(12) United States Patent
Varadarajan et al.

(10) Patent No.: US 11,774,449 B2
(45) Date of Patent: Oct. 3, 2023

(54) INTEGRATED FUNCTIONAL AND MOLECULAR PROFILING OF CELLS

(71) Applicant: University of Houston System, Houston, TX (US)

(72) Inventors: Navin Varadarajan, Houston, TX (US); Gabrielle Romain, Houston, TX (US); Ivan Liadi, Houston, TX (US); Victor Sendra, Cambridge, MA (US); Badrinath Roysam, Houston, TX (US)

(73) Assignee: University of Houston System, Houston, TX (US)

( * ) Notice: Subject to any disclaimer, the term of this patent is extended or adjusted under 35 U.S.C. 154(b) by 228 days.

(21) Appl. No.: 16/995,559

(22) Filed: Aug. 17, 2020

(65) Prior Publication Data
US 2021/0018503 A1    Jan. 21, 2021

Related U.S. Application Data

(63) Continuation of application No. 15/560,018, filed as application No. PCT/US2016/024519 on Mar. 28, 2016, now Pat. No. 10,746,736.
(Continued)

(51) Int. Cl.
*C12Q 1/68* (2018.01)
*G01N 33/569* (2006.01)
(Continued)

(52) U.S. Cl.
CPC ......... *G01N 33/56966* (2013.01); *C12Q 1/68* (2013.01); *C12Q 1/6869* (2013.01); *G01N 33/5005* (2013.01); *G01N 2570/00* (2013.01)

(58) Field of Classification Search
CPC ..................................................... C12Q 1/68
(Continued)

(56) References Cited

U.S. PATENT DOCUMENTS

2006/0073469 A1* 4/2006 Herlyn ................. C12N 5/0697
435/4
2006/0073474 A1* 4/2006 Perez .................. G01N 33/6845
435/6.16
(Continued)

FOREIGN PATENT DOCUMENTS

CN      101135650 A      3/2008
CN      102746986 A      10/2012
EP       1964926 A1      9/2008

OTHER PUBLICATIONS

Mehling et al, Real-time tracking, retrieval and gene expression analysis of migrating human T cells, Lab Chip, 2015,15, 1276-1283, Dec. 10, 2014.*
(Continued)

*Primary Examiner* — Aaron A Priest
(74) *Attorney, Agent, or Firm* — Shackelford, Bowen, McKinley & Norton, LLP

(57) ABSTRACT

Presented herein are methods of evaluating cellular activity by: placing a cell population on an area; assaying for a dynamic behavior of the cell population as a function of time; identifying cell(s) of interest based on the dynamic behavior; characterizing a molecular profile of the cell(s); and correlating the obtained information. The assayed dynamic behavior can include cellular activation, cellular inhibition, cellular interaction, protein expression, protein secretion, cellular proliferation, changes in cellular morphology, motility, cell death, cell cytotoxicity, cell lysis, and combinations thereof. Sensors associated with the area may be utilized to facilitate assaying. Molecular profiles of the cell(s) can then be characterized by various methods, such as DNA analysis, RNA analysis, and protein analysis. The dynamic behavior and molecular profile can then be correlated for various purposes, such as predicting clinical out-
(Continued)

come of a treatment, screening cells, facilitating a treatment, diagnosing a disease, and monitoring cellular activity.

17 Claims, 71 Drawing Sheets

Specification includes a Sequence Listing.

Related U.S. Application Data

(60) Provisional application No. 62/157,174, filed on May 5, 2015, provisional application No. 62/138,813, filed on Mar. 26, 2015.

(51) Int. Cl.
*G01N 33/50* (2006.01)
*C12Q 1/6869* (2018.01)

(58) Field of Classification Search
USPC ......................................................... 435/6.1
See application file for complete search history.

(56) References Cited

U.S. PATENT DOCUMENTS

| | | | | |
|---|---|---|---|---|
| 2008/0300165 | A1* | 12/2008 | Poznansky | A61P 37/04 514/183 |
| 2015/0148705 | A1* | 5/2015 | Baym | A61B 5/443 600/572 |
| 2016/0002731 | A1* | 1/2016 | Robins | C12Q 1/6883 702/19 |
| 2020/0246452 | A1* | 8/2020 | Sampson | C12N 7/00 |

OTHER PUBLICATIONS

Liadi et al., Quantitative high-throughput single-cell cytotoxicity assay for T cells, J Vis Exp. Feb. 2, 2013;(72):e50058. doi: 10.3791/50058.*

Liadi et al., Individual Motile CD4(+) T Cells Can Participate in Efficient Multikilling through Conjugation to Multiple Tumor Cells, Cancer Immunol Res. May 2015;3(5):473-82. doi: 10.1158/2326-6066.CIR-14-0195. Epub Feb. 24, 2015.*

Varadarajan et al., Rapid, efficient functional characterization and recovery of HIV-specific human CD8+ T cells using microengraving, Proc Natl Acad Sci USA. Mar. 6, 2012;109(10):3885-90. doi: 10.1073/pnas.1111205109. Epub Feb. 21, 2012.*

Decision on Rejection for Chinese Patent App. No. 201680030653.1, dated Jan. 13, 2022.

Notice of Rejection for Japanese Pat. App. No. 2017-550160, dated Nov. 6, 2019.

Search Report for EPO App. No. 16769835.6, dated Jan. 27, 2022.

Search Report for EPO App. No. 16769835.6, dated Apr. 9, 2018.

\* cited by examiner

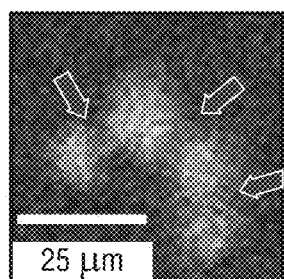 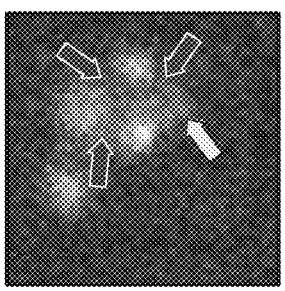 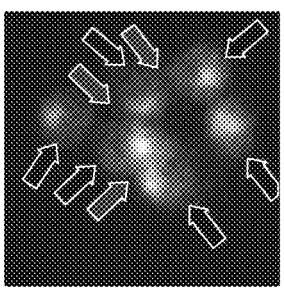 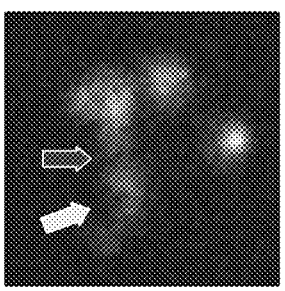
FIG. 3A  FIG. 3B  FIG. 3C  FIG. 3D
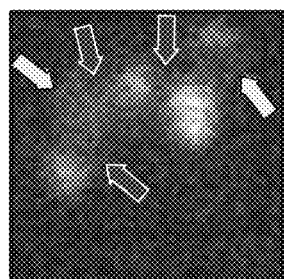 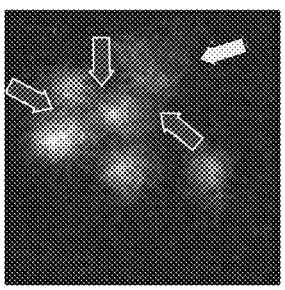 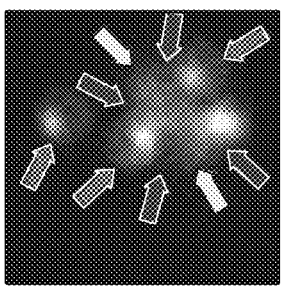 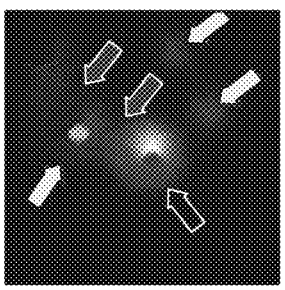
FIG. 3E  FIG. 3F  FIG. 3G  FIG. 3H
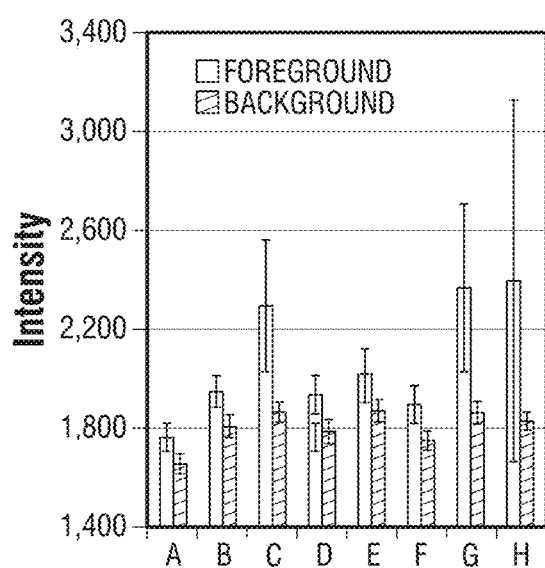 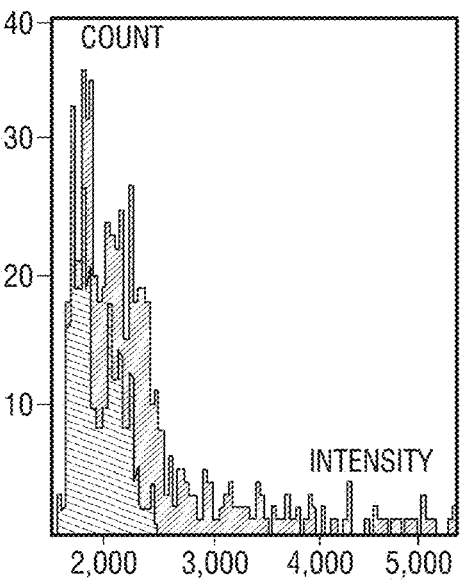
FIG. 3I  FIG. 3J

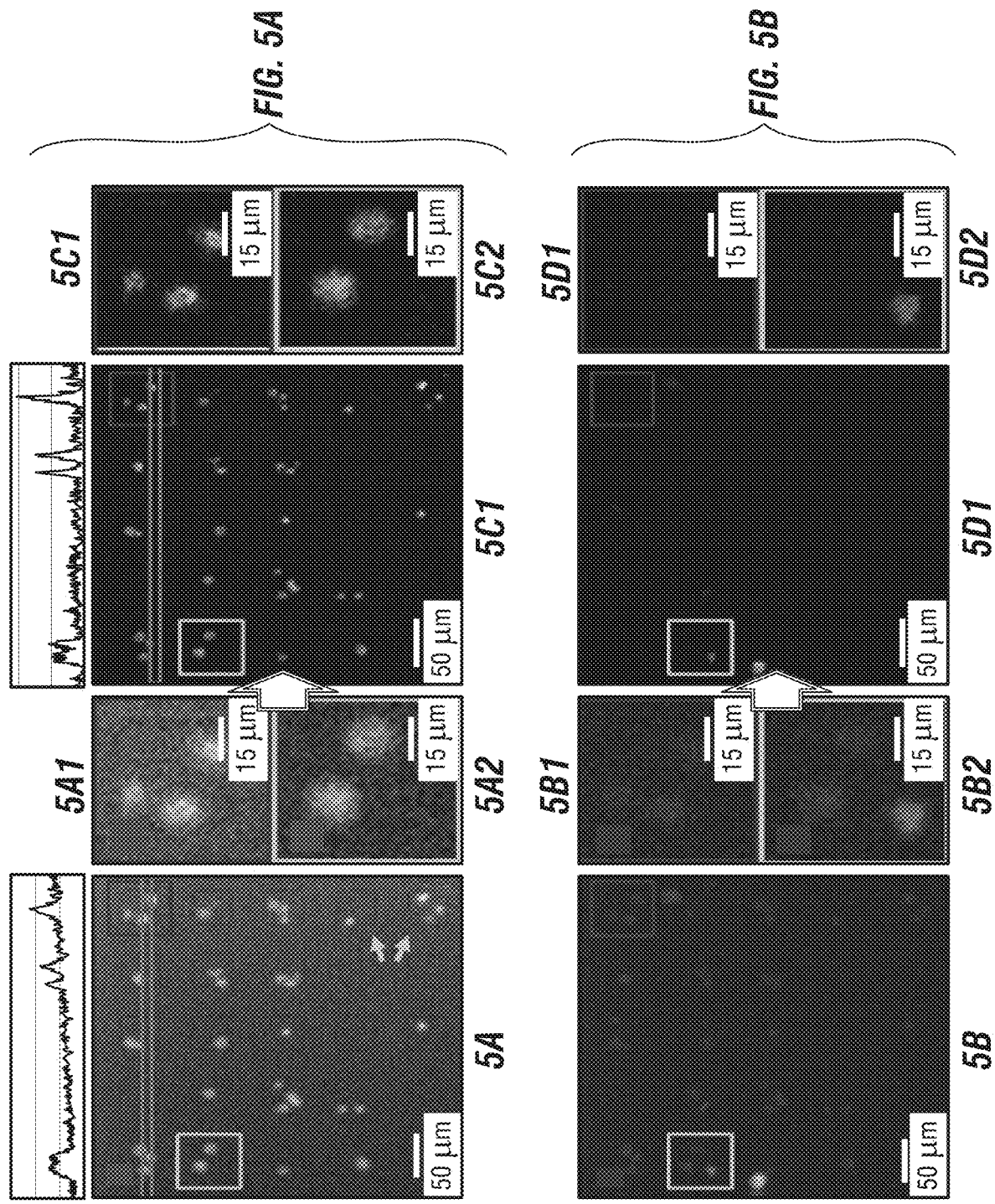

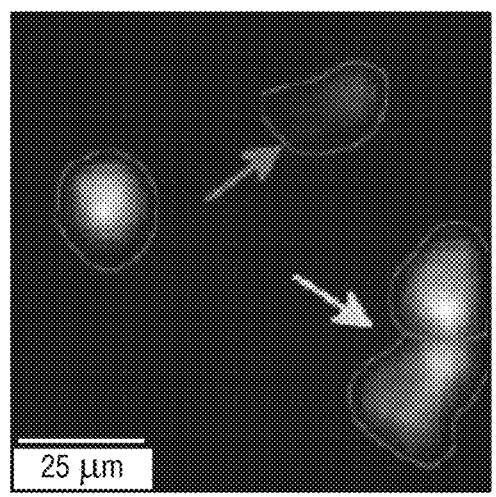
UNDER-SEGMENTATION
FIG. 6A
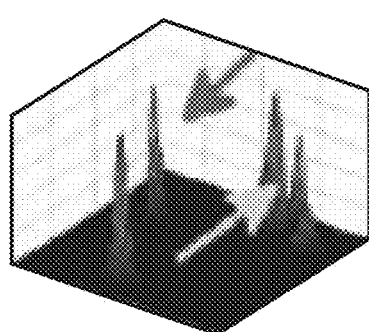 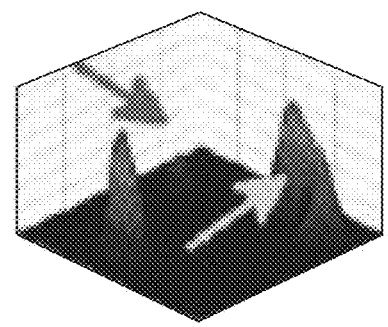
NMTDM | LoG CORRECT SEGMENTATION
FIG. 6B | FIG. 6C
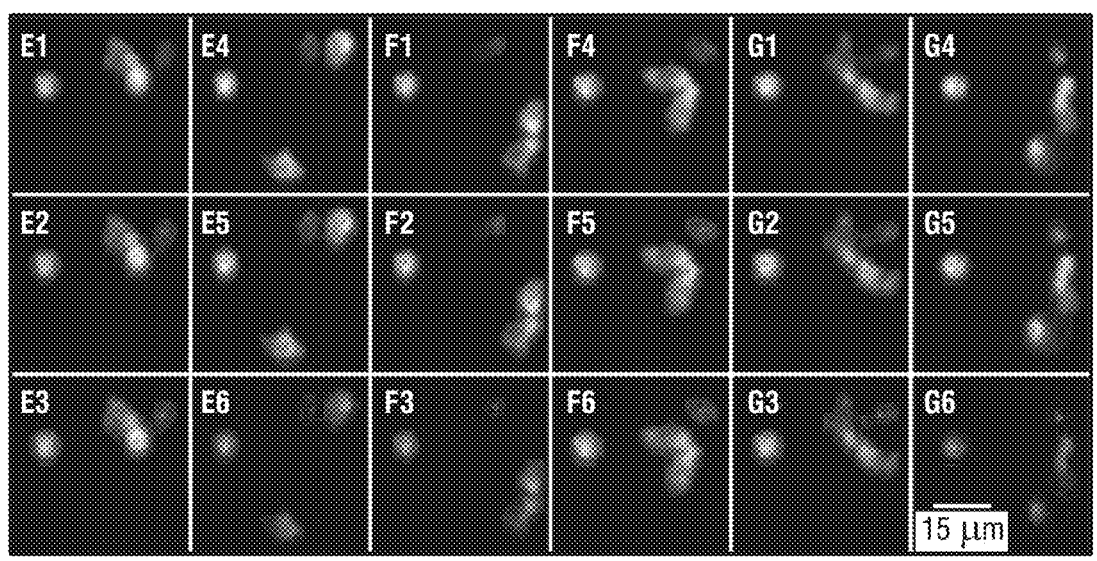
FIG. 6D

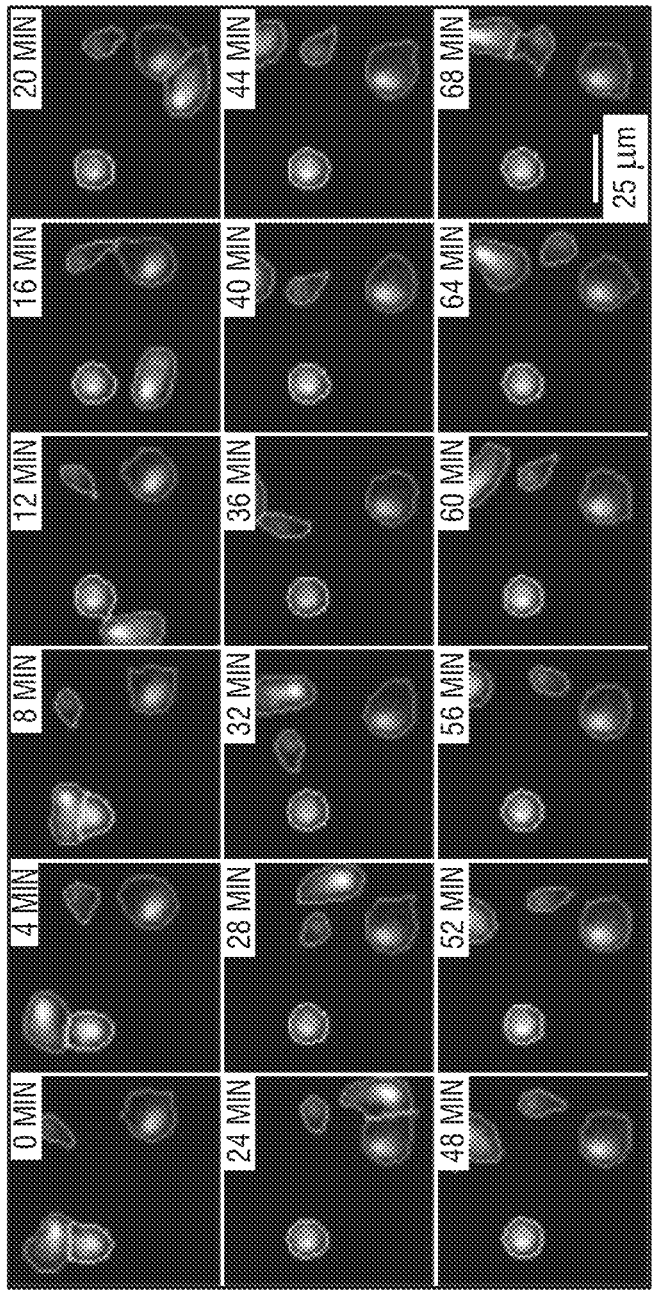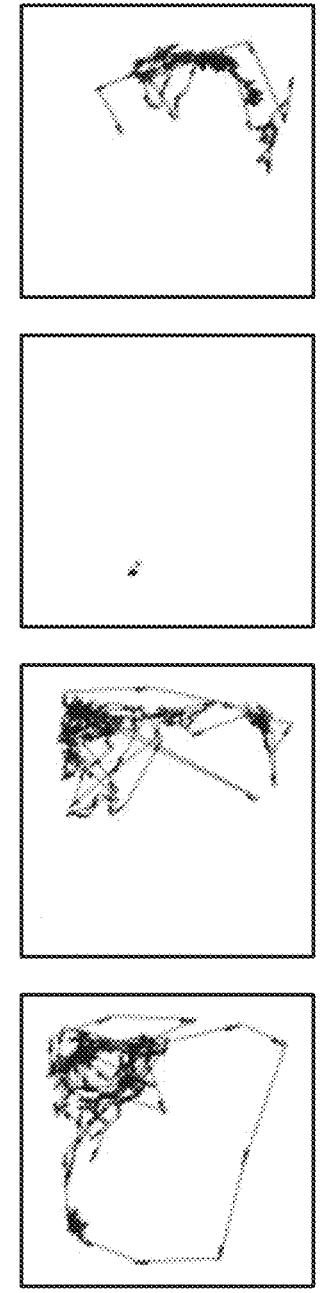

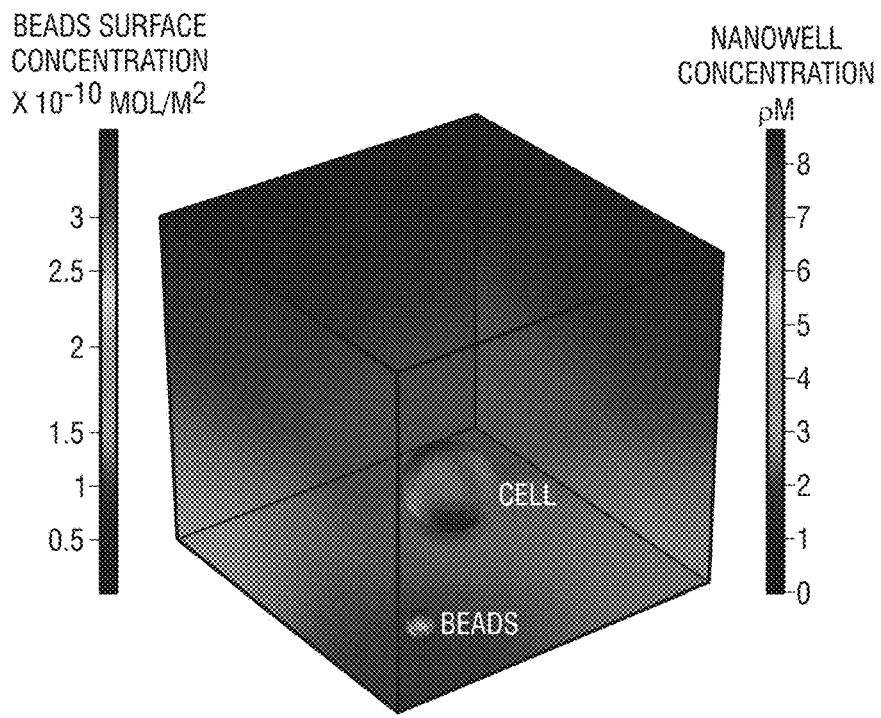
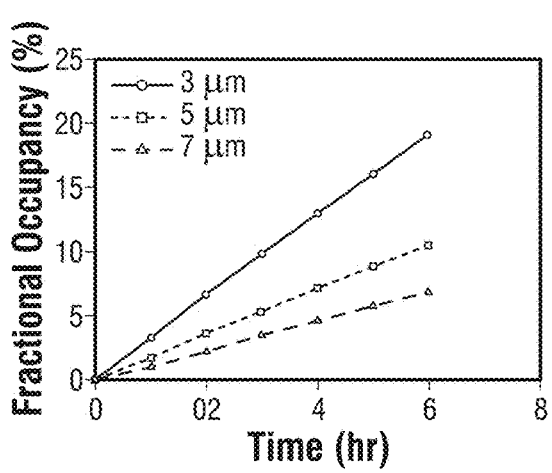
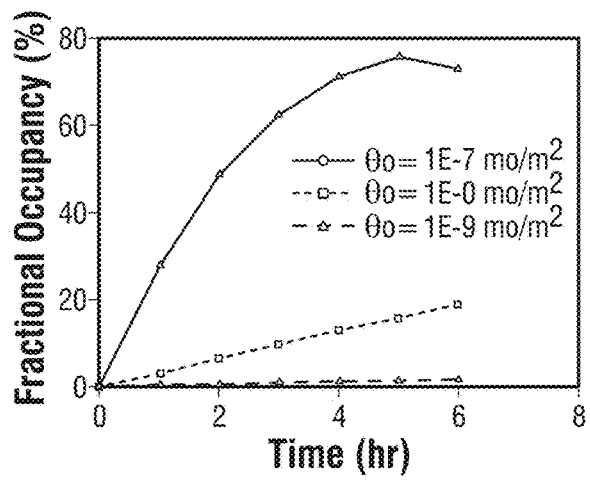
*FIG. 13A*
*FIG. 13B*
*FIG. 13C*

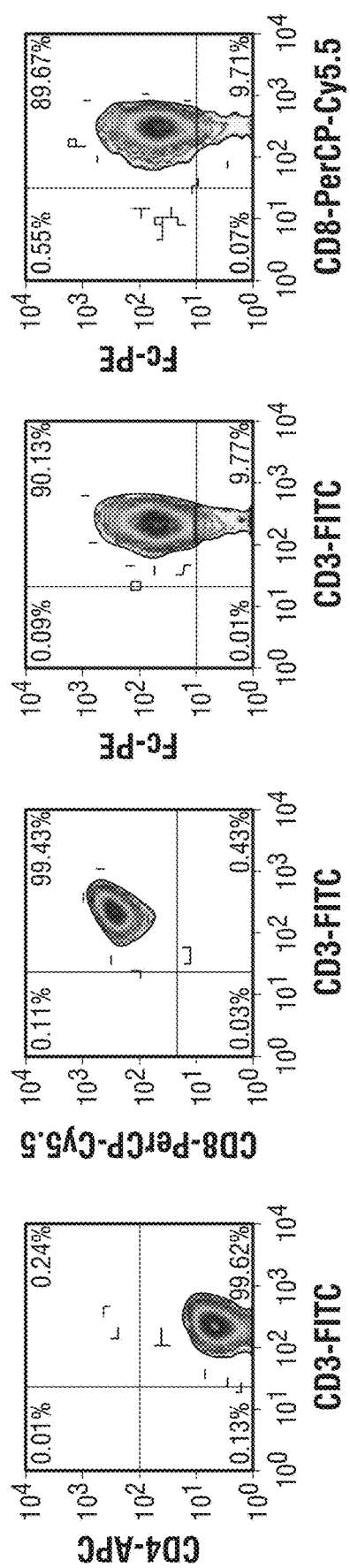
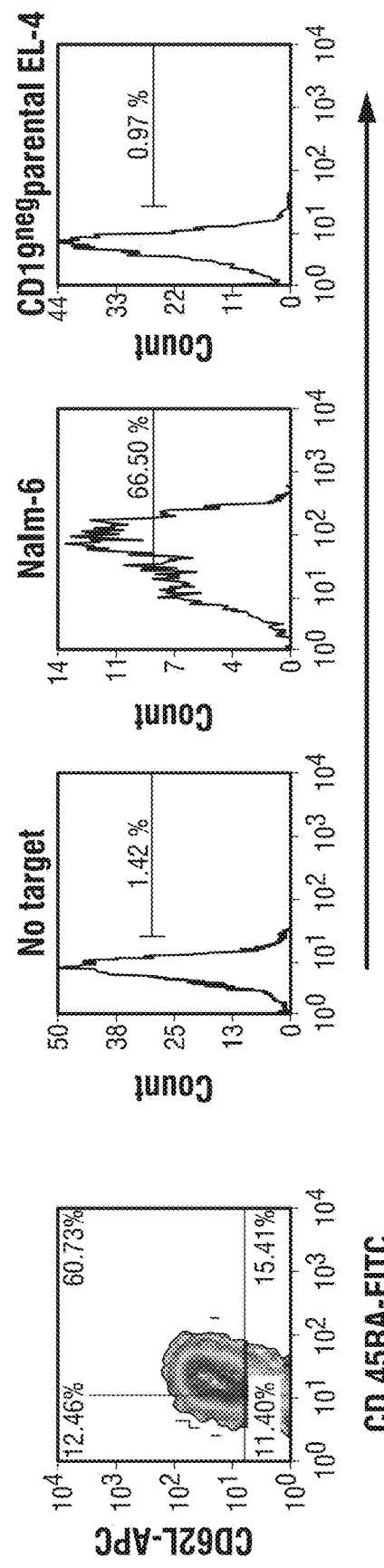
FIG. 15A
FIG. 15B
FIG. 15C

IFNγ secretion

| TARGET | FP | RP | GENE FULL NAME |
|---|---|---|---|
| ALDOA | CCATGGCGACCGTCACA (SEQ ID NO: 1) | TCACTCTGGCCTCCAGACA (SEQ ID NO: 2) | aldolase A, fructose-biphoshate |
| B2M | TCCGTGGCCTTAGCTGTG (SEQ ID NO: 3) | CCCAGACACATAGCAATTCAGG (SEQ ID NO: 4) | beta-2-microglobulin |
| BCL2 | GACAGAGGATCATGCTGTACTT (SEQ ID NO: 5) | CTTGGCATGAGATGCAGGA (SEQ ID NO: 6) | B-cell CLL/lymphoma 2 |
| BCL6B | AACCCCTCAGAGCACACAA (SEQ ID NO: 7) | CGGCCCCGGAAAATTGAATA (SEQ ID NO: 8) | B-cell CLL/lymphoma 6, member B |
| BTLA | TCCCATATCTGGACATCTGGAAC (SEQ ID NO: 9) | CTCCTGCTAAGATGGAGTGTTCA (SEQ ID NO: 10) | B and T lymphocyte associated |
| CCL3 | CCGTCACCTGCTCAGAATCA (SEQ ID NO: 11) | CCATGGTGCAGGAGGAGGAC (SEQ ID NO: 12) | chemokine (C-C motif) ligand 3 |
| CCL4 | CGTGACTGTCCTGTCTCTCC (SEQ ID NO: 13) | TCTACCACAAAGTTGCGAGGAA (SEQ ID NO: 14) | chemokine (C-C motif) ligand 4 |
| CCR1 | AACCCAGAAAGCCCCAGAAA (SEQ ID NO: 15) | GTGGTGTTTGGAGTTTCCATCC (SEQ ID NO: 16) | chemokine (C-C motif) receptor 1 |
| CCR2 | ACATACCAGGACTGCCTGAG (SEQ ID NO: 17) | GTGGATGTACTGGGGAAATGC (SEQ ID NO: 18) | chemokine (C-C motif) receptor 2 |
| CCR4 | CATTGCCTCACAGACCTTCC (SEQ ID NO: 19) | AGGGTGGTGTCTGCTATATCC (SEQ ID NO: 20) | chemokine (C-C motif) receptor 4 |
| CCR5 | TGAGACATCCGTTCCCCTACA (SEQ ID NO: 21) | TGGCAGGGCTCCGATGTATA (SEQ ID NO: 22) | chemokine (C-C motif) receptor 5 |
| CCR6 | AGGCAGCGATGTCTGTGAA (SEQ ID NO: 23) | AGCTCAAGCCCAACATCA (SEQ ID NO: 24) | chemokine (C-C motif) receptor 6 |

*FIG. 21A-1*

| TARGET | FP | RP | GENE FULL NAME |
|---|---|---|---|
| CCR7 | GTGGTTGGGCTCTCCTTGTCA (SEQ ID NO: 25) | TGTGGTTGTGTCTCCGATGTA (SEQ ID NO: 26) | chemokine (C-C motif) receptor 7 |
| CD160 | AGAAGCCAGAAGTCAGGTATCC (SEQ ID NO: 27) | TCCCGTCACTGTGTAGTTCC (SEQ ID NO: 28) | CD160 molecule |
| FAS | AGAAGGGAAGGAGTACACAGAC (SEQ ID NO: 29) | CCGGGGTGCAGTTTATTTCCA (SEQ ID NO: 30) | Fas (TNF receptor superfamily, member 6) |
| CD2 | AGTGCACAGCAGGGAACAA (SEQ ID NO: 31) | AGGCTGCCTCCTCCACATA (SEQ ID NO: 32) | CD2 molecule |
| CD244 | AACCACAGCCCTTCCTTCAA (SEQ ID NO: 33) | GAGCAGGGTTCTGGGCTTTA (SEQ ID NO: 34) | CD244 molecule, natural killer cell receptor 2B4 |
| CD27 | CACTACTGGGCTTCAGGGAAA (SEQ ID NO: 35) | TGCTGGGTCACAGTCCTTCA (SEQ ID NO: 36) | CD27 molecule |
| CD28 | GTCCTGGCTTGCTTATAGCTT (SEQ ID NO: 37) | CATGTAGTCACTGTGCAGGA (SEQ ID NO: 38) | CD28 molecule |
| CD3D | CGTTTCTCTCTGGCCTGGT (SEQ ID NO: 39) | CTCTACCCATGTGATGCTGGTA (SEQ ID NO: 40) | CD3d molecule, delta (CD3-TCR complex) |
| CD3E | GCTACCCCAGAGGAAGCAAA (SEQ ID NO: 41) | TCCATCTCCATGCAGTTCTCAC (SEQ ID NO: 42) | CD3e molecule, epsilon CD3-TCR complex) |
| CD4 | AAAGTTGCATCAGGAAGTGAACC (SEQ ID NO: 43) | CCCACACCCTCACAGGTCAAA (SEQ ID NO: 44) | CD4 molecule |
| CD40LG | GAGGCCAGCAGTAAAACAAC (SEQ ID NO: 45) | AGTTGTTGCTCATGGGTAGTA (SEQ ID NO: 46) | CD40 ligand |

*FIG. 21A-2*

| TARGET | FP | RP | GENE FULL NAME |
|---|---|---|---|
| CD44 | CCGGACACCATGGACAAGTT (SEQ ID NO: 47) | CCTGCAAAGCGGCAGGT (SEQ ID NO: 48) | CD44 molecule (Indian blood group) |
| CD58 | AATCATTTTGACAACCTGTATCCC (SEQ ID NO: 49) | TGTAATTACTGCTAATGGTATGGGTA (SEQ ID NO: 50) | CD58 molecule |
| CD63 | GCAGCCAGCCTTGGGAA (SEQ ID NO: 51) | GCAAGAACTTCACACATTTCATTCC (SEQ ID NO: 52) | CD63 molecule |
| CD69 | TCACCCATGGAAGTGGTCAA (SEQ ID NO: 53) | ACACACTTGTGTCAGACCCTGTA (SEQ ID NO: 54) | CD69 molecule |
| CD80 | TGCTGGCTGGTCTTTCTCA (SEQ ID NO: 55) | GAGTTTGTGCCAGCTCTTCAA (SEQ ID NO: 56) | CD80 molecule |
| CD86 | CGGCCTCCGCAACTCTTATA (SEQ ID NO: 57) | TGGTCTGTGTTCACTCTCTTCC (SEQ ID NO: 58) | CD86 molecule |
| CD8A | ACTTCGTGCCGGTCTTCCT (SEQ ID NO: 59) | GCTGCGACGCGATGGT (SEQ ID NO: 60) | CD8a molecule |
| CSF2 | TGATGGCCAGCCACTACAA (SEQ ID NO: 61) | CAAAGGGGATGACAAGCAGAAA (SEQ ID NO: 62) | colony stimulating factor 2 granulocyte-macrophage |
| CTLA4 | CTTGGGATTTCAGCGGCACAA (SEQ ID NO: 63) | GCTGCTGGCCAGTACCA (SEQ ID NO: 64) | cytotoxic T-lymphocyte-associated protein 4 |
| CX3CL1 | CCACCTTCTGCCATCTGAC (SEQ ID NO: 65) | CGTGATGTTGCATTTCGTCAC (SEQ ID NO: 66) | chemokine (C-X3-C motif) ligand 1 |
| CX3CR1 | GTAGTGTTTGCCCTCACCAAC (SEQ ID NO: 67) | ATCAGACAAGGCCAGGTTCA (SEQ ID NO: 68) | chemokine (C-X3-C motif) receptor 1 |
| CXCL10 | GCTGTACCTGCATCAGCATTA (SEQ ID NO: 69) | CTGGATTCAGACATCTCTTCTAC (SEQ ID NO: 70) | chemokine (C-X-C motif) ligand 10 |
| CXCL12 | AGCCAACGTCAAGCATCTCA (SEQ ID NO: 71) | GCTTCGGGTCAATGCACAC (SEQ ID NO: 72) | chemokine (C-X-C motif) ligand 12 |

FIG. 21B-1

| TARGET | FP | RP | GENE FULL NAME |
|---|---|---|---|
| CXCL9 | AGCCCTTCCTGCGGAGAAAA (SEQ ID NO: 73) | ATCTGCTGAATCTGGGTTTAGACA (SEQ ID NO: 74) | chemokine (C-X-C motif) ligand 9 |
| IL8RA | ATCTCTGACTGCCAGCTCCTA (SEQ ID NO: 75) | TGTCCTCTTCAGTTTCAGCAA (SEQ ID NO: 76) | chemokine (C-X-C motif) receptor 1 |
| CXCR3 | AACTGTGGCCGAGAAAGCA (SEQ ID NO: 77) | TTGAGGCAGCAGTGCATGTA (SEQ ID NO: 78) | chemokine (C-X-C motif) receptor 3 |
| CXCR4 | ATCTTCCTGCCCACCATCTAC (SEQ ID NO: 79) | CCCATGACCAGGATGACCAA (SEQ ID NO: 80) | chemokine (C-X-C motif) receptor 4 |
| FASLG | TGGGGATGTTTCAGCTCTTCC (SEQ ID NO: 81) | CTGTGTGCATCTGGCTGGTA (SEQ ID NO: 82) | Fas ligand (TNF superfamily, member 6) |
| FOXP3 | TGTGGGGTAGCCATGGAAA (SEQ ID NO: 83) | GGGGTGCATGTTGTGGAA (SEQ ID NO: 84) | forkhead box P3 |
| G6PD | GCCGTCACCAAGAACATTCA (SEQ ID NO: 85) | CTCCCGAAGGGCTTCTCC (SEQ ID NO: 86) | glucose-6-phosphate dehydrogenase |
| GAPDH | ACACCATGGGGAAGGTGAAG (SEQ ID NO: 87) | GTGACCAGGGCGCCCAATA (SEQ ID NO: 88) | glyceraldehyde-3-phosphate dehydrogenase |
| GATA3 | CACGGTGCAGAGGTACCC (SEQ ID NO: 89) | AGGGTAGGGATCCATGAAGCA (SEQ ID NO: 90) | GATA binding protein 3 |
| GZMA | GAAGCCCTCCGAGGTGGAA (SEQ ID NO: 91) | GAAAACACCCTGCACAACA (SEQ ID NO: 92) | granzyme A (granzyme 1, cytotoxic T-lymphocyte-associated serine esterase 3) |

FIG. 21B-2

| TARGET | FP | RP | GENE FULL NAME |
|---|---|---|---|
| GZMB | CCCCATCCAGCCTATAATCCTAA (SEQ ID NO: 93) | CTGGGCCTTGTTGCTAGGTA (SEQ ID NO: 94) | granzyme B (granzyme 2, cytotoxic T-lymphocyte-associated serine esterase 1) |
| GZMK | ATCCACAGTGGGTGCTGAC (SEQ ID NO: 95) | AGAGTGTGCGCCTAAAACCA (SEQ ID NO: 96) | granzyme K (granzyme 3; tryptase II) |
| HAVCR2 | GGATCCAAATCCCAGGCATAA (SEQ ID NO: 97) | CTTGGAAAGGCTGCAGTGAA (SEQ ID NO: 98) | hepatitis A virus cellular receptor 2 |
| ICOS | AGTCTGCATTTTGGGATGCA (SEQ ID NO: 99) | GTCGTGCACACTGGATGAA (SEQ ID NO: 100) | inducible T-cell co-stimulator |
| ICOSLG | TTGGCTGCTGCATAGAGAAC (SEQ ID NO: 101) | CTTGTCTCTCTCTCCGATGTCA (SEQ ID NO: 102) | inducible T-cell co-stimulator ligand |
| IFNG | ACTGCCAGGACCCATATGTAA (SEQ ID NO: 103) | GTTCCATTATATCGCTACACTCTGAA (SEQ ID NO: 104) | interferon, gamma |
| IFNGR1 | AAGTTAGGGTTGGACAAAA (SEQ ID NO: 105) | GATATCCAGTTTAGGTGGTCCAA (SEQ ID NO: 106) | interferon gamma receptor 1 |
| IL10 | CCGTGGAGCAGGTGAAGAA (SEQ ID NO: 107) | GTCAAACTCACTCATGGCTTTGTA (SEQ ID NO: 108) | interleukin 10 |
| IL12A | CACAGTGGAGGCCTGTTTA (SEQ ID NO: 109) | TCTGGAATTTAGGCAACTCTCA (SEQ ID NO: 110) | interleukin 12A (natural killer cell stimulatory factor 1, cytotoxic lymphocyte maturation factor 1, p35) |
| IL12B | TCCCTGACATTCTGCGTTCA (SEQ ID NO: 111) | GGTCTTGTCCGTGAAGACTCTA (SEQ ID NO: 112) | interleukin 12B (natural killer cell stimulatory factor 2, cytotoxic lymphocyte maturation factor 2, p40) |

FIG. 21C-1

| TARGET | FP | RP | GENE FULL NAME |
|---|---|---|---|
| IL12RB1 | GCCATATCCGGATGCAGAC (SEQ ID NO: 113) | CAGCTGTGGGACCCTTCATA (SEQ ID NO: 114) | interleukin 12 receptor, beta 1 |
| IL12RB2 | GTCTTGGAAGCTCCTCTTCAC (SEQ ID NO: 115) | TCTAATGTCCACGGAGGAA (SEQ ID NO: 116) | interleukin 12 receptor, beta 2 |
| IL13 | TGCAGTGCCATCGAGAAGAC (SEQ ID NO: 117) | TCGGACATGCAAGCTGGAAA (SEQ ID NO: 118) | interleukin 13 |
| IL15 | AGCCAACTGGGTGAATGTAA (SEQ ID NO: 119) | CACTTTCCGTATATAAAGTAGCATCA (SEQ ID NO: 120) | interleukin 15 |
| IL15RA | TGAGGGCTGTGTCTCTCC (SEQ ID NO: 121) | CCTCCATGGCTTCCATTTCAAC (SEQ ID NO: 122) | interleukin 15 receptor, alpha |
| IL17A | ACTACAACCGATCCACCTCAC (SEQ ID NO: 123) | ACTTTGCCTCCCAGATCACA (SEQ ID NO: 124) | interleukin 17A |
| EOMES | CTGTGGGCAAAGCCGACAATA (SEQ ID NO: 125) | CTCATCCAGTGGGAACCAGTA (SEQ ID NO: 126) | eomesodermin |
| IL17RA | CCAAACCACCAGTCCAAGAA (SEQ ID NO: 127) | CTCATGCATGGCGTGGTTA (SEQ ID NO: 128) | interleukin 17 receptor A |
| IL18 | GACCAAGGAAATCGGCCTCTA (SEQ ID NO: 129) | TCACAGAGATAGTTACAGCCATACC (SEQ ID NO: 130) | interleukin 18 (interferon-gamma-inducing factor) |
| IL18R1 | CGTTCTTCTTGGACCAAAGCTTAA (SEQ ID NO: 131) | AGCAGAGCAGTTGAGCCTTA (SEQ ID NO: 132) | interleukin 18 receptor 1 |
| IL2 | CCCAGGGACTTAATCAGCAATA (SEQ ID NO: 133) | TTCTACAATGGTTGCTGTCTCA (SEQ ID NO: 134) | interleukin 2 |
| IL21R | TGCATCCTGGAAATGTGGAAC (SEQ ID NO: 135) | CCTCGTCCTTCAGCTCTTCATA (SEQ ID NO: 136) | interleukin 21 receptor |

*FIG. 21C-2*

| TARGET | FP | RP | GENE FULL NAME |
|---|---|---|---|
| IL2RA | GCACAGGTGA AATGGAGACC (SEQ ID NO: 137) | GACGAGGCAG GAAGTCTCA (SEQ ID NO: 138) | interleukin 2 receptor, alpha |
| IL2RB | ATGGCCATCC AGGACTTACA (SEQ ID NO: 139) | TTGCATCTGT GGGTCTCCA (SEQ ID NO: 140) | interleukin 2 receptor, beta |
| IL2RG | GCCCAATGGG AATGAAGACA (SEQ ID NO: 141) | TGGAAACACT GAGGGAGTCA (SEQ ID NO: 142) | interleukin 2 receptor, gamma |
| IL4 | CAGCTGATCC GATTCCTGAAA (SEQ ID NO: 143) | GTTGGCTTCC TTCACAGGAC (SEQ ID NO: 144) | interleukin 4 |
| IL4R | GAGCTCCGCC TGTTGTACC (SEQ ID NO: 145) | GCGCCTCCG TTGTTCTCA (SEQ ID NO: 146) | interleukin 4 receptor |
| IL5 | ACTCTGAGGATT CCTGTTCCTGTA (SEQ ID NO: 147) | CCAGTGTGCCT ATTCCCTGAAA (SEQ ID NO: 148) | interleukin5(colony-stimulatingfactor,eosinophil) |
| IL7R | GGAGAAAGTGG CTATGCTCAA (SEQ ID NO: 149) | CTGCGATCCA TTCACTTCCA (SEQ ID NO: 150) | interleukin 7 receptor |
| IRF4 | CTACAACCGC GAGGAGGAC (SEQ ID NO: 151) | TGTCGATGCC TTCCTCGGAAC (SEQ ID NO: 152) | interferon regulatory factor 4 |
| KLF4 | CTGCGGCAAA ACCTACACA (SEQ ID NO: 153) | CGTCCCAGTC ACAGTGGTAA (SEQ ID NO: 154) | Kruppel-like factor 4 (gut) |
| KLRG1 | ACCCAAGCCC AGAATGACTA (SEQ ID NO: 155) | TTGCCACAAG GCAAGAACA (SEQ ID NO: 156) | killer cell lectin-like receptor subfamily G, member 1 |
| LAG3 | TGGAGCCTTT GGCTTTCAC (SEQ ID NO: 157) | GAGGGTGAATC CCTTGCTCTA (SEQ ID NO: 158) | lymphocyte-activation gene 3 |
| LEF1 | AAGAAAGTGCA GCTATCAACCA (SEQ ID NO: 159) | GCTGTCTTTCT TTCCGTGCTA (SEQ ID NO: 160) | lymphoid enhancer-binding factor 1 |
| NANOS2 | TGTCCCATCCT GAGGCACTA (SEQ ID NO: 161) | ACCGTTAAGC GGGCAGTAC (SEQ ID NO: 162) | nanos homolog 2 (Drosophila) |
| NFKB1 | CTGGAACCACG CCTCTAGATA (SEQ ID NO: 163) | AAACTCTGGCTC ATATGGTTTCC (SEQ ID NO: 164) | nuclear factor of kappa lightpolypeptide gene enhancer in B-cells 1 |

*FIG. 21D-1*

| TARGET | FP | | RP | | GENE FULL NAME |
|---|---|---|---|---|---|
| PDCD1 | GCAGCCTGG TGCTGCTA | (SEQ ID NO: 165) | GTGCGCCT GGCTCCTA | (SEQ ID NO: 166) | programmed cell death 1 |
| PRF1 | GTACAGCTTCA GCACTGACAC | (SEQ ID NO: 167) | CTGGGTGGA GGCGTTGAA | (SEQ ID NO: 168) | perforin 1 (pore forming protein) |
| RORA | CAGCAGATAA CGTGGCAGAC | (SEQ ID NO: 169) | GGCACACAAT TGCCCACATCA | (SEQ ID NO: 170) | RAR-related orphan receptor A |
| RORC | CAGACTCATC GCCAAAGCA | (SEQ ID NO: 171) | TTTCCACATG CTGGCTACAC | (SEQ ID NO: 172) | RAR-related orphan receptor C |
| STAT5A | CCCAGGCTCCC TATAACATGTA | (SEQ ID NO: 173) | ATGGTCTCAT CCAGGTCGAA | (SEQ ID NO: 174) | signal transducer and activator of transcription 5A |
| STAT5B | AACAGAGGTT GGTCCGAGAA | (SEQ ID NO: 175) | GTTTCTGGGA CATGGCATCA | (SEQ ID NO: 176) | signal transducer and activator of transcription 5B |
| TCF7 | TTCAATCTGCTC ATGCATTACCC | (SEQ ID NO: 177) | GTGGGCTGTTG AAATGTTCGTA | (SEQ ID NO: 178) | transcription factor 7 (T-cell specific, HMG-box) |
| TGFB1 | CGTCTGCTGAG GCTCAAGTTA | (SEQ ID NO: 179) | TCGCCAGGAAT TGTTGCTGTA | (SEQ ID NO: 180) | transforming growth factor, beta 1 |
| TGFB2 | CAAAAGCCAGA GTGCCTGAA | (SEQ ID NO: 181) | CGCTGGGGTTGG AGATGTTAAA | (SEQ ID NO: 182) | transforming growth factor, beta 2 |
| TGFBR1 | GAAATTGCTCG ACGATGTTCC | (SEQ ID NO: 183) | ACTGATGGGTC AGAAGGTACA | (SEQ ID NO: 184) | transforming growth factor, beta receptor 1 |

*FIG. 21D-2*

| TARGET | FP | RP | GENE FULL NAME |
|---|---|---|---|
| TNFRSF9 | GGGGCAGAAAG AAACTCCTGTA (SEQ ID NO: 185) | TCTGGAAATC GGCAGCTACA (SEQ ID NO: 186) | tumor necrosis factor receptor superfamily, member 9 |
| TNFSF14 | AGGTCTCACG AGGTCAACC (SEQ ID NO: 187) | CCCAGCTGAG TCTCCCATAA (SEQ ID NO: 188) | tumor necrosis factor (ligand) superfamily, member 14 |
| ZAP70 | AAGCGCGATAA CCTCCTCATA (SEQ ID NO: 189) | TTCCGTGTCT GCCTTCTCC (SEQ ID NO: 190) | zeta-chain (TCR) associated protein kinase 70kDa |

FIG. 21E

Effector : Target (E:T) ratio 1:1

| Sample | Single-cell cytotoxicity assay | | | $^{51}$Cr release assay | | |
|---|---|---|---|---|---|---|
| | CD19$^{pos}$ | CD19$^{neg}$ | NALM-6 | CD19$^{pos}$ | CD19$^{neg}$ | NALM-6 |
| PB281848 | 0.22 (2525) | 0.02 (2692) | 0.30 (3102) | 0.17 | 0.00 | 0.16 |
| PB245366 | 0.35 (1523) | 0.01 (990) | 0.37 (401) | 0.39 | 0.05 | 0.40 |

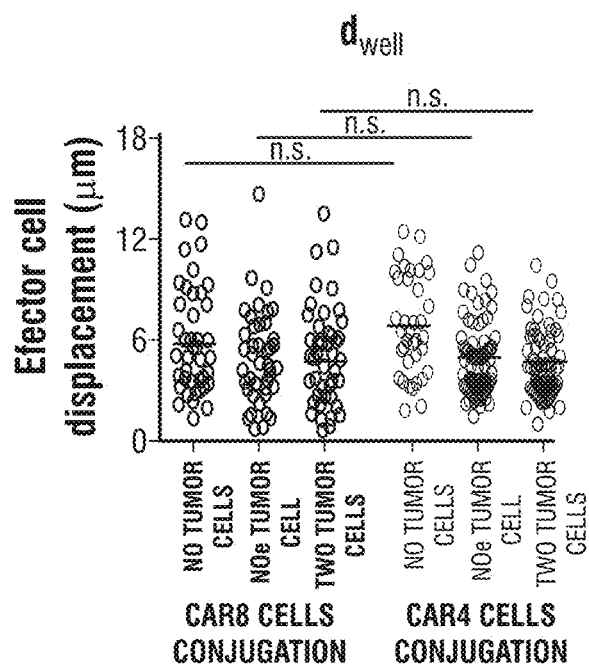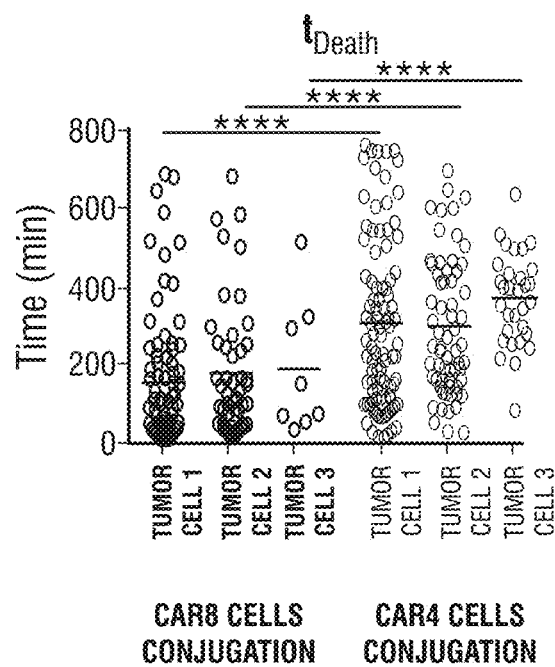
FIG.39A  FIG.39B
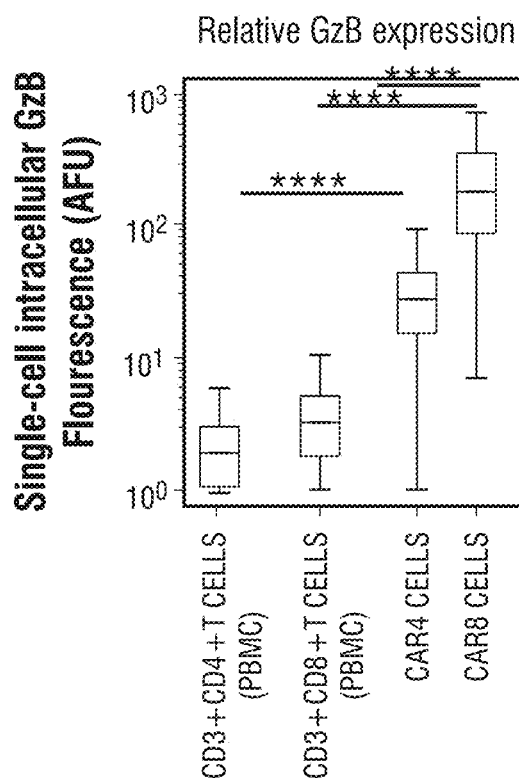
FIG.39C

PB333038

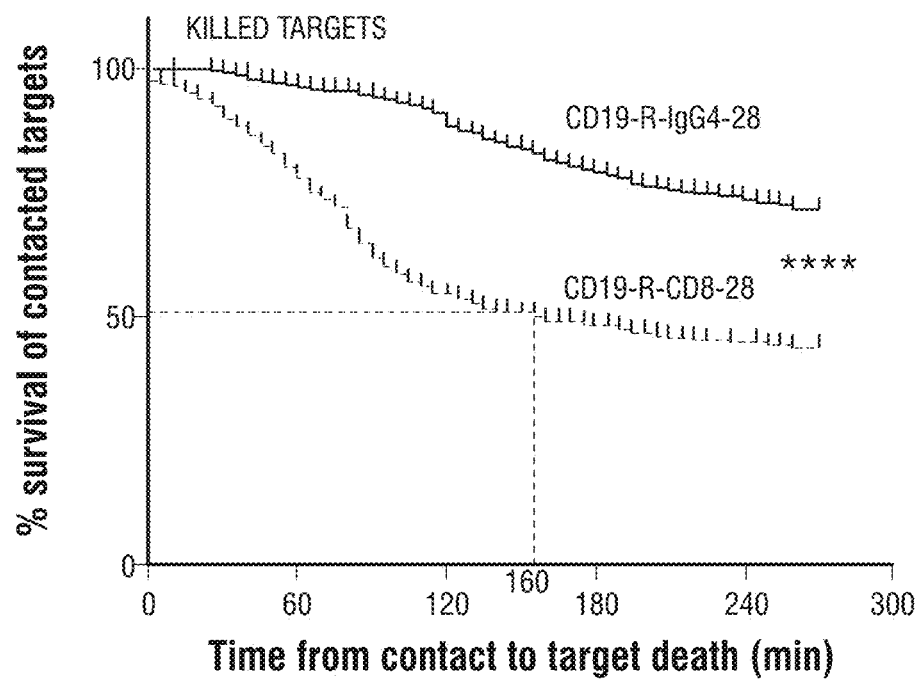
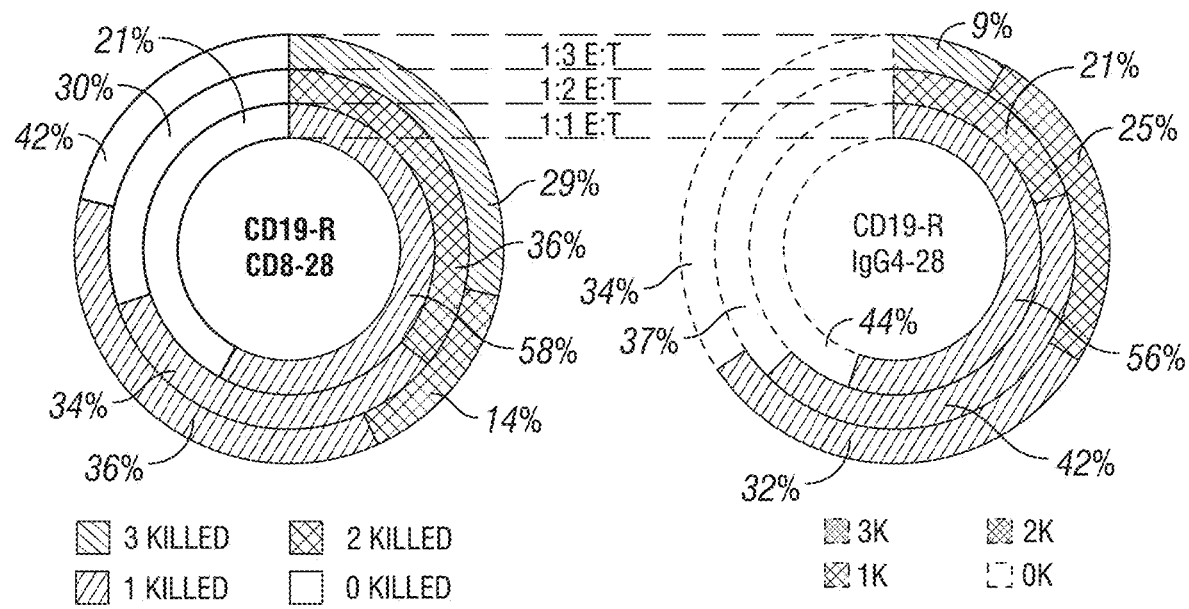
FIG. 43

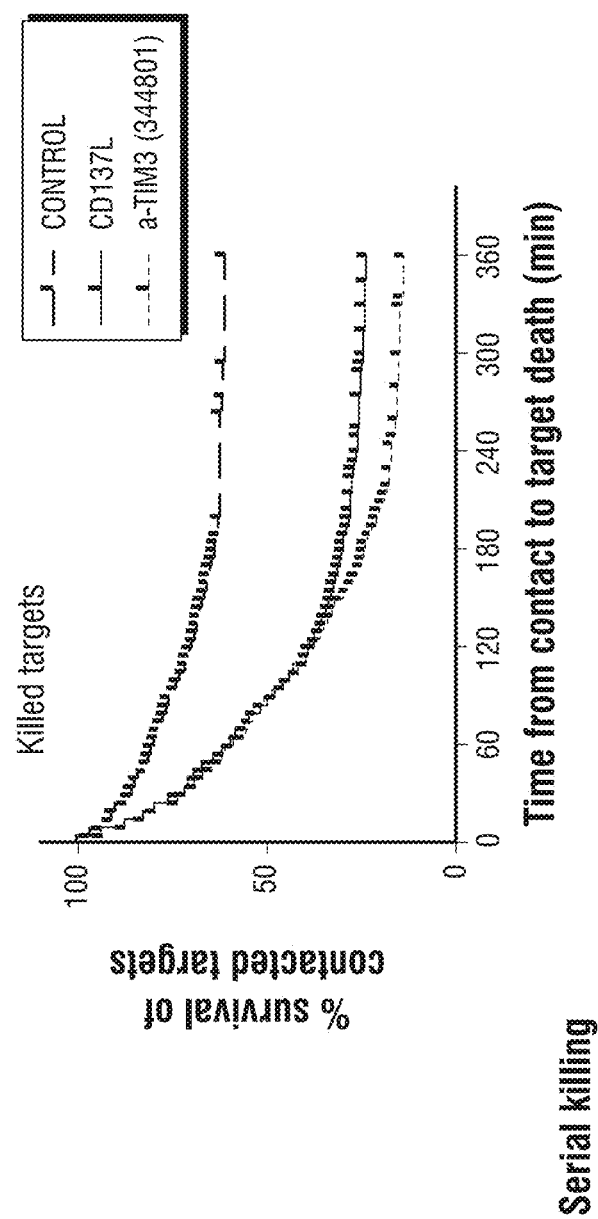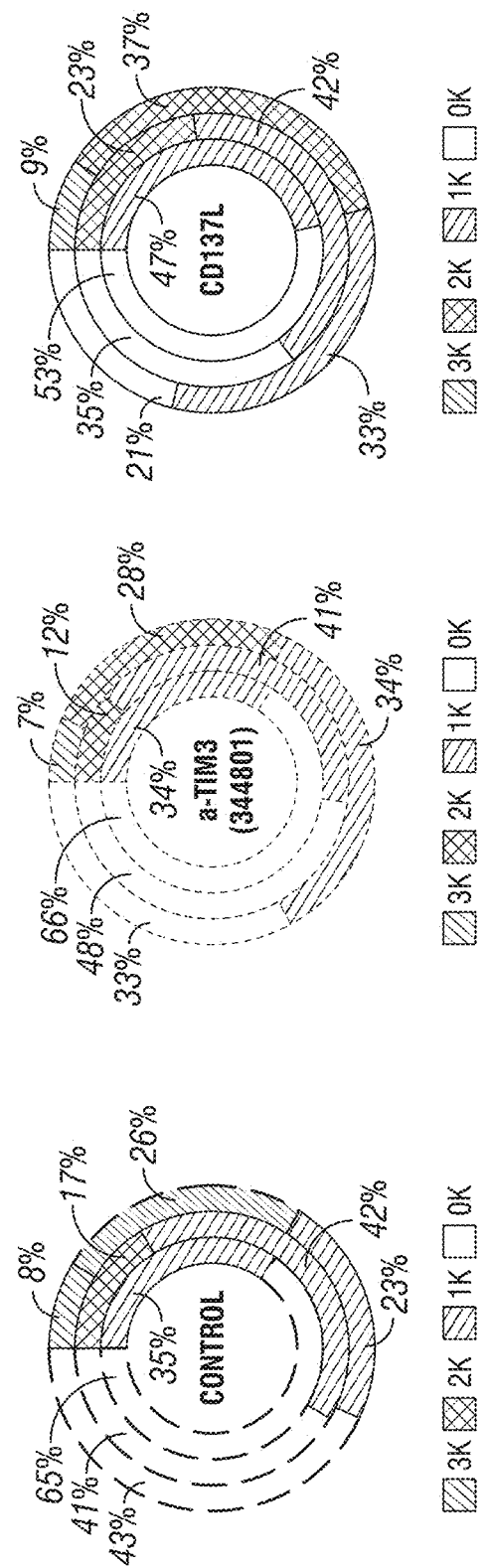
FIG. 49

|  | No. of Targets | | | | |
|---|---|---|---|---|---|
| | | 0 | 1 | 2 | 3 | 4 |
| Effectors | 0 | 160/59.4% | 128/56.2% | 80/51.2% | 69/47.8% | 19/31.6% |
| | 1 | 165/54.6% | 174/45.9% | 98/40.8% | 60/41.7% | 32/15.6% |
| | 2 | 148/47.3% | 111/43.2% | 93/37.6% | 56/35.7% | 21/14.2% |
| | 3 | 57/37.4% | 74/37.8% | 73/35.6% | 29/34.5% | 16/12.5% |
| | 4 | 39/25.6% | 43/13.9% | 29/10.3% | 19/10.5% | 10/0.0% |

FIG. 50

|  | No. of Targets | | | | |
|---|---|---|---|---|---|
| | | 0 | 1 | 2 | 3 | 4 |
| Effectors | 0 | 160/99.4% | 128/98.4% | 80/97.5% | 69/92.8% | 19/89.5% |
| | 1 | 165/98.7% | 174/98.3% | 98/97.9% | 60/91.7% | 32/78.1% |
| | 2 | 148/97.9% | 111/97.3% | 93/96.8% | 56/91.1% | 21/80.9% |
| | 3 | 57/94.7% | 74/94.6% | 73/91.8% | 29/89.7% | 16/81.2% |
| | 4 | 39/87.1% | 43/88.4% | 29/86.2% | 19/84.2% | 10/80.0% |

FIG. 51

| Number of cells | 2 Targets | 3 Targets | 4 Targets |
|---|---|---|---|
| Under-segmentation | 1.2% | 1.4% | 0.1% |
| Over-segmentation | 1.3% | 0.6% | 4.2% |
| Incorrect-correspondence | 0.9% | 0.8% | 3.6% |
| Total cells validated | 816 | 636 | 168 |

FIG. 52

| Parameter | Processing Step | Value (units) |
|---|---|---|
| Median Filter Size $r_m$ | Preprocessing | 3-5 (pixels) |
| Local Max. Clustering $r$ | Nanowell Detection | Well width (pixels) |
| NCC Response Threshold | Nanowell Detection | 0.75 (on 0-1 scale) |
| Number of Mixtures $K$ | Binarization | 3 |
| Thresholding Levels $M$ | Seed Detection | 20 (levels) |
| Local Max. Clustering $r$ | Seed Detection | 8-15 (pixels) |
| Neighborhood $\kappa$ | Spectral Clustering | 2 (pixels) |
| Shape Parameter $\sigma$ | Spectral Clustering | 2 (pixels) |
| Cost Weights $w_1, w_2, w_3$ | Cell Tracking | 1, 10, and 100 |
| $CI$ threshold | Contact Analysis | 0.01 |
| Death marker threshold | Cell Death Analysis | 150 |

*FIG. 53*

SEQUENCE LISTING

<160> NUMBER OF SEQ ID NOS: 190

<210> SEQ ID NO 1
<211> LENGTH: 17
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 1
ccatggcgac cgtcaca                                                17

<210> SEQ ID NO 2
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 2
tcactctggc ctccagaca                                              19

<210> SEQ ID NO 3
<211> LENGTH: 18
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 3
tccgtggcct tagctgtg                                               18

<210> SEQ ID NO 4
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 4
cccagacaca tagcaattca gg                                          22

<210> SEQ ID NO 5
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 5
gacagaggat catgctgtac tt                                          22

```
<210> SEQ ID NO 6
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 6
cttggcatga gatgcagga                                                  19

<210> SEQ ID NO 7
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 7
aacccctcag agcacacaa                                                  19

<210> SEQ ID NO 8
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 8
cggccccgga aaattgaata                                                 20

<210> SEQ ID NO 9
<211> LENGTH: 23
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 9
tcccatatct ggacatctgg aac                                             23

<210> SEQ ID NO 10
<211> LENGTH: 23
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 10
ctcctgctaa gatggagtgt tca                                             23

<210> SEQ ID NO 11
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 11
ccgtcacctg ctcagaatca                                                 20

<210> SEQ ID NO 12
<211> LENGTH: 19
<212> TYPE: DNA
<213> ORGANISM: Artificial Sequence
<220> FEATURE:
```

<223> OTHER INFORMATION: Primer for DELTAgene qPCR assay in Example 2

<400> SEQUENCE: 12
ccatggtgca gaggaggac                                           19

<210> SEQ ID NO 13
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 13
cgtgactgtc ctgtctctcc                                          20

<210> SEQ ID NO 14
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 14
tctaccacaa agttgcgagg aa                                       22

<210> SEQ ID NO 15
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 15
aacccagaaa gccccagaaa                                          20

<210> SEQ ID NO 16
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 16
gtggtgtttg gagtttccat cc                                       22

<210> SEQ ID NO 17
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 17
acataccagg actgcctgag                                          20

<210> SEQ ID NO 18
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 18
gtggatgtac tggggaaatg c                                        21

```
<210> SEQ ID NO 19
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 19
cattgcctca cagaccttcc                                               20

<210> SEQ ID NO 20
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 20
agggtggtgt ctgctatatc c                                             21

<210> SEQ ID NO 21
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 21
tgagacatcc gttcccctac a                                             21

<210> SEQ ID NO 22
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 22
tggcagggct ccgatgtata                                               20

<210> SEQ ID NO 23
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 23
aggcagcgat gtctgtgaa                                                19

<210> SEQ ID NO 24
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 24
agctcaagcc ccaacatca                                                19

<210> SEQ ID NO 25
<211> LENGTH: 19
<212> TYPE: DNA
<213> ORGANISM: Artificial Sequence
<220> FEATURE:
<223> OTHER INFORMATION: Primer for DELTAgene qPCR assay in Example 2
```

<400> SEQUENCE: 25
gtggtggctc tccttgtca                                          19

<210> SEQ ID NO 26
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 26
tgtggtgttg tctccgatgt a                                       21

<210> SEQ ID NO 27
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 27
agaagccaga agtcaggtat cc                                      22

<210> SEQ ID NO 28
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 28
tcccgtcact gtgtagttcc                                         20

<210> SEQ ID NO 29
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 29
agaagggaag gagtacacag ac                                      22

<210> SEQ ID NO 30
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 30
ccgggtgcag tttatttcca                                         20

<210> SEQ ID NO 31
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 31
agtgcacagc agggaacaa                                          19

<210> SEQ ID NO 32
<211> LENGTH: 19

```
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 32
aggctgcctc ctccacata                                              19

<210> SEQ ID NO 33
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 33
aaccacagcc cttccttcaa                                             20

<210> SEQ ID NO 34
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 34
gagcagggtt ctgggcttta                                             20

<210> SEQ ID NO 35
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 35
cactactggg ctcagggaaa                                             20

<210> SEQ ID NO 36
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 36
tgctggtcac agtccttca                                              19

<210> SEQ ID NO 37
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 37
gtcctggctt gctatagctt                                             20

<210> SEQ ID NO 38
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 38
```
catgtagtca ctgtgcagga                                          20

<210> SEQ ID NO 39
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 39
cgtttctctc tggcctggt                                           19

<210> SEQ ID NO 40
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 40
ctctacccat gtgatgctgg ta                                       22

<210> SEQ ID NO 41
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 41
gctaccccag aggaagcaaa                                          20

<210> SEQ ID NO 42
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 42
tccatctcca tgcagttctc ac                                       22

<210> SEQ ID NO 43
<211> LENGTH: 23
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 43
aaagttgcat caggaagtga acc                                      23

<210> SEQ ID NO 44
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 44
cccacacctc acaggtcaaa                                          20

<210> SEQ ID NO 45
<211> LENGTH: 20
<212> TYPE: DNA
<213> ORGANISM: Artificial Sequence

```
<220> FEATURE:
<223> OTHER INFORMATION: Primer for DELTAgene qPCR assay in Example 2

<400> SEQUENCE: 45
gaggccagca gtaaaacaac                                               20

<210> SEQ ID NO 46
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 46
agttgttgct catggtgtag ta                                            22

<210> SEQ ID NO 47
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 47
ccggacacca tggacaagtt                                               20

<210> SEQ ID NO 48
<211> LENGTH: 17
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 48
cctgcaaagc ggcaggt                                                  17

<210> SEQ ID NO 49
<211> LENGTH: 24
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 49
aatcattttg acaacctgta tccc                                          24

<210> SEQ ID NO 50
<211> LENGTH: 26
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 50
tgtaattact gctaatggta tgggta                                        26

<210> SEQ ID NO 51
<211> LENGTH: 17
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 51
gcagccagcc ttgggaa                                                  17
```

<210> SEQ ID NO 52
<211> LENGTH: 25
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 52
gcaagaactt cacacatttc attcc                                              25

<210> SEQ ID NO 53
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 53
tcacccatgg aagtggtcaa                                                    20

<210> SEQ ID NO 54
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 54
acacacttgt cagaccctgt a                                                  21

<210> SEQ ID NO 55
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 55
tgctggctgg tctttctca                                                     19

<210> SEQ ID NO 56
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 56
gagtttgtgc cagctcttca a                                                  21

<210> SEQ ID NO 57
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 57
cggcctcgca actcttata                                                     19

<210> SEQ ID NO 58
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

```
<400> SEQUENCE: 58
tggtctgttc actctcttcc                                              20

<210> SEQ ID NO 59
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 59
acttcgtgcc ggtcttcct                                               19

<210> SEQ ID NO 60
<211> LENGTH: 16
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 60
gctgcgacgc gatggt                                                  16

<210> SEQ ID NO 61
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 61
tgatggccag ccactacaa                                               19

<210> SEQ ID NO 62
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 62 caaagggat gacaagcaga aa                                            22

<210> SEQ ID NO 63
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 63
cttggatttc agcggcacaa                                              20

<210> SEQ ID NO 64
<211> LENGTH: 17
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 64
gctgctggcc agtacca                                                 17

<210> SEQ ID NO 65
```

<210> SEQ ID NO 65
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 65
ccaccttctg ccatctgac                                          19

<210> SEQ ID NO 66
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 66
cgtgatgttg catttcgtca c                                       21

<210> SEQ ID NO 67
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 67
gtagtgtttg ccctcaccaa c                                       21

<210> SEQ ID NO 68
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 68
atcagacaag gccaggttca                                         20

<210> SEQ ID NO 69
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 69
gctgtacctg catcagcatt a                                       21

<210> SEQ ID NO 70
<211> LENGTH: 23
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 70
ctggattcag acatctcttc tac                                     23

<210> SEQ ID NO 71
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 71
agccaacgtc aagcatctca            20

<210> SEQ ID NO 72
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 72
gcttcgggtc aatgcacac             19

<210> SEQ ID NO 73
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 73
agcccttcct gcgagaaaa             19

<210> SEQ ID NO 74
<211> LENGTH: 24
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 74
atctgctgaa tctgggttta gaca       24

<210> SEQ ID NO 75
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 75
atctctgact gcagctccta            20

<210> SEQ ID NO 76
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 76
tgtcctcttc agtttcagca a          21

<210> SEQ ID NO 77
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 77
aactgtggcc gagaaagca             19

<210> SEQ ID NO 78
<211> LENGTH: 20
<212> TYPE: DNA

<213> ORGANISM: Artificial Sequence
<220> FEATURE:
<223> OTHER INFORMATION: Primer for DELTAgene qPCR assay in Example 2

<400> SEQUENCE: 78
ttgaggcagc agtgcatgta          20

<210> SEQ ID NO 79
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 79
atcttcctgc ccaccatcta c          21

<210> SEQ ID NO 80
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 80
cccatgacca ggatgaccaa          20

<210> SEQ ID NO 81
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 81
tggggatgtt tcagctcttc c          21

<210> SEQ ID NO 82
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 82
ctgtgtgcat ctggctggta          20

<210> SEQ ID NO 83
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 83
tgtggggtag ccatggaaa          19

<210> SEQ ID NO 84
<211> LENGTH: 18
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 84
gggtcgcatg ttgtggaa          18

-continued

<210> SEQ ID NO 85
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 85
gccgtcacca agaacattca                                              20

<210> SEQ ID NO 86
<211> LENGTH: 18
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 86
ctcccgaagg gcttctcc                                                18

<210> SEQ ID NO 87
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 87
acaccatggg gaaggtgaag                                              20

<210> SEQ ID NO 88
<211> LENGTH: 18
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 88
gtgaccaggc gcccaata                                                18

<210> SEQ ID NO 89
<211> LENGTH: 18
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 89
cacggtgcag aggtaccc                                                18

<210> SEQ ID NO 90
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 90
agggtaggga tccatgaagc a                                            21

<210> SEQ ID NO 91
<211> LENGTH: 18
<212> TYPE: DNA
<213> ORGANISM: Artificial Sequence
<220> FEATURE:

<223> OTHER INFORMATION: Primer for DELTAgene qPCR assay in Example 2

<400> SEQUENCE: 91
gaagcctccg aggtggaa                                              18

<210> SEQ ID NO 92
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 92
gaaaacaccc tcgcacaaca                                            20

<210> SEQ ID NO 93
<211> LENGTH: 23
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 93
ccccatccag cctataatcc taa                                        23

<210> SEQ ID NO 94
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 94
ctgggccttg ttgctaggta                                            20

<210> SEQ ID NO 95
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 95
atccacagtg ggtgctgac                                             19

<210> SEQ ID NO 96
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 96
agagtgtgcg cctaaaacca                                            20

<210> SEQ ID NO 97
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 97
ggatccaaat cccaggcata a                                          21

```
<210> SEQ ID NO 98
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 98
cttggaaagg ctgcagtgaa                                              20

<210> SEQ ID NO 99
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 99
agtctgcatt ttgggatgca                                              20

<210> SEQ ID NO 100
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 100
gtcgtgcaca ctggatgaa                                               19

<210> SEQ ID NO 101
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 101
ttggctgctg catagagaac                                              20

<210> SEQ ID NO 102
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 102
cttgtctctc tctccgatgt ca                                           22

<210> SEQ ID NO 103
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 103
actgccagga cccatatgta a                                            21

<210> SEQ ID NO 104
<211> LENGTH: 26
<212> TYPE: DNA
<213> ORGANISM: Artificial Sequence
<220> FEATURE:
<223> OTHER INFORMATION: Primer for DELTAgene qPCR assay in Example 2
```

```
<400> SEQUENCE: 104
gttccattat atccgctaca tctgaa                                          26

<210> SEQ ID NO 105
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 105
aagttagggt tggacaaaa                                                  19

<210> SEQ ID NO 106
<211> LENGTH: 23
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 106
gatatccagt ttaggtggtc caa                                             23

<210> SEQ ID NO 107
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 107
ccgtggagca ggtgaagaa                                                  19

<210> SEQ ID NO 108
<211> LENGTH: 24
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 108
gtcaaactca ctcatggctt tgta                                            24

<210> SEQ ID NO 109
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 109
cacagtggag gcctgttta                                                  19

<210> SEQ ID NO 110
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 110
tctggaattt aggcaactct ca                                              22

<210> SEQ ID NO 111
<211> LENGTH: 20
```

-continued

```
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 111
tccctgacat tctgcgttca                                              20

<210> SEQ ID NO 112
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 112
ggtcttgtcc gtgaagactc ta                                           22

<210> SEQ ID NO 113
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 113
gccatatccg gatgcagac                                               19

<210> SEQ ID NO 114
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 114
cagctgtggg accctcata                                               19

<210> SEQ ID NO 115
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 115
gtcttggaag ctcctcttca c                                            21

<210> SEQ ID NO 116
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 116
tctaatgtcc cacggaggaa                                              20

<210> SEQ ID NO 117
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 117
```
tgcagtgcca tcgagaagac					20

<210> SEQ ID NO 118
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 118
tcggacatgc aagctggaaa					20

<210> SEQ ID NO 119
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 119
agccaactgg gtgaatgtaa					20

<210> SEQ ID NO 120
<211> LENGTH: 26
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 120
cactttccgt atataagta gcatca					26

<210> SEQ ID NO 121
<211> LENGTH: 18
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 121
tgagcgctgt gtctctcc					18

<210> SEQ ID NO 122
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 122
cctccatggc ttccatttca ac					22

<210> SEQ ID NO 123
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 123
actacaaccg atccacctca c					21

<210> SEQ ID NO 124
<211> LENGTH: 20
<212> TYPE: DNA
<213> ORGANISM: Artificial Sequence

```
<220> FEATURE:
<223> OTHER INFORMATION: Primer for DELTAgene qPCR assay in Example 2

<400> SEQUENCE: 124
actttgcctc ccagatcaca                                            20

<210> SEQ ID NO 125
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 125
ctgtggcaaa gccgacaata                                            20

<210> SEQ ID NO 126
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 126
ctcatccagt gggaaccagt a                                          21

<210> SEQ ID NO 127
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 127
ccaaaccacc agtccaagaa                                            20

<210> SEQ ID NO 128
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 128
ctcatgcatg gcgtggtta                                             19

<210> SEQ ID NO 129
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 129
gaccaaggaa atcggcctct a                                          21

<210> SEQ ID NO 130
<211> LENGTH: 25
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 130
tcacagagat agttacagcc atacc                                      25
```

<210> SEQ ID NO 131
<211> LENGTH: 24
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 131
cgttcttctt ggaccaaagc ttaa                                          24

<210> SEQ ID NO 132
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 132
agcagagcag ttgagcctta                                               20

<210> SEQ ID NO 133
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 133
cccagggact taatcagcaa ta                                            22

<210> SEQ ID NO 134
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 134
ttctacaatg gttgctgtct ca                                            22

<210> SEQ ID NO 135
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 135
tgcatcctgg aaatgtggaa c                                             21

<210> SEQ ID NO 136
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 136
cctcgtcctt cagctcttca ta                                            22

<210> SEQ ID NO 137
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 137
gcacaggtga aatggagacc                                           20

<210> SEQ ID NO 138
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 138
gacgaggcag gaagtctca                                            19

<210> SEQ ID NO 139
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 139
atggccatcc aggacttaca                                           20

<210> SEQ ID NO 140
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 140
ttgcatctgt gggtctcca                                            19

<210> SEQ ID NO 141
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 141
gcccaatggg aatgaagaca                                           20

<210> SEQ ID NO 142
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 142
tggaaacact gagggagtca                                           20

<210> SEQ ID NO 143
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 143
cagctgatcc gattcctgaa a                                         21

<210> SEQ ID NO 144

```
<210> SEQ ID NO 144
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 144
gttggcttcc ttcacaggac                                                 20

<210> SEQ ID NO 145
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 145
gagctccgcc tgttgtacc                                                  19

<210> SEQ ID NO 146
<211> LENGTH: 18
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 146
gcgcctccgt tgttctca                                                   18

<210> SEQ ID NO 147
<211> LENGTH: 24
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 147
actctgagga ttcctgttcc tgta                                            24

<210> SEQ ID NO 148
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 148
ccagtgtgcc tattccctga aa                                              22

<210> SEQ ID NO 149
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 149
ggagaaagtg gctatgctca a                                               21

<210> SEQ ID NO 150
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 150
```
ctgcgatcca ttcacttcca                                          20

<210> SEQ ID NO 151
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 151
ctacaaccgc gaggaggac                                           19

<210> SEQ ID NO 152
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 152
tgtcgatgcc ttctcggaac                                          20

<210> SEQ ID NO 153
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 153
ctgcggcaaa acctacacaa                                          20

<210> SEQ ID NO 154
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 154
cgtcccagtc acagtggtaa                                          20

<210> SEQ ID NO 155
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 155
acccaagccc agaatgacta                                          20

<210> SEQ ID NO 156
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 156
ttgccacaag gcaagaaca                                           19

<210> SEQ ID NO 157
<211> LENGTH: 19
<212> TYPE: DNA

```
<213> ORGANISM: Artificial Sequence
<220> FEATURE:
<223> OTHER INFORMATION: Primer for DELTAgene qPCR assay in Example 2

<400> SEQUENCE: 157
tggagccttt ggctttcac                                               19

<210> SEQ ID NO 158
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 158
gagggtgaat cccttgctct a                                            21

<210> SEQ ID NO 159
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 159
aagaaagtgc agctatcaac ca                                           22

<210> SEQ ID NO 160
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 160
gctgtctttc tttccgtgct a                                            21

<210> SEQ ID NO 161
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 161
tgtcccatcc tgaggcacta                                              20

<210> SEQ ID NO 162
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 162
accgttaagc gggcagtac                                               19

<210> SEQ ID NO 163
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 163
ctggaaccac gcctctagat a                                            21
```

```
<210> SEQ ID NO 164
<211> LENGTH: 23
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 164
aaactctggc tcatatggtt tcc                                          23

<210> SEQ ID NO 165
<211> LENGTH: 17
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 165
gcagcctggt gctgcta                                                 17

<210> SEQ ID NO 166
<211> LENGTH: 16
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 166
gtgcgcctgg ctccta                                                  16

<210> SEQ ID NO 167
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 167
gtacagcttc agcactgaca c                                            21

<210> SEQ ID NO 168
<211> LENGTH: 18
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 168
ctgggtggag gcgttgaa                                                18

<210> SEQ ID NO 169
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 169
cagcagataa cgtggcagac                                              20

<210> SEQ ID NO 170
<211> LENGTH: 20
<212> TYPE: DNA
<213> ORGANISM: Artificial Sequence
<220> FEATURE:
```

<223> OTHER INFORMATION: Primer for DELTAgene qPCR assay in Example 2

<400> SEQUENCE: 170
ggcacacaat tgccacatca                                           20

<210> SEQ ID NO 171
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 171
cagactcatc gccaaagca                                            19

<210> SEQ ID NO 172
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 172
tttccacatg ctggctacac                                           20

<210> SEQ ID NO 173
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 173
cccaggctcc ctataacatg ta                                        22

<210> SEQ ID NO 174
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 174
atggtctcat ccaggtcgaa                                           20

<210> SEQ ID NO 175
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 175
aacagaggtt ggtccgagaa                                           20

<210> SEQ ID NO 176
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 176
gtttctggga catggcatca                                           20

```
<210> SEQ ID NO 177
<211> LENGTH: 23
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 177
ttcaatctgc tcatgcatta ccc                                          23

<210> SEQ ID NO 178
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 178
gtgggctgtt gaaatgttcg ta                                           22

<210> SEQ ID NO 179
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 179
cgtctgctga ggctcaagtt a                                            21

<210> SEQ ID NO 180
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 180
tcgccaggaa ttgttgctgt a                                            21

<210> SEQ ID NO 181
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 181
caaaagccag agtgcctgaa                                              20

<210> SEQ ID NO 182
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 182
cgctgggttg gagatgttaa a                                            21

<210> SEQ ID NO 183
<211> LENGTH: 21
<212> TYPE: DNA
<213> ORGANISM: Artificial Sequence
<220> FEATURE:
<223> OTHER INFORMATION: Primer for DELTAgene qPCR assay in Example 2
```

-continued

<400> SEQUENCE: 183
gaaattgctc gacgatgttc c						21

<210> SEQ ID NO 184
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 184
actgatgggt cagaaggtac a						21

<210> SEQ ID NO 185
<211> LENGTH: 22
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 185
ggggcagaaa gaaactcctg ta					22

<210> SEQ ID NO 186
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 186
tctggaaatc ggcagctaca						20

<210> SEQ ID NO 187
<211> LENGTH: 19
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 187
aggtctcacg aggtcaacc						19

<210> SEQ ID NO 188
<211> LENGTH: 20
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 188
cccagctgag tctcccataa						20

<210> SEQ ID NO 189
<211> LENGTH: 21
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 189
aagcgcgata acctcctcat a						21

<210> SEQ ID NO 190
<211> LENGTH: 19

```
<212> TYPE: DNA
<213> ORGANISM: Artificial Sequence
<220> FEATURE:
<223> OTHER INFORMATION: Primer for DELTAgene qPCR assay in Example 2

<400> SEQUENCE: 190
ttccgtgtct gccttctcc                                                        19
```

INTEGRATED FUNCTIONAL AND MOLECULAR PROFILING OF CELLS

CROSS-REFERENCE TO RELATED APPLICATIONS

This application is a continuation of U.S. Nonprovisional application Ser. No. 15/560,018 filed on Sep. 20, 2017, which claims priority to International Application No. PCT/US2016/024519 filed on Mar. 28, 2016, which claims priority to U.S. Provisional Patent Application No. 62/138,813 filed on Mar. 26, 2015; and U.S. Provisional Patent Application No. 62/157,174 filed on May 5, 2015. The entirety of each of the aforementioned applications is incorporated herein by reference.

STATEMENT REGARDING FEDERALLY SPONSORED RESEARCH

This invention was made with government support under Grant No. CA174385, awarded by the National Institutes of Health (NIH). The government has certain rights in the invention.

BACKGROUND

Current methods of studying cellular activity lack the ability to integrate dynamic cellular behavior with molecular behavior at the single-cell level. The present disclosure addresses the aforementioned deficiency in the art.

SUMMARY

In some embodiments, the present disclosure pertains to methods of evaluating cellular activity by: (a) placing a cell population on an area; (b) assaying for a dynamic behavior of the cell population as a function of time; (c) identifying one or more cells of interest based on the dynamic behavior; (d) characterizing a molecular profile of the one or more identified cells; and (e) correlating the information obtained from steps (b) and (d). In some embodiments, the methods of the present disclosure also include a step of obtaining the cell population from a source, such as a tissue or a blood sample.

In some embodiments, the cell population includes immune cells. In some embodiments, the cell population includes, without limitation, T cells, B cells, monocytes, macrophages, neutrophils, dendritic cells, natural killer cells, fibroblasts, stromal cells, stem cells, progenitor cells, tumor cells, tumor stem cells, tumor infiltrating lymphocytes, and combinations thereof. In some embodiments the cell population includes T cells.

In some embodiments, the cell population is placed on an area as individual cells. In some embodiments the area includes a plurality of containers. In some embodiments the containers are in the form of at least one of wells, channels, compartments, and combinations thereof. In some embodiments, the containers are in the form of an array of nanowells.

In some embodiments, the dynamic behavior to be assayed includes, without limitation, cellular activation, cellular inhibition, cellular interaction, protein expression, protein secretion, metabolite secretion, changes in lipid profiles, microvesicle secretion, exosome secretion, microparticle secretion, changes in cellular mass, cellular proliferation, changes in cellular morphology, motility, cell death, cell cytotoxicity, cell lysis, cell membrane polarization, establishment of a synapse, dynamic trafficking of proteins, granule polarization, calcium activation, metabolic changes, small molecule secretion, proton secretion, and combinations thereof. In some embodiments, the assaying occurs by visualizing the dynamic behavior by various methods, such as time-lapse imaging microscopy.

For instance, in some embodiments, the motility of a cell population is assayed by evaluating at least one of cellular location, cellular movements, cellular displacement, cellular speed, cellular movement paths on the area, cellular infiltration, cellular trafficking, and combinations thereof. In some embodiments, the cell cytotoxicity of a cell population is assayed by evaluating release of cytotoxic molecules from the cell population. In some embodiments, the cellular interaction of a cell population is assayed by evaluating duration of cellular interactions, number of cellular interactions, calcium activation, granule polarization, protein localization, motility during cellular interaction, termination of cellular interaction, and combinations thereof.

In some embodiments, the assaying includes the use of a sensor associated with an area. In additional embodiments, the present disclosure pertains to methods of evaluating cellular activity by: (a) placing a cell population on an area that is associated with a sensor; and (b) assaying for a dynamic behavior of the cell population as a function of time.

In some embodiments, the sensor is in the form of a bead. In some embodiments, the bead includes diameters that range from about 3 μm to about 5 μm. In some embodiments, the sensor includes an analyte binding agent that is directed against an analyte of interest (e.g., secreted proteins, cell lysate components, cellular receptors, and combinations thereof).

In some embodiments, the sensor is utilized to assay the dynamic behavior of a single cell in the cell population in real-time. For instance, in some embodiments, protein expression is assayed by the sensors of the present disclosure through capture of cell lysate components. In some embodiments, protein secretion is assayed by the sensors of the present disclosure through capture of secreted proteins. In some embodiments, the sensors of the present disclosure are utilized as a fiduciary marker to enable auto-focusing of the cell population during the assaying. In some embodiments the cell population is lysed prior to incubation with the sensors.

Various methods may also be utilized to identify one or more cells of interest based on an assayed dynamic cellular behavior. For instance, in some embodiments, one or more cells are identified automatically through the use of algorithms. Thereafter, various molecular profiles of the identified cells can be characterized.

In some embodiments, the characterized molecular profiles can include, without limitation, transcription activity, transcriptomic profile, gene expression activity, genomic profile, protein expression activity, proteomic profile, protein interaction activity, cellular receptor expression activity, lipid profile, lipid activity, carbohydrate profile, microvesicle activity, glucose activity, metabolic profile, and combinations thereof. In some embodiments, the characterizing occurs by a method that includes, without limitation, DNA analysis, RNA analysis, protein analysis, lipid analysis, metabolite analysis, mass spectrometry, and combinations thereof.

Various methods may also be utilized to correlate the obtained information. For instance, in some embodiments the correlating includes integrating the assayed dynamic behavior and the characterized molecular profile. In some embodiments, the correlating includes correlating the motility of the one or more identified cells to gene expression or transcription activities of the one or more identified cells. In some embodiments, the correlating includes correlating the motility of the one or more identified cells to protein interaction activity of the one or more identified cells. In some embodiments, the correlating includes correlating the cellular interaction activity of the one or more identified cells to protein expression activity of the one or more identified cells.

The correlated information may be utilized for various purposes. For instance, in some embodiments, the correlated information can be utilized for at least one of predicting clinical outcome of a treatment (e.g., immunotherapy), screening cells (e.g., multi-killer T cells), retrieving cells (e.g., by micromanipulation) for further evaluation (e.g., further study or expansion), facilitating a treatment, diagnosing a disease, monitoring cellular activity, and combinations thereof.

DESCRIPTION OF THE FIGURES

FIG. 2A shows an array of 168×70 nanowells arranged in blocks of 7×7 (with 5×5 usable inner nanowells/block). FIG. 2B shows enlarged views of five blocks highlighted by the red box in Panel A. FIG. 2C shows time-series data at 5-minute intervals for the nanowell highlighted by the red box in Panel B. FIG. 2D shows enlargement of a single frame of the time-lapse series for the nanowell shown in Panel C, showing 3 NALM-6 target cells (green), one CD19-specific CAR$^+$ T-cell (red, lower right) in contact with a target cell (contact region appears yellow), and a red fluorescent debris particle that is rejected in the analysis (left edge).

FIGS. 3A-3J illustrate automated image analysis challenges. FIGS. 3A-H show examples of image frames. The red arrows indicate unclear boundaries between adjacent cells. The yellow arrows highlight low-intensity cells that are difficult to detect. The green arrows highlight cells that are difficult to segment due to non-uniform fluorescence. FIGS. 3A, 3B, 3D, 3E, and 3F exemplify frames with low contrast and SNR. FIG. 3I shows mean and standard deviation (error bars) of the background intensity (dark gray) and the foreground intensity (light gray) for the images in FIGS. 3A-H. FIG. 3J shows variation in fluorescence distribution both across the pixels associated with one cell, and across cells. The red and blue histograms correspond to the cell indicated by the red and blue dots respectively in FIG. 3H.

FIG. 4A shows examples of nanowells showing artifacts. FIG. 4B shows normalized cross-correlation (NCC) for the best-fitting template. FIG. 4C shows estimated nanowell cropping regions.

FIGS. 5A-5B illustrate the pre-processing (leveling, smoothing, unmixing, illumination correction) for a sample 5×5 nanowell block. FIG. 5A shows the presence of well outlines in the target (NALM-6 cells) channel. Panels 5A1 & 5A2 show close-up views of two selected nanowells. FIG. 5B shows the corresponding effector (CAR$^+$ T cells) channel. Panels 5B1 & 5B2 correspond to the same nanowells highlighted in 5A1 & 5A2, respectively. Panels 5C1 & 5C2 and 5D1 & 5D2 show the target and effector channels after pre-processing. The histograms on top of the images illustrate the uneven illumination in the raw image that is corrected after preprocessing.

FIGS. 6A-6D illustrate the ability of the confinement-constrained cell segmentation method to recover a nanowell movie that cannot be segmented by conventional methods. FIG. 6A shows a sample image frame for a single nanowell containing four effector (NK) cells. The red arrow points to a cell with very low contrast that is missed by conventional algorithms. The yellow arrow points to two cells that are difficult to separate due to non-uniform fluorescence. FIG. 6B shows the proposed normalized multi-threshold distance map (NMTDM) improves upon the Laplacian of Gaussian (Log) response in FIG. 6C. FIG. 6D provides a histogram of cell counts showing a variable number of cells, implying that this nanowell cannot be automatically segmented without error. The confinement-constrained algorithm uses the peak of this histogram (correctly at 4) to re-segment the entire movie correctly. Panels E, F, and G in FIG. 6D provide examples of re-segmentation results for under-, correct-, and over segmentation scenarios.

FIGS. 7A-7E illustrate confinement-constrained cell tracking. FIG. 7A shows a sample tracking of NK cells in a nanowell. The cell outlines are colored by cell identity. FIGS. 7B-E show color-coded sample cell movement paths illustrating the ability to track effector and target cells with diverse movement patterns.

FIG. 8A shows spatial regions used to compute CI for a target cell (K562 cell, green) and effector (NK cell, red). FIG. 8B shows contact event for which CI=0.3. FIG. 8C shows non-contact for which CI=0.02. FIG. 8D shows sample frames over 10 hours every 30 minutes. FIG. 8E shows the contact measure CI over time for target cells T1 and T2. The red dotted lines correspond to the sampling times in FIG. 8D.

FIG. 10A shows the distribution of cumulative time in contact between effector cells and target cell, before and after cell death. FIG. 10B shows distributions of displacements of NK cells before (free) or during contact with their target. The bars indicate comparisons, along with their significance (*=$p<0.05$, =$p<0.01$, *=$p<0.001$, ****=$p<0.0001$).

FIG. 12A provides a schematic of beads assay and antibodies sandwich to detect cytokine secreted from single-cell. Effector cells and target cells were labeled with PKH67 and PKH26 (Sigma) respectively and cytokine-positive beads fluoresced in red (Streptavidin-PE). FIG. 12B provides background-corrected mean fluorescence intensity (MFI) detected from a minimum of 30 IFNγ-positive beads, as a function of IFNα analyte concentration. FIG. 12C provides a comparison of the bead assay with ELISpot for detection of single-cell IFNα secretion of different effector cells (PBMC and TIL) at varying level of antigenic stimulation (viral peptide pools and PMA/ionomycin). Linear regression show that both approaches are significantly correlated ($r^2$=0.87, p-value=0.0008).

FIGS. 13A-13C provide a finite element analysis to model the efficiency of capture of analyte secreted from single cells in open-well systems. FIG. 13A provides a snapshot of heat maps showing analyte concentration in liquid phase across the well (right) and on the bead surface (left) after 5 hours of secretion in a 40 μm nanowell. Simulation parameters were shown on the table on the right. FIG. 13B provides a fractional occupancy of beads of different sizes as a function of incubation time and their ability to capture analyte secreted from single cells. FIG. 13C provides a fractional occupancy of 3 μm beads as a function of incubation time when the binding site density was varied across three orders of magnitude. For a single-cell secreting at a constant rate, beads with lowest binding site density possess highest fractional occupancy.

FIGS. 15A-15C provide flow cytometry characterization of the phenotype and function of CAR$^+$ T cells. FIG. 15A provides a phenotypic characterization of CAR$^+$ T cells with flow cytometry, showing that the cells were predominantly CD8$^+$ with over 90% expression of CAR.

FIG. 15B shows dot plots obtained by staining with CD62L and CD45RA, showing that the dominant subset of CAR$^+$ T cells (60.73%) were naïve-like. FIG. 15C provides intracellular staining analysis, which confirms the ability of CAR$^+$ T cells to specifically upregulate IFNα expression upon recognition of target cells expressing cognate antigen. The effector: target ratio was 1:5.

FIG. 16A demonstrates how TIMING is utilized to quantify T-cell intrinsic behavior like motility and the nature of their interaction leading to induction of apoptosis within tumor cells. Effector (blue) and target (red) cells were labeled, and apoptosis was detected by Annexin V (green-yellow). FIG. 16B shows that, at the conclusion of the TIMING assay, the IFNα molecules captured onto the beads during TIMING are revealed by using appropriate fluorescently labeled antibodies.

FIG. 17A provides a Venn Diagram showing breakdown of CD8$^+$ T cell functionality based on killing (no kill, kill one, and kill multiple) and/or IFNγ secretion for nanowells containing exactly one effector and multiple (2-5) tumor cells interactions (N=1178). FIG. 17B provides cumulative contact duration between effector and targets (minutes) leading to the different functional outcomes. Effector cells that only secrete IFNα (monofunctional) exhibited longer contact duration compared to cells that kill one or serial, irrespective of whether they secrete IFNγ. Kinetics of killing based on $t_{Contact}$ (FIG. 17C) and $t_{Death}$ (FIG. 17D) are also shown for mono-killer and multi killer cells (first, second, and third target killed respectively) for subsets of effector that participate in killing and/or IFNγ secretion. FIG. 17E provides data relating to average displacement, $d_{well}$ (μm), calculated for different combination of functionality of killing and IFNγ secretion of CAR$^+$ T cell. All p-values for all multiple comparisons were computed using parametric one-way ANOVA and each dot represents a single effector cell. P-value designations are as follows: *<0.05, <0.01, *<0.001, and ****<0.0001.

FIG. 19A provides a $t_{Contact}/t_{Death}$ comparison for multi-killer cells and mono-killer T cells. It was observed that $t_{Contact}$ was significantly lower than $t_{Death}$, demonstrating that T-cell detachment preceded tumor-cell Annexin V staining. P-values were determined using parametric one-way ANOVA. FIG. 19B shows a comparison of duration of conjugation of killers and non-killer T cells, (irrespective of IFNγ secretion). P values were determined using t-test. Note that a non-killer T cells have a population of cells, indicated by the green arrow, that were conjugated to the tumor cell for the entire duration of observation and hence the values represent an underestimate of the true duration of conjugation.

FIGS. 21A-1-21E provide a list of targeted genes and primer designs for DELTAgene quantitative PCT (qPCR) assays in Example 2.

FIG. 22A provides representative examples of high and low motility cell tracks during the 3 hour TIMING experiment. X, Y coordinates are shown in microns relative to initial cell position set to the origin. Color map represents aspect ratio of cell polarization with red denoting circular cells and increasing shades of green and blue denoting elongated cells. M2 and M3 denote the cells for which corresponding supplementary movies are shown. FIG. 22B shows a volcano plot demonstrating the significance (t-test) and magnitude of fold-change comparing high and low motility CD8$^+$ T cells. FIG. 22C shows unsupervised hierarchical bi-clustering of samples and of the genes identified as having a significant difference (p-value<0.05) and net foldchange of >1.5. * and + denote the individual motile and non-motile cells whose tracks are shown in panel A. FIG. 22D shows that trend discovery with STrenD allows selecting the genes that are the most relevant for description of the progressive states between cells. FIG. 22E shows the visualization of the consecutives states in a tree shape structure illustrating how each gene localizes differentially with high or low motility cells. FIG. 22F shows a protein interaction network analysis using Genemania of differentially expressed genes demonstrating their segregation into T cell activation and cell migration pathways.

FIG. 27C shows that CD2 and CD58 expression are linearly correlated at the single-cell level. FIG. 27D shows that LAG3, CD244 (2B4), GATA3 and IL18R1 transcripts are more highly expressed in high motility in comparison to low motility cells.

FIG. 29A provides a schematic of second-generation CD19-specific CAR (CD19RCD28) that signals through chimeric CD28/CD3-ζ. FIG. 29B provides representative composite micrographs illustrating the ability of single $CAR^+$ T cells to kill, and to undergo apoptosis, when incubated with tumor cells confined within nanowells. Scale bar 50 μm. FIG. 29C provides phenotypic characterization of the $CAR^+$ T cells from two separate donors. The total $CD3^+CAR^+$ population was gated to reveal the frequencies of $CD4^+$ and $CD8^+$ $CAR^+$ T-cell populations. FIG. 29D provides a comparison of the cytolytic responses measured by the single-cell assay and population-level $^{51}Cr$ release assay, at an E:T ratio of 1:1. The numbers in parentheses for the single-cell assay report the total number of events observed. FIG. 29E shows donut plots summarizing the frequency of killing outcomes of the interaction between $CAR^+$ T cells, derived from these two donors, and CD19±EL4 target cells. Representative micrographs illustrating each of these interactions are shown in FIG. 31.

FIG. 34A show a timeline, where the red bar indicates periods of conjugation, the blue arrow indicates timepoint at which conjugation was first observed, and green line indicates time to target death since first conjugation. FIG. 34B shows an aspect ratio of polarization that describes the ratio of major and minor axis fitted to an ellipse. FIG. 34C shows an illustration of a net displacement of a T-cell centroid ($d_{Well}$), which represents the average displacement of the centroid of the effector cell between successive seven minute time points. Also shown are the mean motility (FIG. 34D), time to first conjugation (FIG. 34E), and killing efficiency (FIG. 34F), of single CAR8 cells in each of three different subgroups. Each circle represents a single cell.

P-values for multiple comparisons were computed using parametric one-way ANOVA.

Figure 35:
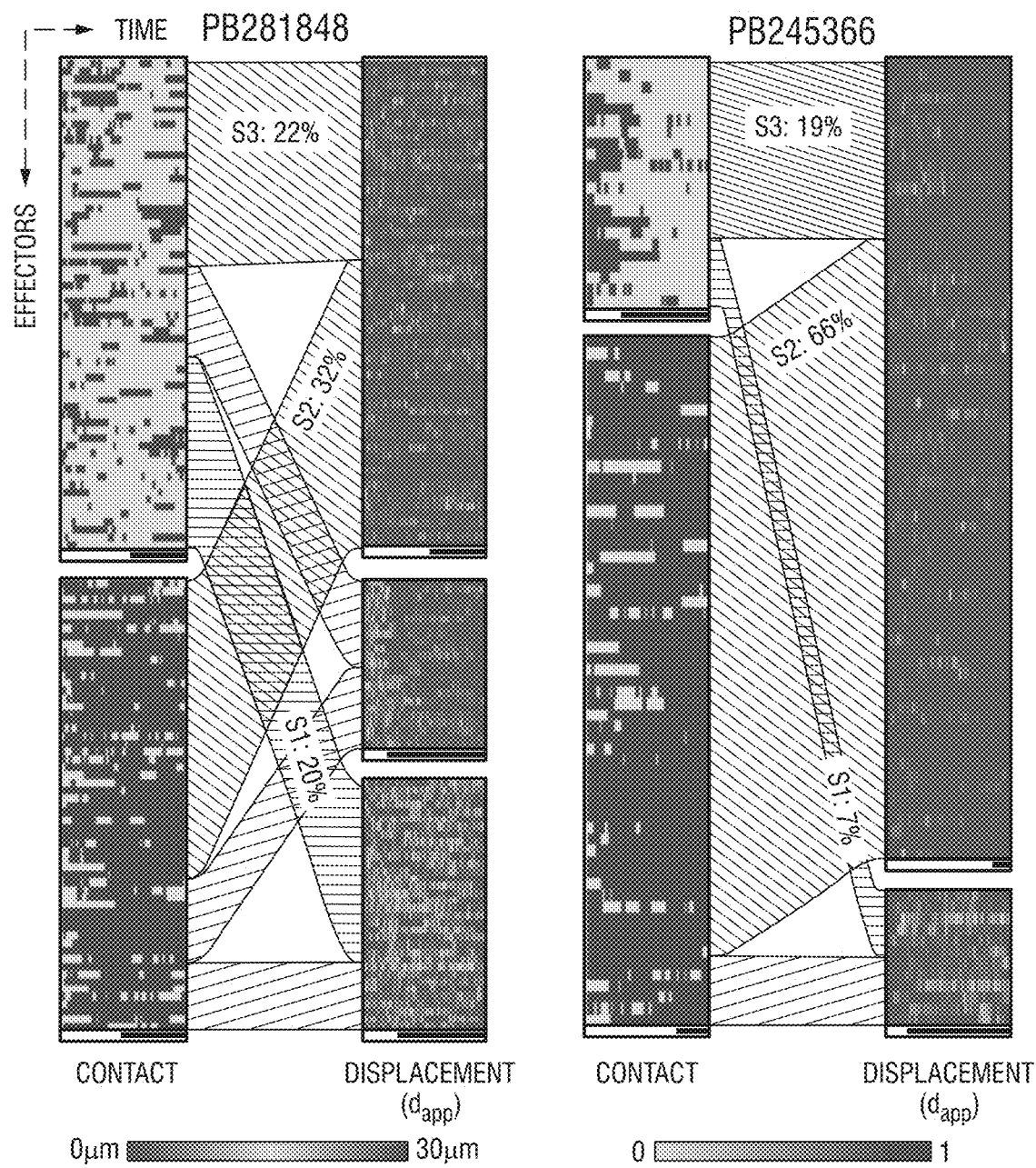

FIG. 35 shows the identification of subgroups of killer CAR8 cells based on their motility and contact behavior with tumor cells at an E:T ratio of 1:1. The time series of the contact pattern of CAR8 cells in their interaction with NALM-6 cells was clustered using K-means clustering (Euclidean distance, complete linkage) to identify low and high contact duration subsets. The displacement ($d_{well}$, of) the CAR8 cells was independently clustered to yield two or three subsets using K-means (Euclidean distance, complete linkage). Since these are features of the same cells, Caleydo was used to visualize the linkage between the clusters (gray cables) at single-cell resolution. The frequency of each of the three subsets, S1-S3, is highlighted in orange.

Figure 36A:
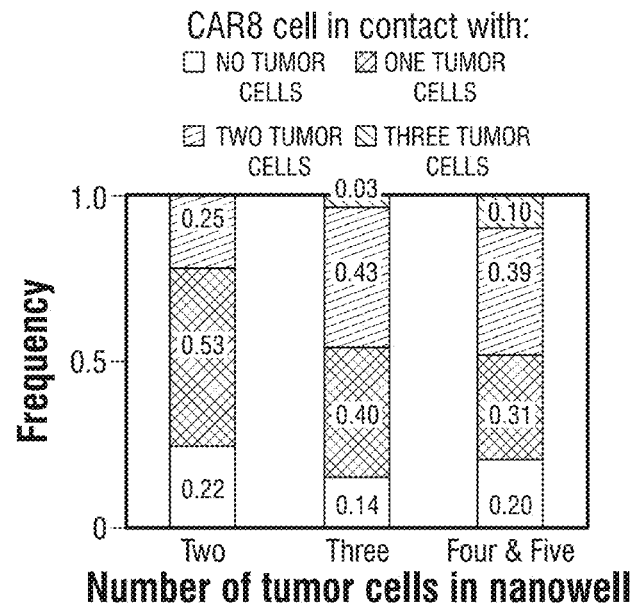

FIGS. 36A-36D show that multi-killer CAR8 cells engage in simultaneous conjugations leading to multiplexed killing (E:T 1:2-5). FIG. 36A shows a distribution of the number of simultaneous conjugations of individual CAR8 cells when incubated with increasing number of NALM-6 tumor cells. The mean motility (FIG. 36B), time to first conjugation (FIG. 36C), and killing efficiency (FIG. 36D), of individual multi-killer CAR8 cells are also shown. P-values for multiple comparisons were computed using parametric one-way ANOVA.

Figure 37A:
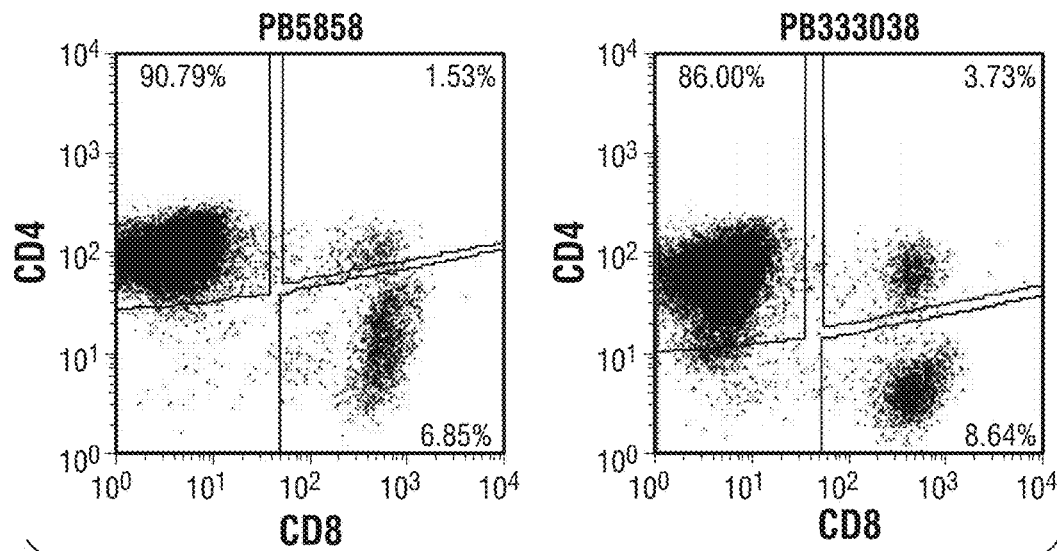
Figure 37B:
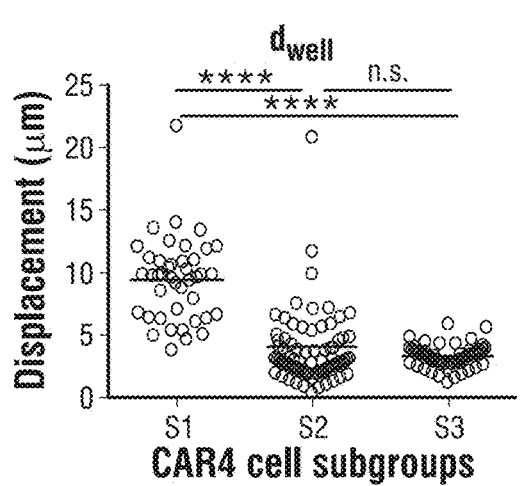
Figure 37C:
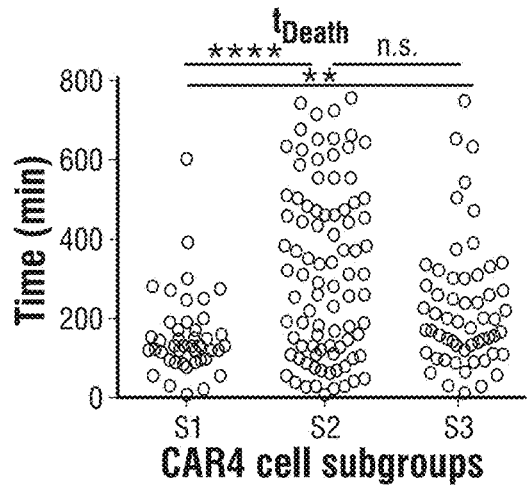
Figure 37D:
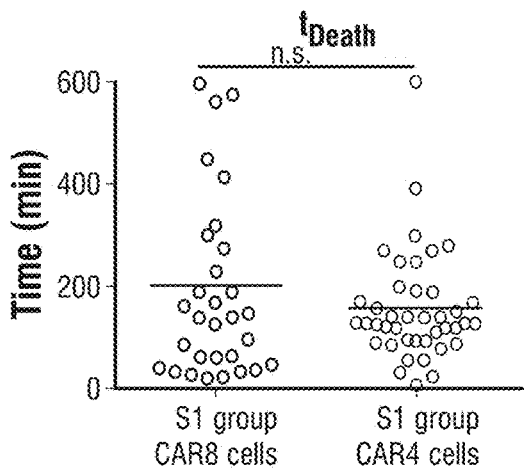
Figure 37E:
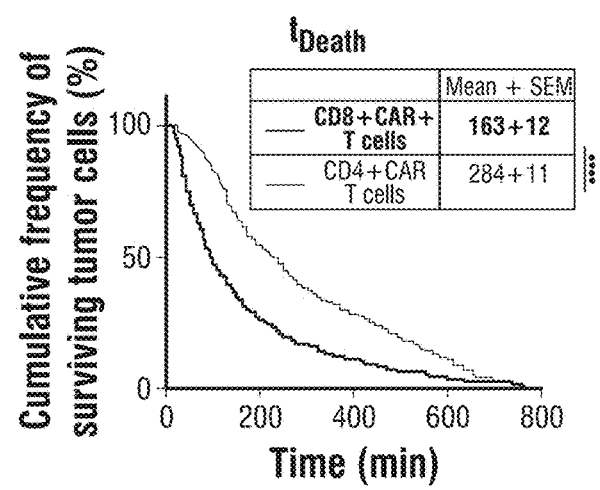

FIGS. 37A-37E show a subpopulation of CAR4 cells, identified based on their motility, can engage in efficient killing (E:T 1:1). FIG. 37A shows a phenotypic characterization of the CAR$^+$ T cells from two separate donors that comprise of predominantly CD4$^+$CAR$^+$ T cells. The mean motility (FIG. 37B), killing efficiency (FIG. 37C) of single CAR4 cells in each of three different subgroups are also shown. FIG. 37D provides a comparison of the means of the killing efficiencies between single CAR8 and CAR4 cells within the 51 subgroups. Each circle represents a single cell in panels B-D. CAR4 cells are represented using grey circles and CAR8 cells are represented using black circles. FIG. 37E provides a comparative Kaplan-Meier estimators depicting the differences in killing efficiencies of the entire population of CAR4 cells and CAR8 cells. P-values for multiple comparisons (B/C) were computed using a parametric one-way ANOVA, and dual comparisons (D/E) computed using unpaired two-tailed t-test.

Figure 38:
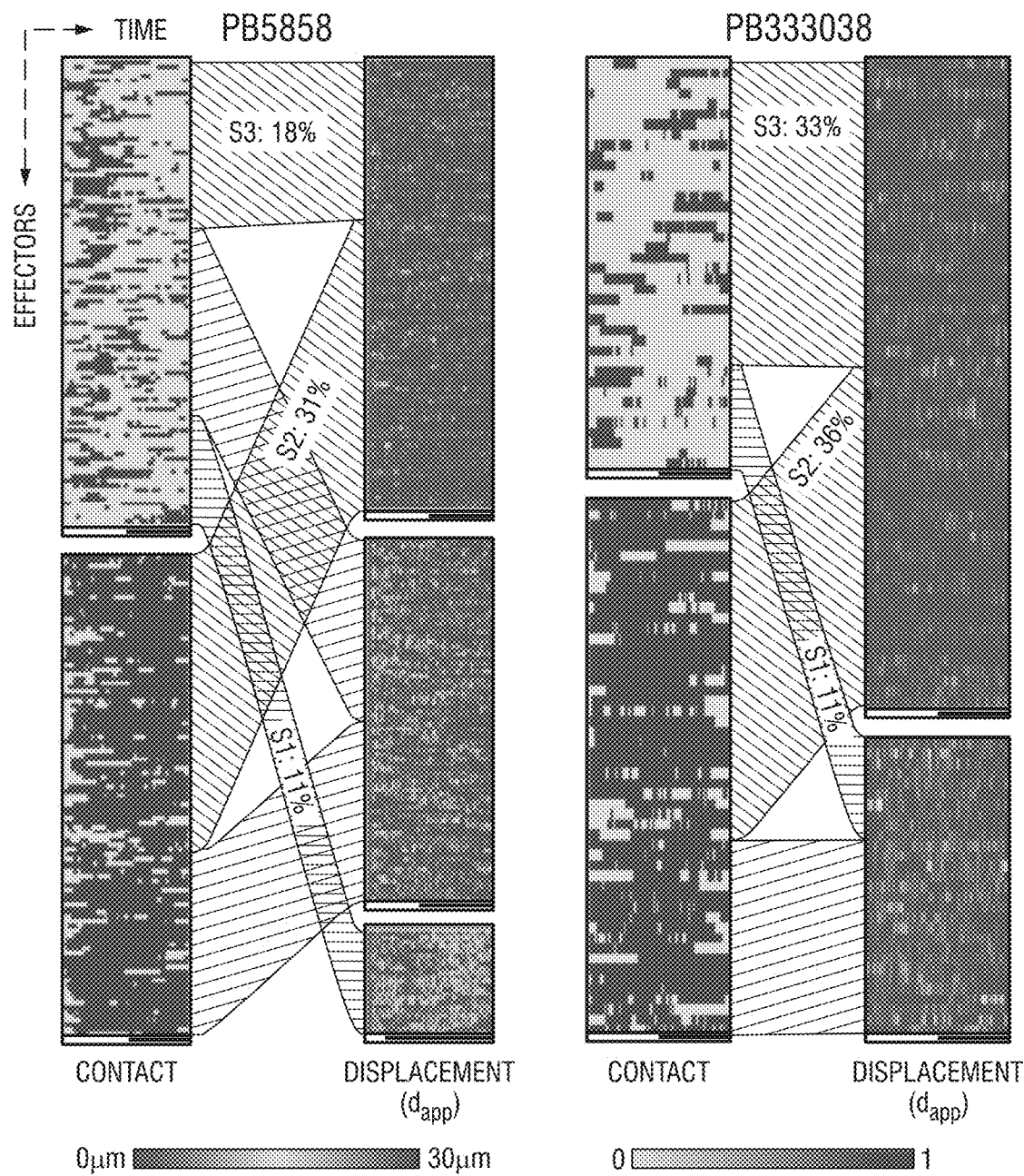

FIG. 38 provides the identification of subgroups of killer CAR4 cells based on their motility and contact behavior with tumor cells at an E:T ratio of 1:1. The time series of the contact pattern of CAR4 cells in their interaction with NALM-6 cells was clustered using K-means clustering (Euclidean distance, complete linkage) to identify low and high contact duration subsets. The displacement ($d_{well}$, of) the CAR4 cells was independently clustered to yield two or three subsets using K-means (Euclidean distance, complete linkage). Since these are features of the same cells, Caleydo was used to visualize the linkage between the clusters (gray cables) at single-cell resolution. The frequency of each of the three subsets, S1-S3, is highlighted in orange.

Figure 1:
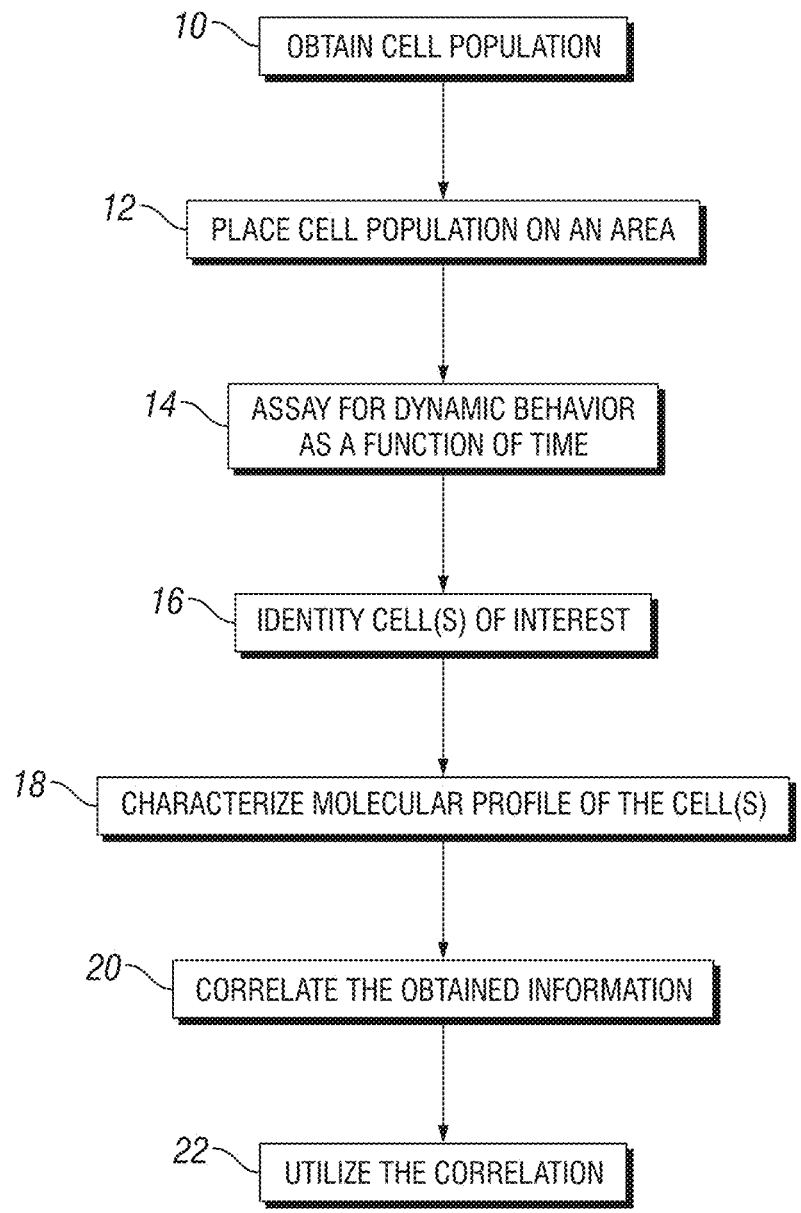
FIG. 1 illustrates a scheme of a method of evaluating cellular activity.
Figures 1, 39D:
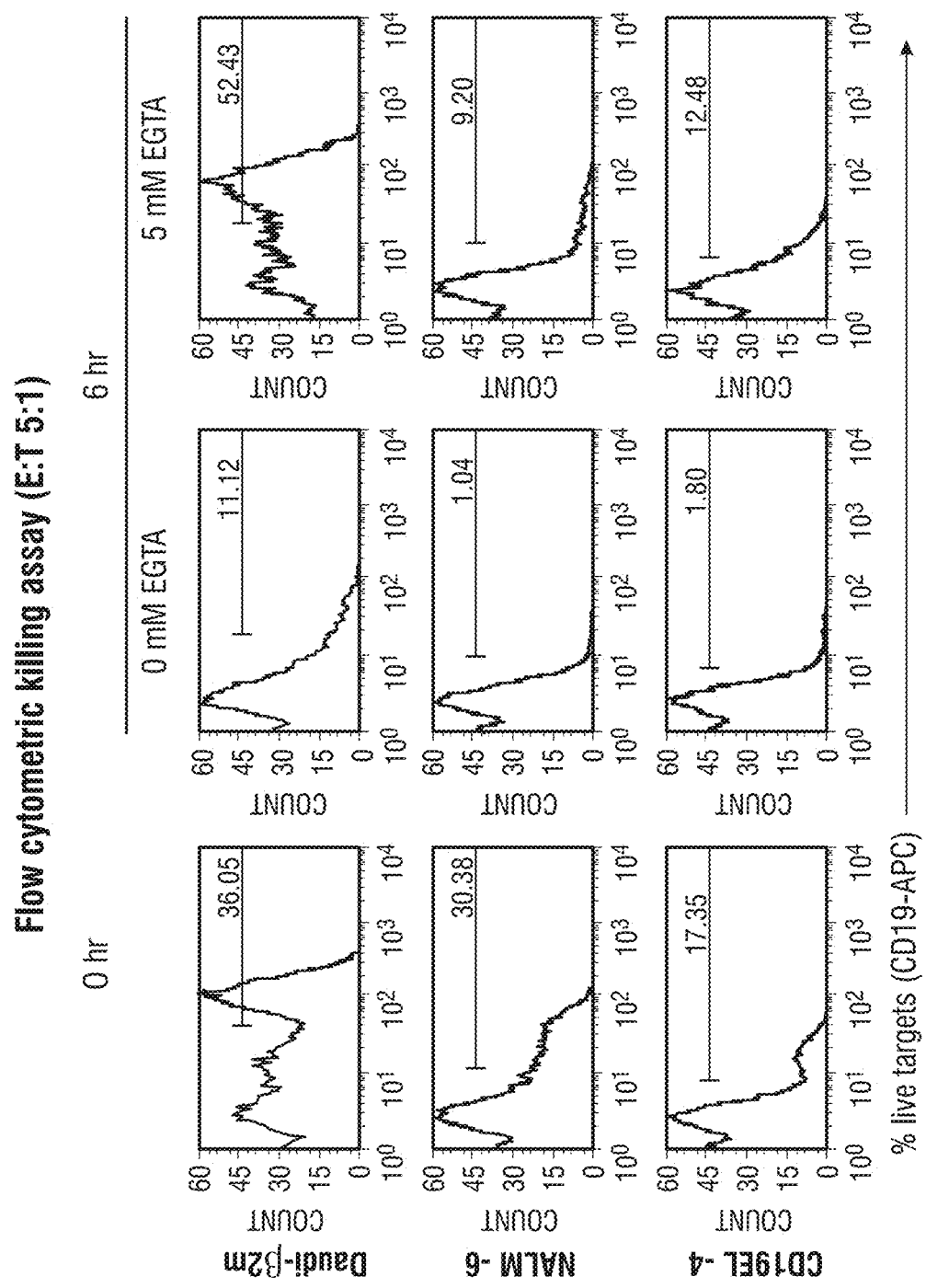
Figures 2, 39D:
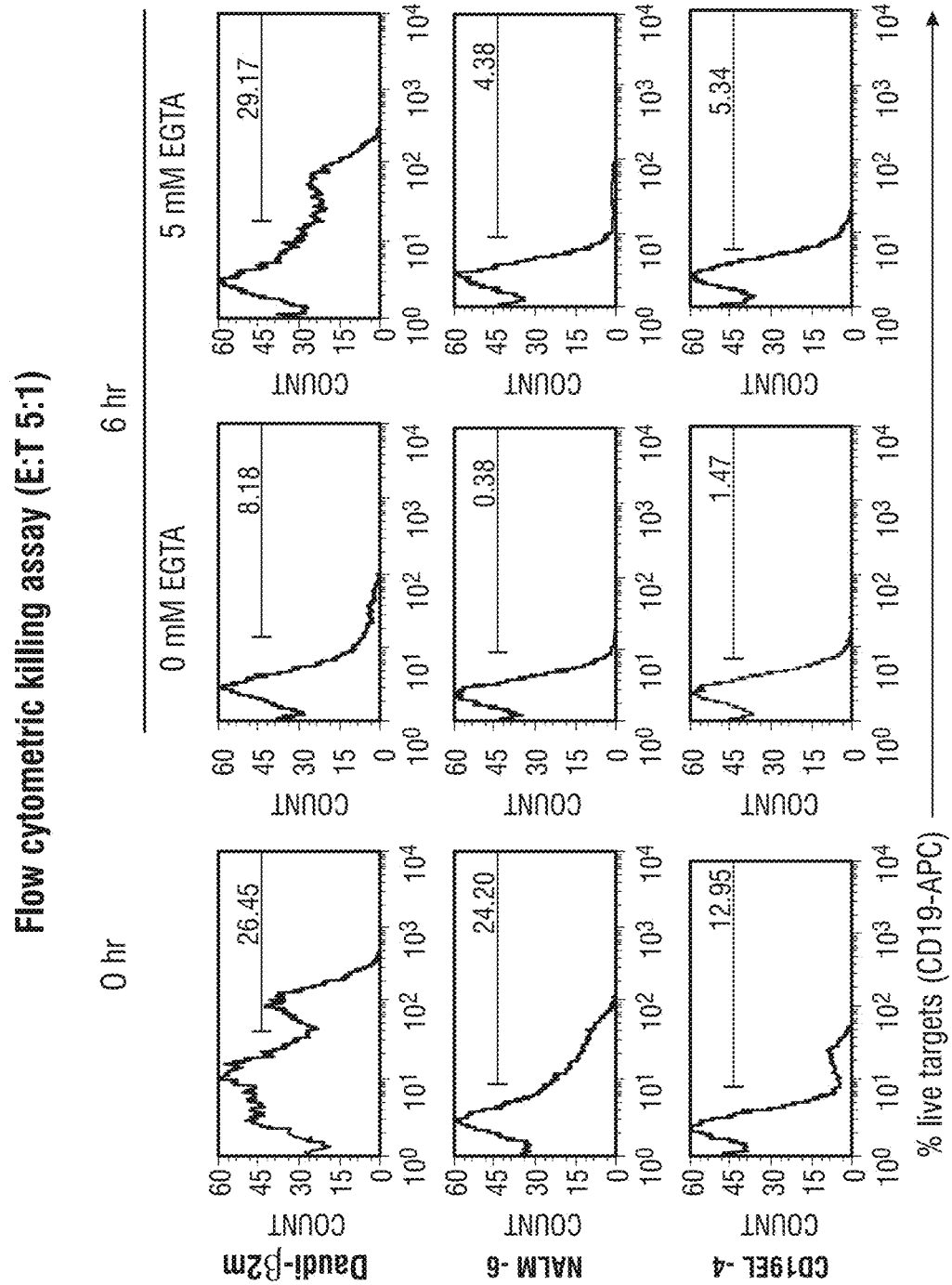

FIGS. 39A-39D-2 show that multi-killer CAR4 cells demonstrated delayed kinetics of killing in comparison to CAR8 cells (E:T 1:2-5). Comparisons between the mean motility (FIG. 39A), and killing efficiency (FIG. 39B) are also shown. FIG. 39C provides a box and whisker plots (extremities indicate 99% confidence intervals) displaying intracellular expression of Granzyme B identified by immunofluorescent staining and flow-cytometry. CAR4 cells (from donors PB5858 and PB333038) and CAR8 cells (from donors PB243566 and PB281848) were profiled using mAb against CD4/CD8/CAR and GzB. P-values were computed using parametric one-way ANOVA for multiple comparisons or t-tests for dual comparisons. FIGS. 39D-1-39D-2 show flow cytometric killing assay (E:T=5:1) of CAR4 cells incubated with three separate target cell lines (Daudi-β2m, NALM-6 and CD19$^+$EL4) in the absence or presence of 5 mM EGTA blockade.

Figure 40A:
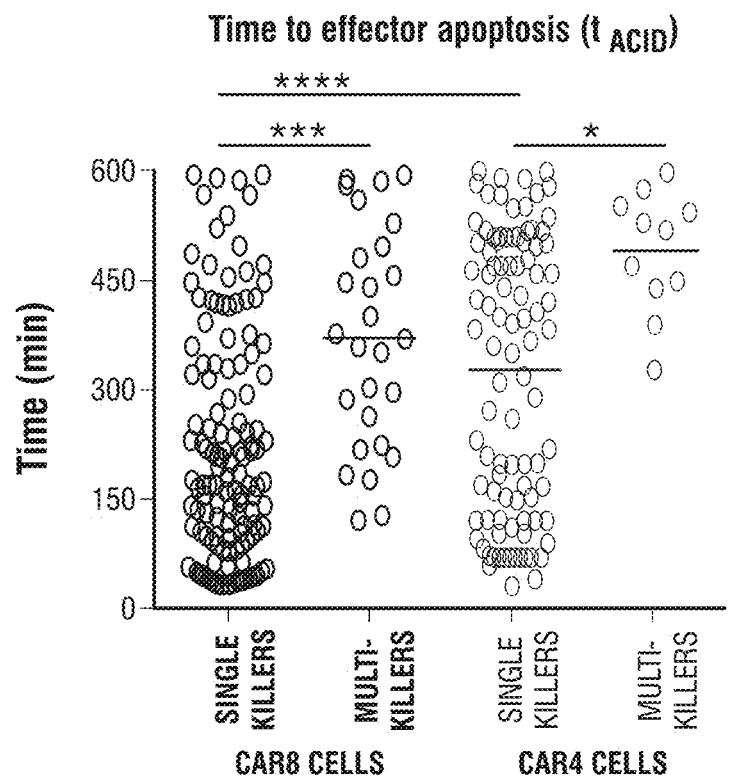
Figure 40B:
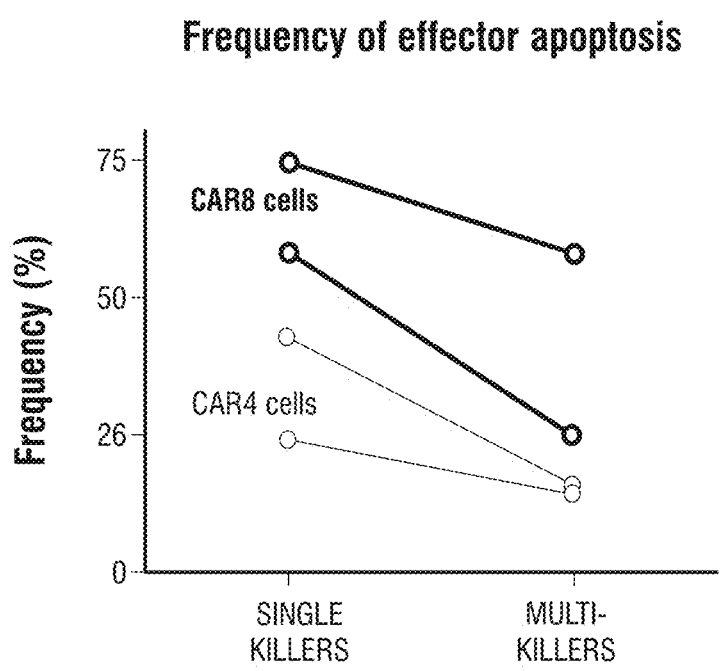

FIGS. 40A-40B show that the frequency and kinetics of killer-cell apoptosis are dependent on functional conjugations with multiple NALM-6 tumor cells. FIG. 40A provides comparisons of the mean kinetics of effector apoptosis of individual single killer CAR$^+$ T cells (E:T 1:1) with multi-killer CAR$^+$ T cells (E:T 1:2-5). Each circle represents a single-cell. CAR4 cells are represented using grey circles and CAR8 cells are represented using black circles. FIG. 40B shows the frequency of killer-cell apoptosis as a function of tumor cell density.

Figure 41:
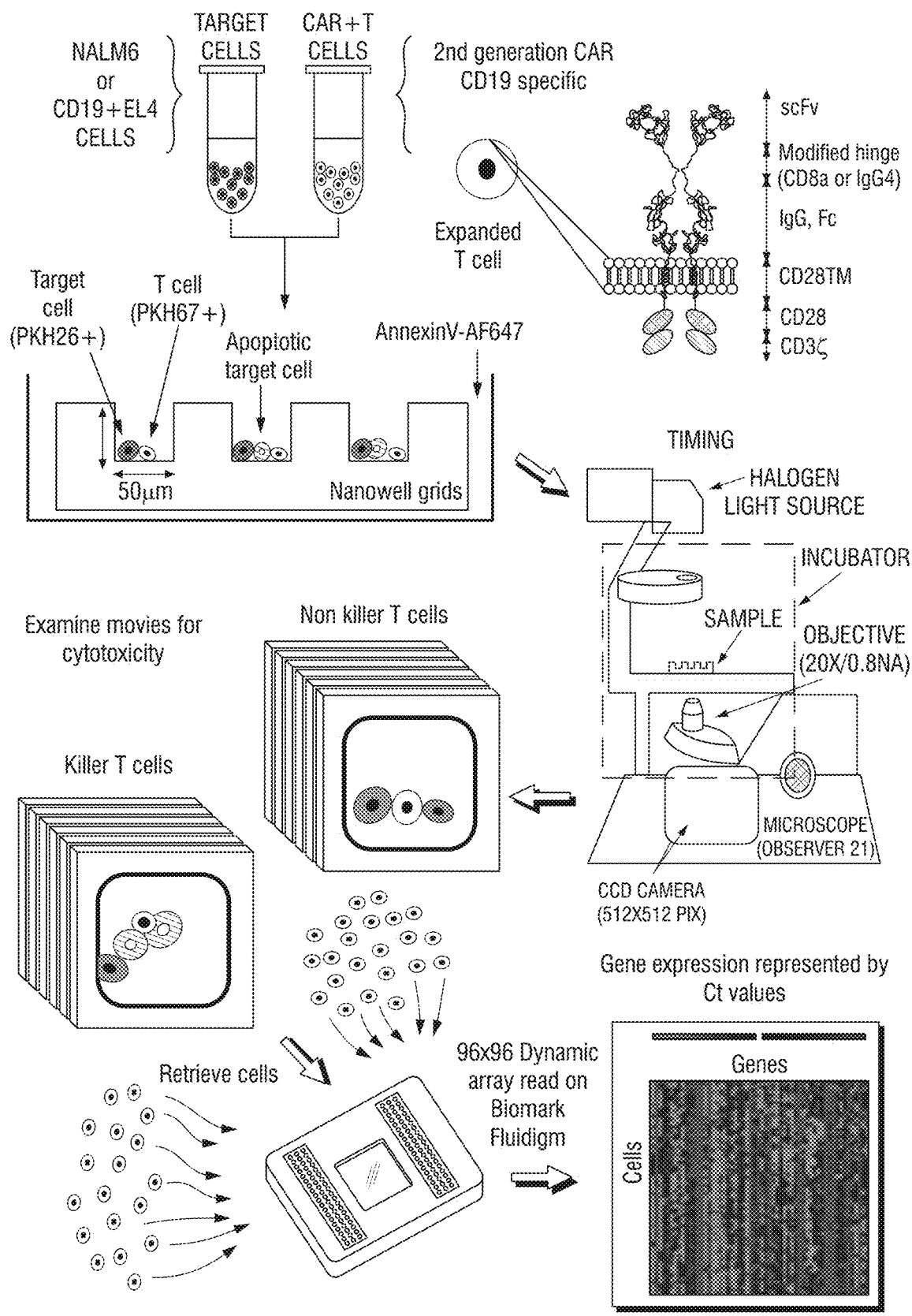

FIG. 41 provides a scheme of a TIMING assay followed by single-cell gene expression profiling.

Figure 42:
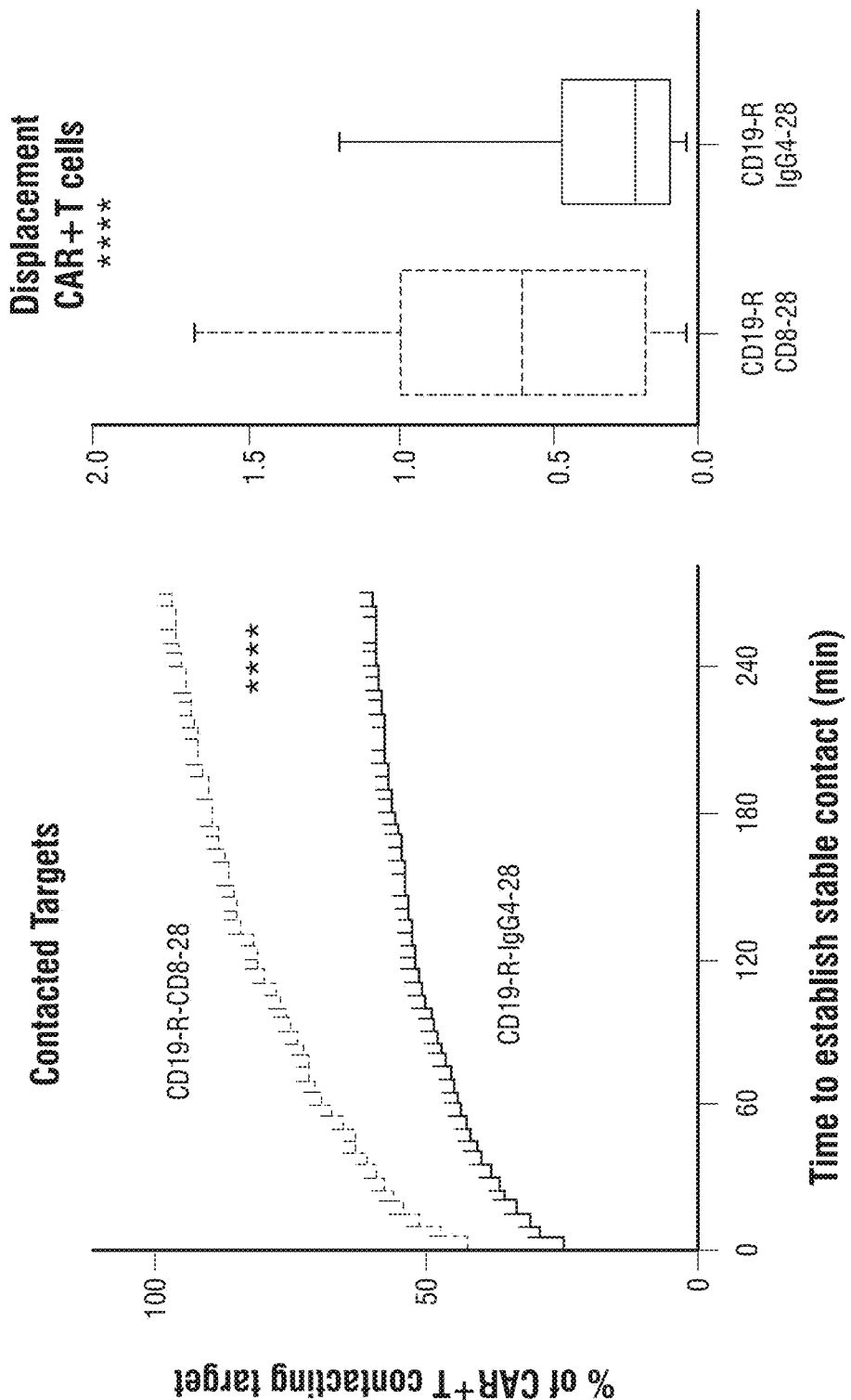

FIG. 42 provides motility data for CAR$^+$ T cell constructs in vitro.

FIG. 43 provides cytotoxicity data for CAR$^+$ T cell constructs in vitro.

Figure 44:
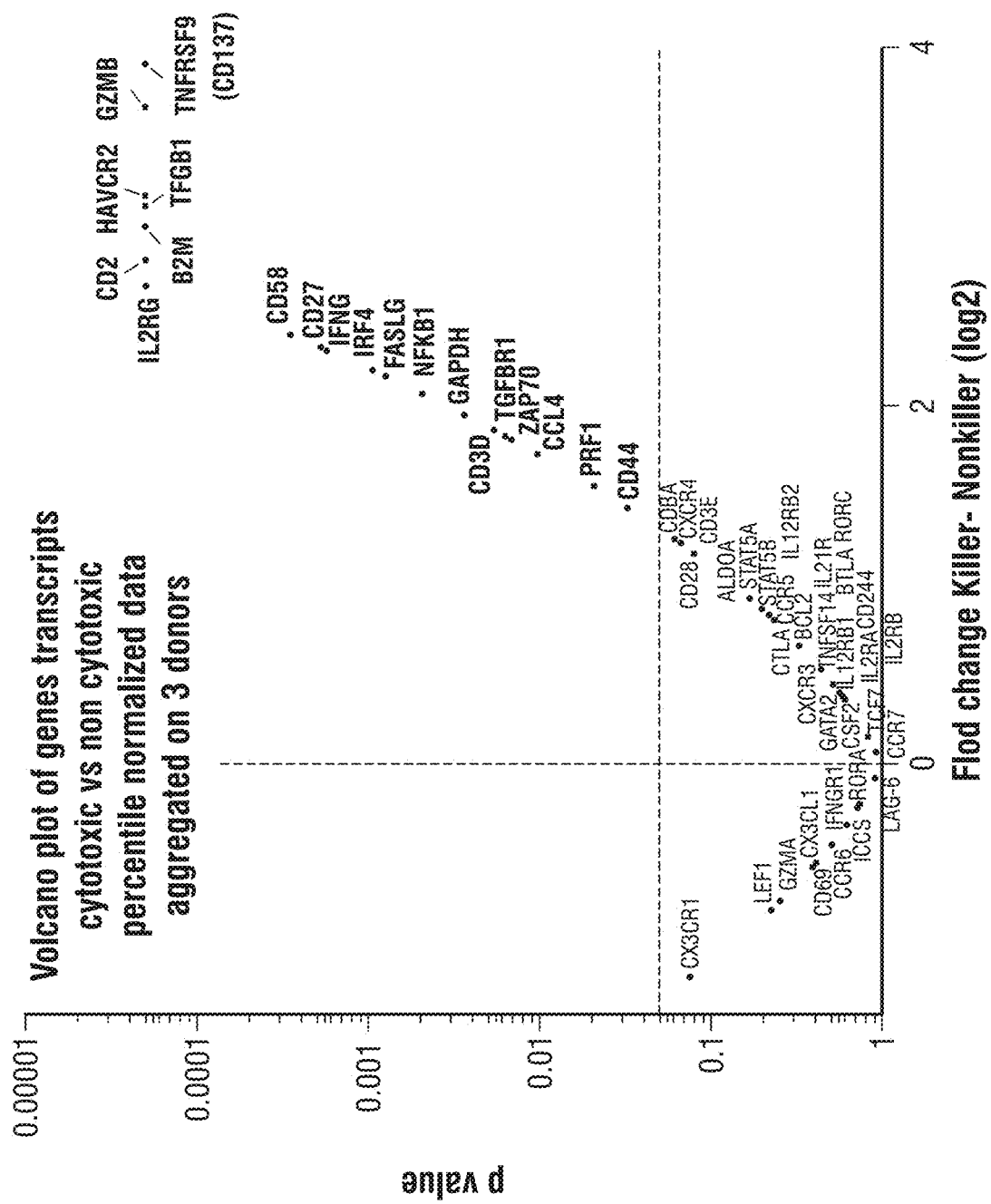

FIG. 44 provides a gene expression profile of CAR$^+$ T cells.

Figure 45:
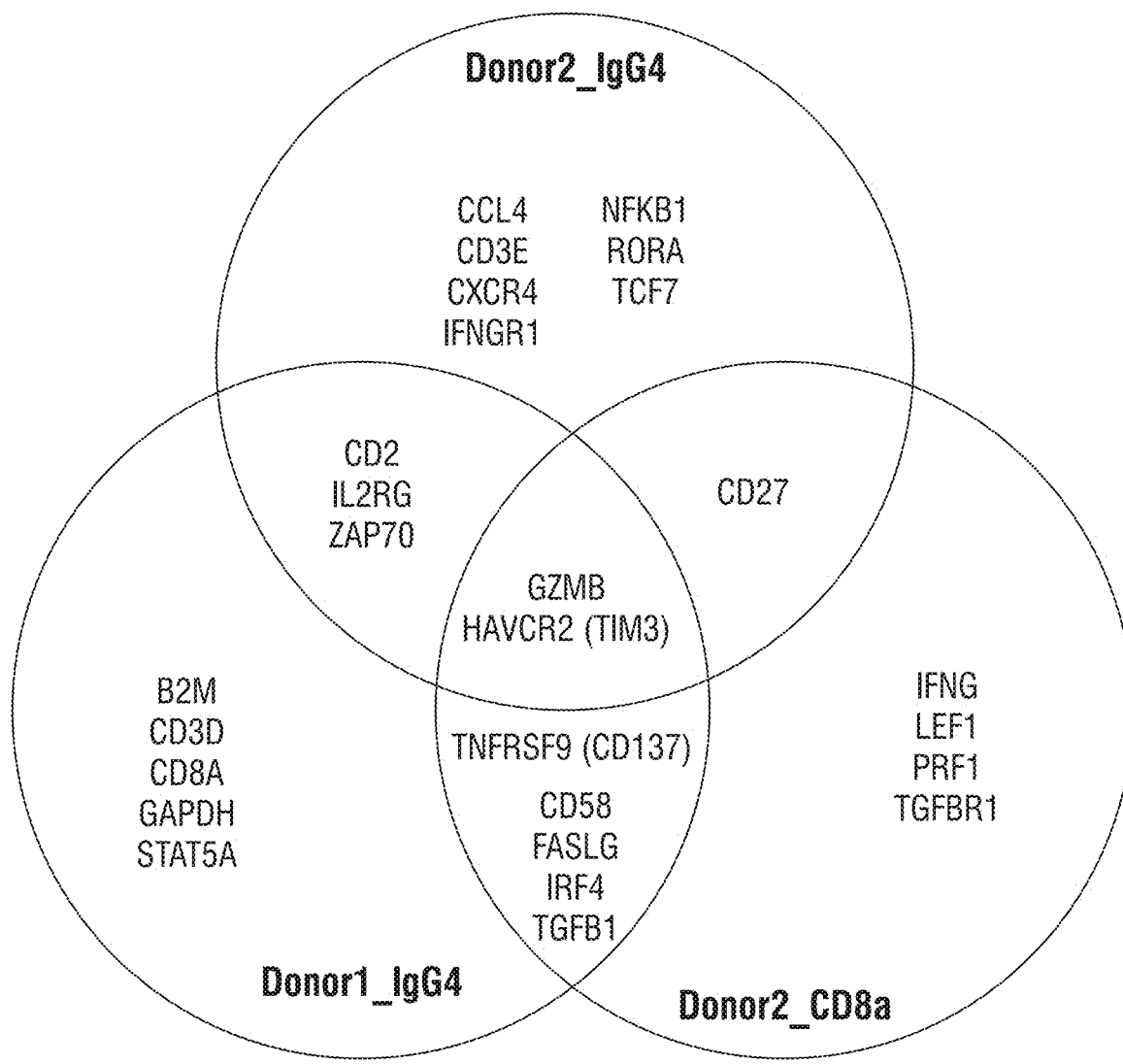

FIG. 45 provides a Venn diagram of differentially expressed genes from three donors.

Figure 46:
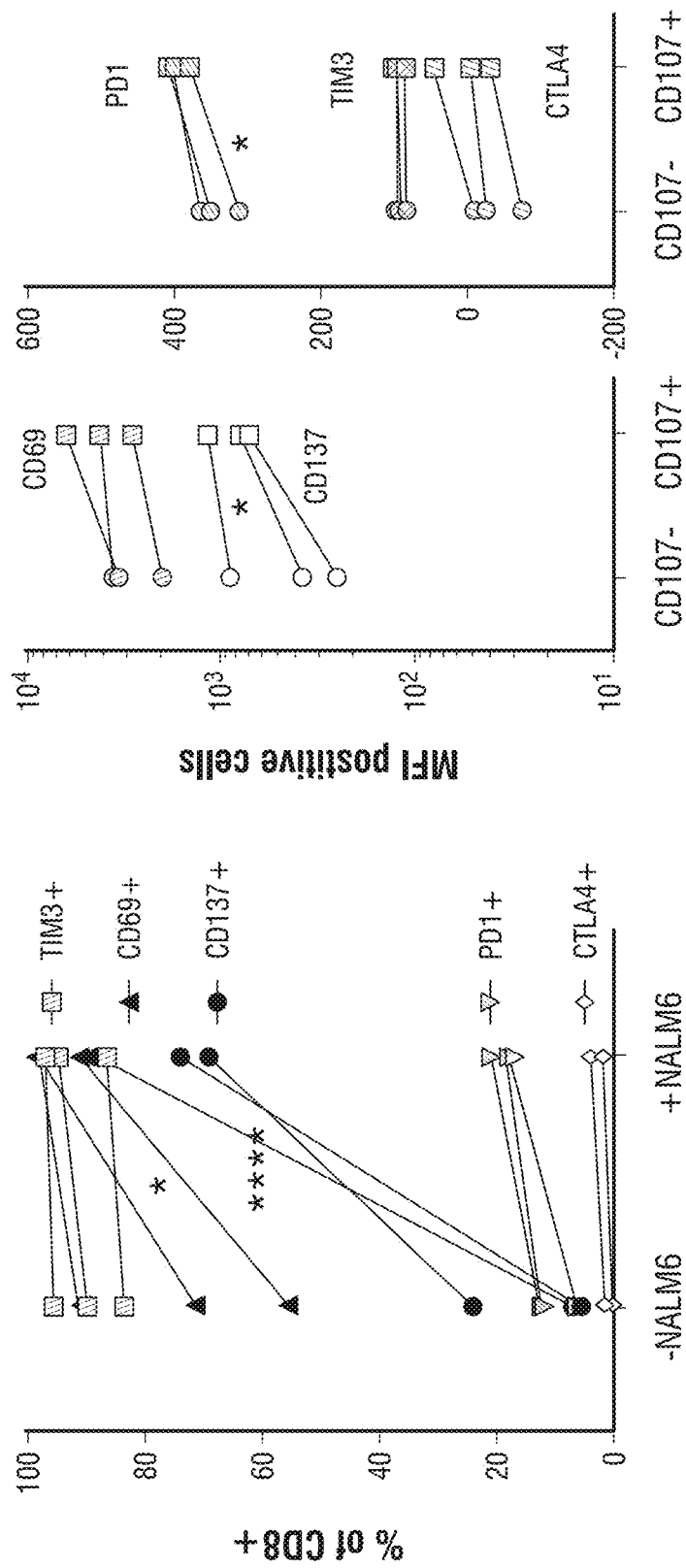

FIG. 46 provides data indicating that CD137 is expressed at higher levels in activated CAR$^+$ T cells and in degranulating CAR$^+$ Tcells.

Figure 47:
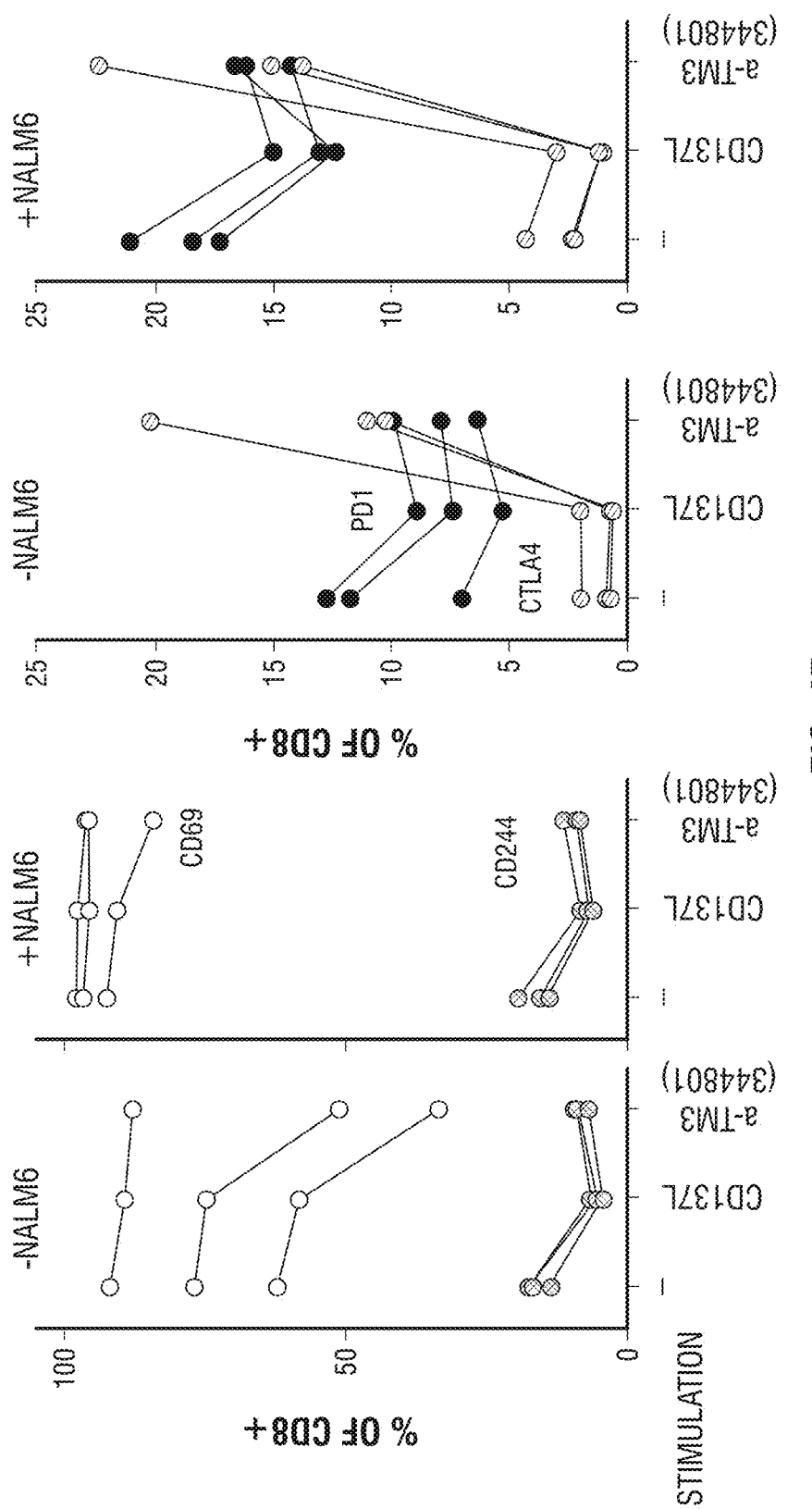

FIG. 47 provides data indicating that CD137 stimulation decreases exhaustion markers while TIM3 targeting induces CTLA4.

Figure 48:
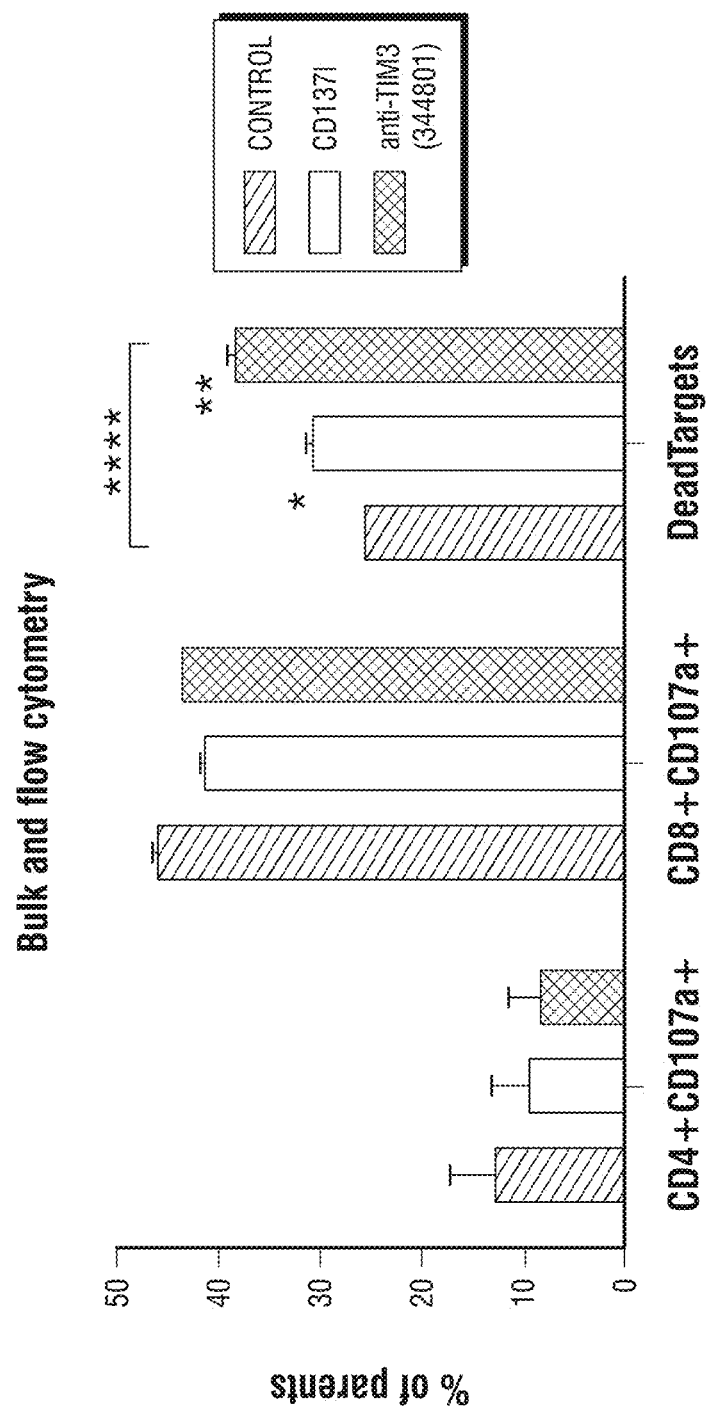

FIG. 48 provide data indicating that targeting CD137 and TIM3 increases cytotoxicity of CAR$^+$ Tcells.

FIG. 49 provides data indicating that the targeting of CD137 and TIM3 increases CAR$^+$ T cell cytotoxicity.

FIG. 50 provides a summary of yield from traditional automated segmentation. The first entry indicates the number of nanowells containing the corresponding cell distribution (manually verified), and the second entry indicates the corresponding yield.

FIG. 51 provides a summary of error-free nanowell yield using the confinement constrained cell detection method.

FIG. 52 provides frequency of cell segmentation and tracking errors.

FIG. 53 provides a list of parameter settings.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Integrative quantification of single-cell dynamic functional behavior and the underlying mechanisms responsible for the functions is important for developing a comprehensive understanding of cellular behaviors. For instance, quantifying the heterogeneity at the single-cell level in high-throughput across multiple biological dimensions from the genome and transcriptome, to intracellular and extracellular signaling, and to interaction with other kinds of cells can have a direct impact in improving therapeutic discovery in biotechnology, diagnosis of diseases, and in facilitating immunotherapy.

While flow cytometry is an optimal tool for providing snapshots of the cellular phenotype, it is not well suited for studying continuous dynamic cellular behaviors. To characterize the complete identity of individual single cells, it is desirable to have a modular method that can quantify and screen for cellular functionality such as motility, interaction with other cells, and protein secretion; and the ability to integrate these parameters with single-cell multiplexed molecular platforms.

The study of such cell behaviors are of vital interest in many fields, including immunology, cancer biology, and stem cell engineering. For instance, T cells are an essential component of the adaptive immune response against pathogens and tumors. A critical hallmark of a robust adaptive immune response against pathogens and tumors is the ability of individual T cells to participate in multiple functions (polyfunctionality).

T cells play an important role in mediating anti-tumor immunity. Moreover, the presence of tumor infiltrating lymphocytes (TILs) is a positive clinical prognostic marker for certain tumors. Among the most well described functional attributes of T-cell anti-tumor efficacy are motility (tumor-trafficking and infiltration), direct cytotoxicity (release of cytotoxic molecules) and secretion of the pro-inflammatory cytokines like IFN-γ.

Unlike cytotoxicity that only influences the target cell that is directly conjugated to the T cell, secretion of IFN-γ has a more profound influence on all cells within the microenvironment by multiple mechanisms including elevated expression of HLA-class I molecules, induction of chemokines that promote immune cell infiltration, mediation of angiostasis, and prevention of the outgrowth of antigen-loss variants. In addition, secretion of IFN-γ can induce adaptive resistance mechanisms in tumors by inducing the expression of T-cell suppressive molecules and down-modulation of tumor antigen expression.

Direct measurement of all of the aforementioned T cell functions at the single-cell level requires the simultaneous monitoring of multiple parameters, including cell-cell interactions, cell migration, gene expression, the ability to detect secreted proteins, and the survival of the effector cells. These challenges have been tackled by measuring just a subset of these effector functions and relying on correlative studies to establish a link to cellular functionality.

Indeed, while multi-photon microscopy is useful for studying T-cell motility and cytotoxicity in situ or in vivo, the number of T cells that can be simultaneously tracked is small and limited to the field-of-view, potentially leading to sampling bias. In vitro dynamic imaging systems may be better suited for studying the longitudinal interactions between T cells and target cells at single-cell resolution, in a defined environment and high-throughput.

Likewise, microfabricated nanowell arrays are ideal for tracking both the motility and interaction between cells. While elegant methods like microengraving and the single-cell barcode chip (SCBC) have been reported for the analysis of cytokines secreted by single cells, these methods require capture of the secreted cytokine on a separate glass substrate via encapsulation. Significantly, there are as yet no reports documenting the simultaneous measurement of motility, T-cell target-cell interaction parameters including the kinetics of killing, and cytokine secretion quantified within the same timeframe.

Automated time-lapse microscopy of live cells in vitro is a well-established method for spatiotemporal recording of cells and biomolecules, and tracking multi-cellular interactions. Unfortunately, most conventional methods assess limited numbers (e.g., 10-100) of manually sampled "representative" cell pairs, leading to subjective bias. Therefore, such methods lack the ability to quantify the behaviors of statistically under-represented cells reliably. The aforementioned limitation is significant because many biologically relevant cellular subpopulations (e.g., tumor stem cells, multi-killer immune cells, and biotechnologically relevant protein secreting cells) are rare.

As such, there is a need for improved and real-time methods of studying cellular activity that integrate dynamic cellular behavior with molecular behavior at the single-cell level. The present disclosure addresses the aforementioned need.

In some embodiments, the present disclosure pertains to methods of evaluating cellular activity. In some embodiments illustrated in FIG. 1, the methods of the present disclosure include one or more of the following steps: obtaining a cell population (step 10); placing the cell population on an area (step 12); assaying for a dynamic behavior of the cell population as a function of time (step 14); identifying one or more cells of interest based on the dynamic behavior (step 16); characterizing a molecular profile of the one or more identified cells (step 18); correlating the obtained information (step 20); and utilizing the correlated information (step 22).

In some embodiments, the methods of the present disclosure may utilize a sensor. In additional embodiments, the present disclosure pertains to methods of evaluating cellular activity by placing a cell population on an area that is associated with a sensor, and assaying for a dynamic behavior of the cell population as a function of time. As set forth in more detail herein, the methods of the present disclosure can have numerous embodiments.

Obtaining Cell Populations

The methods of the present disclosure can obtain cell populations from various sources. For instance, in some embodiments, cell populations are obtained from a tissue. In some embodiments, cell populations are obtained from a blood sample. In some embodiments, cell populations are obtained from an in vitro expanded blood cell population. In some embodiments, cell populations are obtained directly from a patient's blood before or after a treatment.

The methods of the present disclosure can also utilize various methods to obtain cell populations. For instance, in some embodiments, cell populations are obtained by a method that includes, without limitation, flow cytometry, positive flow sorting, negative flow sorting, magnetic sorting, and combinations thereof. In some embodiments, cell populations are obtained by using a micromanipulator (e.g., an automated or manual micromanipulator). In some embodiments, cell populations are obtained by using a magnetic head after the incubation of cells with magnetic particles specific for a particular cell population phenotype.

Cell Populations

The methods of the present disclosure can obtain and utilize various cell populations. For instance, in some embodiments, the cell populations include, without limitation, plant cells, fungi cells, bacterial cells, prokaryotic cells, eukaryotic cells, unicellular cells, multi-cellular cells, immune cells, and combinations thereof. In some embodiments, the cell populations include immune cells. In some embodiments, the immune cells are obtained from a patient's blood before or after a treatment. In some embodiments, immune cells are expanded in vitro.

In some embodiments, the cell populations include, without limitation, T cells, B cells, monocytes, macrophages, neutrophils, dendritic cells, natural killer cells, fibroblasts, stromal cells, stem cells, progenitor cells, tumor cells, tumor stem cells, tumor infiltrating lymphocytes, and combinations thereof. In some embodiments, the cell population includes T cells. In some embodiments, the T cells include, without limitation, helper T cells, cytotoxic T cells, natural killer T cells, genetically modified T cells, chimeric antigen receptor (CAR) modified T cells, and combinations thereof. In some embodiments, the T cells include, without limitation, $CD3^+$ T cells, γδ T cells ($V\gamma9^+, V\gamma2^+$), natural killer T cells ($CD1d^+$, $V\alpha24^+$), and combinations thereof.

In some embodiments, the cell populations include natural killer cells. In some embodiments, the natural killer cells include, without limitation, $CD16^+$ natural killer cells, natural killer T cells, $CD1d^+/V\alpha24^+$ natural killer T cells, and combinations thereof.

In some embodiments, the cell populations include tumor cells. Tumor cells may be derived from various sources. For instance, in some embodiments, the tumor cells are derived from at least one of cancer stem cells, melanoma, pancreatic cancer, ovarian cancer, leukemia, lymphoma, breast cancer, glioblastoma, neuroblastoma, prostate cancer, lung cancer, and combinations thereof. In some embodiments, the tumor cells include NALM cells.

The cell populations of the present disclosure can be homogenous or heterogenous. For instance, in some embodiments, the cell populations are homogenous. In some embodiments, the cell populations are heterogenous. In some embodiments, the heterogenous cell populations include tumor cells and immune cells. In some embodiments, the heterogenous cell populations include tumor cells and cytotoxic T cells.

Placement of Cell Populations on an Area

The cell populations of the present disclosure can be placed on various areas for dynamic behavior analysis. For instance, in some embodiments, the area is non-encapsulated. In some embodiments, the area is an open system.

In some embodiments, the area includes a volume bounded container. In some embodiments, the area includes a plurality of containers. In some embodiments, the containers are in the form of at least one of wells, channels, compartments, and combinations thereof. In some embodiments, the containers include nanowells. In some embodiments, the containers are in the form of an array.

In some embodiments, are area may include containers that have a volume capacity of about 1 nL to about 100 nL. In some embodiments, the containers have a volume capacity of less than about 1 nL. In some embodiments, the area is in the form of a patterned array of micro or nanowells. In some embodiments, the area is associated with fluid flow to permit gas and nutrient exchange.

In some embodiments, the area includes a number of individual arrays on a microfluidic chip with a plurality of individual containers (e.g., from about 10 containers to about 1,000,000 containers). In some embodiments, the areas of the present disclosure include microfluidic chips that contain arrays of nanowells with volume capacities of less than about 1 nL per well.

The areas of the present disclosure may be fabricated from various materials. For instance, in some embodiments, the areas of the present disclosure include, without limitation, polydimethylsiloxane (PMDS), polymethylmethacrylate (PMMA), silicon, glass, polyethylene glycol (PEG), and combinations thereof.

Cell populations can be placed on the areas of the present disclosure in various manners. For instance, in some embodiments, cell populations are placed on an area as individual cells. In some embodiments, cell populations are placed on an area as an aggregate of cells. In some embodiments, cell populations are placed on an area as a small number of cells (e.g., 2-6 cells per container). In some embodiments, cell populations are placed on the area in the form of droplets.

In some embodiments, cell populations are placed on an area manually. In some embodiments, cell populations are placed on an area in an automated manner. In some embodiments, cell populations are placed on an area by semi-automated cell retrieval methods. In some embodiments, cell populations are placed on an area by sorting specific droplets of cells.

Dynamic Behavior

The methods of the present disclosure may be utilized to assay various dynamic behaviors of cell populations on an area. For instance, in some embodiments, the assayed dynamic behavior includes, without limitation, cellular activation, cellular inhibition, cellular interaction, protein expression, protein secretion, metabolite secretion, changes in lipid profiles, microvesicle secretion, exosome secretion, microparticle secretion, changes in cellular mass, cellular proliferation, changes in cellular morphology, motility, cell death, cell cytotoxicity, cell lysis, cell membrane polarization, establishment of a synapse, dynamic trafficking of proteins, granule polarization, calcium activation, metabolic changes, and combinations thereof.

In some embodiments, the assayed dynamic behavior includes protein secretion. In some embodiments, the assayed dynamic behavior includes motility. In some embodiments, the assayed dynamic behavior includes cell death, such as activation induced cell death.

In some embodiments, the assayed dynamic behavior includes cellular interaction. In some embodiments, the cellular interaction includes, without limitation, heterologous cellular interaction, homologous cellular interaction, and combinations thereof.

In some embodiments, the assayed dynamic behavior includes the combination of cell death and cellular interaction. In some embodiments, the assayed dynamic behavior includes, without limitation, motility, cell cytotoxicity, cell death, protein secretion, cellular interaction, and combinations thereof. For instance, in some embodiments, the dynamic behavior to be assayed includes secretion of cytokines from a T-cell (e.g., pro-inflammatory cytokines, such as IFN-γ), the motility of the T-cell, and the interaction of the T-cell with a target cell, dynamic monitoring of T-cell/target cell death, and combinations thereof.

In some embodiments, the assayed dynamic behavior includes a change in cellular morphology. In some embodiments, the change in cellular morphology includes, without limitation a change in cell shape, a change in cell volume, a change in cell mass, a change in cell size, a change in cell polarization, and combinations thereof.

Assaying of Dynamic Behaviors

Various methods may be utilized to assay the dynamic behavior of cells. In some embodiments, the assaying occurs at a single cell level. In some embodiments, the assaying occurs by visualizing the dynamic behavior. In some embodiments, the visualizing occurs by a method that includes, without limitation, microscopy, time-lapse imaging microscopy, fluorescence microscopy, multi-photon microscopy, quantitative phase microscopy, surface enhanced Raman spectroscopy, videography, manual visual analysis, automated visual analysis, and combinations thereof.

In some embodiments, the visualizing of dynamic behavior occurs by time-lapse imaging microscopy. In some embodiments, the visualizing is recorded as an array of multi-channel movies. In some embodiments, the visualizing occurs through high-throughput time-lapse imaging microscopy in nanowell grids. In some embodiments, the visualizing occurs by utilizing time-lapse microscopy through at least one of bright field microscopy, phase contrast microscopy, fluorescence microscopy, quantitative phase microscopy, surface enhanced Raman spectroscopy, and combinations thereof.

In some embodiments, the assaying of a dynamic behavior includes quantification of the dynamic behavior. In some embodiments, the assaying occurs manually. In some embodiments, the assaying occurs automatically. In some embodiments, the assaying occurs automatically through the use of algorithms. For instance, in some embodiments, the assaying occurs through the use of automated quantification of a dynamic behavior through automated algorithms that measure the onset time, duration, frequency, and extent of the dynamic behavior.

The assaying of the dynamic behavior of cells can have various embodiments. For instance, in some embodiments, the cellular morphology of a cell population is assayed by measuring the eccentricity of a best-fitting ellipse.

In some embodiments, the motility of a cell population is assayed by evaluating at least one of cellular location, cellular movement, cellular displacement, cellular speed, cellular movement paths on an area, cellular infiltration, cellular trafficking, and combinations thereof. In some embodiments, cell positions can be tracked by automated image analysis and graphed using a Matlab surface function.

In some embodiments, cell death is assayed by detecting apoptosis markers. In some embodiments, cellular toxicity is assayed by measuring release of cytotoxic molecules from the cell population.

In some embodiments, cellular interaction of a cell population is assayed by measuring duration of cellular interactions, number of cellular interactions, calcium activation, granule polarization, protein localization, motility during cellular interaction, termination of cellular interaction, and combinations thereof. In some embodiments, the assaying of the cellular interaction also includes the detection and quantification of cell-cell contacts.

In some embodiments, the combination of cell death and cellular interaction are assayed by evaluating various parameters. Such parameters can include, without limitation, time between first cellular contact and death, the number of cellular contacts prior to cell death, cumulative duration of cellular interactions between first cellular contact and target cell death ($t_{Contact}$), time between first cellular contact and target cell death ($t_{Death}$), time between termination of cellular contact and target cell death, number of cell deaths caused by an individual cell, and combinations thereof.

The assaying methods of the present disclosure can also include additional steps. For instance, in some embodiments, the assaying includes labeling the cell population. In some embodiments, the cell population is labeled by staining cells with fluorescent-based detection reagents. In some embodiments, the labeling can provide information on various dynamic behaviors, such as cell death, motility, or protein secretion. For instance, in some embodiments, intracellular staining analysis can be utilized to assay protein expression (e.g., up-regulation of IFNγ expression using fluorescent immune-affinity reagents, such as antibodies). In some embodiments, the labeling of cells with fluorescent dyes can be utilized to indicate the viability of the cells.

In some embodiments, the assaying includes pre-treating the cell population with an active agent. In some embodiments, the active agent includes, without limitation, small molecules, drugs, antibodies, cytokines, chemokines, growth factors, and combinations thereof.

In some embodiments, the assaying includes pre-treating the cell population with other cells. In some embodiments, the other cells can include cells of the same species, pathogens or symbiotes. In some embodiments, the other cells can include, without limitation, viruses, bacteria, parasites, and combinations thereof.

The assaying methods of the present disclosure can occur under various conditions. For instance, in some embodiments, the step of assaying the dynamic behavior of cells is performed at 37° C. and 5% $CO_2$. In some embodiments, the step of assaying the dynamic behavior of cells is performed at varying concentrations of molecular oxygen (e.g., 0-5%). In some embodiments, the step of assaying the dynamic behavior of cells is performed at varying concentrations of metabolites. In some embodiments, the metabolites include, without limitation, glucose, glutamine, lactate, branched chain amino acids and pyruvate. Additional conditions can also be envisioned.

Assaying of Dynamic Behavior as a Function of Time

The dynamic behavior of cells can be assayed for various periods of time. For instance, in some embodiments, the assaying occurs at sequential intervals for a period of time. In some embodiments, the period of time ranges from about 1 minute to about 96 hours. In some embodiments, the period of time ranges from about 1 minute to about 24 hours. In some embodiments, the period of time ranges from about 1 hour to about 24 hours. In some embodiments, the period of time ranges from about 5 hours to about 24 hours. In some embodiments, the period of time ranges from about 12 hours to about 14 hours.

In some embodiments, the sequential intervals range from about 1 minute to about 60 minutes. In some embodiments, the sequential intervals range from about 1 minute to about 10 minutes. In some embodiments, the sequential intervals range from about 5 minutes to about 10 minutes. In some embodiments, the sequential intervals range from about 5 minutes to about 6 minutes.

In some embodiments, the dynamic behavior of cells are assayed for 12-13 hour periods at sequential intervals that last from about 5 minutes to about 10 minutes per interval. In some embodiments, the dynamic behavior of cells are assayed for about 8 hours at sequential intervals that last for about 6 minutes per interval.

Sensors

In some embodiments, the assaying of the dynamic behavior of a cell population occurs by the use of sensors. In some embodiments, the sensor to be used for assaying a dynamic behavior is associated with the area that contains the cell population. In some embodiments, the sensor is immobilized on the area.

The sensors of the present disclosure can include various components. For instance, in some embodiments, the sensor includes an analyte binding agent. In some embodiments, the analyte binding agent is associated with one or more regions on a surface of the sensor. In some embodiments, the analyte binding agent includes, without limitation, genes, nucleotide sequences, interference RNA (RNAi), antisense oligonucleotides, peptides, antisense peptides, antigene peptide nucleic acids (PNA), proteins, antibodies, and combinations thereof.

In some embodiments, the analyte binding agent on a sensor is directed against an analyte of interest (i.e., an analyte associated with a dynamic behavior of a cell). In some embodiments, the analyte of interest includes, without limitation, secreted proteins, cell lysate components, cellular receptors, metabolites, lipids, microvesicles, exosomes (e.g., exosomes with diameters of less than about 200 nm), microparticles (e.g., microparticles with diameters between about 200 nm and about 5 μm), small molecules, protons, carbohydrates, and combinations thereof. In some embodiments, the analyte of interest is a cytokine.

In some embodiments, the analyte of interest is captured by the sensors of the present disclosure. In some embodiments, the captured analytes of interest are subsequently characterized. The captured analytes of interest may be characterized by various methods. In some embodiments, such methods can include, without limitation, mass spectrometry, sequencing, microscopy, nucleic acid hybridization, immunoassay-based detection (e.g., enzyme-linked immunosorbent assay (ELISA)), and combinations thereof.

The sensors of the present disclosure can be in various forms. For instance, in some embodiments, the sensor is in the form of a bead. In some embodiments, the bead is coated with an antibody directed against an analyte (e.g., antibody-coated beads to profile cytokine secretion, as detected with fluorescently labeled secondary antibodies).

The beads of the present disclosure can have various diameters. For instance, in some embodiments, the beads include diameters that range from about 100 nm to about 100 μm. In some embodiments, the beads include diameters that range from about 500 nm to about 10 μm. In some embodiments, the beads include diameters that range from about 1 μm to about 10 μm. In some embodiments, the beads include diameters that range from about 500 nm to about 5 μm. In some embodiments, the beads include diameters ranging from about 1 μM to about 6 μM. In some embodiments, the beads include diameters that range from about 3 μm to about 5 μm. In some embodiments, the beads include diameters that range from about 1 μm to about 3 μm. In some embodiments, the beads include diameters of about 3 μm.

The beads of the present disclosure can include various analyte binding densities. For instance, in some embodiments, the beads include a binding site density ranging from about $10^{-10}$ mol/m$^2$ to about 10 mol/m$^2$. In some embodiments, the beads include a binding site density ranging from about $10^{-9}$ mol/m$^2$ to about $10^{-1}$ mol/m$^2$. Additional binding site densities can also be envisioned.

The beads of the present disclosure can also include various compositions. For instance, in some embodiments, the beads can include polymeric beads, silicon beads, glass beads, and combinations thereof.

The beads of the present disclosure can be modified with an analyte binding agent through various methods. For instance, in some embodiments, the beads may be co-incubated with an antibody against an analyte of interest. This can then result in the adhesion of the antibodies to the surfaces of the beads. The beads can then be used to assay a dynamic behavior of a cell population.

Use of Sensors to Assay Dynamic Behavior

The sensors of the present disclosure can be utilized to assay the dynamic behavior of cells in various manners. For instance, in some embodiments, the sensors of the present disclosure are utilized to assay the dynamic behavior of a cell population in real-time. In some embodiments, the sensors of the present disclosure are utilized to assay the dynamic behavior of a single cell in a cell population in real-time.

The sensors of the present disclosure can be utilized to assay various dynamic behaviors of a cell population. Such dynamic behaviors and assaying methods were described previously. For instance, in some embodiments, the dynamic behavior to be assayed by the sensors of the present disclosure can include, without limitation, cellular activation, cellular inhibition, protein secretion, microvesicle secretion, exosome secretion, microparticle secretion, metabolite secretion, small molecule secretion, proton secretion, protein expression, and combinations thereof.

In some embodiments, protein expression is assayed by the sensors of the present disclosure through capture of cell lysate components. In some embodiments, protein secretion is assayed by the sensors of the present disclosure through capture of secreted proteins. The capture of the cell lysate components or secreted proteins can then be visualized by various methods, such as the use of fluorescent secondary antibodies.

The sensors of the present disclosure can also have secondary uses in assaying dynamic behavior. For instance, in some embodiments, the sensor is utilized as a fiduciary marker to enable auto-focusing of a cell population during imaging. In some embodiments that utilize quantitative phase imaging, the invariant size of the sensor bead is used as a reference object.

The cell populations of the present disclosure can be exposed to the sensors of the present disclosure by various methods. For instance, in some embodiments, the cell population is incubated with the sensors. In some embodiments, the cell population is lysed prior to incubation with the sensors.

Identifying One or More Cells of Interest

The assayed dynamic behavior of a cell population can be utilized to identify one or more cells of interest. For instance, in some embodiments, one or more cells of interest can be identified based on their assayed motility, cell cytotoxicity, cell death, protein secretion, cellular interaction, and combinations thereof. In some embodiments, a single cell is identified based on the assayed dynamic behavior. In some embodiments, a plurality of cells are identified based on the assayed dynamic behavior.

Cell identification can occur by various methods. For instance, in some embodiments, the one or more cells are identified manually. In some embodiments, the one or more cells are identified automatically. In some embodiments, the one or more cells are identified automatically through the use of algorithms. In some embodiments, the one or more cells are identified through the use of automated segmentation and tracking algorithms.

In some embodiments, the one or more identified cells may be isolated. In additional embodiments, the methods of the present disclosure may include a step of isolating the one or more identified cells. Various methods may be used to isolate the one or more identified cells. For instance, in some embodiments, the one or more identified cells are isolated by micromanipulation (e.g., manual or automated micromanipulation), magnetic retrieval, dielectrophoretic retrieval, acoustic retrieval, laser based retrieval, and combinations of such steps.

Molecular Profile Analysis

Once one or more cells are identified based on an assayed dynamic behavior (and optionally isolated), their molecular profile can be characterized. Various molecular profiles of the one or more identified cells can be characterized. For instance, in some embodiments, the molecular profile can include, without limitation, transcription activity, transcriptomic profile, gene expression activity, genomic profile, protein expression activity, proteomic profile, protein interaction activity, cellular receptor expression activity, lipid profile, lipid activity, carbohydrate profile, microvesicle activity, glucose activity, metabolic profile (e.g., by using mass spectrometry or other methods), and combinations thereof.

In some embodiments, the characterized molecular profile includes cellular receptor expression activity. In some embodiments, the profiled cellular receptor includes, without limitation, T cell receptors, immunoglobulin receptors, killer immunoglobulin receptors (KIR), B cell receptors (BCR), chemokine receptors (e.g., CXCR3), transcription factor receptors (e.g., GATA3), and combinations thereof. In some embodiments, the characterized molecular profile includes one or more apoptosis markers of a cell.

Various methods may be utilized to characterize the molecular profile of cells. For instance, in some embodiments, the molecular profile characterization occurs by DNA analysis, RNA analysis, protein analysis, lipid analysis, metabolite analysis (e.g., glucose analysis), mass spectrometry, and combinations thereof.

In some embodiments, the molecular profile characterization occurs by DNA analysis. In some embodiments, the DNA analysis includes amplification of DNA sequences from one or more identified cells. In some embodiments, the amplification occurs by the polymerase chain reaction (PCR).

In some embodiments, the molecular profile characterization occurs by RNA analysis. In some embodiments, the RNA analysis includes RNA quantification. In some embodiments, the RNA quantification occurs by reverse transcription quantitative PCR (RT-qPCR), multiplexed qRT-PCR, fluorescence in situ hybridization (FISH), and combinations thereof.

In some embodiments, the molecular profile characterization occurs by RNA or DNA sequencing. In some embodiments, the RNA or DNA sequencing occurs by methods that include, without limitation, whole transcriptome analysis, whole genome analysis, barcoded sequencing of whole or targeted regions of the genome, and combinations thereof. In some embodiments, the microvesicles, exosomes or microparticles secreted by the individual cells or aggregates are detected by RNA-sequencing or antibody-based methods.

In some embodiments, the molecular profile characterization occurs by protein analysis. In some embodiments, the protein analysis occurs at the proteomic level. In some embodiments, the protein analysis occurs by multiplexed fluorescent staining. In some embodiments, the comprehensive metabolic profile of single cells is achieved by using mass spectrometry.

Correlation of the Obtained Information

Various procedures may be utilized to correlate the information obtained through the methods of the present disclosure. For instance, in some embodiments, the correlating includes integrating the assayed dynamic behavior and the characterized molecular profile of the one or more identified cells.

In some embodiments, the correlating includes correlating the motility of the one or more identified cells to gene expression or transcription activities of the one or more identified cells. In some embodiments, gene analyses algorithms (e.g. Trend discovery with STrenD) can be utilized to select genes that are correlated with high or low motility cells. Likewise, in some embodiments, bi-clustering algorithms may be utilized to identify over-expressed genes that are associated with high or low motility cells.

In some embodiments, the correlating includes correlating the cellular interaction activity of one or more identified cells to the protein expression activity of the one or more identified cells. In some embodiments, the correlating includes correlating the motility of the one or more identified cells to the protein interaction activity of the one or more identified cells. For instance, in some embodiments, a protein interaction network analysis of one or more identified cells can be performed by using a Genemania algorithm that correlates the protein interaction activity of one or more identified cells to the motility of the one or more identified cells. In some embodiments, the correlating involves linking the ability of immune cells to participate in killing or serial killing with the genes associated with these cells using single-cell RNA-seq or qPCR profiling.

Application of Obtained Information

The correlated information obtained from the methods of the present disclosure can be utilized for various purposes. For instance, in some embodiments, the correlated information can be utilized for at least one of predicting clinical outcome of a treatment, screening cells, retrieving cells for further evaluation, facilitating a treatment, diagnosing a disease, monitoring cellular activity, and combinations thereof.

In some embodiments, the correlated information can be utilized to facilitate a treatment. In some embodiments, the treatment includes immunotherapy. For instance, in some embodiments, the ability to dynamically profile interactions between immune cells and tumor cells and performing subsequent proteomic/transcriptomic profiling on the immune cells allows for engineering of better immunotherapies.

In some embodiments, the correlated information can be utilized to monitor cellular activity. In some embodiments, the monitored cellular activity includes an immune response.

In some embodiments, the correlated information can be utilized to screen cells, such as the screening of cells for clinical efficacy. For instance, in some embodiments, the screened cells include multi-killer T cells. In some embodiments, the functional and molecular characteristics of the multi-killer T-cells are evaluated before selecting subsets for preclinical and clinical tests.

In some embodiments, the correlated information can be utilized to predict clinical outcome, such as the outcome of an immunotherapy. For instance, in some embodiments, the observed ability of a T cell to persist and participate in serial killing of tumor cells can be utilized as a predictor of the therapeutic success of the identified T-cell in cancer therapy. Likewise, the characterized protein expression activity of the identified T-cell can be utilized to introduce various markers (e.g., immune-receptors) onto the T-cell in order to enhance therapeutic success in vivo.

In some embodiments, the correlated information can be utilized to retrieve cells for further evaluation. In some embodiments, cells are retrieved by various methods, such as micromanipulation. Thereafter, the cells are evaluated for various purposes. In some embodiments, the cells are evaluated in additional studies. In some embodiments, the cells are evaluated through cellular expansion.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Automated Profiling of Individual Cell-Cell Interactions from High-Throughput Time-Lapse Imaging Microscopy in Nanowell Grids (TIMING)

In this Example, fluorescently labeled human T cells, Natural Killer cells (NK), and various target cells (NALM6, K562, EL4) were co-incubated on PDMS arrays of sub-nanoliter wells (nanowells), and imaged using multi-channel time-lapse microscopy. Novel cell segmentation and tracking algorithms that account for cell variability and the nanowell confinement property increased the yield of correctly analyzed nanowells from 45% (existing algorithms) to 98% for wells containing one effector and a single target. This enabled reliable automated quantification of cell locations, morphologies, movements, interactions, and deaths. Automated analysis of recordings from 12 different experiments demonstrated automated nanowell delineation accuracy of more than 99%, automated cell segmentation accuracy of more than 95%, and automated cell tracking accuracy of 90%, with default parameters, despite variations in illumination, staining, imaging noise, cell morphology, and cell clustering. Analysis of a dataset with more than 10,000 nanowells revealed that NK cells efficiently discriminate between live and dead targets by altering the duration of conjugation. The data also demonstrated that cytotoxic cells display higher motility than non-killers, both before and during contact.

Recent advances have enabled the fabrication of large arrays of sub-nanoliter wells (nanowells) cast onto transparent biocompatible polydimethylsiloxane (PDMS) substrates. Small groups of living cells from clinical samples, and laboratory-engineered cells can be confined to nanowells, and imaged over extended durations by multi-channel time-lapse microscopy, allowing thousands of controlled cellular events to be recorded as an array of multi-channel movies. Applicants refer to this method as Time-lapse Imaging Microscopy In Nanowell Grids (TIMING). The spatial confinement can enable a rich sampling of localized cellular phenomena, including cell movements, cellular alterations, and cell-cell interaction patterns, along with the relevant intra-cellular event markers.

TIMING is thus ideally suited for tracking cell migration and interactions at short distances. However, if cell migratory patterns over larger distances are of interest, arrays with larger wells can be fabricated. Similarly, if unconfined migratory behavior of cells is desired, other methods have been described. The promise and challenge of nanowell arrays, is high throughput, eliminating the need for user selection of events of interest, and the ability to repeatedly follow the same cell(s) over time.

For instance, FIGS. 2A-2D illustrate a TIMING dataset consisting of 11,760 nanowells containing fluorescently tagged human $CAR^+$ T-cells (red) and NALM-6 tumor cells (green) that were imaged by time-lapse microscopy over 130 time points at 5-minute intervals to yield an array of 4-channel movies, one per nanowell. The border nanowells from each block are discarded, yielding 25 usable nanowells per block. TIMING datasets vary in size between 200 GB-1.5 TB, depending upon the array size, and number of time points. Production datasets are often of lower quality than the example in FIGS. 2A-2D (e.g., FIGS. 3A-5B) and contain confounds including natural cellular variability, variations in signal to noise ratio (SNR), staining variations, focus drift, spectral overlap between fluorochromes, and photobleaching.

In this Example, Applicants demonstrate the development of highly automated algorithms that can reliably segment and track the cells in TIMING datasets with minimal parameter tuning, and yield a sufficiently large and rich set of cellular-scale measurements for statistical profiling, without the need for manual proofreading. A direct application of general-purpose segmentation and tracking algorithms is not a viable strategy since their yield (number of nanowells analyzed with zero errors in segmentation and tracking) is low, and their parameter tuning needs are high.

For example, a direct application of a prior segmentation algorithm with a reported accuracy of more than 95% that is the core of the open-source FARSIGHT toolkit (farsight-toolkit.org) to the dataset in FIGS. 2A-2D produce an error-free yield of only 43% of the nanowells for the basic case when a nanowell contains one effector and one target (FIG. 50).

The situation with tracking algorithms is similar. For example, in analyzing one sample block containing 36 nanowells, out of which 21 contained at least one cell, a state-of-the art algorithm accurately tracked xx nanowells with zero errors (yield of 28%). When the yield falls below 90%, burdensome manual proofreading is preferred to identify the nanowells that were tracked accurately. If on the other hand, the automated accuracy is at least 90%, the user can simply accept the automated results, and the modest error that they entail.

As such, general-purpose segmentation and tracking algorithms do not exploit powerful constraints that are germane to TIMING datasets, specifically, the spatial confinement of cells, and rarity of cell divisions. They also lack mechanisms to cope with the higher morphological variability and non-uniform fluorescence of cell bodies compared to cell nuclei that were heavily studied in the prior literature.

In this Example, Applicants present algorithms that exploit the confinement and cell-cycle constraints, and utilize novel segmentation approaches to increase the yield to 98% for the basic case noted above (compare FIG. 50 vs. FIG. 51), and deliver high tracking accuracies (FIG. 52). At this level of performance, the quantitative measurements derived from automated segmentation and tracking can be directly utilized for statistical studies without the need for manual proofreading. FIG. 50 provides a summary of yield from traditional automated segmentation. The first entry indicates the number of nanowells containing the corresponding cell distribution (manually verified), and the second entry indicates the corresponding yield. FIG. 51 provides a summary of error-free nanowell yield using the confinement constrained cell detection method.

Example 1.1. Specimen Preparation and Imaging

The TIMING datasets were derived from ongoing studies in which human T cells (genetically engineered to express chimeric antigen receptor CAR) and Natural Killer (NK) cells were used as effectors. Human leukemic lines NALM6, K562 or mouse EL4 cells expressing the appropriate ligands were used as targets (T).

Both cell types were washed once in serum-free medium, suspended to ~2 million/mL and labeled with PKH67 Green and PKH26 Red dyes respectively, as directed by the manufacturer (Sigma-Aldrich). Approximately 100,000 effector (E) cells were loaded onto the nanowell array, followed by ~200,000 target cells. Cells were allowed to settle into the nanowells for 5 minutes, and excess cells were washed away.

Next, 50 μL of Annexin V-Alexa Fluor 647 (AnnV-AF647, Life Technologies) was mixed in 3 mL of complete culture medium (RPMI-1640+10% FBS, containing no phenol red, Cellgro) and pipetted onto the nanowell array plate, thus immersing the array in the medium throughout the image acquisition while allowing for nutrition and gas exchange (37° C., 5% $CO_2$). The nanowell array is much wider than the field of view of the microscope. Therefore, a computer-controlled microscope stage (AxioObserver Z1, Carl Zeiss) was used to scan the array spatially. Images were collected over 12-13 hour periods at 5-10 minute intervals. This temporal sampling rate is in the range of times described between first contact and killing in previous in vitro observations. The stage movements from one block to the next require ~100 ms, negligible compared to the sampling interval.

Applicants used an LD Plan Neofluar 20×/0.4NA Korr Ph1 Ph2 M27 (Carl Zeiss) objective lens combined with an optovar of 1× Tubulens, yielding a total magnification of 200×, and a resolution of 0.325 μm/pixel (pixel size). A Peltier-cooled (−10° C.) digital scientific CMOS camera (ORCA-Flash 4.0 V2 C11440-22CU), or Hamamatsu EM-CCD camera were used for recording the images.

Example 1.2. Automatic Nanowell Localization

Figure 4A:
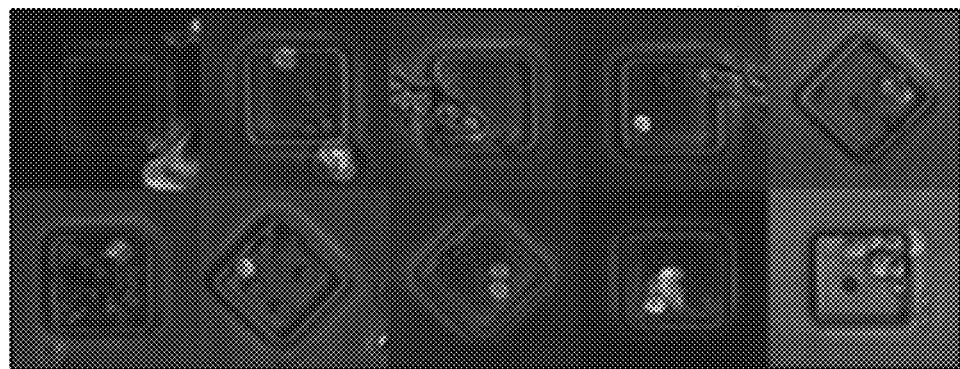
FIGS. 4A-4C illustrate automated localization of nanowells.

Automatic localization of nanowells is preferred for delineating the cell confinement regions, correcting for stage re-positioning errors, and breaking up the overall TIMING dataset into a large number of motion-corrected video sequences, one per nanowell. Preferably, this operation is reliable since a single well-detection error can render the nanowell unusable for analysis, reducing the experimental yield. Preferably, the operation must also be robust to focus drift (accounting for shrinkage/swelling/irregularity of the polymer substrate), wells with compromised geometry, illumination variations, ringing artifacts, and debris or air bubbles that may move, and abruptly appear/disappear from the camera view over time (FIG. 4A).

Content-independent image registration methods like SIFT matching were neither sufficiently reliable nor practical for TIMING data. They required multiple parameter adjustments, and failed in the presence of artifacts. Therefore, Applicants adopted a normalized cross-correlation (NCC) based template fitting method that is robust to illumination variations and artifacts. Applicants exploited the fact that the geometry of nanowells is known from the fabrication process, and they are always visible in the phase-contrast channel.

Figure 2A:
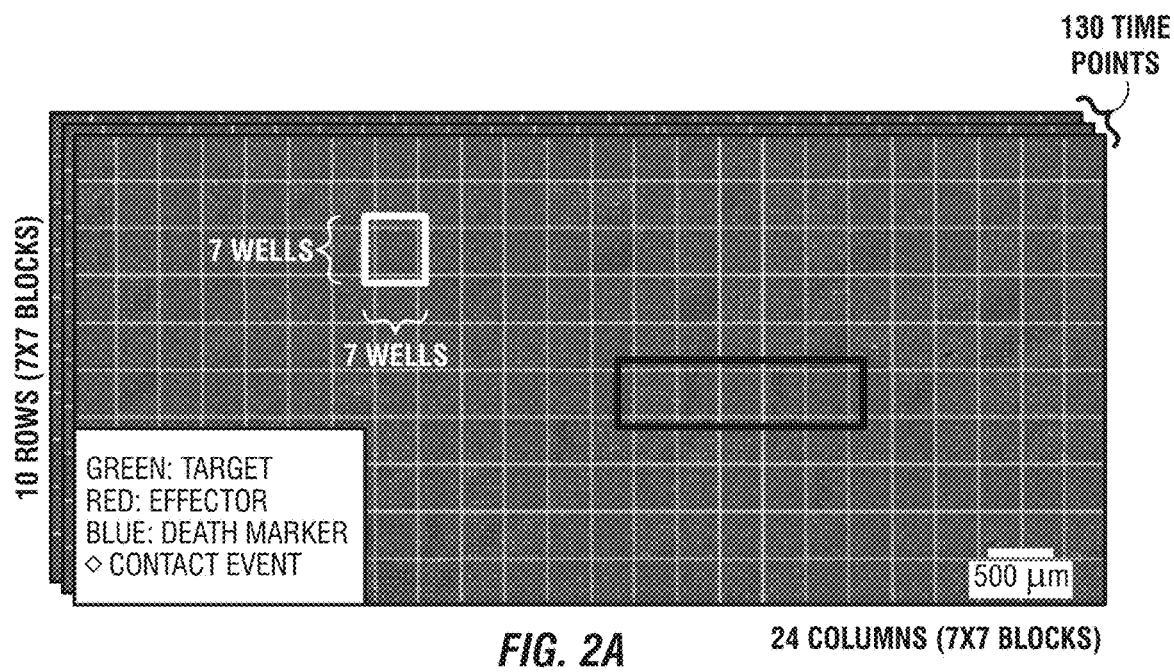
FIGS. 2A-2D illustrate a small dataset based on a time-lapse imaging microscopy in Nanowell Grids (TIMING) assay.
Figure 2B:
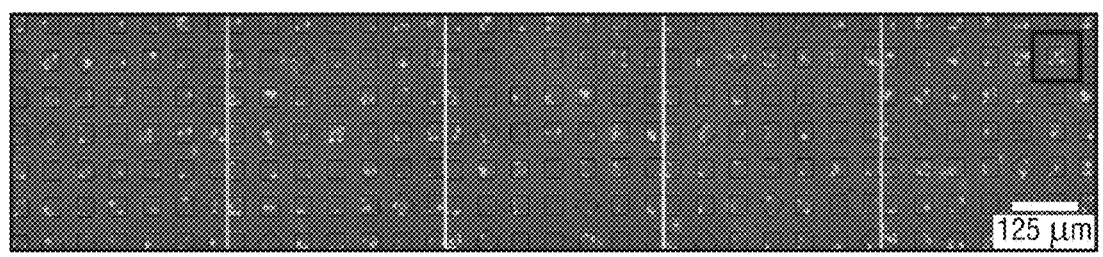
Figure 2C:
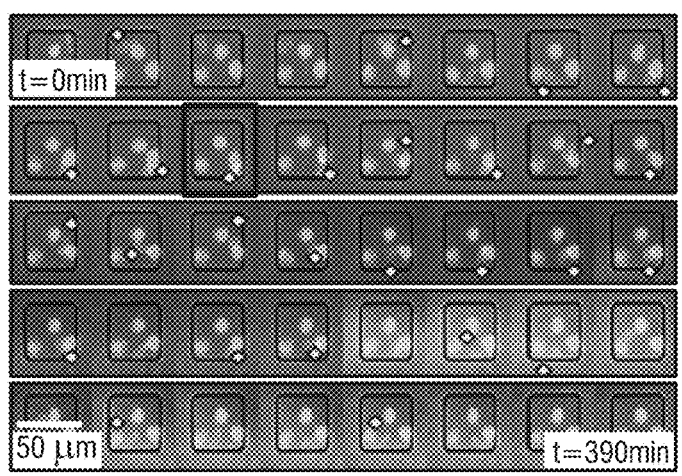
Figure 2D:
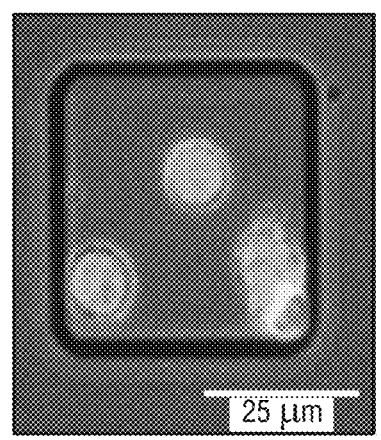

For instance, FIG. 2B shows that some of the nanowells are intentionally rotated by 45° for implementing a coding strategy designed to uniquely locate individual wells in an array. Therefore, Applicants select two empty wells (regular, and rotated by 45°) from the dataset being analyzed and use them as templates that are fitted to the image data. The NCC responses are in the range of (−1, +1), with −1 indicating a poor match, and +1 a perfect match.

Figure 4B:
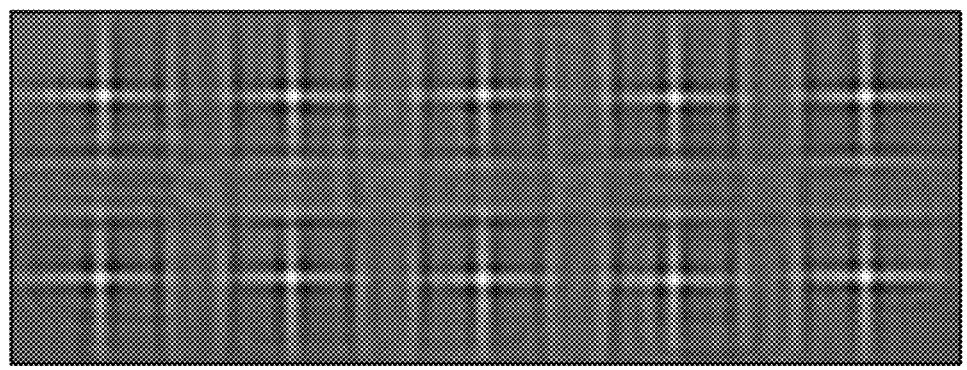
Figure 4C:
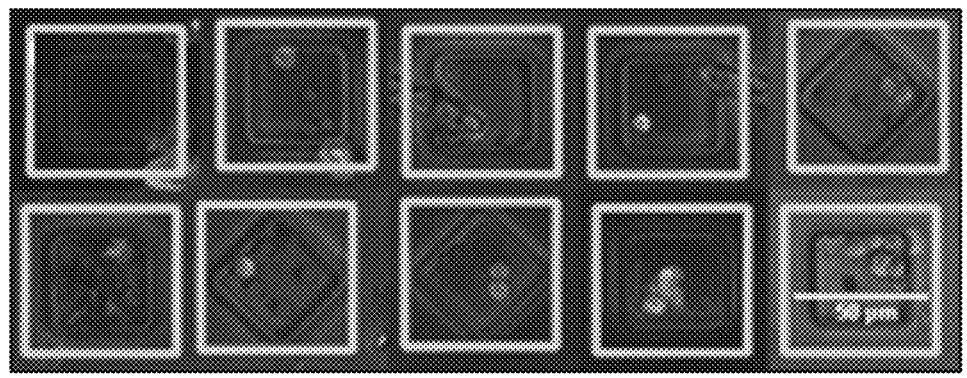
Figure 8A:
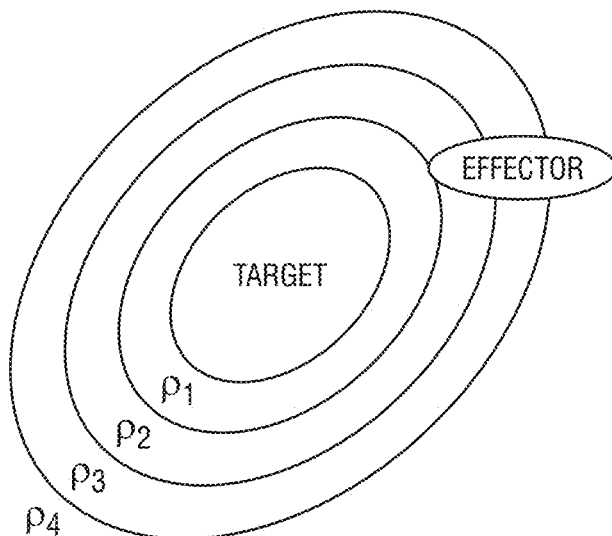
FIGS. 8A-8E show a cell interaction analysis.
Figure 8B:
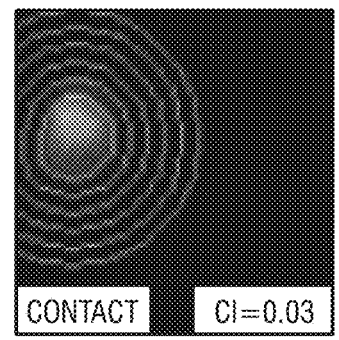
Figure 8C:
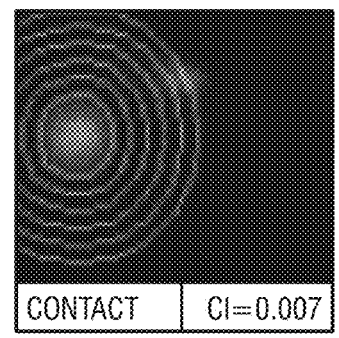
Figure 8D:
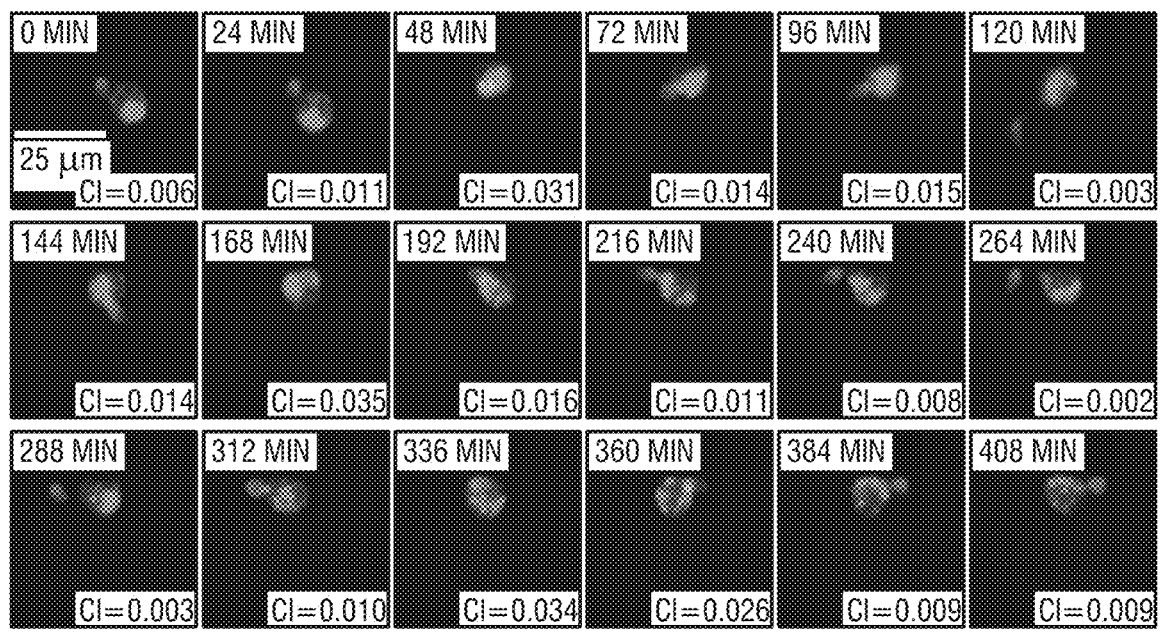
Figure 8E:
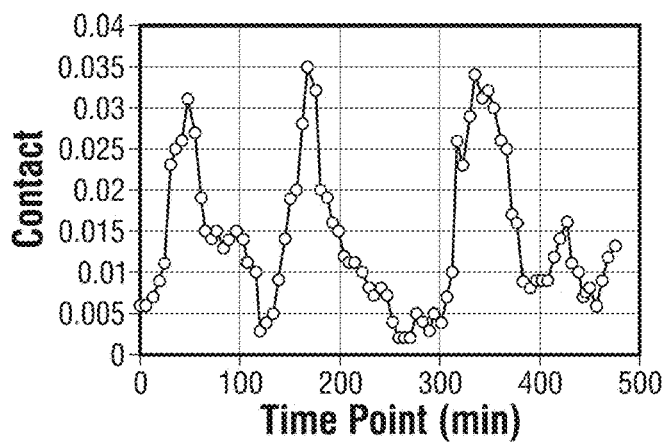

To speed up NCC, Applicants used a Fourier implementation, and performed the normalization in the spatial domain. FIG. 4B shows the NCC responses of the example wells in FIG. 4A to the best-fitting (of the two) templates in FIG. 4A. Applicants used the local maximum clustering algorithm on the best-fitting NCC response to detect well centers, and used the known spacing between nanowells to filter out invalid responses, yielding a robust localization of wells with more than 99% accuracy.

To cope with artifacts, Applicants discarded the nanowell videos whose maximum NCC response falls below a pre-defined threshold (typ. 0.75). The resulting rigid spatial transformation estimates (FIG. 4C) were used to generate cropped motion-corrected nanowell video recordings.

Example 1.3. Image Pre-Processing

Each image frame of every video sequence was leveled to correct illumination variations by subtracting the local background estimated at each pixel using a Gaussian kernel with σ=15 (FIG. 5C). Next, Applicants corrected for spectral overlap between the emission spectra of the PKH67 and PKH26 dyes used to label the effector and target cells. The columns of the mixing matrix were estimated offline using principal component analysis (PCA) for a 7×7 block of nanowell videos, and then re-used across the rest of the array. The unmixing was performed by a linear inverse method.

Finally, Applicants smooth the images using a median filter with a radius $r_m=3$ while preserving cell boundaries. As noted by other authors, such pre-processing is preferred for reducing high-throughput cell segmentation errors.

Even after pre-processing, cells exhibit variability in shape and intra-cellular fluorescence (FIG. 6A), and this is a challenge for cell detection and separation of touching/overlapping cell bodies. The widely used multi-scale Laplacian of Gaussian (LoG) map misses the dim cell indicated by the red arrow, and is unable to separate the pair of cells indicated by the yellow arrow that exhibit non-round shapes and non-uniform intensities (FIG. 6C). Moreover, gradient-weighted watershed algorithms have difficulty separating cells with weak edges.

In order to overcome the aforementioned limitations, Applicants propose a normalized multi-threshold distance map (NMTDM) (FIG. 6C) that is designed to detect cell bodies that works as follows. The normalized pixel intensity distributions p(i) of Applicants' pre-processed images are modeled by a mixture of 3 Gaussian distributions in accordance with Equation 1.

$$p(i)=\Sigma_{k=1}^{K}w_k g(i|\mu_k,\sigma_k)$$ Eq. 1

In Equation 1, parameters $(\mu_k,\sigma_k)$ and weights $w_k$, k=1, 2, 3 capture the dim background, intermediate foreground, and hyper-fluorescent foreground pixels, respectively. Applicants used the k-means algorithm with deterministic seeding for estimating the mixture weights since it is fast, requires few initialization parameters, converges reliably, and produces comparable results to expensive expectation maximization algorithms, making it ideal for Applicants' high-throughput analysis.

Clusters 2 & 3 together capture the image foreground, where $L_{min}$ and $L_{max}$ denote the minimum and maximum pixel intensity values for this foreground. Applicants define a series of M threshold values (typ. 20) denoted between $L_{min}$ and $L_{max}$ separated by $\delta=(L_{max}-L_{min})/M$, where $i=L_{min}$, $L_{min}+\delta, L_{min}+2\delta, \ldots, L_{max}$. Each of these thresholds is used to generate a corresponding binary mask denoted $B_i(x,y)$ and a corresponding Euclidean distance map $D_i(x,y)$. Each of these binary masks are subjected to connected components analysis, yielding a set of connected components denoted $R^h$, $h=1, \ldots, H$.

Next, Applicants normalized the Euclidean distance maps for each connected component by the corresponding maximum value within $R_h$, to ensure that the distance maps at different levels contribute equally to the final response. With this, the normalized multi-threshold distance map (NMTDM) for a connected component $R_h$ can be written in accordance with Equation 2.

$$R((x,y) \in R_h) = \frac{1}{M} \times \sum_l \frac{D_l((x,y) \in R_h)}{\max_{(x,y)} D_l((x,y) \in R_h)} \quad \text{Eq. 2}$$

The NMTDM exhibits clear peaks, one per cell, unlike the multi-scale LoG (FIG. 6B vs. 6C). Moreover, local maxima clustering over this map yields a more reliable estimate of the cell count than the multi-scale LoG filter. This step requires only two parameter settings: the number of levels M and the clustering radius r for selecting the peaks. Using this, Applicants estimate the number of cells independently for each frame, and compute a histogram over the time series (FIG. 6D). Knowing that the number of cells in a nanowell stays constant (cell divisions are rare within the observation period), the presence of more than one non-zero entry in this histogram implies that conventional segmentation & tracking results would be error prone for this nanowell, and require proofreading. However, the histogram exhibits a peak at the correct cell count.

Applicants found that the histogram peak is a reliable indicator of cell counts over a time-lapse sequence, despite errors in individual frames. Moreover, the height of the peak of the normalized histogram is a reliable measure of Applicants' confidence in the cell count. For this illustration, the peak reaches 82%. Applicants discard nanowells for which the peak falls below 75%.

Example 1.4. Confinement Constrained Cell Re-Segmentation

Although the above-described method is effective for estimating the correct number of cell bodies, it does not yield precise cell location estimates and cell segmentations because it assumes that the cells are brighter closer to their centers. Applicants' strategy to overcome this limitation is to use the histogram-based cell count estimate to re-segment the cells de novo by a normalized spectral clustering of image pixels. This method can detect cells of diverse shapes, and tends to estimate clusters (cells) with similar sizes—a reasonable assumption when handling ambiguous images.

Given N foreground pixel coordinates $[x_i]_{i=1,\ldots,N}$, Applicants compute a similarity matrix $W \in R_{N \times N}$ in accordance with Equation 3.

$$w(i,j) = \begin{cases} \exp\left(-\frac{\|x_i - x_j\|^2}{2\sigma^2}\right), & \text{if } \|x_i - x_j\| < \varepsilon; \\ 0 & \text{otherwise} \end{cases} \quad \text{Eq. 3}$$

In Equation 3, c is a user-defined constant representing the maximum distance between a pixel and its neighbors, $|\cdot|$ is the Euclidean norm, and $\sigma$ controls the neighborhood width. Next, Applicants compute the degree matrix D and the un-normalized graph Laplacian matrix $L=D-W$, where D is a diagonal matrix defined in Equation 4.

$$D(i,j) = \Sigma_{j=1}^N W(i,j). \quad \text{Eq. 4}$$

In Equation 4, Applicants form the matrix $U=[u_1, \ldots, u_K] \in R_{N \times N}$ by computing the first K eigenvectors $u_1, \ldots, u_K$ of the generalized eigenvalue problem $Lu=\lambda Du$. Finally, Applicants cluster the points $\{y_i\}_{i=1,\ldots,N}$ corresponding to the rows of U into clusters $C_i$, $i=1, \ldots, K$, and re-label the foreground pixels $\{x_i\}_{i=1,\ldots,N}$ accordingly. This method (FIGS. 6A-6D) enables cells in video sequences to be re-segmented accurately, despite errors on individual frames.

Applicants are guaranteed to obtain a fixed number of cells across each movie, and this simplifies cell tracking. Interestingly, the confinement constrained cell re-segmentation algorithm also enables efficient editing of incorrect segmentation & tracking results. If needed, a user can re-run the spectral clustering based re-segmentation with the corrected cell count, and this yields the correct results in most cases.

Example 1.5. Confinement-Constrained Cell Tracking

Reliable cell tracking is needed to quantify the complex motile behaviors of cells at high throughput. The low temporal sampling rate (5-10 minutes/frame) implies that cells can undergo significant displacements and shape changes between frames. In addition, the effect of the nanowell walls makes it difficult to predict cell movements. Importantly, Applicants wish to avoid the need for manual proofreading.

With these considerations in mind, Applicants propose a confinement-constrained tracking method that is fast, fully automated, and reliable. It is formulated globally over the entire movie, rather than on a successive frame-by-frame basis. It does not require any initialization, and requires only 3 parameters. Note that Applicants' algorithm is not intended for general-purpose cell tracking problems. Rather, it is designed specifically for confinement-constrained data. For general problems, sophisticated cell-tracking methods have been described and compared in the literature. The approaches include particle filtering, Kalman filtering that require a motion model and an observation model, but do not need prior segmentations. Contour based, mean-shift, and level-set methods, are preferable when high-temporal resolution data are available, and some can handle merging and splitting of cells implicitly. Optimization-based approaches require objects to be detected/segmented a priori and are preferred for low temporal resolution data. When objects can enter/exit the field, cells divide or die, or when the segmentation is unreliable, elaborate methods are described to handle appearance, disappearance, merge and split, and automatic correction of segmentation errors. For TIMING data, Applicants are unconcerned with such complications because of the nanowell confinement property. Therefore, Applicants' formulation is a streamlined formulation.

Applicants formulated the tracking of K cells over T frames as a globally optimal edge selection problem on a directed graph. A node $n_j^t$ in the graph represents cell j at frame t, and is described by an attribute vector $d_j^t = \{c_j^t, a_j^t, r_j^t\}$, where $c_j^t = (x_j^t, y_j^t)$ is the centroid; $a_j^t$ is the area of the cell; and $r_j^t$ denotes the pixels defining cell j. An edge $e_{i,j}^t = \{n_i^{t-1} n_j^t\}$ associates cell i at frame t−1 to cell j at frame t, and Applicants compute an association cost $\sigma_{i,j}^t$ that measures the dissimilarity between cell regions i and j. An edge selection variable $\gamma_{i,j}^t \in \{0,1\}$ indicates if a given edge is selected in the final solution. Using integer programming, Applicants seek the solution $\gamma \in \{0,1\}^N$, where $N=(T-1) \times K \times K$ that minimizes the following sum of association costs over each nanowell.

$$\Gamma = \operatorname*{argmin}_{\gamma \in \{0,1\}^N} \sum_{t=2}^{T} \sum_{j=2}^{K} \sum_{i=1}^{K} \varphi_{i,j}^t \gamma_{i,j}^t \qquad \text{Eq. 5}$$

$$\text{s.t.} \begin{cases} \sum_{i=1}^{K} \gamma_{i,j}^t \leq 1 & \text{for } \begin{array}{l} j=1, \ldots, K, \\ t=2, \ldots, T. \end{array} \\ \sum_{k=1}^{K} \gamma_{i,k}^{t+1} \leq 1 & \text{for } \begin{array}{l} j=1, \ldots, K, \\ t=2, \ldots, T-1 \end{array} \end{cases}.$$

The cell confinement constraint is implicit in Equation 5. The inequality constraints ensure that each node $n_j^t$ is associated with a maximum of one node in the previous frame, and the next frame, respectively. In computing $\varphi_{i,j}^t$, Applicants ignore shape and texture features since cell morphologies and intensity profiles vary over time. Applicants compute a weighted sum of the Euclidean distance between cell centroids $g(c_i, c_j)$, the area difference between cells $g(a_i, a_j) = |a_i - a_j|$, and the set-theoretic distance between the pixels $(r_i, r_j)$ for the two cells described in Equation 6.

$$g(r_i, r_j) = \begin{cases} 1 - \frac{a_{overlap}}{\min(a_i, a_j)} & \text{if } v_{overlap} > 0 \\ \min(dist(r_i, r_j)), & \text{otherwise} \end{cases}, \qquad \text{Eq. 6}$$

In Equation 6, $a_{overlap}$ is the overlapping area, and min$(dist(r_i, r_j))$ is the shortest distance between the cells' pixels. The overall cost is written as $\varphi_{i,j} = w_1 \times g(c_i, c_j) + w_2 \times g(a_i, a_j) + w_3 \times g(r_i, r_j)$, where the weights $w_1$, $w_2$, and $w_3$ can be adjusted if needed. Applicants used the default values $w_1=1$, $w_2=10$, and $w_3=100$. One can increase $w_3$ when high temporal resolution data and good segmentation results are available. Applicants solve the integer program in Equation 5 by using the branch-and-bound algorithm. Although the theoretical worst-case running time can grow exponentially, this is not a concern since Applicants are processing small cohorts of cells in each nanowell.

FIG. 7A illustrates the results of automated tracking for a nanowell containing only effector cells, showing our ability to cope with large inter-frame movements. FIGS. 7B-7E depict sample cell trajectories for effector and target cells with diverse motion patterns. Additional examples are presented in FIG. 9.

Example 1.6. Detection and Quantification of Cell-Cell Contacts

Detecting contacts between effectors and targets, and measuring the contact parameters (e.g., onset time, duration, frequency, extent) is needed for understanding how cell behaviors predict subsequent events of interest, especially the killing of targets by effectors. Approaches using the spatial proximity of cell segmentations can be unreliable for TIMING data since they require much higher resolution imaging, and are sensitive to segmentation errors. With this in mind, Applicants define a soft cell interaction measure GI for quantifying the interaction of a cell with its surrounding cells, as follows.

First, Applicants compute the normalized effector fluorescence signal $I_N^j(x,y)$ in each nanowell j. Next, Applicants define a series of ring-like compartments using a Euclidean distance map $D(x,y)$ with respect to the segmented target cells, as illustrated in FIG. 8. Pixels with distances between k and k+1 pixels form compartments $b_k$ with inner radii $k=\{1,2,\ldots,n\}$, where n is the maximum distance needed to cover the complete nanowell. Applicants sum the fluorescence intensities over each compartment, and normalize them by their radii k that are proportional to the compartment areas. With this, the cell interaction measure CI(t) is the following weighted intensity summation in Equation 7.

$$CI(t) = \sum_{k=1}^{n} \left[ \frac{1}{k} \sum (x,y) \in b_k I_N^j(x,y) \right] \qquad \text{Eq. 7}$$

FIGS. 8A-8E show how CI(t) captures cell contacts in a graded manner over an image sequence. This measure can be thresholded to detect cell contact events with a desired sensitivity. The threshold is set and verified manually by an immunologist based on visual verification of at least 30 nanowells for each TIMING dataset, starting with a default value (typ. 0.01). Applicants consider this visual verification to be valuable due diligence. A full manual annotation of the contacts by five independent observers over 156 nanowell videos showed a 90.4% concordance with the default threshold. In order to definitely assign contact, it is defined to occur when the threshold criterion is met for two successive frames. CI(t) is defined above for a single cell and its neighbors. It can be extended to handle multiple cells by using segmentation masks.

Example 1.7. Feature Computation

For each cell, the automated segmentation and tracking operations produce multiple time series of primary features including cell location (x,y), area a(t), instantaneous speed v(t), cell shape as measured by the eccentricity of the best-fitting ellipse e(t), and the contact measure CI(t). In addition, target cell death events (apoptosis) are detected using Annexin V, whose summed fluorescence intensity $i_d(t)$, is measured as another primary feature. Next, Applicants compute cellular features at the scale of each nanowell, specifically, the number of effector cells $n_e$, target cells $n_t$, dead effectors $n_{ed}$, contacted targets $n_{tc}$, and killed targets $n_{tk}$. These measurements can be used to profile the nanowells.

The primary cellular features capture important aspects of the cellular activities within each nanowell, but they have two disadvantages. First, they have a variable dimensionality, since the number of time points varies across TIMING experiments. Second, a long experiment can result in unnecessarily high dimensional feature data. With the intent of deriving meaningful lower-dimensional representations of cellular events independent of the number of time points, Applicants derive a set of eight secondary features for each cell. For each cell, Applicants compute the average speed prior to first contact $\bar{v}_{free}$, average speed during the contact phase $\bar{v}_{contact}$, average cell eccentricity prior to first contact $\bar{e}_{free}$, average eccentricity during the contact phase $\bar{e}_{contact}$, time elapsed between first contact and death $\Delta t_d$, total contact duration between first contact and death $\Delta t_{cd}$, time duration before first contact $\Delta t_{free}$, and the number of conjugations prior to target cell death $n_{cd}$.

Example 1.8. Experimental Results

The proposed method was evaluated on 12 TIMING experiments involving combinations of target cells (NALM6, K562, and EL4) and effector cells (NK cells or CAR+T cells), to evaluate its ability to cope with biological and imaging variability, different cell types, experimental durations, and changes in instrumentation. All the datasets were analyzed using the parameter settings summarized in FIG. 53.

Figure 9:
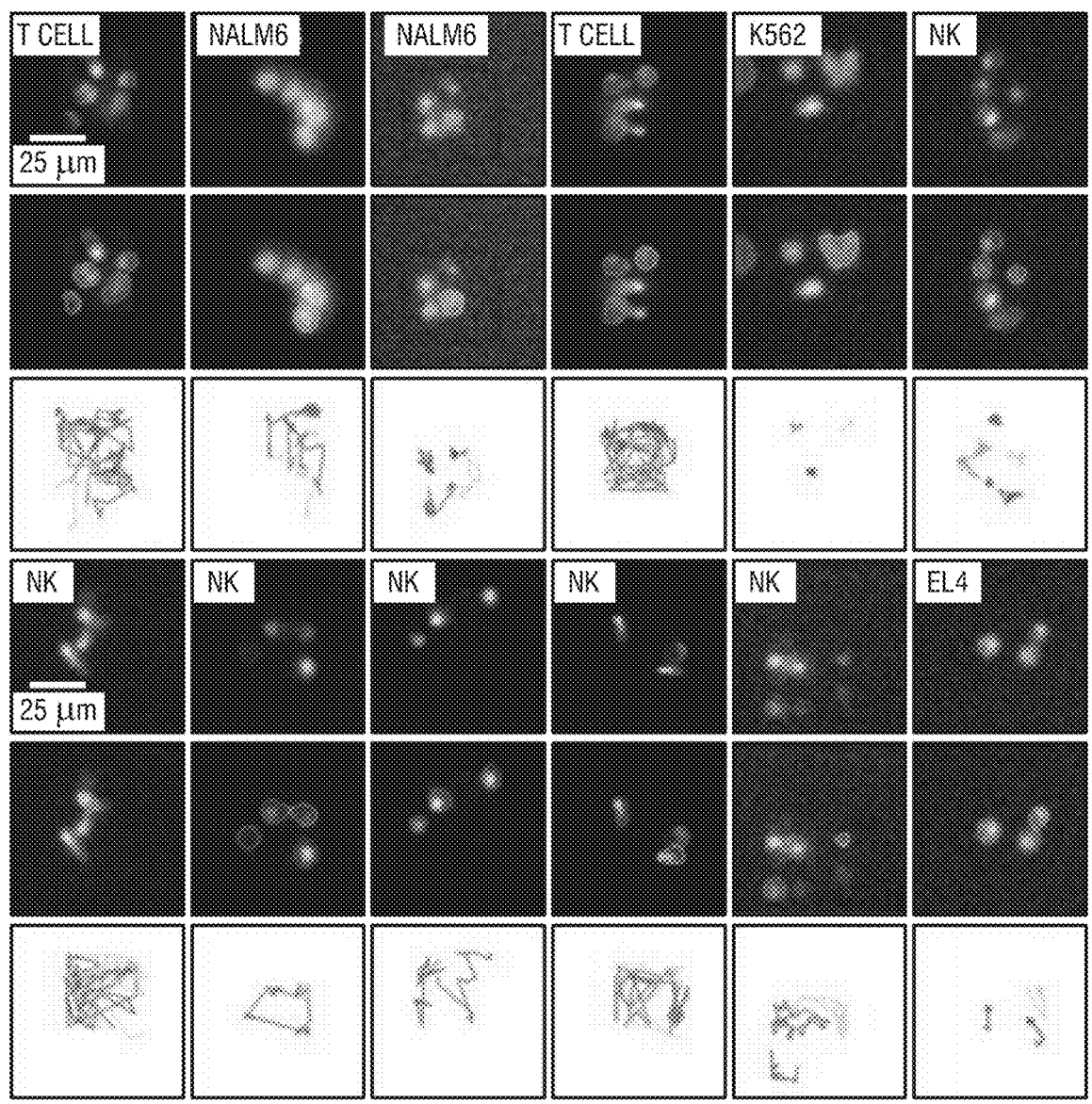
FIG. 9 shows a visual summary of segmentation and tracking results involving various target cells (NALM6, K562, and EL4) and effector cells (NK cell or CAR$^+$ T cell) from 12 TIMING experiments, all run with identical parameter settings (FIG. 53, Example 1). The upper rows show sample frames. The middle rows show segmentations. The bottom rows show the cell tracks.

Given the sheer volume of the data, Applicants start by presenting a visual summary of sample segmentation and tracking results in FIG. 9. Overall, the algorithms and parameter settings proved reliable for automated analysis. As a detailed example, Applicants present results of manually validating the segmentation and tracking on a small dataset with 2,000 nanowells containing CAR+T cells and NALM6 cells imaged over 130 time points. Of these, 157 nanowells had >4 effectors or targets. These larger cohorts are irrelevant for the current biological study of interest, so they were omitted from further analysis. An additional 33 wells (1.7%) were discarded because the confidence in cell counts (histogram peak) was below 75%. Of the remaining 1,803 nanowells, only 7 were not detected accurately due to air bubbles, so Applicants' overall nanowell detection accuracy exceeded 99%.

Example 1.9. Improvement in Yield

In order to assess the fraction of wells with zero cell detection errors, Applicants manually validated the results over the 1,803 remaining nanowells using the proposed method and a prior algorithm as a benchmark. The results are summarized in FIG. 51.

For the entries with more than 90 wells, Applicants manually validated 40% of wells, and the full set of wells for the remaining entries. Comparing the corresponding entries in FIGS. 50 and 51 show that the proposed method dramatically increased the number of usable wells. The few errors were due to persistently dim fluorescent cells that were missed, or because a cell was persistently occluded by another cell for more than 80% of the recording duration. For perspective, yield rates of less than 90% render the automated image analysis results unusable, since the user has to manually analyze an excessive number of nanowells. With a yield close to 98%, the user can simply accept the automated results, and the modest error that they entail.

Example 1.10. Cell Segmentation and Tracking Performance

Nearly 5,061 cells were segmented and tracked in this dataset. The automated segmentation and tracking results were overlaid on the movies and presented to an immunologist, and the errors were scored as: under-segmentation; over-segmentation; and incorrect association. Over-segmentation errors appear when a cell is identified as two or more objects. Under-segmentation occurs when the same label is assigned to multiple cells. Both of these errors can occur if the cell count is incorrect. Incorrect correspondence occurs when the tracking fails, usually due to segmentation errors.

Applicants consider a single association error sufficient to render the tracking results for a nanowell movie unusable. Despite this stringent requirement and the high volume of data, the algorithm is extremely accurate (FIG. 52, frequency of cell segmentations and tracking errors).

Next, Applicants compared automatic segmentations of 30 randomly selected target and effector cells against manual segmentations. The Jaccard similarity index for target cells was 0.86±0.12 (mean±std.) and 0.78±0.17 for effector cells, indicating good segmentation accuracy.

Example 1.11. Data Analysis

Applicants analyzed a TIMING dataset containing 11,520 nanowells (320 blocks of 6×6 wells) in which Applicants imaged the dynamics of killing of K562 cells by in-vitro expanded NK cells for 8 hours at 6 minute intervals. From the automatically extracted features, Applicants selected only the nanowells containing exactly 1 effector and 1 target cell, showing a stable effector-target contact of at least 6 minutes (2 successive frames), and in the case of target death, contact by effector prior to death. This resulted in a cohort of 552 nanowells that is ideal for analyzing the dynamic behaviors of effectors, without the confounds associated with multi-effector cooperation or serial killing.

Figure 10A:
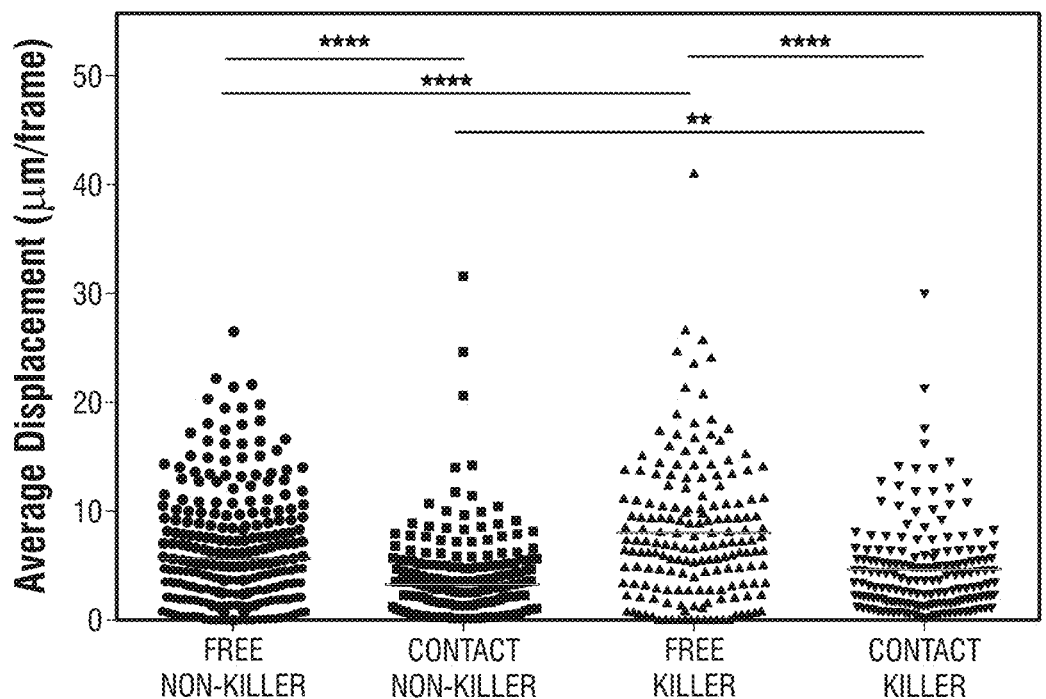
FIGS. 10A-10B illustrate TIMING feature analysis.

Comparisons of the out-of-contact motility and the velocity during tumor cell conjugation demonstrated that NK cells that participated in killing displayed higher motility during both phases (FIG. 10A), consistent with Applicants' recent report that demonstrated that motility might be a biomarker for activated immune cells (see Example 2). Furthermore, for NK cells, the change in speed and arrest upon target cell ligation is well-documented.

Figure 10B:
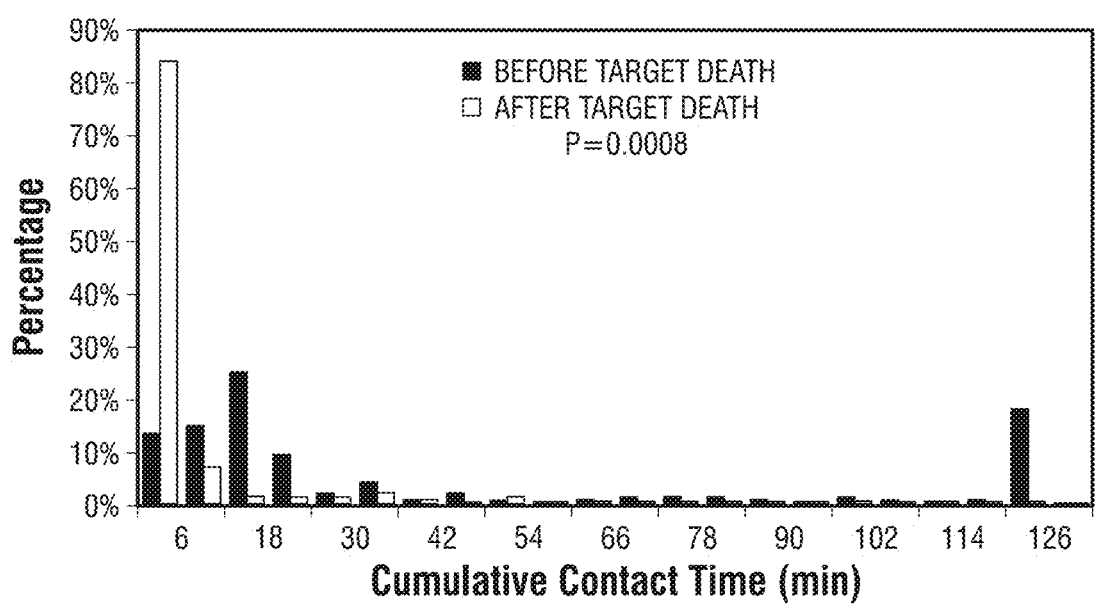

Second, Applicants were interested in quantifying differences in NK cell behavior in interacting with live or dead cells. Of all the NK cells that participated in killing, only 18% re-conjugated to target cells subsequent to apoptosis, and when they did, their duration of conjugation of 18±14 minutes was significantly shorter than conjugations mediated by the same NK cells to live tumor cells (52±72 minutes) (FIG. 10B). These results suggest that NK cells largely avoided conjugating to dead target cells, and even when they did, made an early decision to terminate the conjugation.

Example 1.12. Implementation

For a block with 36 wells and 60 cells, the processing time is 9-10 seconds/block per time point on a Dell 910 PowerEdge server with 40 CPU cores, 1 TB of RAM, and a RAID 5 storage system. The cell tracking took 1.1 secs/block. Segmentation took 3.1 secs/block. Well detection took 1.5 secs/block. Feature computation took 3.5 secs/block. The algorithms were implemented in Python & C++, except for the spectral clustering that used a compiled MATLAB executable.

Example 1.13. Conclusions

The combined TIMING system consisting of the nanowell arrays and Applicants' automated confinement-constrained image analysis methods enable a far more comprehensive sampling of cellular events than is possible manually. The proposed algorithms dramatically improved the yield and accuracy of the automated analysis to a level at which the automatically generated cellular measurements can be utilized for biological studies directly, with little to no editing. Most segmentation and/or tracking errors (mostly due to persistently low fluorescence, or occlusion over extended durations) can be detected based on the confidence metric, and the corresponding nanowells can either be ignored or edited. Applicants' method is scalable to multi-terabyte TIMING datasets, and does not require elaborate initialization or careful parameter tuning.

Example 2. Integrated Single-cell Functional and Molecular Profiling of Dynamic T Cell Behavior In this Example, Applicants demonstrate the development and validation of a scalable single-cell methodology that integrates responses based upon microbead molecular biosensors for detecting protein secretion, automated time-lapse microscopy to monitor cell motility and cell-cell interactions, and microfluidic quantitative polymerase chain reaction (qPCR) for highly multiplexed transcriptional profiling. Analysis of 1,178 single tumor-reactive T cells interacting with 3,122 tumor target cells over a period of 5 hours revealed that the integrated behavior of polyfunctional T cells having both target killing and IFN-γ secretion was similar to that of serial killers without IFN-γ secretion. This suggested that cytolysis was the dominant determinant of the interaction behavior and that killing enables faster synapse termination.

In particular, Applicants have validated an integrated methodology that combines microbead-based molecular sensors for detecting cytokine secretion from single T cells concurrently with Timelapse Imaging In Nanowell Grids (TIMING) to monitor T-cell motility and cytotoxicity, without the need for encapsulation. TIMING was used to combine functional and molecular screening at the single-cell level, by performing multiplexed transcriptional profiling (96 genes) on CD19-specific CAR$^+$ T cells. Simultaneous quantification of the interaction between individual tumor-specific CD8$^+$ T cells and multiple target cells demonstrated that IFN-γ was the most common function elicited. However, CD8$^+$ T cells with killing ability, especially serial killing ability, required shorter durations of target cell conjugation in comparison to IFN-γ secreting mono-functional cells, indicating rapid synapse termination by T cells capable of killing versus cytokine secretion. The behavioral interaction of polyfunctional T cells exhibiting both killing and IFN-γ secretion was similar to that of serial killers without IFN-γ secretion, suggesting that killing was the dominant determinant of the interaction behavior.

Tracking the velocities of these cells by longitudinal time-lapse imaging revealed that these serial killer T cells (with or without IFN-γ secretion) may be identified based on their higher out-of-contact basal motility. Single-cell multiplexed transcriptional profiling of T cells identified only by their basal motility, confirmed that the motile cells expressed an activated phenotype with significantly increased amounts of perforin and other genes associated with chemotaxis.

Without being bound by theory, Applicants propose an integrated model of functional CD8$^+$ T-cell behavior based on these results. Moreover, these results establish Applicants' methodology as an investigational tool for combining multiplexed functional and molecular screening at the single-cell level, and suggest that motility might be a surrogate biomarker for identifying T cells with killer phenotype which has potential implications for immunotherapy.

Figure 11:
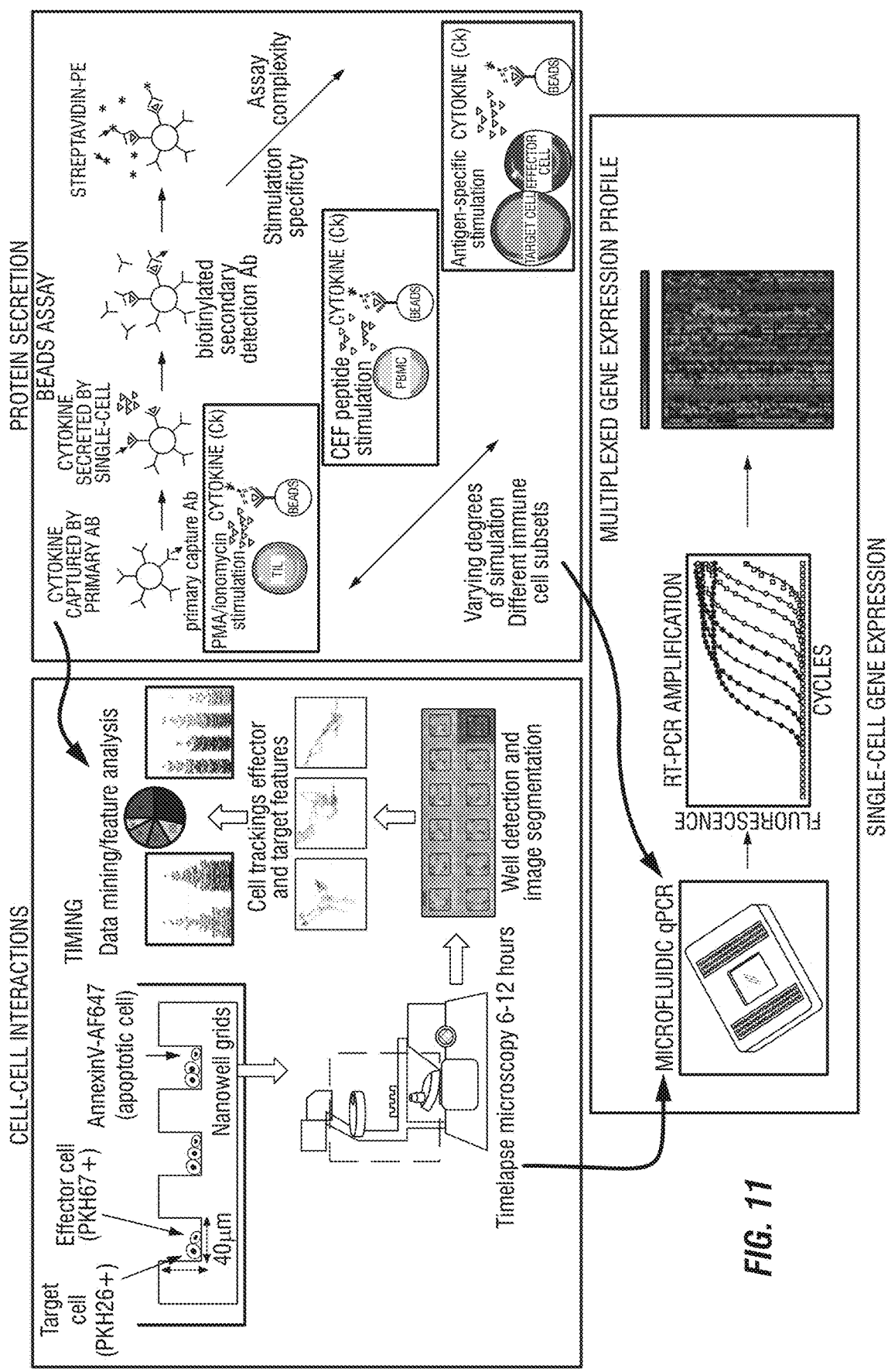
FIG. 11 provides a schematic of modules for high-throughput multiplexed functional and molecular profiling of single cells as achieved through combination of beads assay (protein secretion), TIMING (cell-cell interaction analytics) and microfluidic qPCR (single-cell gene expression).
Figure 12A:
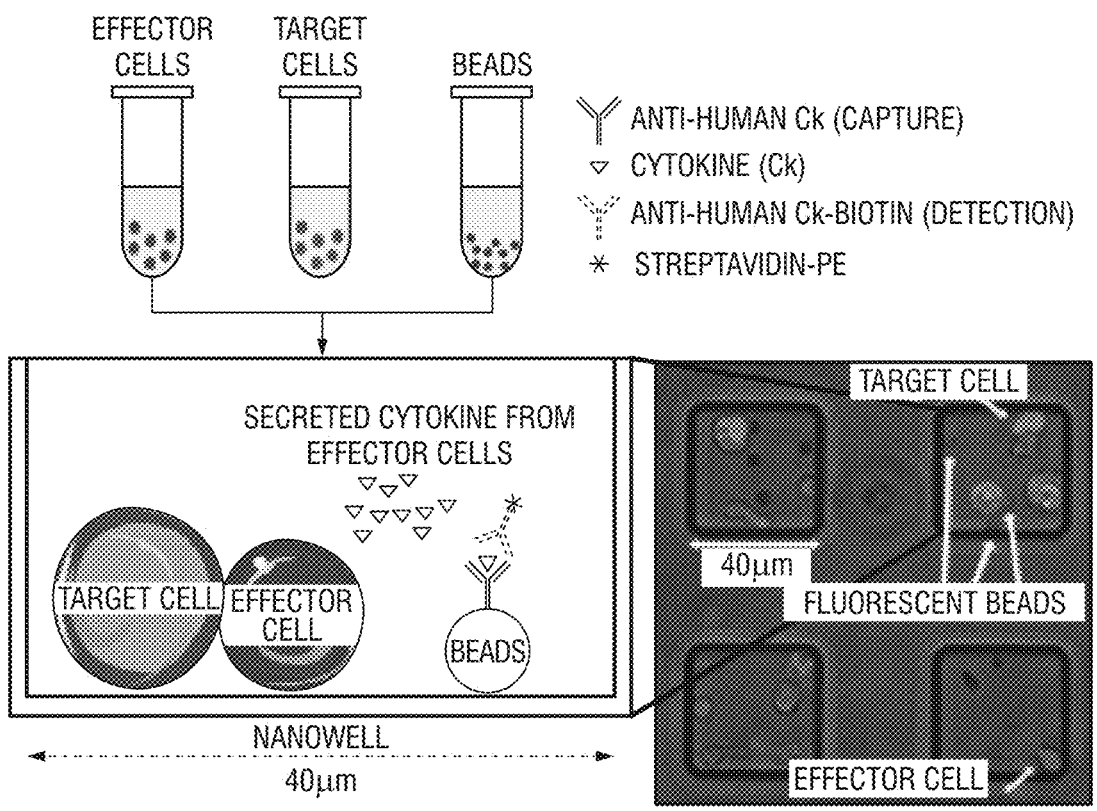
FIGS. 12A-12C illustrate that the frequency of IFNγ-secreting T cells enumerated by functionalized microbeads within nanowell arrays is correlated to the same responses determined using ELISpot.

Example 2.1. Design of an Integrated Platform for Simultaneous Profiling of Protein Secretion and Dynamic Cell-Cell Interactions In this Example, Applicants designed an integrated method that had the ability to add or remove independent modules in determining the polyfunctional nature of the T cells: cytokine secretion, dynamics of interaction with target cells, cytotoxicity, and molecular profiling (FIG. 11). Starting with Applicants' recently reported TIMING assay (Example 1), Applicants implemented functionalized beads as biosensors of the local microenvironment within individual nanowells to profile cytokine secretion (FIG. 12A), and microfluidic qPCR to facilitate gene expression profiling. This integrated approach could thus be used to profile cytokine secretion simultaneously with cytotoxicity, on one unified microscope platform.

Figure 12B:
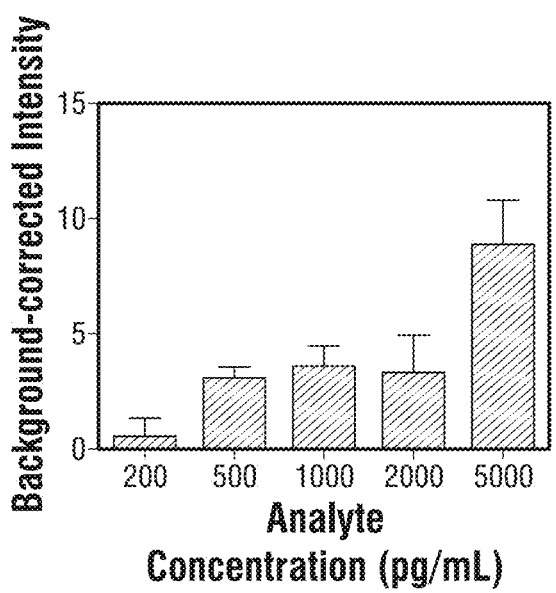

Example 2.2. Frequency of IFNγ-Secreting T Cells Enumerated by Functionalized Microbeads within Nanowell Arrays is Correlated to the Same Responses Determined Using ELISpot Applicants first tested the ability of functionalized microbeads to efficiently capture proteins secreted by single cells after incubation in individual nanowells by measuring the limit of detection (LoD) of functionalized beads at different concentrations of the analyte. Briefly, antibody-coated beads were incubated with varying concentrations of IFN-γ (0-5000 pg/mL) for a period of two hours at 37° C., loaded onto nanowell arrays, and subsequently detected with a fluorescently labeled secondary antibody. The background corrected mean fluorescent intensity (MFI) quantified across a minimum of 30 beads confirmed that IFN-γ was detectable at a concentration of 500 pg/mL (FIG. 12B).

Figure 12C:
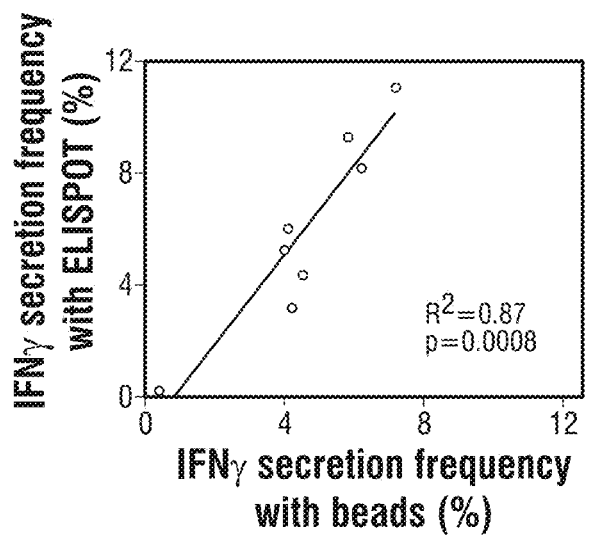

Next, the correlation between the nanowell encapsulated bead assay and ELISpot for quantifying frequencies of single T cells secreting IFN-γ upon activation was determined. To account for variations in stimulus and the diversity of T-cell populations, the frequency of IFN-γ secreting single T cells was enumerated under three sets of conditions: stimulation of peripheral blood mononuclear cells (PBMC) with HLA-class I peptide pools targeting common viral antigens; stimulation of PBMC with phorbol 12-myristate 13-acetate (PMA)/ionomycin; and stimulation of in vitro expanded, melanoma-specific TIL with PMA/ionomycin. An aliquot of $10^6$ cells were stimulated for a period of 3-5 hours and an aliquot of ~100,000 cells was loaded onto a nanowell array (84,672 nanowells, 125 pL each). A suspension of 200,000 beads pre-coated with anti-IFN-γ was subsequently loaded onto the nanowell array and incubated for a period of 2 hours at 37° C. By analyzing an average of 10,182±8,589 (mean±s.d.) single cells matched to one or more beads within the nanowells, the frequency of the activated T-cell IFN-γ response was determined to be 0.40-7.8%. The magnitude of these responses were similar to those recorded by ELISpot [0.20-11.2%], and results of both assays were significantly correlated ($r^2$=0.87, p-value=0.0008), demonstrating that beads can be efficiently utilized to capture cytokine secretion from single cells (FIG. 12C). In the absence of stimulation, the frequency of IFN-γ beads detected when incubated with T cells was <1 in 10,000 and this set the limit of detection of our assay at 0.01%.

Example 2.3. In Open-Well Systems, Fractional Occupancy of Analyte on Beads Increases as the Density of the Antibody Used to Capture Analyte Decreases As opposed to encapsulated systems, open-well configurations can be advantageous for the long term monitoring of cell fate and function since they allow continuous exchange of gases and nutrients. Furthermore, they avoid potential alterations of cellular behavior that can arise from the artificially high local concentrations of analytes commonly found in closed systems.

A disadvantage of open-well systems is that the analyte secreted by an individual cell within a nanowell is subjected to persistent diffusion into the bulk medium, potentially lowering the sensitivity. Therefore, Applicants sought to quantify the efficiency of analyte capture on beads by modeling a simplified open-well system using finite element simulations (FIG. 13A). The concentration of analyte in liquid media (C) can be described using Fick's $2^{nd}$ law, as illustrated in Equation 8.

$$\frac{\partial C}{\partial t} = D\nabla^2 C \qquad \text{Eq. 8}$$

In Equation 8, D represents the diffusion coefficient of the analyte. Since the walls of the PDMS can be assumed to be largely impermeable to proteins, the flux at these boundaries was set to zero. At a constant rate of analyte secretion from the cell (10 molecules/seconds), the mass balance of analyte concentration on bead surface ($C_s$) was determined by Equation 9.

$$\frac{\partial C_s}{\partial t} = D_s \nabla^2 C_s + k_{on} C(\theta_0 - C_s) - k_{off} C_s \qquad \text{Eq. 9}$$

In Equation 9, $D_s$ represents diffusivity of analyte on bead surface, $k_{on}$ and $k_{off}$ represent kinetic binding constants determined by strength of capture antibody—analyte interaction and $\theta_0$ represents number of capture antibodies available per unit surface area of the bead. The choice of parameter values (FIG. 13A) was based on commercially available antibody binding affinities, the known rates of cytokine secretion from T cells, and previously reported numerical simulations of closed systems. Initial concentrations of analyte in liquid media and bead surface were set to zero and increase in fractional occupancy $$\left(\oiint \frac{C_s}{\theta_0}\right)$$

of the bead with time as the cell secretes the analyte was modeled.

Upon validating the model with previously published data, Applicants sought to optimize two key tunable variables, the size of beads and the surface density of capture antibodies to maximize fractional occupancy (and therefore the fluorescent pixel intensity). The simulations demonstrated that the fractional occupancy of all three bead sizes increased linearly as a function of time (1-6 hours), and that regardless of the incubation time, the 3 μm bead had a 1.8-fold and 2.7-fold higher fractional occupancy in comparison to the 5 μm and 7 μm beads (FIG. 13B).

When the bead diameter was held constant (3 μm), but the binding site density was varied across three orders of magnitude, the beads with the lowest binding site density ($10^{-9}$ mol/m$^2$) had the highest fractional occupancy (FIG. 13C). These results show that increased fractional occupancy is observed when the total number of binding sites is decreased by either decreasing the bead size, or binding site density, and are consistent with ambient analyte theory that predicts that higher sensitivity can be achieved by lowering the number of antibodies used to capture the analyte.

Furthermore, for a nanomolar binder at low fractional occupancy (neglecting desorption), the simulations predicted that the kinetics of analyte capture is diffusion limited (FIG. 13A), in agreement with previous studies on antibody microspots, closed-well systems, and two-compartment mathematical models. It should however be noted that, unlike microspot assays, the present system does not conform to ambient analyte conditions as depletion of analyte by capture on the bead surface is not negligible in comparison to total analyte available.

Example 2.4. Simultaneous Quantification of Cytotoxicity and IFN-γ Secretion in Tumor-Specific CD8$^+$ CAR$^+$ T Cells Using TIMING Since the end-point experiments confirmed the ability to detect IFN-γ from single T cells upon activation, and the modeling suggested that the beads should work well in an open-well system, Applicants integrated the beads into the TIMING workflow to enable measurement of effector target interactions while also capturing any secreted IFN-γ protein, at single-cell resolution.

Figure 14:
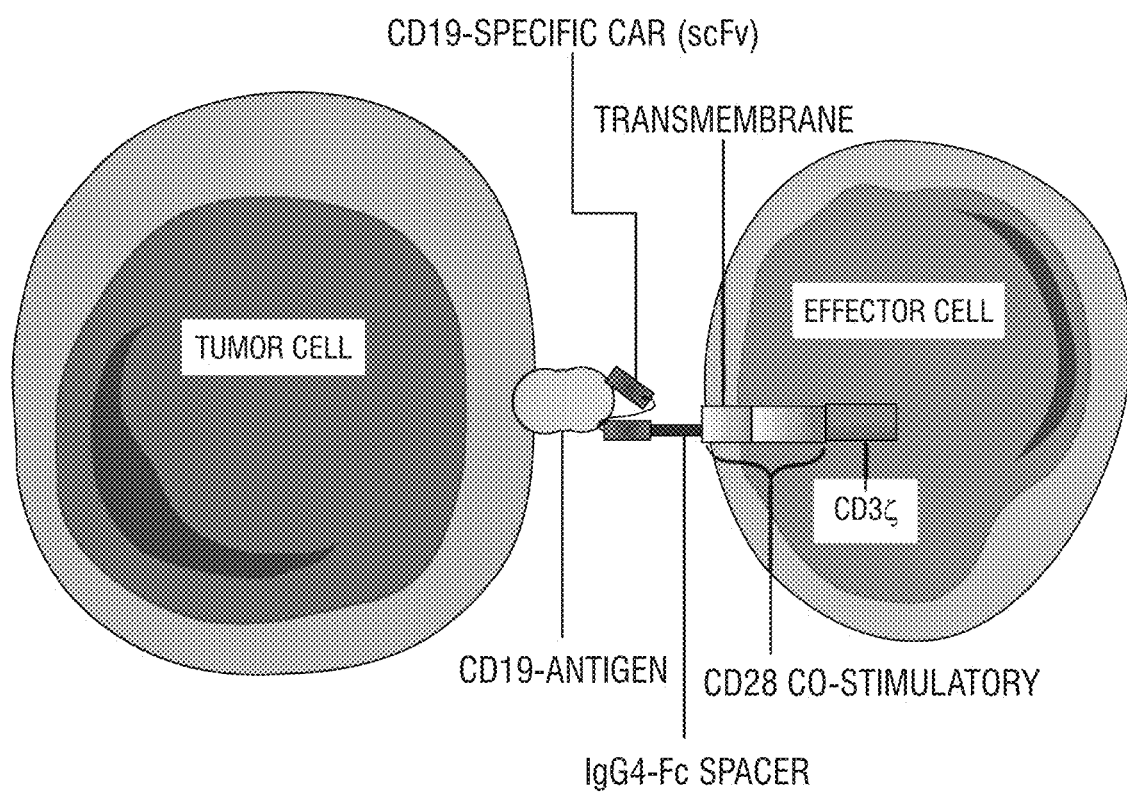
FIG. 14 provides a schematic of an effector cell (blue) that recognizes a CD19 antigen on a tumor cell (red) with a second generation chimeric antigen receptor (CAR) that activates through CD3ζ and CD28 endodomains.

Applicants chose to interrogate the polyfunctionality of tumor-specific individual CD8$^+$ T cells with regards to cytokine secretion and cytotoxicity. Genetically modified and propagated T cells were generated from the peripheral blood mononuclear cells (PBMC) of a healthy donor to enforce expression of a second generation CD19-specific CAR (designated CD19RCD28) that activates T cells via a chimeric CD3 and CD28 endodomain (FIG. 14). Subsequent to numeric expansion on activating and propagating cells (AaPC) for a period of four weeks, the CAR$^+$ T cells were predominantly CD8+(>99%, FIG. 15A). Phenotypic characterization of the CD8$^+$CAR$^+$ T cells demonstrated that the dominant subset of T cells were naïve like (CD45RA$^+$ CD62L$^+$, 60.7%, FIG. 15B). The ability of these T cells to specifically secrete IFN-γ upon interaction with cells presenting CD19 antigen was confirmed by co-incubating with both NALM-6 tumor cells (CD19 positive) and EL4 cells (CD19 negative, FIG. 15C).

Figure 16A:
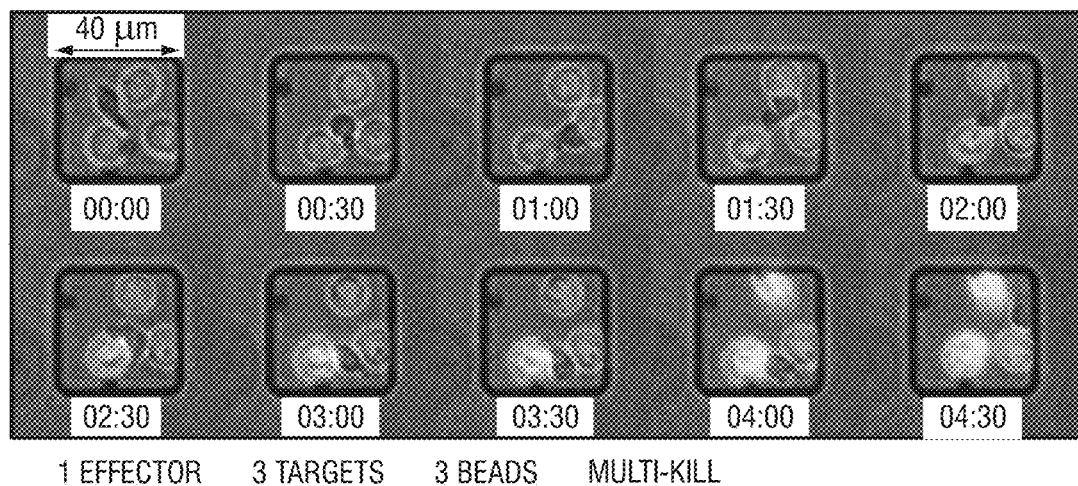
FIGS. 16A-16B provide data relating to combining TIMING with bead based assays to interrogate multi-functionality of CAR$^+$ T cells at the single-cell level.
Figure 16B:
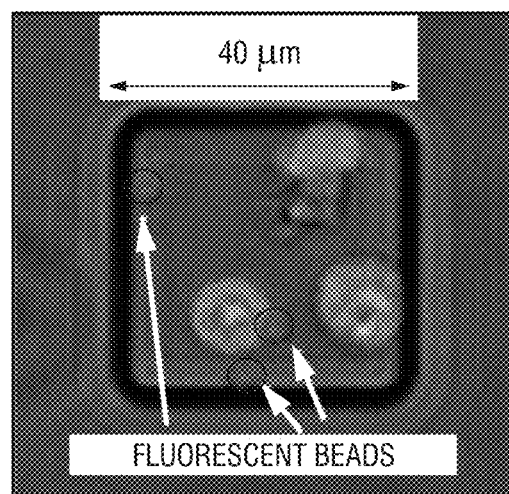

CAR$^+$ T cells as effectors, NALM-6 tumor cells as targets, and pre-functionalized beads coated with IFN-γ capture antibody as cytokine sensors, were loaded sequentially onto a nanowell grid array. Effector-mediated tumor lysis was detected using Annexin V staining and every individual nanowell (14,400 wells, 64 pL each) was profiled for a period of 5 hours (FIG. 16A), and cytokine secretion was quantified by the formation of immune-sandwiches on beads (FIG. 16B).

Applicants modified previously-reported image analysis algorithms to not only enable the automated segmentation and tracking of cells, but to now facilitate the identification of fluorescence intensity on the beads to report on the secretion of IFN-γ. After a simple diameter-based gating, Applicants identified 1,178 wells of interest containing a single T cell, 2 to 5 tumor cells, and one or more beads. Nanowells containing multiple tumor cells were specifically chosen to allow observation of individual T cells participating in multiple killing events. Within this subset, since every T cell was incubated with multiple tumor cells, three separate functional definitions were employed: serial killer cells that killed at least two tumor cells, mono-killer cells that killed exactly one tumor cell, and IFN-γ secreting cells.

Figure 17A:
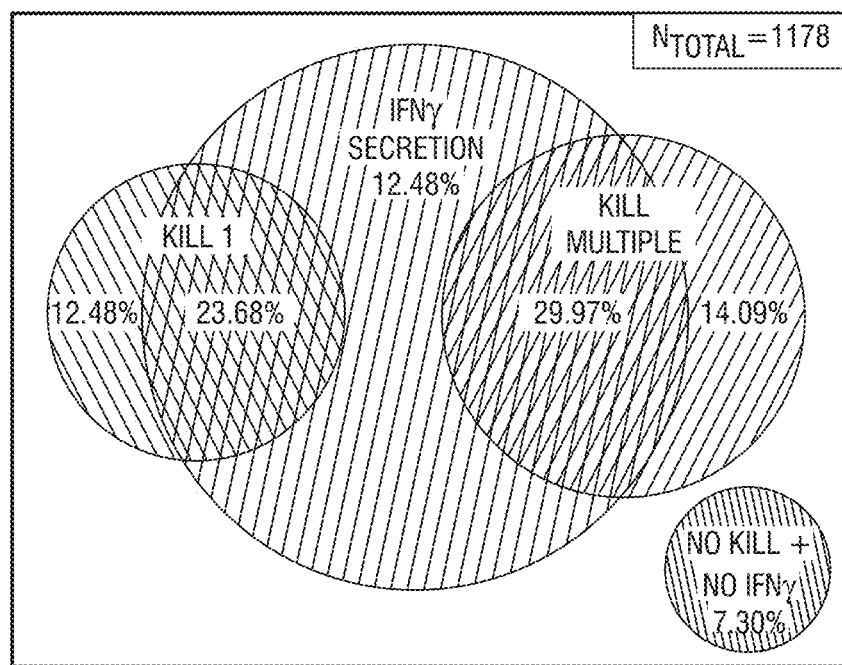
FIGS. 17A-17E provide quantitative comparisons of the intrinsic and interaction behaviors of monofunctional and polyfunctional CAR$^+$ T cells.

Subsequent to conjugation to one or more tumor cells, IFN-γ secretion was the most commonly observed function recorded in single T cells (64.2%, FIG. 17A). Polyfunctional cells defined as either CAR$^+$ T cells that killed multiple tumor cells (44.1%) or cells that were able to kill at least one tumor cell and simultaneously secrete IFN-γ was only slightly lower (53.6%, FIG. 17A). The subset of cells capable of both multi-killing and IFN-γ secretion comprised 30% of the population.

Figure 17B:
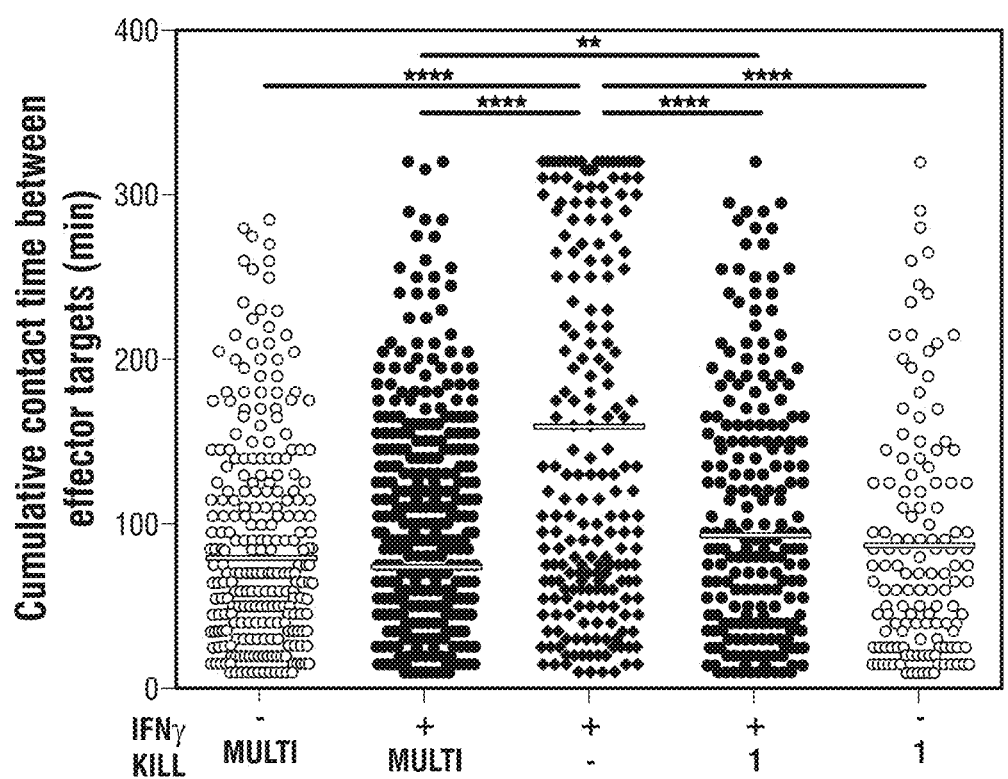

Example 2.5. Killer CAR$^+$ T Cells Detach Faster from Target Cells in Comparison to IFN-γ Secreting Cells Since TIMING assays, as described above, have the ability to monitor both conjugate formation and functional readouts, and since the CD8$^+$ T cells uniformly expressed the high-affinity immunoreceptor, Applicants quantified the threshold for activation by analyzing the total duration of conjugation prior to functional readout. T cells that only secreted IFN-γ (monofunctional), exhibited the longest conjugation durations of all functional T cells (159±8 min). This duration was significantly longer than cells that killed either only one tumor cell with (94±5 minutes) or without IFN-γ (89±6 minutes) secretion, or multiple tumor cells with (74±2 minutes) or without IFN-γ (79±4 minutes) (FIG. 17B).

Figure 18:
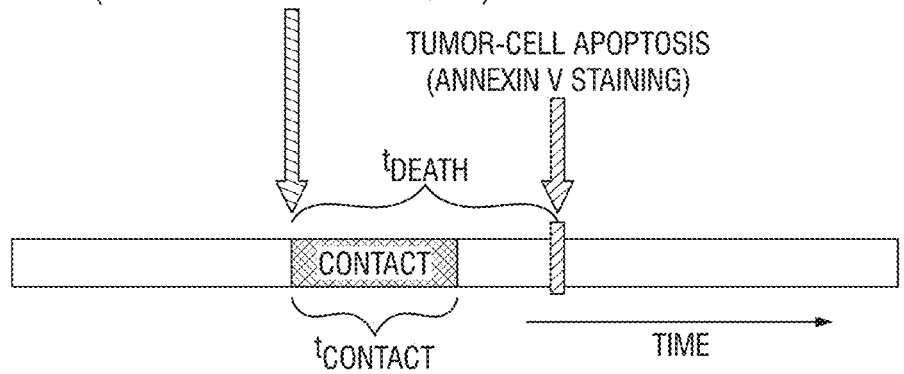
FIG. 18 provides a schematic depicting the effector parameters used to describe their interaction with single NALM-6 tumor cells. The red bar indicates periods of conjugation, the blue arrow indicates timepoint at which conjugation was first observed, and the green line indicates time to target death since first conjugation.

These results suggest that the duration of conjugation between T cells and tumor cells that results in killing has a lower threshold for functional activation in comparison to IFN-γ (monofunction). To define the kinetics of the interaction between individual T cells and tumor cells that lead to subsequent killing, two interaction parameters, $t_{Contact}$, cumulative duration of conjugation between first contact to target death; and $t_{Death}$, time between first contact and target apoptosis, were computed (FIG. 18). The $t_{Contact}$ parameter reflects the duration of stable conjugation and $t_{Death}$ reflects the kinetics of target apoptosis.

Figure 19A:
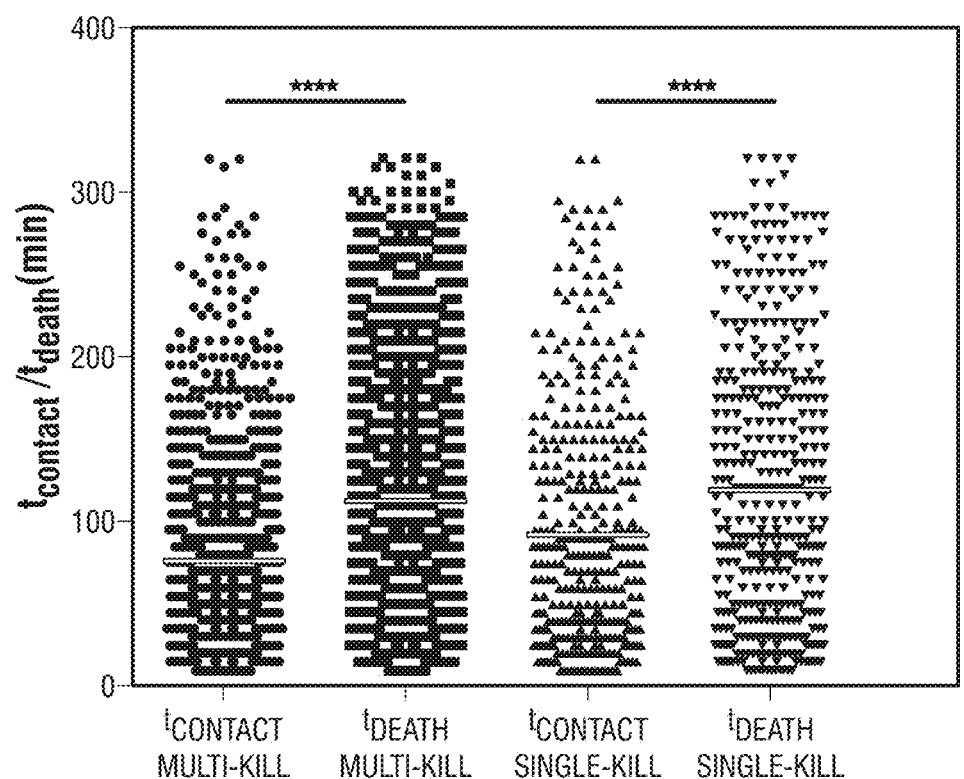
FIGS. 19A-19B provide additional data relating to the motility of T cells.

For both mono-killers and serial killers, $t_{Contact}$ was significantly lower than $t_{Death}$ demonstrating that T cell detachment preceded tumor-cell Annexin V staining (FIG. 19A). Second, the total duration of conjugation of all killer T cells (81±2 minutes) was lower than non-killer T cells (154±6 minutes) (p-value<0.0001, FIG. 19B).

The aforementioned results suggest that, at the single-cell level, the relationship between exact time at which single T cells terminate the synapse and time of target cell apoptosis is heterogeneous. In aggregate, killer T cells terminated the synapse upon initiation of killing but prior to appearance of the apoptosis markers on tumor cells.

No significant differences were observed in the $t_{Contact}$ when comparing serial killer CAR$^+$ T cells, with or without IFN-γ secretion (FIG. 17C), suggesting that killing is the dominant behavior in determining duration of conjugation. The frequency of individual serial killer T cells that either secreted IFN-γ (353/1178=30%) or did not secrete IFN γ (166/1178=14%) was not significantly different from T cells that only secreted IFN-γ (147/1178=12%) (Fisher 2×2 test, p-value=0.2) confirming that shorter duration of conjugation still provided sufficient activation for cytokine secretion.

Next, Applicants compared mono-killers and serial killers, with and without concomitant IFN-γ secretion, measured by $t_{Contact}$ and $t_{Death}$. In order to facilitate direct comparisons, each of the targets killed by the serial killer T cells was sorted based on the order in which they made contact with the effector cell. In the absence of IFN-γ secretion, serial killer effector cells showed no significant differences in either $t_{Contact}$ (69±5 minutes) or $t_{Death}$ (94±6 minutes) in killing of the first target encountered, in comparison to mono-killers ($t_{Contact}$: 89±6 minutes, $t_{Death}$: 117±7 minutes, FIGS. 17C-17D).

Figure 17C:
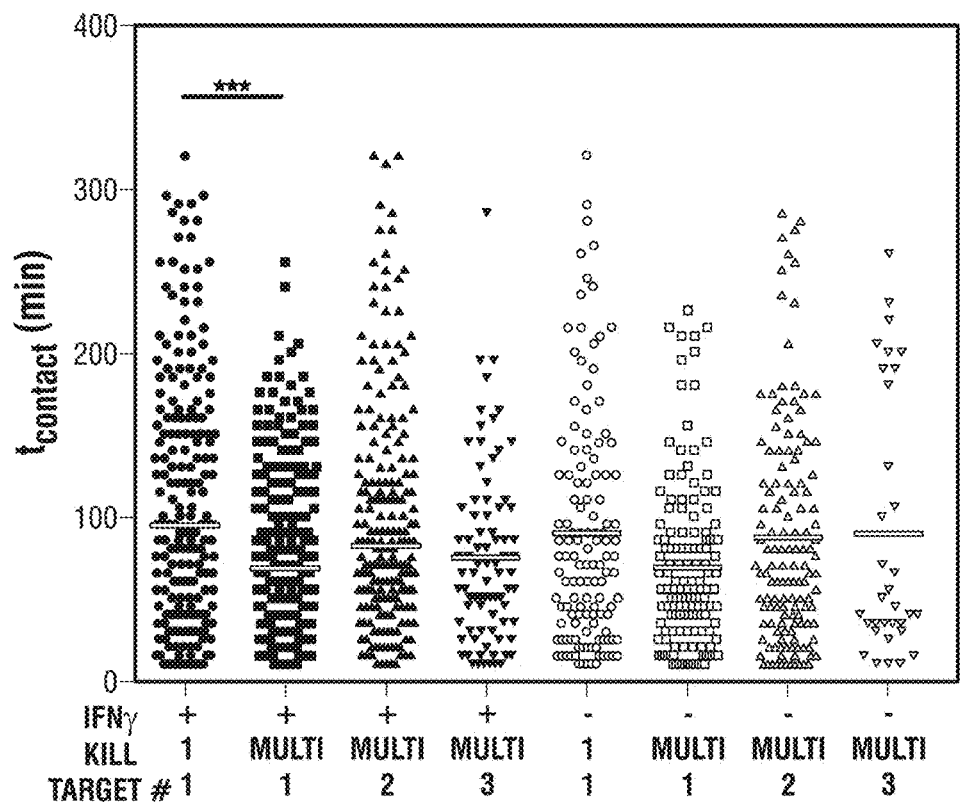
Figure 17D:
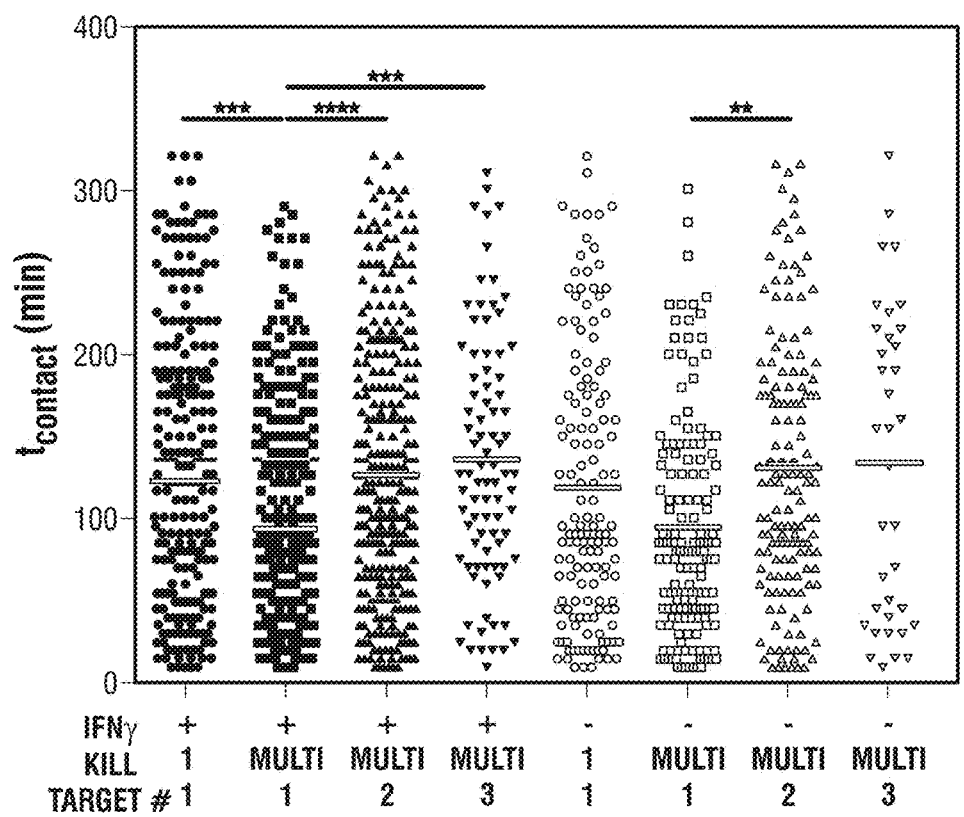

In contrast, serial killer effector cells that also secreted IFN-γ showed a decreased duration of conjugation ($t_{Contact}$: 68±3 minutes) and an increased efficiency of killing ($t_{Death}$: 93±4 minutes) in killing of the first target encountered, in comparison to mono-killers that secreted IFN-γ ($t_{Contact}$: 94±5 min, $t_{Death}$: 121±5 min). This difference was only observed for the first target since subsequent targets killed by the serial killers did not show significant differences in either $t_{Contact}$ or $t_{Death}$ (FIGS. 17C-17D). In summary, these results showed that polyfunctional T cells that are able to participate in both serial killing and secrete IFN-γ, have a lower threshold for the duration of activation prior to a functional response.

Example 2.6. Basal Motility when not in Target Cell Contact May be Used to Identify Serial Killer Polyfunctional CAR$^+$ T Cells Next, Applicants investigated if intrinsic T-cell behavioral parameters like basal motility ($d_{well}$: average mean displacement within the nanowell over 5 minute periods) prior to tumor cell conjugation, might offer insights into their functional capacity subsequent to tumor cell conjugation. Individual CAR$^+$ T cells that failed to display any functionality (killing/IFN-γ secretion) upon tumor cell conjugation also had the least out-of-contact motility ($d_{well}$: 1.3±0.1 μm) of the T cells subgroups profiled (FIG. 17E).

Figure 17E:
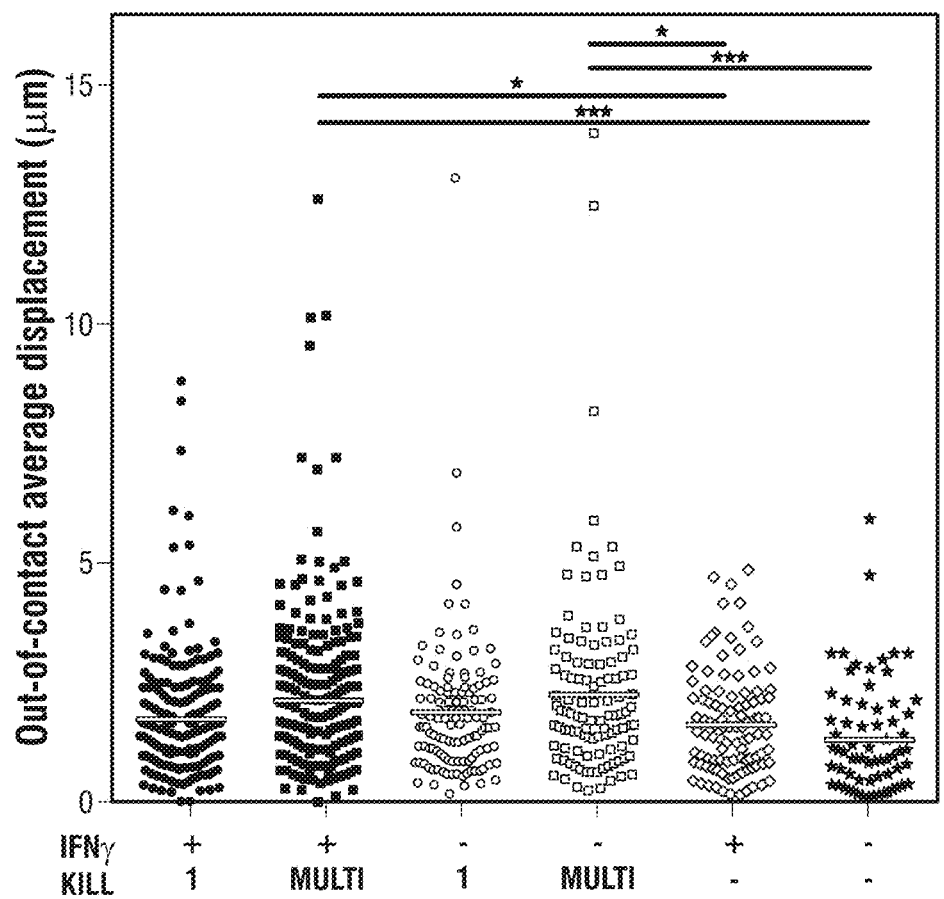

In contrast, effector cells that were able to kill multiple tumor cells and secrete IFN-γ exhibited a significantly higher out-of-contact motility ($d_{well}$: 2.2±0.1 μm) compared to those that only secreted IFN-γ without killing ($d_{well}$: 1.6±0.1 μm), and the aforementioned non-functional T cells (p-value=0.043 and 0.002 respectively) (FIG. 17E).

Figure 20:
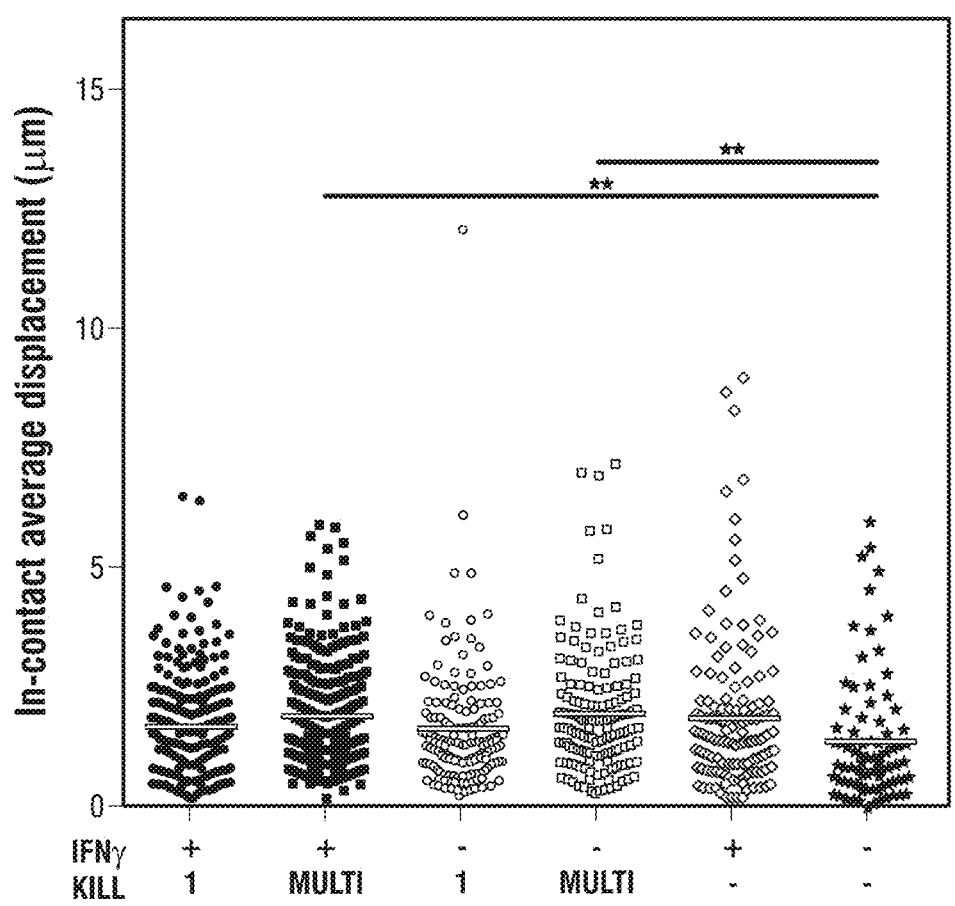
FIG. 20 shows average displacements of effector cells during conjugation of effector with target cells per frame interval (5 minutes) at an E:T ratio of 1:2-5. Effector cells that kill multiple targets irrespective of whether they secrete IFNγ are significantly more motile compared to non-functional effectors that do not kill or secrete IFNγ. Each marker represents single-cell and red bar represents the mean of the population. P-values were determined using one-way ANOVA.

This observation of higher motility was also recorded with serial killer effector cells that did not secrete IFN-γ ($d_{Well}$: 2.4±0.2 μm) in comparison with effector cells that only secreted IFN-γ or non-functional cells (p-value=0.007 and 0.0002 respectively). Remarkably, these observations, however were not true for effector cells that were only capable of killing one tumor cell, as their average displacement were not significantly higher compared to those that did not kill, suggesting that serial killers perhaps benefit from the high motility allowing for rapid discovery of targets within the local micro-environment. These observations were only true for the out-of-contact motility and not surprisingly, regardless of the function elicited, all functional effector cells showed no differences in motility during conjugation with the tumor cell (FIG. 20).

Figure 22A:
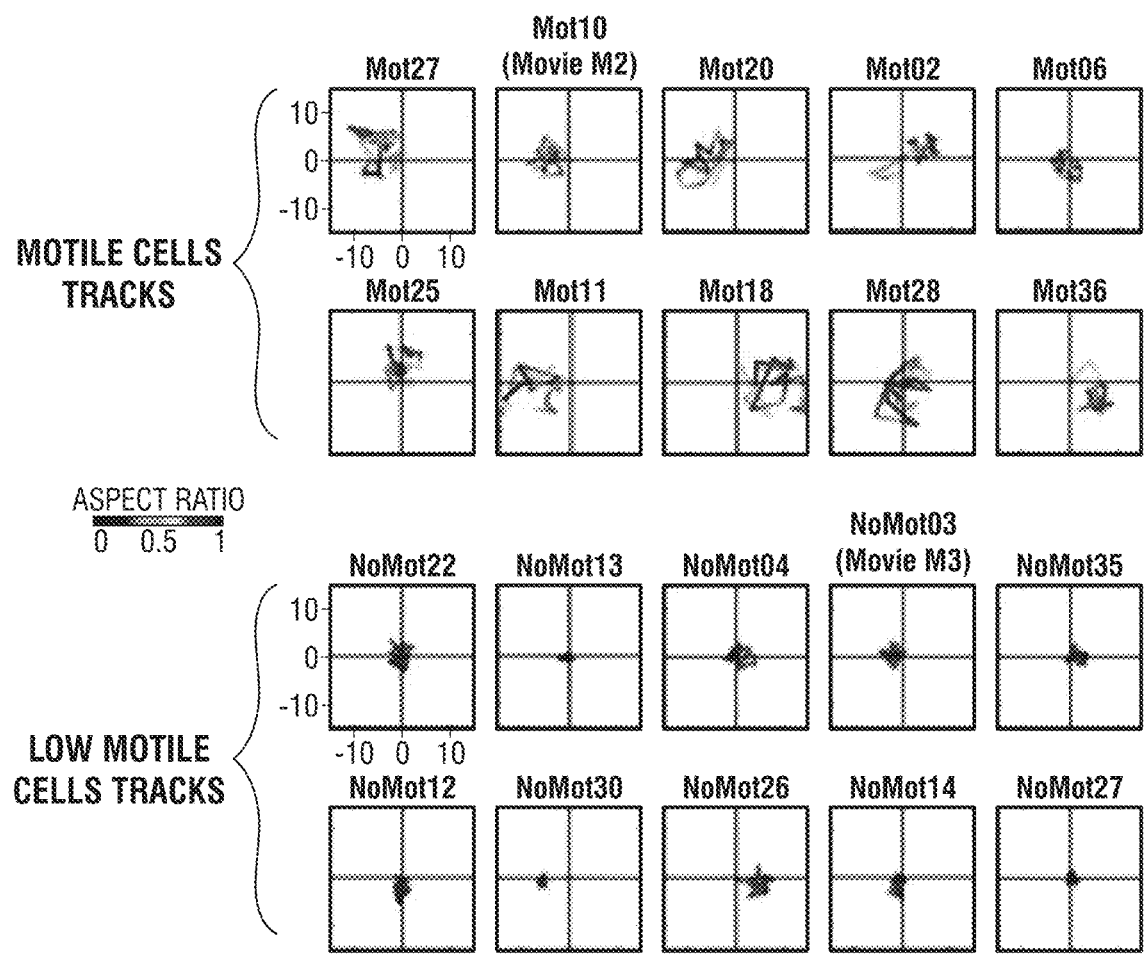
FIGS. 22A-22F provide data indicating that motile CD8$^+$ CAR$^+$ T cells display an activated transcriptional profile.
Figure 22B:
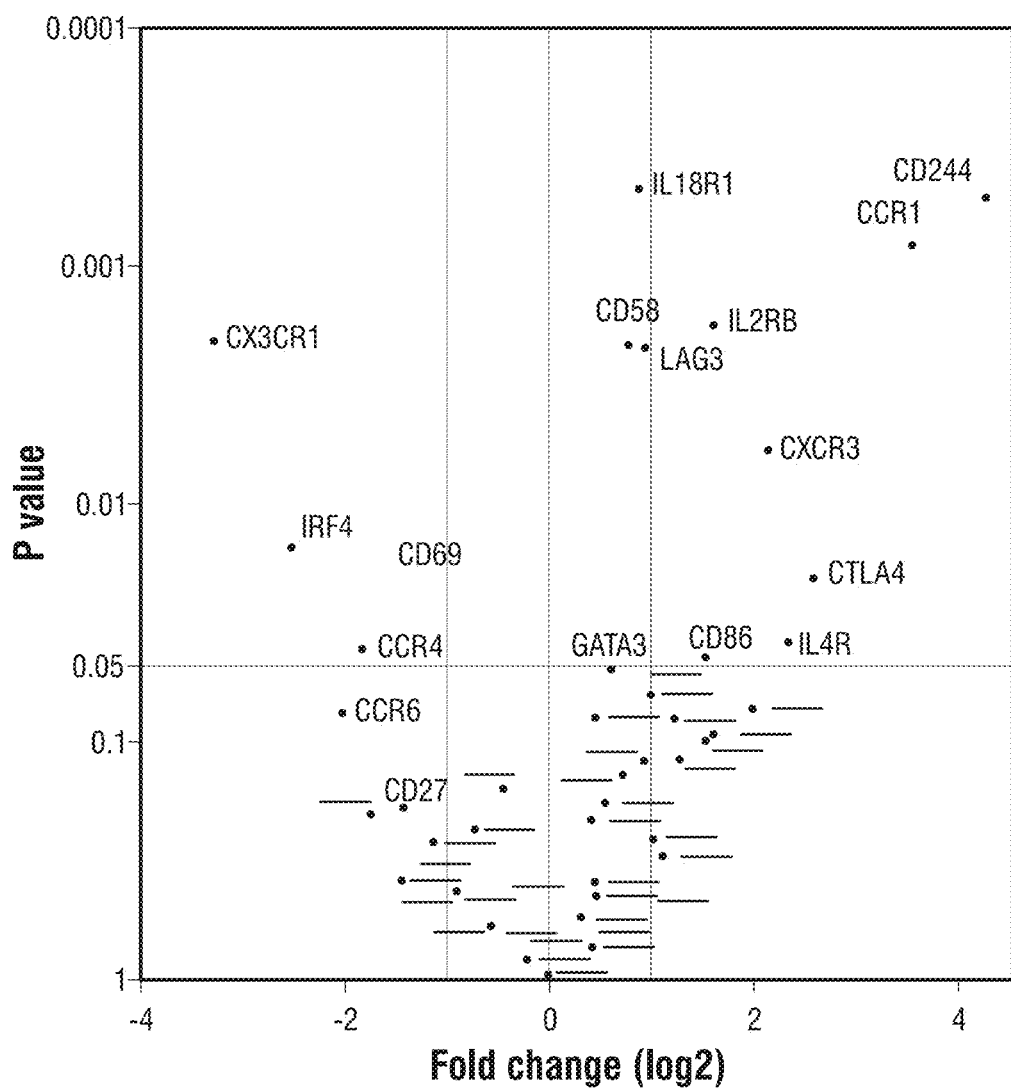
Figure 22C:
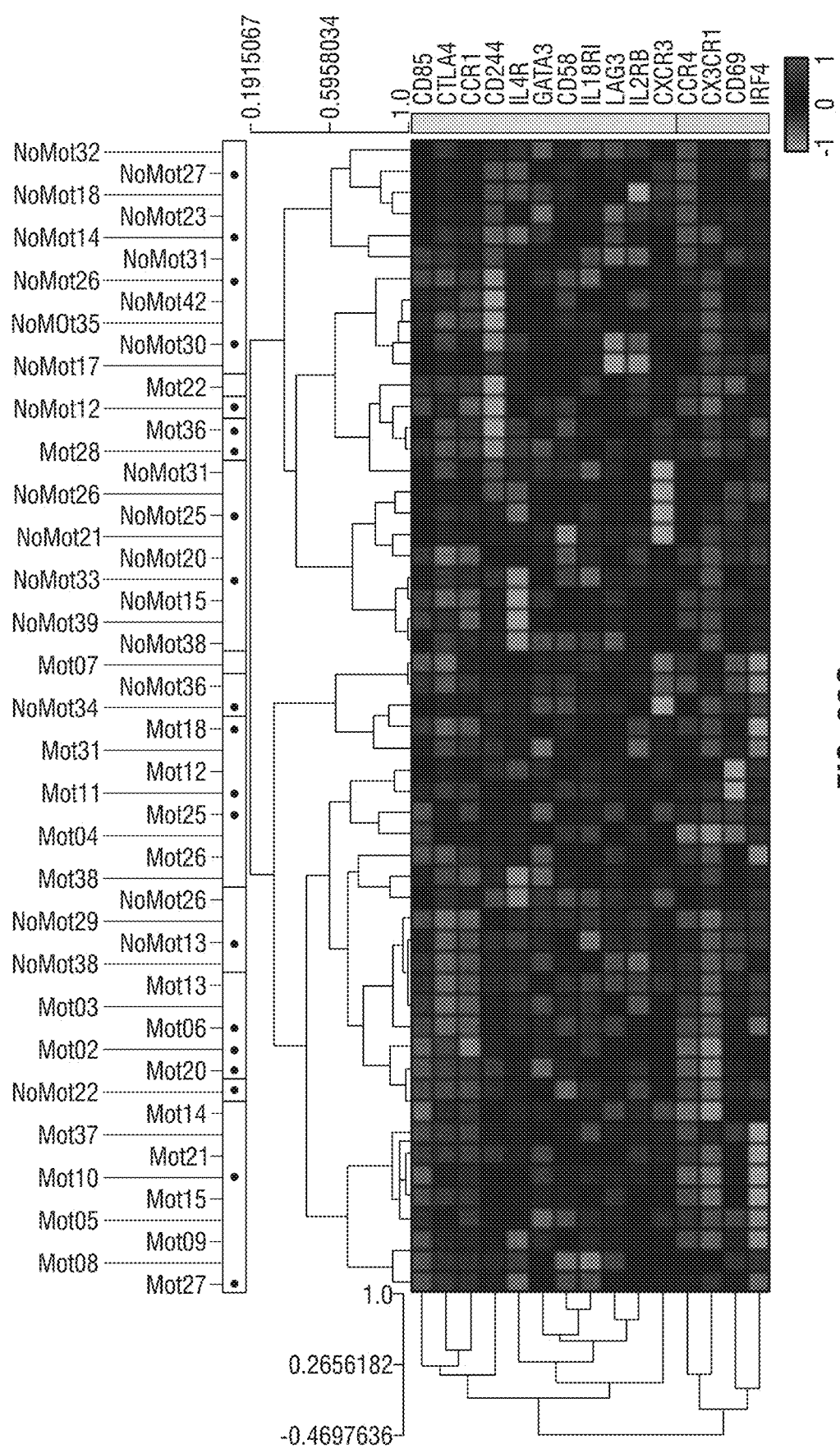
Figure 23:
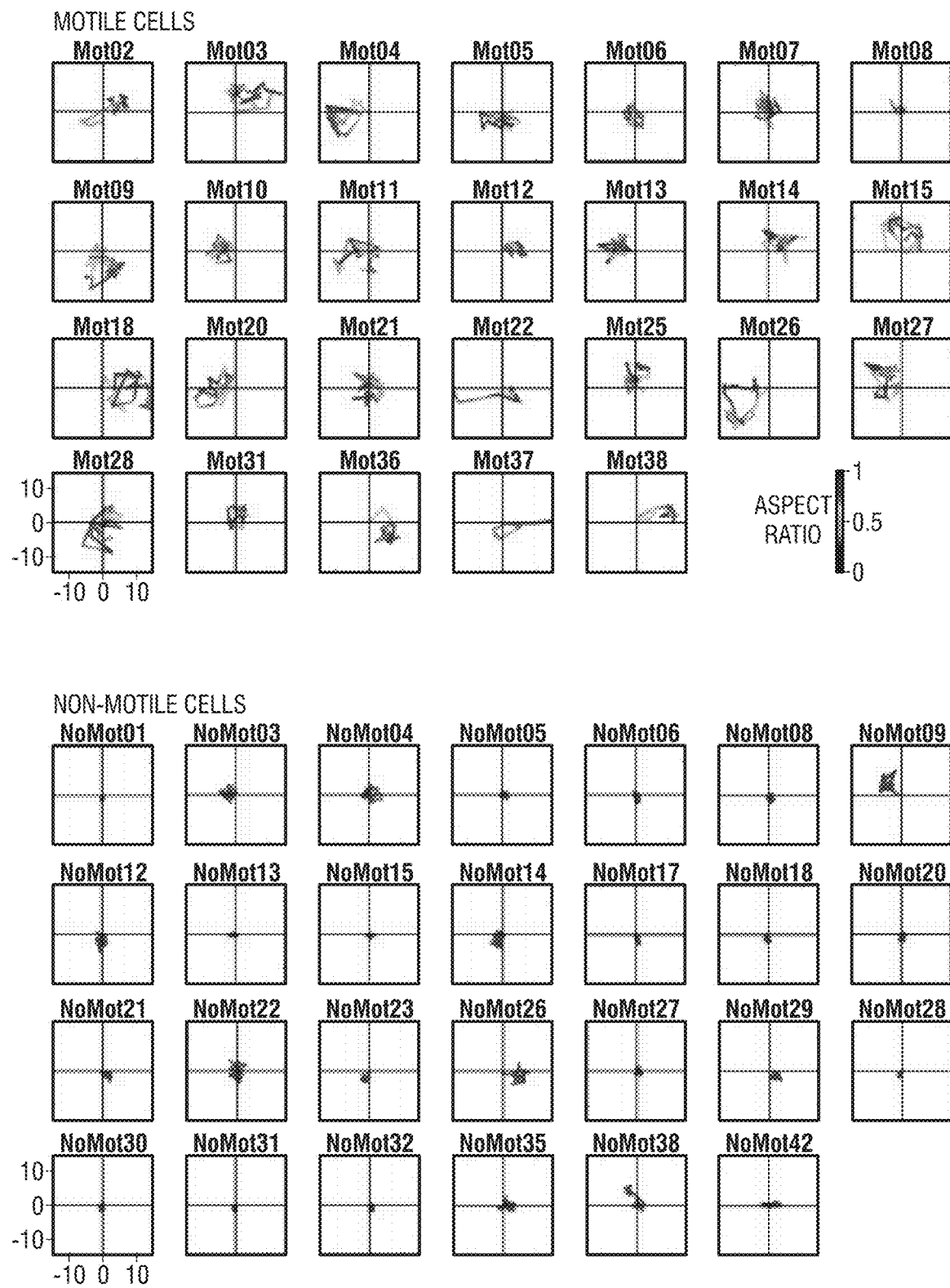
FIG. 23 shows position tracks of high and low motility CD8$^+$ T cells during 3 hours of TIMING experiments. Shown are larger scanning area and lower circularity of high motility cells as compared to low motility cells. Cell positions were tracked by automated image analysis and graphed using the Matlab surface function. X, Y coordinates are listed in microns relative to cell initial position. Color map represents aspect ratio (circularity) values. Red denotes circular cells and increasing shades of green and blue indicate elongated cells.

Example 2.7. Transcriptional Profiling of Motile CAR$^+$ T Cells Reveals an Activated Phenotype Since the TIMING results indicated that the basal motility may be able to identify polyfunctional killer cells, Applicants next sought to define the underlying molecular profile of motile CD8$^+$ T cells. Accordingly, a set of 90 genes relevant to T-cell function were identified, and multiplexed, single cell, RT-qPCR was performed (FIGS. 21A-1-21E). In order to study the basal motility of these CD8+ T cells, a TIMING experiment was set up to track individual live T cells without the influence of the tumor cells. Single cells were picked up based on their motility profile: "motile or high motility" ($d_{well}$: 2.6±0.8 µm, n=41) or "non-motile or low motility" ($d_{well}$: 0.8±0.4 µm n=43) and their transcriptional profile determined (FIGS. 6A and 23). After microfluidic qPCR, and subsequent to filtering, t-test comparisons of 62 genes between the motile and non-motile groups showed that 15 genes had significantly altered level of expression (p<0.05) and more than a 1.5 fold change: CD244, CD58, LAG3, CTLA4, CD86 (activation markers); CCR1, CXCR3, IL18R1, IL2RB, IL4R (chemokine and cytokine receptors), and GATA3 (transcription factor) were upregulated, while CX3CR1, CCR4 (chemokine receptors); CD69 (activation marker), and IRF4 (transcription factor) and were down-regulated (FIG. 22B). Unsupervised hierarchical clustering was performed with gene- and cell-normalized data of these 15 genes, and the sample clustering achieved a classification according to the known categories (motile vs. non motile) with 83% accuracy (FIG. 22C).

Figure 22D:
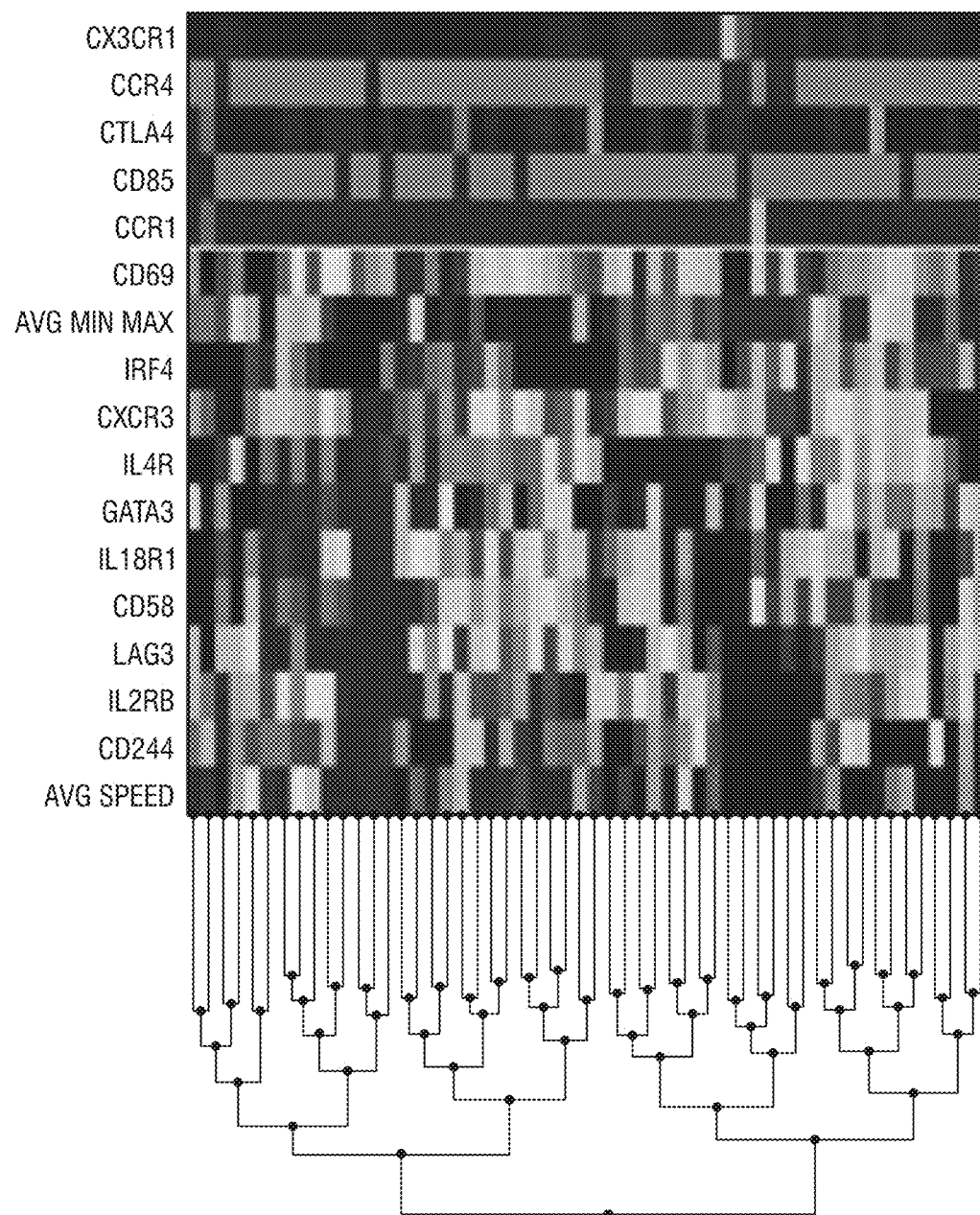
Figure 24:
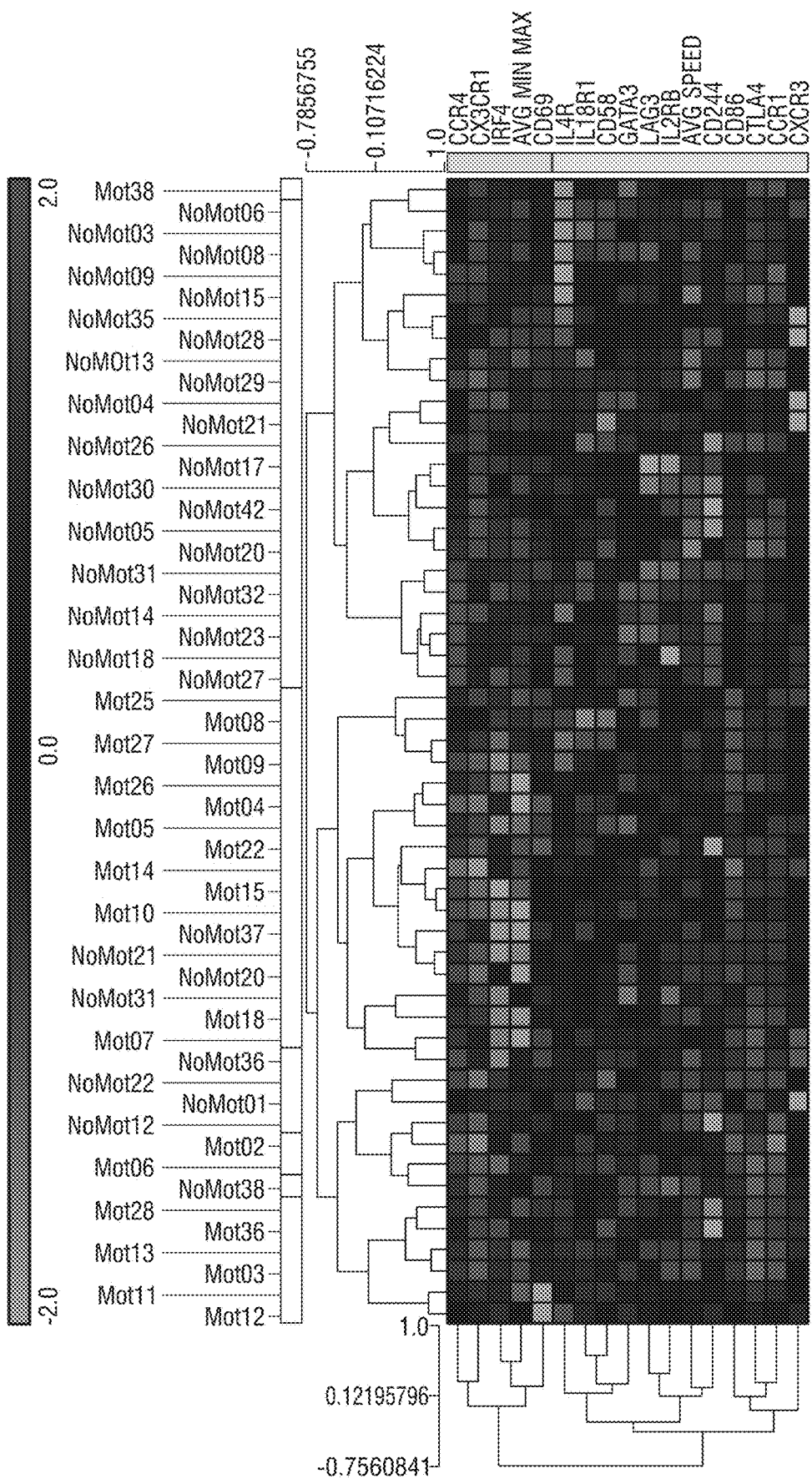
FIG. 24 provides unsupervised hierarchical bi-clustering represented as heatmap of samples and of the genes along with the average speed and average aspect ratio (Min/Max) of the individual T cells. Only genes and features identified as having a significant difference (p-value<0.05) and net fold-change of >1.5 are used in the clustering. Compared to clustering without speed and shape features (FIG. 22C), the samples and the genes are clustered in a similar manner when using these features: similar accuracy in sample segregation and gene ordering.

When Applicants repeated the agglomerative clustering with the motility-specific features $d_{well}$ and aspect ratio (AR, ratio of minor/major axes) along the genes, the cluster tree structure was largely unaltered and $d_{well}$ was closely clustered with expression of CD244 and IL2RB, while AR was highly correlated to IRF4 (FIG. 24). While the comparisons of transcriptional profiles with Student's t-test and hierarchical clustering enabled Applicants to infer differences between the motile and non-motile groups, Applicants hypothesized that the heterogeneity of this cell population could be also described as a progression of cells characterized by gradual changes in gene expression from cell to cell. The set of fifteen differentially expressed genes and the two motility parameters, $d_{well}$ and AR, were used as the base set for the subspace trend discovery tool STrenD that identified ten genes considered to support the progression (FIG. 22D). With the selected genes and features, STrenD outputs a tree structure representing the progression of cells identified by the input features (FIG. 22E).

Figure 22E:
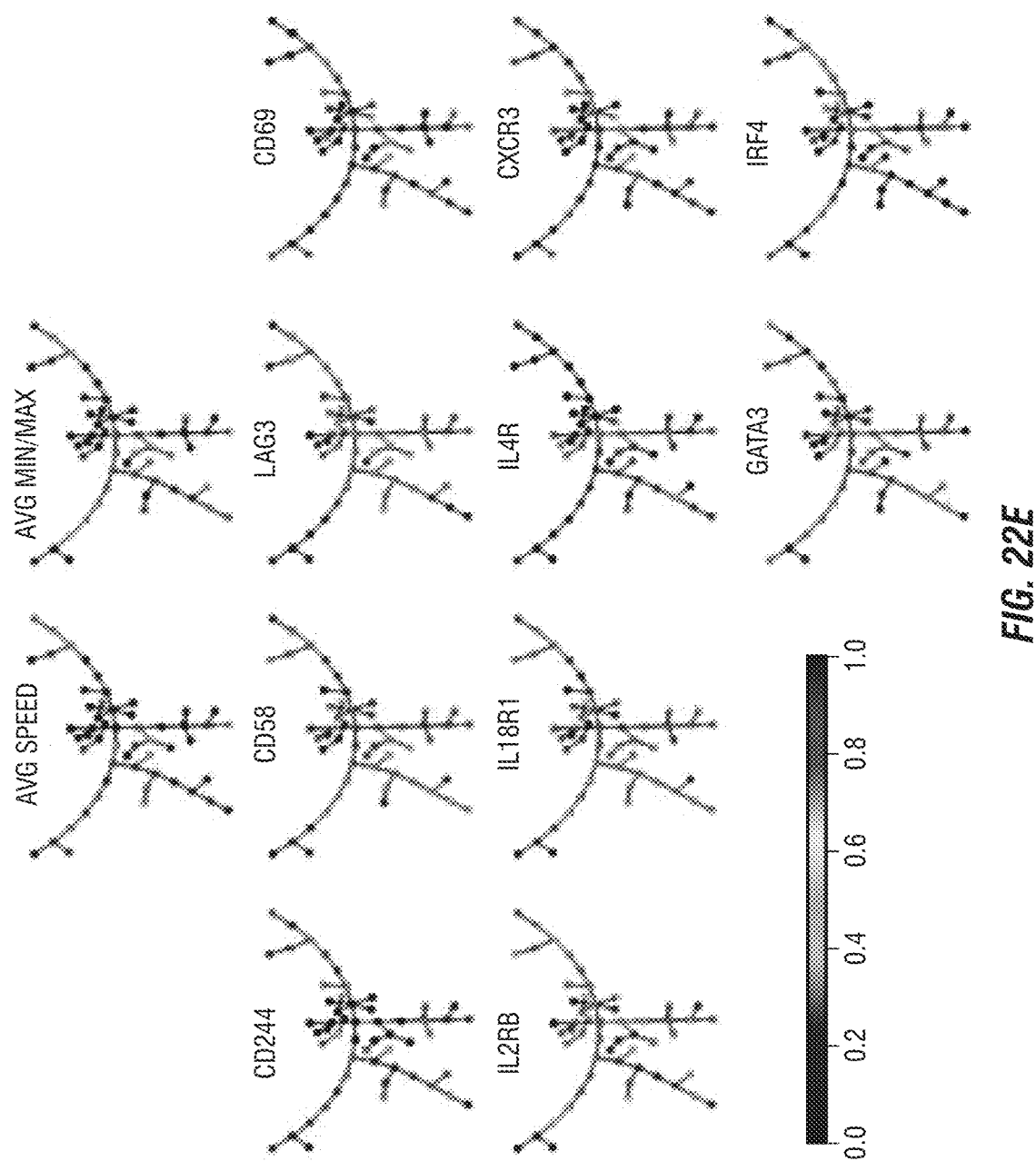

By visualizing and coloring the tree using TreeVis, Applicants can clearly identify non motile cells clustered together at the center-right side of the tree, while motile cells split out of this pool into two branches, one with high expression of IL2RB, IL18R1, CD58, LAG3 and GATA3 (FIG. 22E, upper left branch), one with low expression of these and with very low expression of IRF4, but still with high motility and high CD244 expression (FIG. 22E, lower left branch).

Figure 22F:
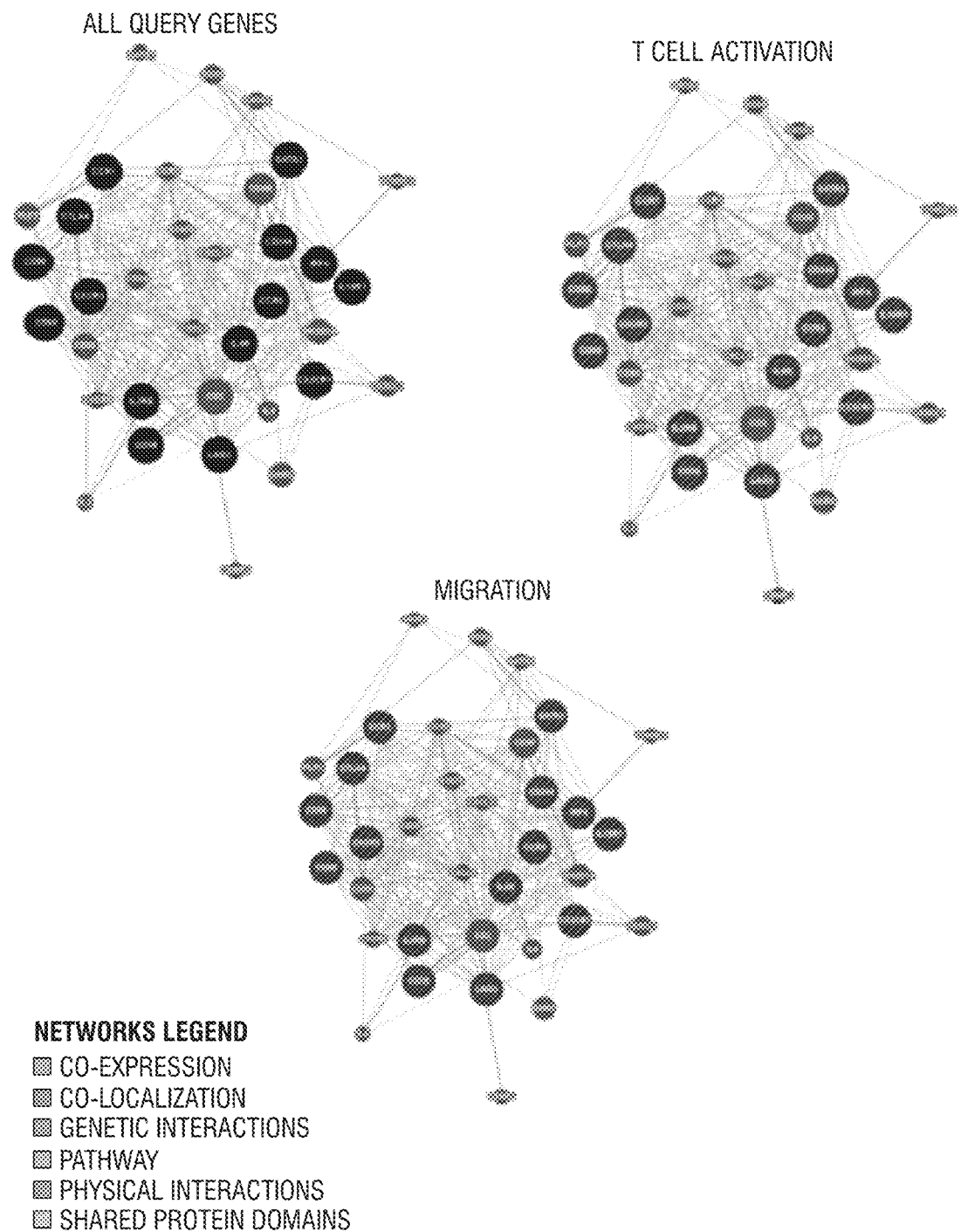

Consistent with the observations outlined here, network analysis using GeneMania confirmed that the major pathways associated with the identified transcripts were related to positive T-cell activation and lymphocyte migration (FIG. 22F). Lastly, since one of the major mechanisms of immediate cytotoxicity mediated by CD8+ T cells is through the granzyme B/Perforin pathway, and since Applicants' TIMING results indicated that polyfunctional serial killer CD8+ T cells had a higher basal motility, Applicants quantified the differences in expression of these specific transcripts within motile and non-motile cells. Although GZMB was not significantly differentially expressed, PRF1 transcripts were detected at significantly higher levels in motile cells (p-value=0.03, FIG. 25).

Example 2.8. Discussion

Applicants have demonstrated in this Example an integrated and modular high-throughput analytical pipeline for combined functional and molecular profiling of T-cell behaviors. This single-cell assay provides an integrated method which not only tracks the key functional attributes of T cells including motility, cytotoxicity, and cytokine secretion directly, but also serves as a front-end screen for identifying functional attributes that can be interrogated at the molecular level using multiplexed transcriptional profiling. Although Applicants have demonstrated the application of this method in the context of T-cell behaviors, the platform can be adapted to other cell types for monitoring combined cellular behaviors, protein secretion, and transcriptional profiling.

Figure 19B:
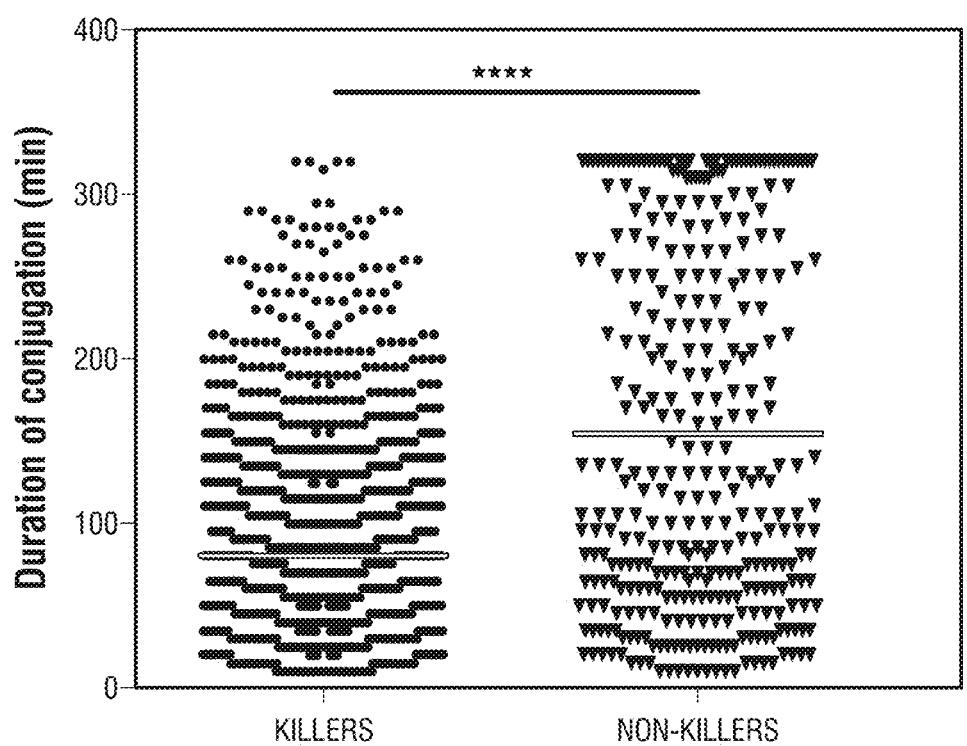
Figure 26:
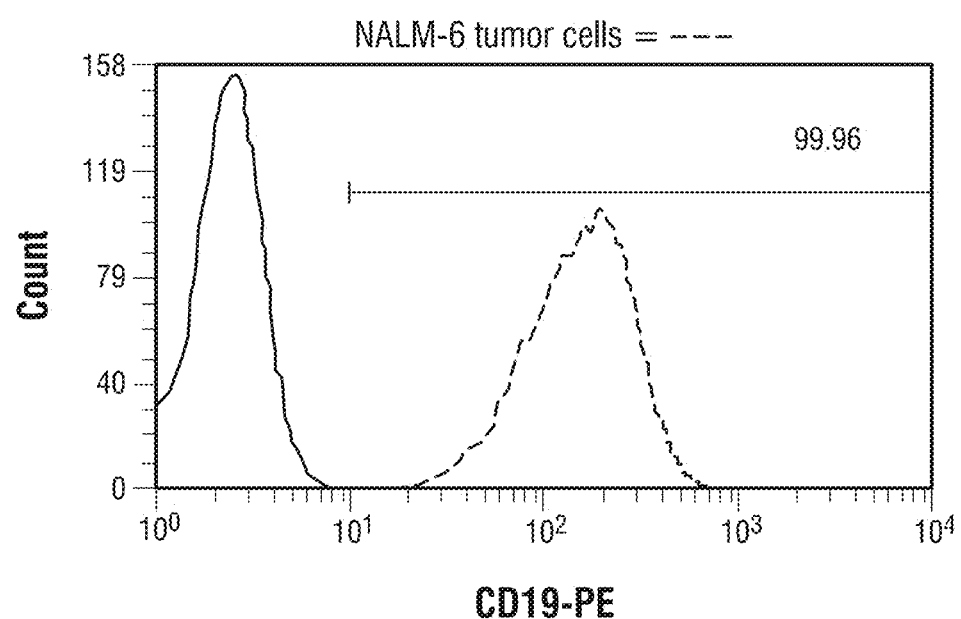
FIG. 26 shows CD19 expression on NALM-6 tumor cells as determined by immunofluorescent staining. The EL4 cell line (CD19negative) was used as a negative control (black lines).

The polyfunctionality of tumor-specific individual CD8+ CAR+ T cells, with regards to IFN-γ secretion and killing (and multi-killing) upon ligation with tumor cells was evaluated. Among all functional T cells, the group that secreted IFN-γ as a monofunction displayed the longest duration of conjugation to the tumor cell, in comparison to the T cells that participated in lysis of target cells. Since all T cells were uniformly modified with the CAR, and since the concentration of antigen on the target cells was uniform (FIG. 26), Applicants' results reveal that the duration of stable conjugation leading to different functional outcomes (IFN-γ vs. killing) can be heterogeneous. Applicants' results thus complement previous studies obtained by titrating antigen concentration to show that CD8+ T cells can form a short lytic synapse at low antigen densities, and a long stable stimulatory synapse leading to IFN-γ at high antigen densities. Significantly, Applicants' results at the single-cell level suggest that detachment from target cells might be enabled by killing, and the decision to terminate conjugation can occur prior to Annexin V staining (FIGS. 19A-19B).

In tracking the frequencies of serial killer T cells with and without simultaneous IFN-γ secretion, no significant differences were observed, suggesting that the early termination of conjugation did not affect T-cell activation for IFN-γ secretion. Applicants' results demonstrate at the single-cell level that the duration of conjugation of T cells to target cells might reflect different functional outcomes, in concordance with a recent report combining population level functional studies and single-cell calcium activation on mouse/human T cells which showed that failed target detachment can lead to prolonged IFN-γ hyper-secretion from T cells and that initiation of caspase within target cells likely enabled T cells to terminate the synapse.

Figure 25:
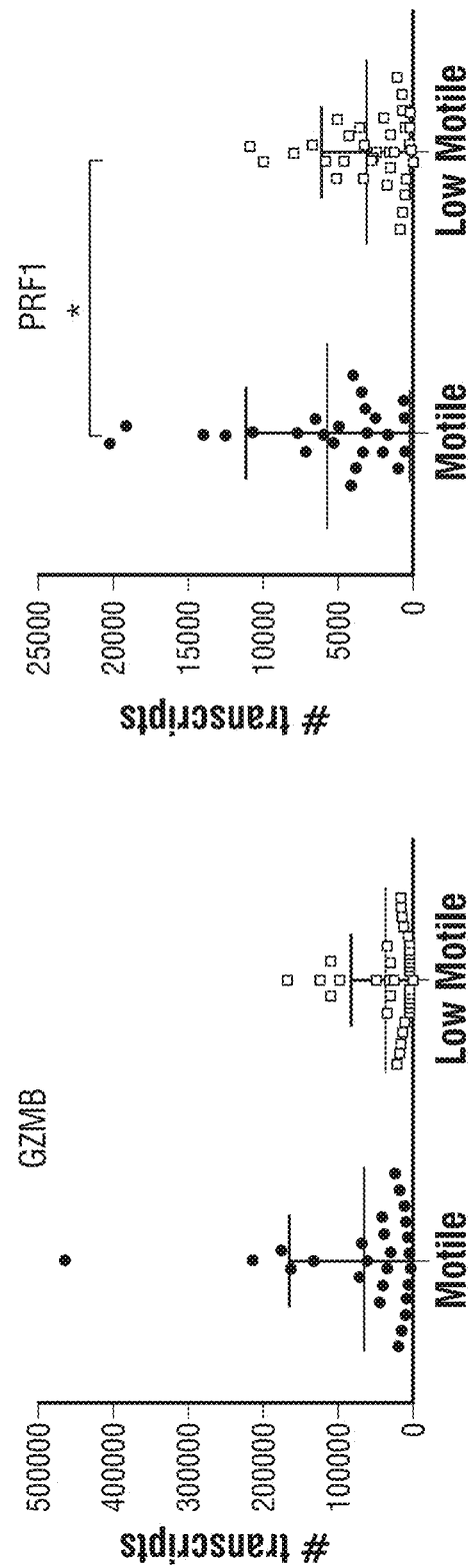
FIG. 25 provides comparisons of relative number of Granzyme B and perforin transcripts in high and low motility $CD8^+$ T cells. Transcript numbers were calculated as $2^{(Log2Ex)}$ in an idealized manner, assuming a maximum efficacy of the qPCR assays. Granzyme B is not differentially expressed, whereas perforin shows a significant difference between the two groups (p-value=0.03).

In addition, tracking the displacement of CD8+CAR+ T cells revealed that polyfunctional cells and specifically serial killer T cells, exhibited elevated out-of-contact basal motility in comparison to either non-functional T cells, or those effector cells that only secreted IFN-γ. In order to gain molecular insights into the immunological state of highly motile cells, multiplexed transcriptional profiling was performed at the single-cell level, targeting genes associated with T-cell activation, differentiation and memory. Combined statistical testing using t tests and hierarchical clustering followed by progression discovery modeling identified a core set of immunological genes that may be useful in distinguishing motile and non-motile T cells. Consistent with TIMING observations that motile T cells are enriched within the polyfunctional subset, molecular profiling indicated that markers associated with recent activation including CD244 (2B4), CD58, LAG3, IL2RB (CD122), IL18R1, the chemokine receptor CXCR3 and the transcription factor GATA3 were upregulated within motile cells. Similarly, the transcripts for the pore forming protein, perforin, required for immediate cytotoxicity mediated by CD8+ T cells, were also upregulated within motile T cells (FIG. 25).

Figure 27A:
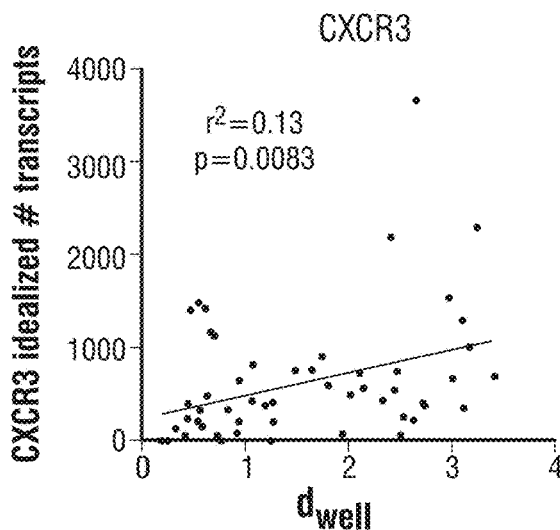
FIGS. 27A-27D show a correlation between idealized numbers of transcripts and average speed of the cell (dwell). It is shown that CXCR3 (FIG. 27A) and CD2 (FIG. 27B) expression increase with motility of $CD8^+$ T cells.
Figure 27B:
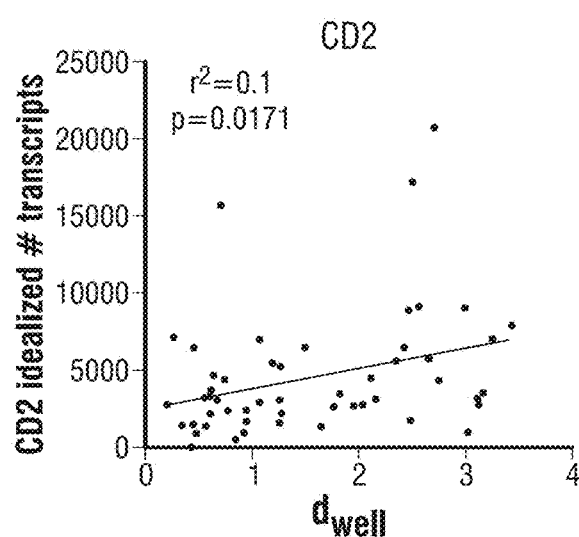

Individual T cells with increased motility also showed a matched increase in CXCR3 transcripts (FIG. 27A) which is one of the major chemokine receptors associated with trafficking to the tumor microenvironment and is expressed on activated TILs in diverse cancers including breast cancer and melanoma. The expression of CXCR3 is up-regulated upon CD8$^+$ T-cell activation, and in addition to its functional role in chemotaxis, CXCR3 derived signaling is believed to also affect the development of both effector and memory CD8$^+$ T cells. Similarly, the number of CD2 transcripts showed a positive correlation with T-cell motility (FIG. 27B).

Figure 27C:
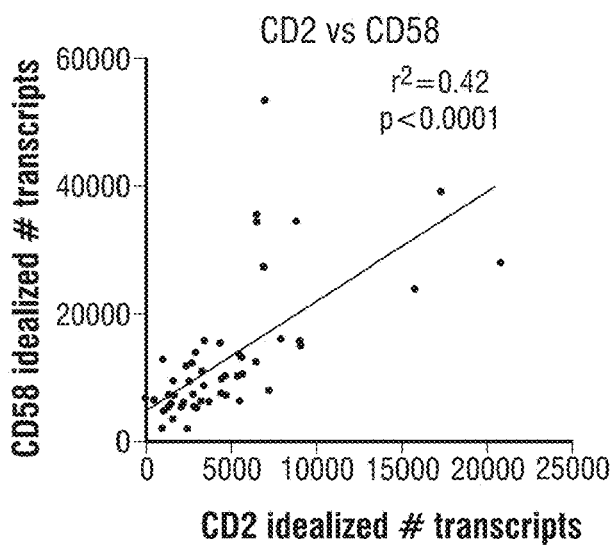
Figure 27D:
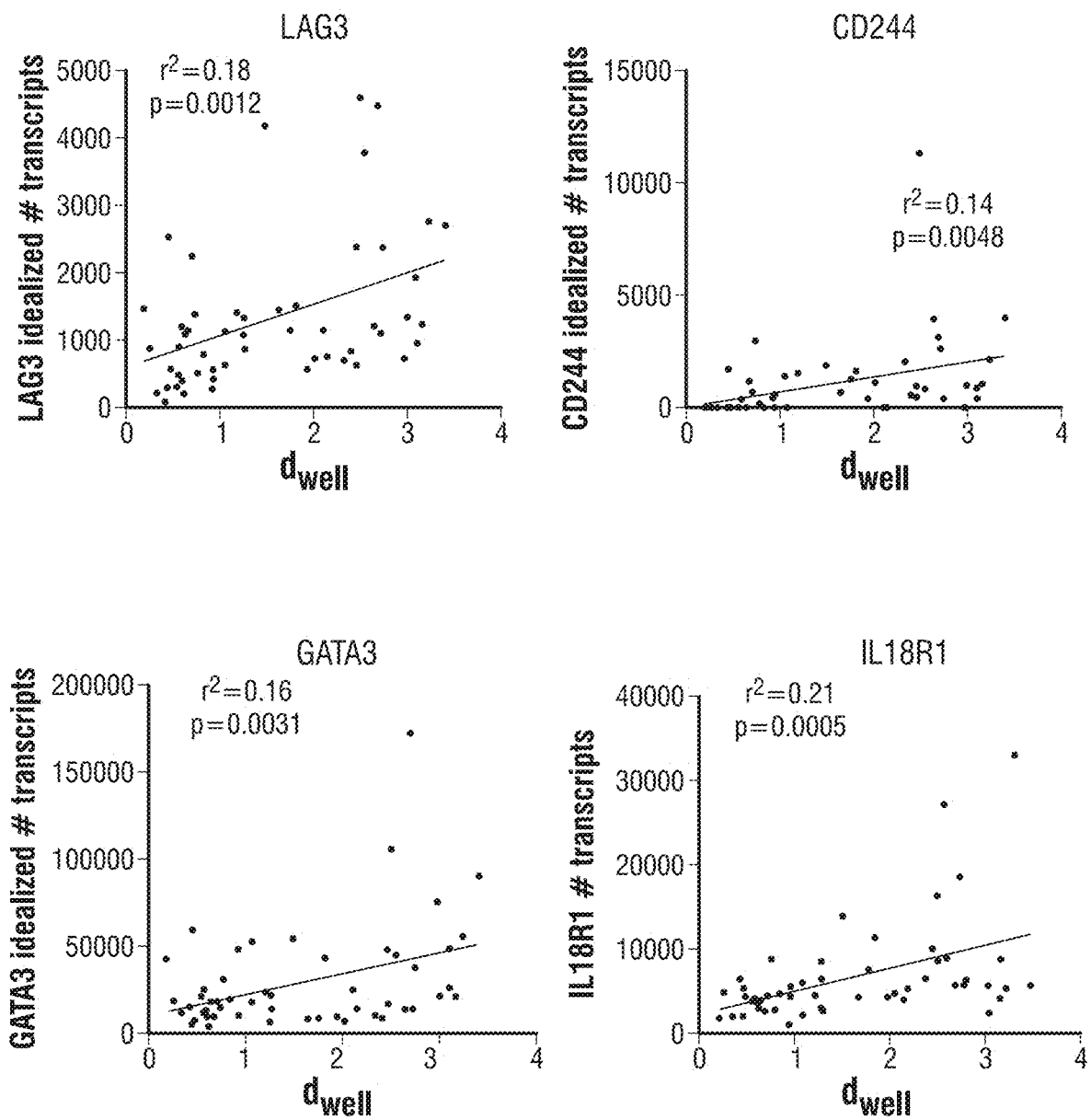
Figure 28:
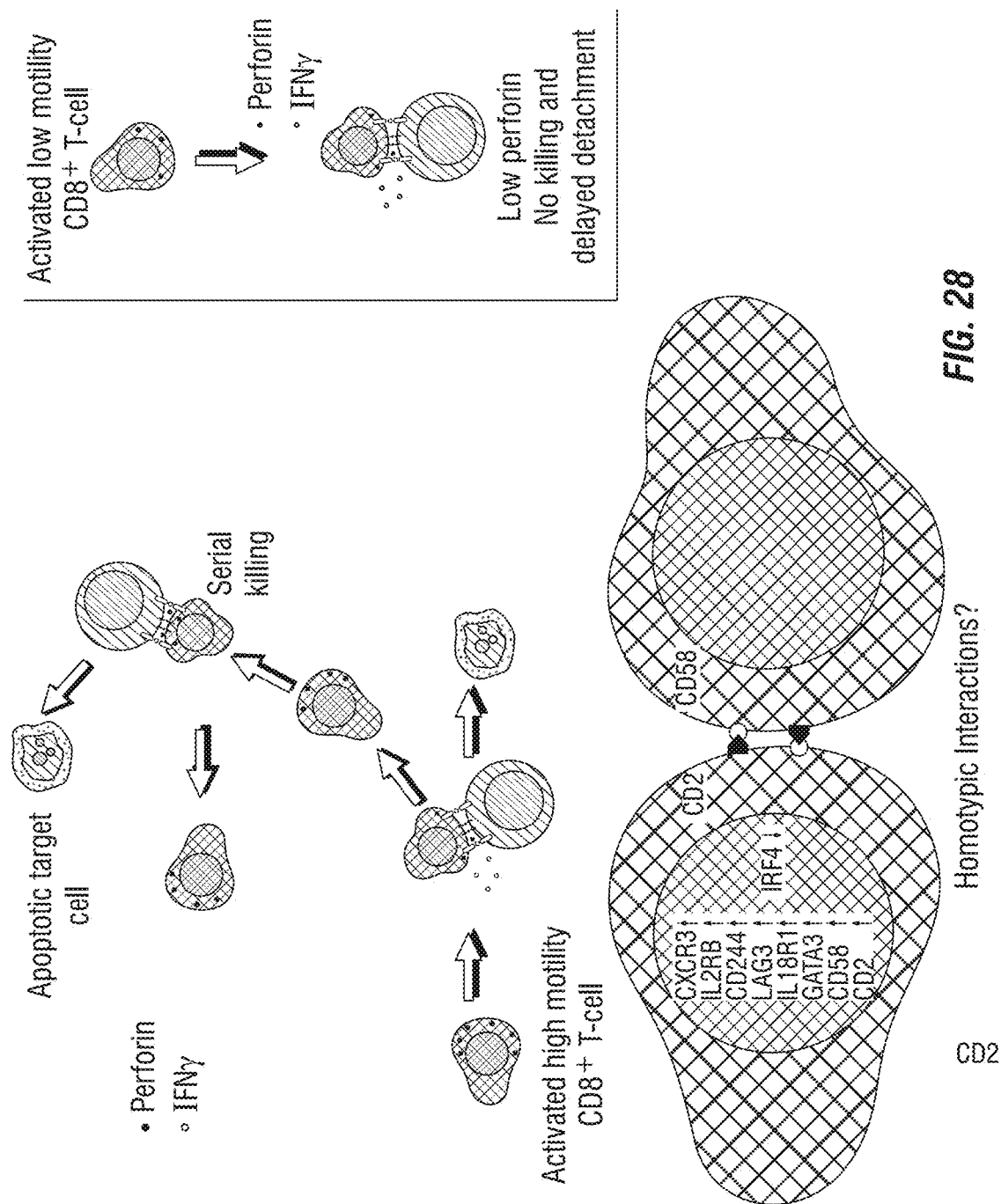
FIG. 28 provides a schematic summarizing integrated T-cell functionality. A subset of polyfunctional $CD8^+$ $CAR^+$ T cells participated in both serial killing of tumor cells and secreted IFNγ. T cells participating in killing and serial killing detach faster from their targets and possessed a higher out of contact motility that enabled them to sample the local microenvironment. By contrast, T cells that failed to kill the attached target cell demonstrated low out of contact motility and did not initiate detachment but were still able to secrete IFNγ. Gene expression profiling showed that high motility T cells had higher numbers of transcripts of perforin, and of molecules implicated in cell activation and chemokine migration, in comparison to low motility T cells.

The dynamic molecular interaction between CD2 and its binding partner CD58 facilitates T-cell recognition by stabilization of inter-cell contacts. Since the single-cell transcriptional profiling indicated a matched up-regulation of CD58 and CD2 on motile T cells (FIG. 27C), it is possible that these molecules can mediate homotypic T-cell/T-cell interactions and cluster formation, both of which are known to promote T-cell activation, proliferation and differentiation in vitro and in vivo. Of note, CD244 was also upregulated on motile T cells and is a similar adhesion molecule that can regulate T-cell homotypic interactions by binding to CD48 (FIG. 27D). Applicants thus propose an integrated model that summarizes all of Applicants' results integrating motility, serial killing, IFN-γ secretion and transcriptional profiling (FIG. 28).

In summary, Applicants' integrated methodology combining functional and molecular screening enables investigation of complex cellular behaviors at single-cell resolution. Applicants' modular and scalable method is suitable for screening combinations of the different T cell functions that might be required for the efficacy of T cells engineered with a panel of CARs and predicting whether an introduced immunoreceptor will result in therapeutic success in vivo. The therapeutic potential of CAR$^+$ T cells for treatment of B-cell malignancies raises the question whether similarly-engineered T cells with alternative specificities will also have anti-tumor effects in humans. Thus, the study of genetically modified CD19-specific T cells serves as a foundation to advance our understanding of CAR$^+$ T cells that target other hematologic malignancies and solid tumors.

Currently, most investigators rely on mouse experiments to inform on which CAR design and TIL population to advance to human application, but this is not readily amenable to scale up. As demonstrated here, Applicants propose that high throughput in vitro systems can be employed to evaluate the functional characteristics of panels of T cells before selecting subsets for preclinical and clinical translation. The implementation of the microscopy tools revealed in this report and the observation that motility correlates with killing of tumor cells may provide investigators with an approach to identify genetically modified T cells without the need for testing in small animals.

Example 2.9. Cell Lines, Primary T Cells, TILs, and Reagents

Human pre-B cell line NALM-6 (ATCC) and CAR$^+$ T cells were cultured as described previously. The cell lines were routinely tested to ensure that they were free of *mycoplasma* contamination and flow-cytometry was utilized to confirm the expression of CD19. TILs were isolated and expanded as previously described. Briefly, initial TIL expansion was performed in 24-well plates from either small 3-5 mm$^2$ tumor fragments or from enzymatic digestion, followed by centrifugation with FICOLL. TILs were then allowed to propagate for 3-5 weeks in TIL-complete media containing 6000 IU/mL human recombinant IL-2 (Prometheus). Once desired number of TIL was achieved, Rapid Expansion Protocol (REP) was performed in which TIL was cultured together with PBMC feeder cells (1 TIL: 200 feeders) preloaded with anti-CD3 (OKT3, eBioscience) in a G-REX 100M flask until the desired number of cells were achieved and harvested.

Example 2.10. Beads Preparation: Coating Beads with Primary Capture Antibody

About 1 μL of Promag 3 Series goat anti-mouse IgG-Fc beads (~2.3×10$^5$ beads) in solution was washed with 10 μL of PBS, and re-suspended in 19.6 μL PBS (~0.05% solids). Mouse anti-human IFN-γ (clone 1D1K) was then added to beads at final concentration of 10 μg/mL and incubated for 30 min at room temperature (RT), followed by washing and re-suspension in 100 μL PBS.

Example 2.11. ELISpot Assays

ELISpot assay was performed with fresh PBMC and TIL as previously described. Briefly, microwell plates were coated with capture antibody anti-human IFNγ-1D1K at 10 μg/mL overnight at 4° C. The next day, the plates were washed twice in PBS and blocked with RPMI-PLGH+10% FBS for 45 minutes at 37° C. Cells were prepared, as follows, in triplicates: (1) 4,000 PBMC stimulated with 10 ng/mL PMA/1 μg/mL ionomycin per well (2) 4,000 melanoma-specific TIL stimulated with 10 ng/mL PMA/1 μg/mL ionomycin per well (3) 200,000 PBMC stimulated with 2 μg/mL CEF peptide (4) Corresponding non-stimulated cells. Next, cells were incubated for 18 hours at 37° C./5% $CO_2$, followed by five washes with PBS and 2 hour incubation with biotinylated detection anti-human IFNγ 7-B61 at 37° C./5% $CO_2$ in PBS+0.5% FBS. After washing with PBS seven times, the immunosandwich was completed with subsequent addition of extravidin-alkaline phosphatase (1 hour incubation at 37° C./5% $CO_2$ [Sigma-Aldrich]). The plate was washed five times with PBS, and BCIP/NBT (Sigma-Aldrich) substrate was added and incubated for 15 minutes at 37° C./5% $CO_2$. The plate was subsequently read with ELISpot reader (C.T.L. counter) while taking into account background measurement.

Example 2.12. Nanowell Array Fabrication and Cell Preparation

Nanowell array fabrication for interrogation of effector functions at single-cell level was performed as described previously. Approximately 1 million effector cells and target cells were both spun down at 400 xg for 5 minutes followed by labeling with 1 μM PKH67 and PKH26 fluorescent dyes respectively according to manufacturer's protocol. Excess unbound dyes were then washed away and cells were re-suspended at ~2 million cells/mL concentration in complete cell-culture media (RPMI+10% FBS).

Example 2.13. Finite Element Simulations

The system of partial differential equations to model variation of analyte concentrations, C and $C_s$, with time, was solved using Transport of diluted species interface, Chemical reaction engineering module in COMSOL Multiphysics 4.1. Mass balance equation involving Cs was solved using its weak form. Change in positions of cell and bead, convective transport, diffusion on the bead surface ($D_s=10^{-25}$ m²/s), non-specific adsorption on walls and degradation of analyte were neglected to simplify numerical simulations.

Example 2.14. TIMING Assays for Multiplex Study of Effector Cytolytic Phenotypes and IFN-γ Secretion Capture antibody coated beads and labeled effector and target cells were loaded consecutively onto nanowell arrays. Whenever necessary, arrays were washed with 500 µL of cell culture media to remove excess beads or cells. Next, detection solution containing Annexin V-Alexa Fluor 647 (AF647) (Life Technologies) (for detection of target apoptosis) were prepared by adding 50 µL solutions from stock to 2.5 mL of complete cell-culture media without phenol red. Nanowell arrays were then imaged for 5 hours at intervals of 5 minutes using LEICA/ZEN fluorescent microscope utilizing a 20×0.45 NA objectives and a scientific CMOS camera (Orca Flash 4.0). Subsequently, mouse anti-human IFN-γ biotin was added to 2.5 mL cell media above at 1:1000 dilution. This was incubated for 30 minutes followed by washing and incubation with 5 µg/mL Streptavidin—R-Phycoerythrin (PE). The entire chip was again imaged to determine the intensity of PE signal on the microbeads and the two datasets were matched using custom informatics algorithms.

Example 2.15. Image Processing, Cell Segmentation and Tracking, and Data Analytics Image analysis and cell segmentation/tracking were performed as described previously. The pipeline of image processing and cell segmentation ends with statistical data analysis based on the tabular spatio-temporal measurement data generated by the automated segmentation and cell tracking algorithms. Nanowells containing 1 effector and 2-5 tumor cells were selected for further analysis. Next, Applicants partitioned all these events based on the functionalities of the cells (i.e. mono-kill, serial kill, and IFNγ secretions). A size-exclusion filter based on maximum pixel areas were used to effectively differentiate cells from beads (i.e., beads were much smaller than cells). Where specified, cell tracks were represented using MATLAB (Mathworks Inc. MA).

Example 2.16. Gene Expression Profiling

PKH green stained CD8$^+$ T cells were loaded on a nanowell array, immersed with Annexin-AF647 (Life Technologies) containing phenol red free complete cell-culture medium and imaged for 3 hours using TIMING exactly as described above. After carefully washing the cells on the chip 3 times with cold PBS (4° C.), cells were kept at 4'C until retrieval. Time-lapse sequences were manually analyzed to identify live high and low motility cells. The cells were individually collected using an automated micro-manipulating system (CellCelector, ALS) and deposited in nuclease free microtubes containing 5 µL of 2× CellsDirect buffer and RNAse Inhibitor (Invitrogen). Single cell RT-qPCR was then performed using the protocol ADP41 developed by Fluidigm. Ninety-two cells (48 motile and 44 non motile) were assayed, along with bulk samples of 10 and 100 cells, and with no-cell and no-RT controls. The panel of 95 genes (FIGS. 21A-1-21E) included genes relevant to T cell activation, signaling and gene regulation, and was designed and manufactured by Fluidigm D3 AssayDesign.

For data analysis, Applicants first extracted Log 2Ex value by subtracting Ct values from a threshold of 29, as described previously. Applicants then excluded data from i) cells that had less than 40% of genes that were amplified and had a mean of Log 2Ex out of the range of population mean±3SD and from ii) genes that were amplified in <10% of cells. Post-process analysis was done using Excel (Microsoft), Prism (GraphPad), MeV, STrenD (https://github.com/YanXuHappygela/STrenD-release-1.0) and Genemania webtool (http://www.genemania.org/).

Example 3. Individual Motile CD4$^+$ T Cells can Participate in Efficient Multi-Killing Through Conjugation to Multiple Tumor Cells In this Example, Applicants implemented TIMING to provide direct evidence that CD4$^+$CAR$^+$ T cells (CAR4 cells) can engage in multi-killing via simultaneous conjugation to multiple tumor cells. Comparisons of the CAR4 cells and CD8$^+$ CAR+ T cells (CAR8 cells) demonstrate that while CAR4 cells can participate in killing and multi-killing, they do so at slower rates, likely due to the lower Granzyme B content. Significantly, in both sets of T cells, a minor sub-population of individual T cells identified by their high motility, demonstrated efficient killing of single tumor cells. By comparing both the multi-killer and single killer CAR$^+$ T cells, it appears that the propensity and kinetics of T-cell apoptosis was modulated by the number of functional conjugations. T cells underwent rapid apoptosis. Moreover, at higher frequencies (i.e., when T cells were conjugated to single tumor cells in isolation), this effect was more pronounced on CAR8 cells.

Applicants' results suggest that the ability of CAR$^+$ T cells to participate in multi-killing should be evaluated in the context of their ability to resist activation induced cell death (AICD). Applicants anticipate that TIMING may be utilized to rapidly determine the potency of T-cell populations and may facilitate the design and manufacture of next-generation CAR$^+$ T cells with improved efficacy.

Example 3.1. Cell Lines and Antibodies

All antibodies were purchased from Biolegend (San Diego, Calif.). Human pre-B cell line NALM-6 (ATCC), Daudi-β2m (ATCC), T-cell lymphoma EL-4 (ATCC) and modified CD19$^+$EL-4 cells were cultured as described previously. The cell lines were routinely tested to ensure that they were free of *mycoplasma* contamination and flow-cytometry was utilized to confirm the expression of CD19.

Example 3.2. Genetic Modification and Propagation of Cells

PBMC from healthy volunteers were electroporated using Nucleofector II (Amaxa/Lonza) with DNA plasmids encoding for second generation CAR (designated CD19RCD28) and SB11 transposase and co-cultured with γ-irradiated K562 aAPC (clone 4) for 28 days along with cytokines (IL-2 and IL-21) in a 7-day stimulation cycle as described previously. For single cell analysis, frozen CAR$^+$ T cells were revived and re-stimulated with irradiated K562 aAPC before using them in experiments.

Example 3.3. Flow Cytometry

Cells were stained for cell surface markers (CAR, CD4, CD8, CD3), fixed and permeabilized (Cytofix/Cytoperm, BD Biosciences) for 20 minutes at 4° C. Cells were subsequently stained for intracellular granzyme B in perm/wash buffer at 4° C. for 30 minutes, acquired on a FACS Calibur, and analyzed using FCS Express/FlowJo as previously described Statistical analyses for determining GzB expression were performed within R.

Example 3.4. End-Point Cytotoxicity Assay

Nanowell array fabrication and the corresponding cytotoxicity assay to interrogate effector-target interaction at single-cell level were performed as described previously. Briefly, CAR$^+$ T cells labeled with 1 µM of red fluorescent dye, PKH26 (Sigma) and target cells labeled with 1 µM of green fluorescent dye PKH67 were co-loaded onto nanowell arrays at a concentration of $10^6$ cells/mL. Images were acquired on a Carl Zeiss Axio Observer fitted with a Hamamatsu EM-CCD camera using a 10×0.3 NA objective. Automated image acquisition of the entire chip was performed at 0 and 6 hour and apoptosis was identified by staining with AnnexinV conjugated to Alexa-647 (Life Technologies, Carlsbad, Calif.).

Example 3.5. TIMING Assays

Nanowell grids were fixed in position on a 60 mm petridish. The cells were labeled and loaded exactly as described for the end-point assay and imaged on a Zeiss Axio Observer using a 20×0.45 NA objective. Images were acquired for 12-16 hours at intervals of 7-10 minutes.

Example 3.6. Flow Cytometry Based Cytotoxicity Assays

CAR4 cells ($1 \times 10^6$ cells) were incubated with CD19$^+$ target cells (0.2×10$^6$ cells; Daudiβ$_2$m, NALM-6, CD19EL-4) at E:T ratio of 5:1 in the presence or absence of 5 mM EGTA in 24-well plates in 5% $CO_2$ at 37° C. for 6 hours. Following incubation cells were stained for CD3 (T cells) and CD19 (tumor targets), acquired on a FACS Calibur (BD Biosciences) and analyzed using FCS Express version 3.00.007 (Thornhill, Canada).

Example 3.7. Image Processing and Cell Segmentation

In order to permit accurate computation of cell displacements despite camera and stage movements, the individual nanowells were detected automatically with >99% accuracy by correlating pre-constructed shape templates at the expected range of orientations and magnification values. The correlation value is a maximum at the well centers, and these points are detected using a local maxima clustering algorithm. The cells in each image channel are analyzed automatically using a 3-step method. First, each pixel is stratified as bright foreground, intermediate foreground, and dark background based on modeling image intensities as a mixture of three Gaussian distributions. The foreground pixels are subjected to multi-level thresholding (Applicants used 10 equally-spaced levels between the maximum and minimum foreground intensity values). The cell centers are detected using a local maxima clustering on the average of Euclidean distance maps computed at each threshold. Using these cell centers, the image foreground is partitioned into individual cell regions using the normalized cuts algorithm, allowing cell sizes and shapes to be quantified. Spectral overlap between the dyes used under the imaging conditions were eliminated during image processing through an automatic "unmixing" cess, and this is performed independently for each set of experiments. In addition, the segmentation scripts calculate an integrated fluorescence intensity by averaging on all the pixels associated with a given cell and thus eliminated any ambiguity in effector/target classification due to the diffusion of dyes across the cell membrane during contact.

Example 3.8. Cell Tracking

The detected cells, denoted $C_{i=1 \ldots N}^{t=1 \cdots T}$, where N is the number of cells in the well and T is the number of frames, are tracked from frame to frame using a graph-theoretic edge selection algorithm on a directed graph where cells correspond to vertices and edges represent temporal association hypotheses. The association cost for each edge $f_{i,j}^t$ between object t at time t and object j at time t+1 is calculated based on cell location and size. The temporal correspondences are identified using an integer programming algorithm that maximizes the total association cost subject to constraints to ensure that each cell in a given frame is associated with a maximum of one cell in the subsequent frame, and vice versa.

Example 3.9. Production and Phenotype of CAR$^+$ T Cells

Figure 29A:
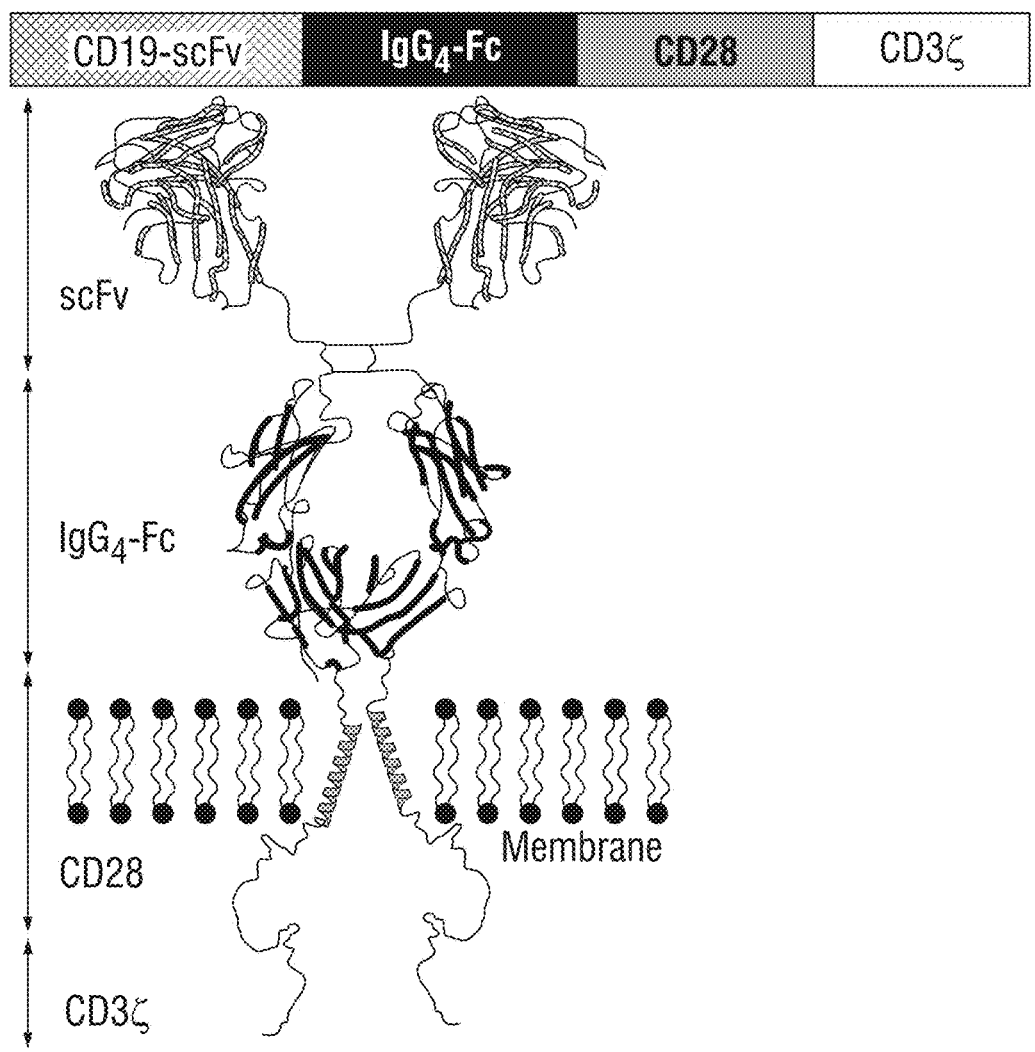
FIGS. 29A-29E provide high-throughput single-cell analysis of $CAR^+$ T-cell cytolytic functionality in nanowell grids.
Figure 29B:
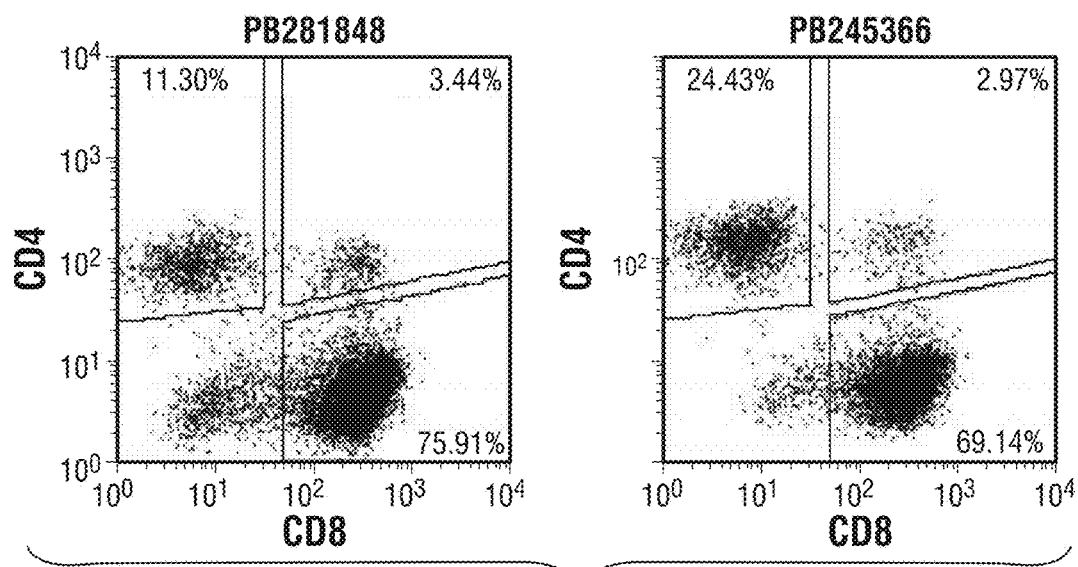

Genetically modified and propagated T cells were generated from the peripheral blood mononuclear cells (PBMC) of healthy volunteer donors derived using the Sleeping Beauty (SB) system[27] to enforce expression of a second generation CD19-specific CAR (designated CD19RCD28) that activates T cells via a chimeric CD3 and CD28 endodomain (FIG. 29A). Subsequent to expansion, CAR$^+$ T cells from two separate donors contained predominantly CD8$^+$ T cells (FIG. 29B).

Figures 29C, 29D:
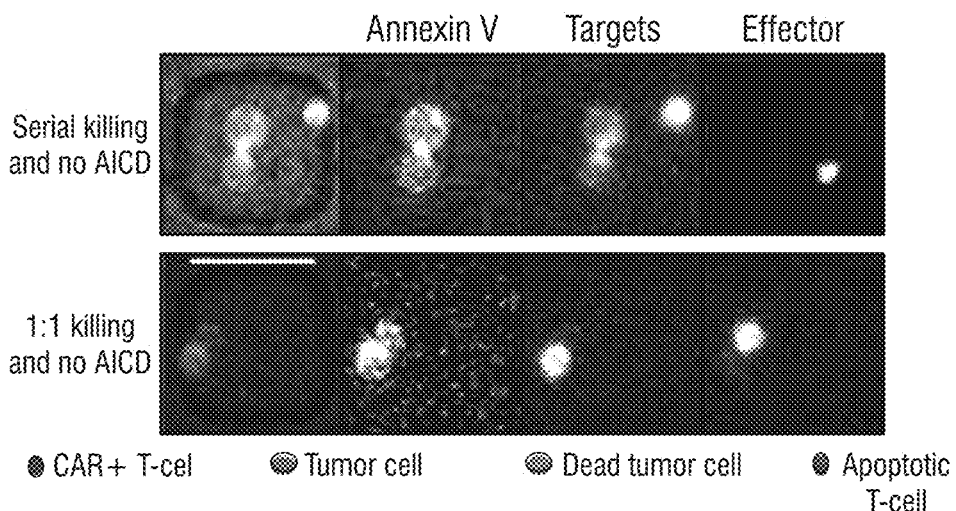
Figure 30:
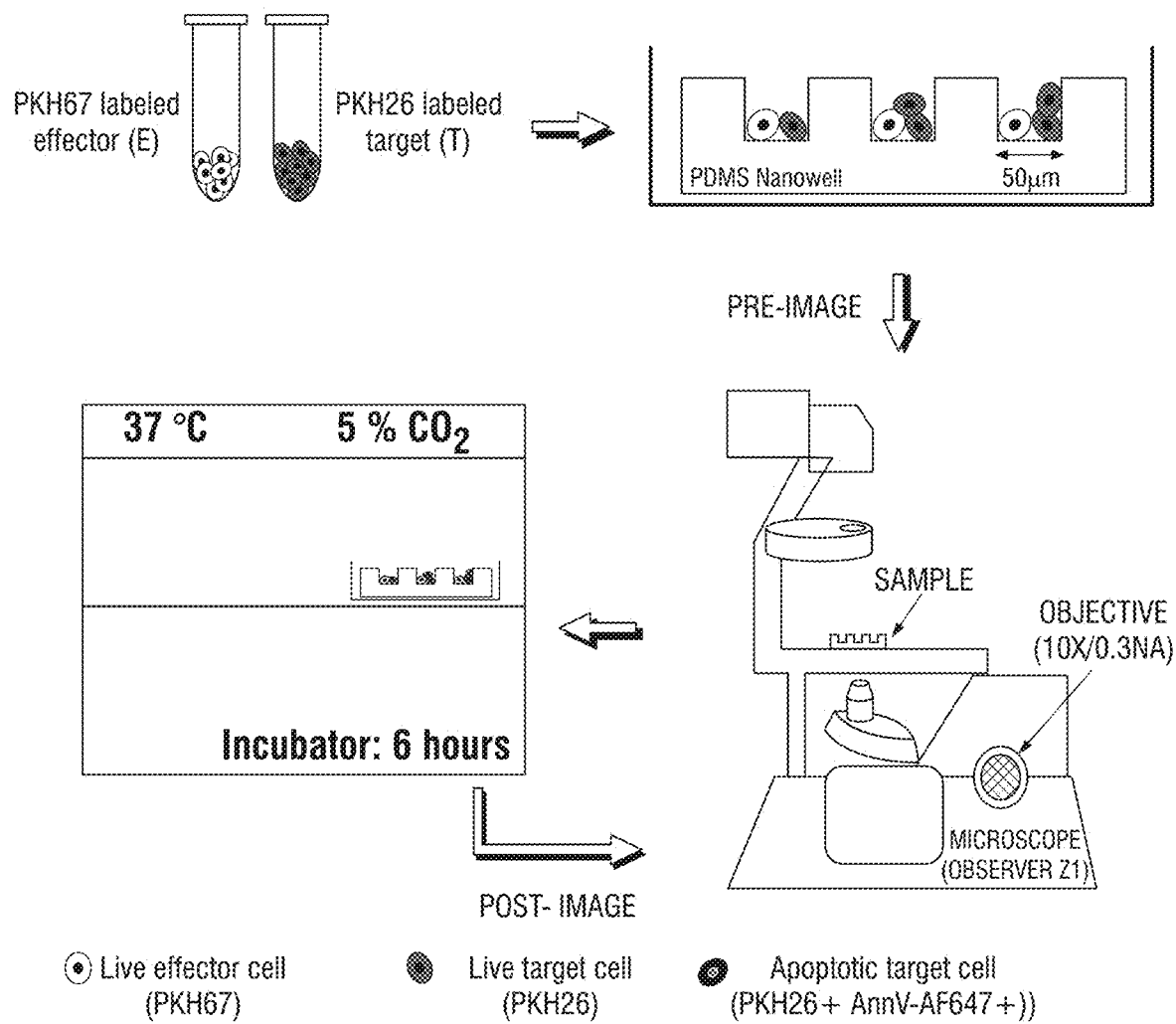
FIG. 30 illustrates a high-throughput cytotoxicity assay for monitoring T-cell target cell interactions in nanowell grids. Labeled effectors and target cells are loaded onto a nanowell array (~85,000 individual wells, 125 pL each well) to enable monitoring of T-cell function at the single-cell level. Subsequent to loading and washing steps, the entire chip is immersed in cell-culture media containing AnnexinV. A pre-image is acquired on the microscope to determine the occupancy of every single nanowell and to exclude cells dead at the start of the assay. The array is then transferred to the incubator for 6 hours to enable cell-cell interactions and a second post-image is acquired. In house image segmentation programs are used to automatically process the images and database matching is employed to determine killing. In parallel, a separate nanowell array is loaded with targets only to determine the death rate in the absence of effectors, over the same period of time. The killing assay results are corrected for the background killing rate determined by the target only arrays.

Example 3.10. The Cytotoxic Potential, Specificity and Multi-Killing Ability of Individual CAR$^+$ T Cells Donor-derived CAR$^+$ T-cell populations were evaluated for their ability to lyse CD19$^+$EL4 target cells, by co-culture within nanowell grids (FIGS. 29C and 30). At an E:T of 1:1, averaged across both donors, 29% of single CAR$^+$ T cells induced apoptosis of (number of events, $N_{total}$=4,048) CD19$^+$EL4 cells within six hours, whereas they induced apoptosis of just 1% ($N_{total}$=3,682) of CD19$^-$EL4 cells in the same time frame. The >29-fold increase of lysis of CD19$^+$ versus CD19$^-$ targets confirms TAA-specific lysis (FIG. 29D, p-value<0.0001, Fisher's 2×2 test). In parallel, a conventional 4-hour $^{51}$Chromium release assay (CRA) was performed at the same E:T ratio (1:1) and reported a similar overall magnitude of target cells killing (mean 14-fold increase of lysis of CD19$^+$ versus CD19$^-$EL4 cells), albeit without single-cell resolution (FIG. 29D). The ability to redirect specificity to lyse human CD19$^+$ tumor cells was confirmed using the pre-B cell line NALM-6 (data not shown).

Figure 31:
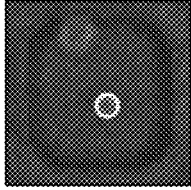
FIG. 31 provides composite micrographs illustrating representative examples of the interactions between single $CAR^+$ T cells (E) and one or more NALM-6 tumor (T) cells. The tumor-cells are colored red, the $CAR^+$ T cells are labeled blue with an artificial white exterior. Killing is determined by the colocalization of Annexin V staining (green) on red target cells. Scale bar 50 μm.

When averaged across both donors, within six hours of observation, individual CAR$^+$ T cells induced apoptosis in 34% ($N_{total}$=3,503) of NALM-6 target cells at an E:T ratio of 1:1. Across all of the samples tested, single cell assay demonstrated a linear correlation to the CRA (FIG. 29D, $r^2$=0.84, p-value=0.01). The ability of individual T cells to eliminate more than one target cell was quantified by analyzing nanowells containing multiple targets (FIG. 31). Averaged across both donors, at an E:T ratio of 1:2, within six hours, 21% ($N_{total}$=2,294) of single CAR$^+$ T cells killed exactly one CD19$^+$EL4 target-cell whereas 23% killed both targets (FIG. 29E).

Figure 29E:
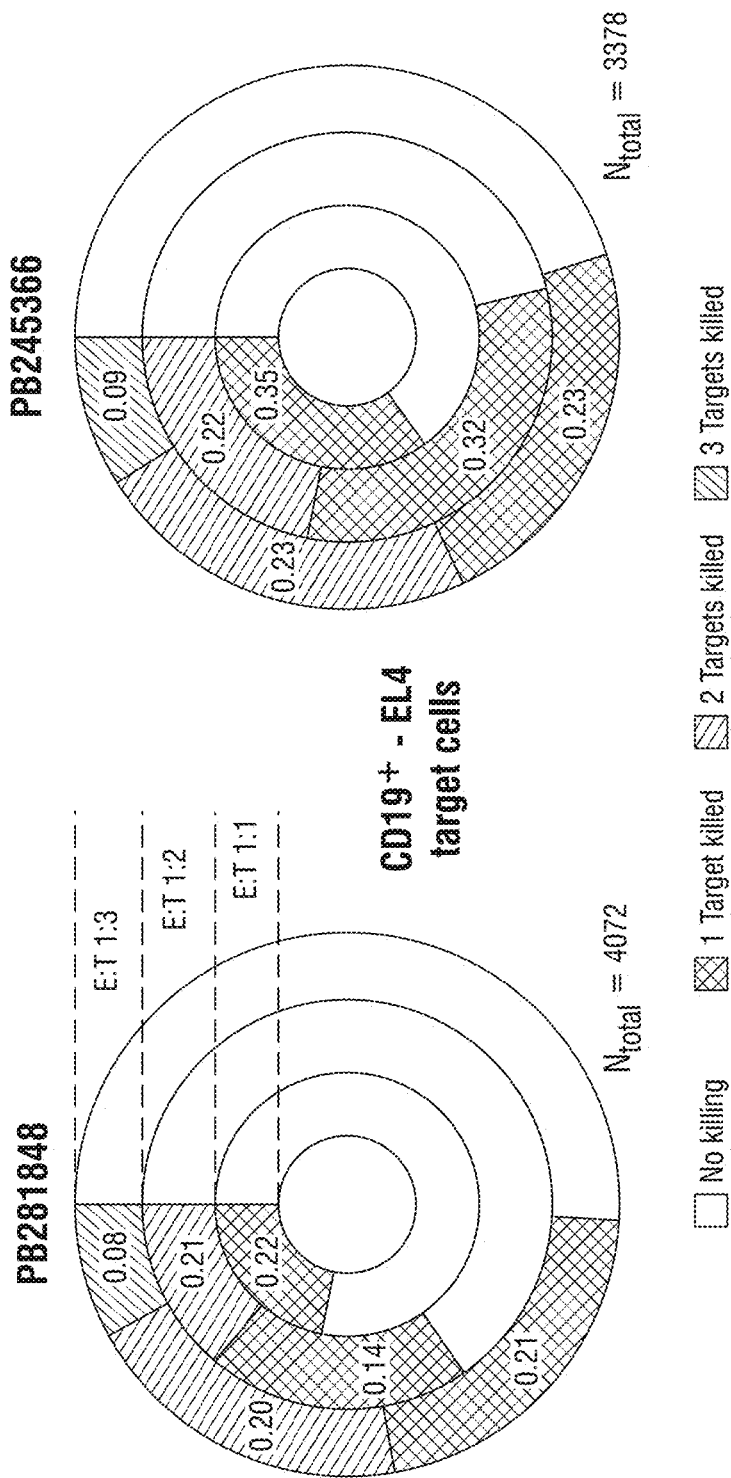

During this same timeframe, at an E:T ratio of 1:3, 22% ($N_{total}$=1,108) of single CAR$^+$ T cells killed exactly one target, 22% killed exactly two targets, and 9% killed all three targets (FIG. 29E). Thus, within a defined observation window, the likelihood that an individual CAR$^+$ T cell killed more than one tumor cell improved as the number of targets within the nanowell increased, even though this might reflect higher frequency of interactions at higher cell densities.

Figure 32:
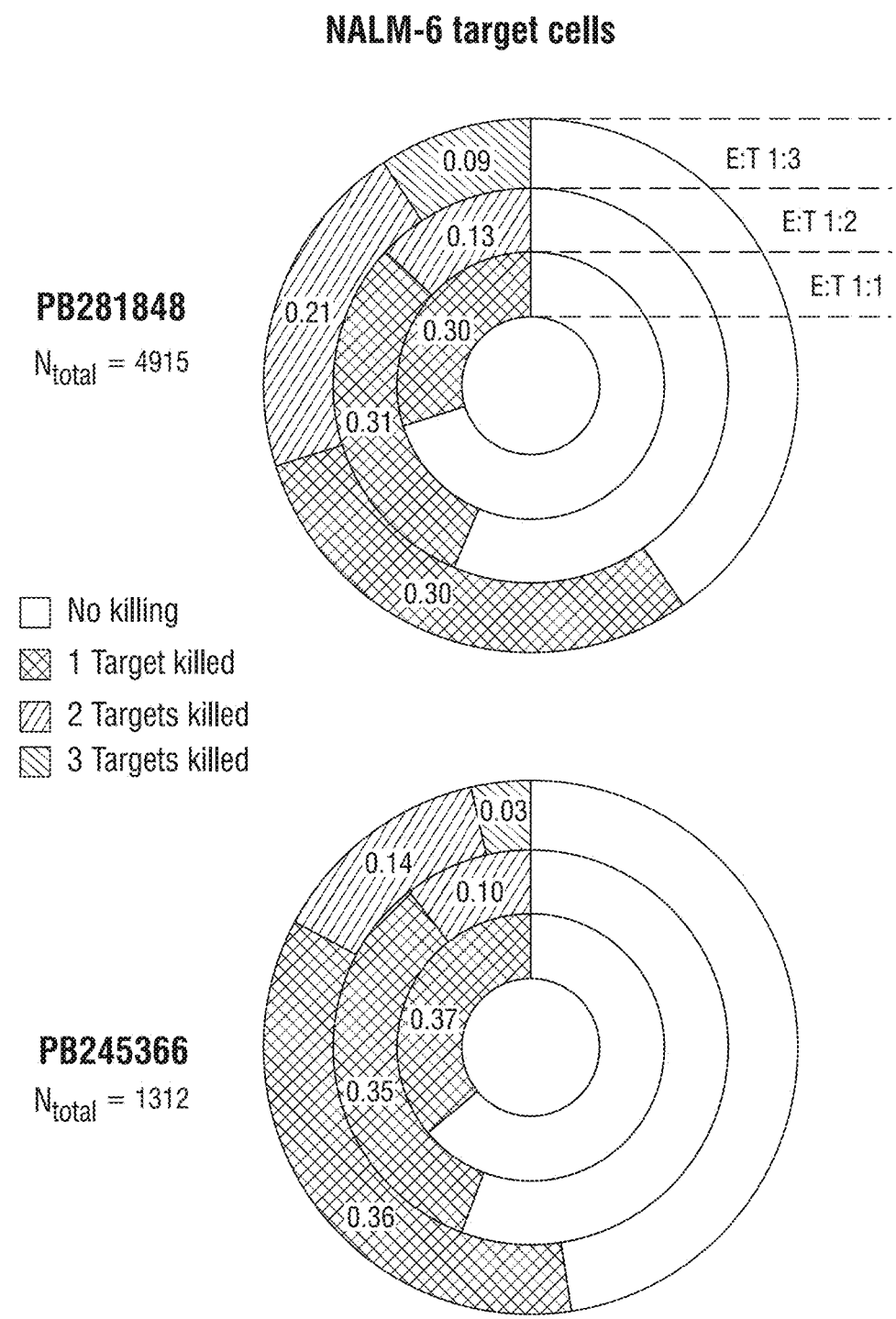
FIG. 32 shows donut plots summarizing the outcomes of the interaction between individual CAR8 cells and 1-3 $CD19^+$-NALM-6 tumor cells.

The aforementioned findings were also observed when substituting NALM-6 as target cells, albeit with diminished frequency of multi-killing after 6 hours of co-culture (FIG. 32). In aggregate, these data demonstrate that the responses measured by the single-cell assay are consistent with the results of CRA, and that multi-killer CAR$^+$ T cells (ability to lyse at least two targets) comprised 20% ($N_{total}$=3,402) of the CAR$^+$ T-cell population.

Example 3.11. Motile CD8$^+$ Cytotoxic T Cells are Efficient Killers with Decreased Potential for Activation Induced Cell Death (AICD)

Figure 33:
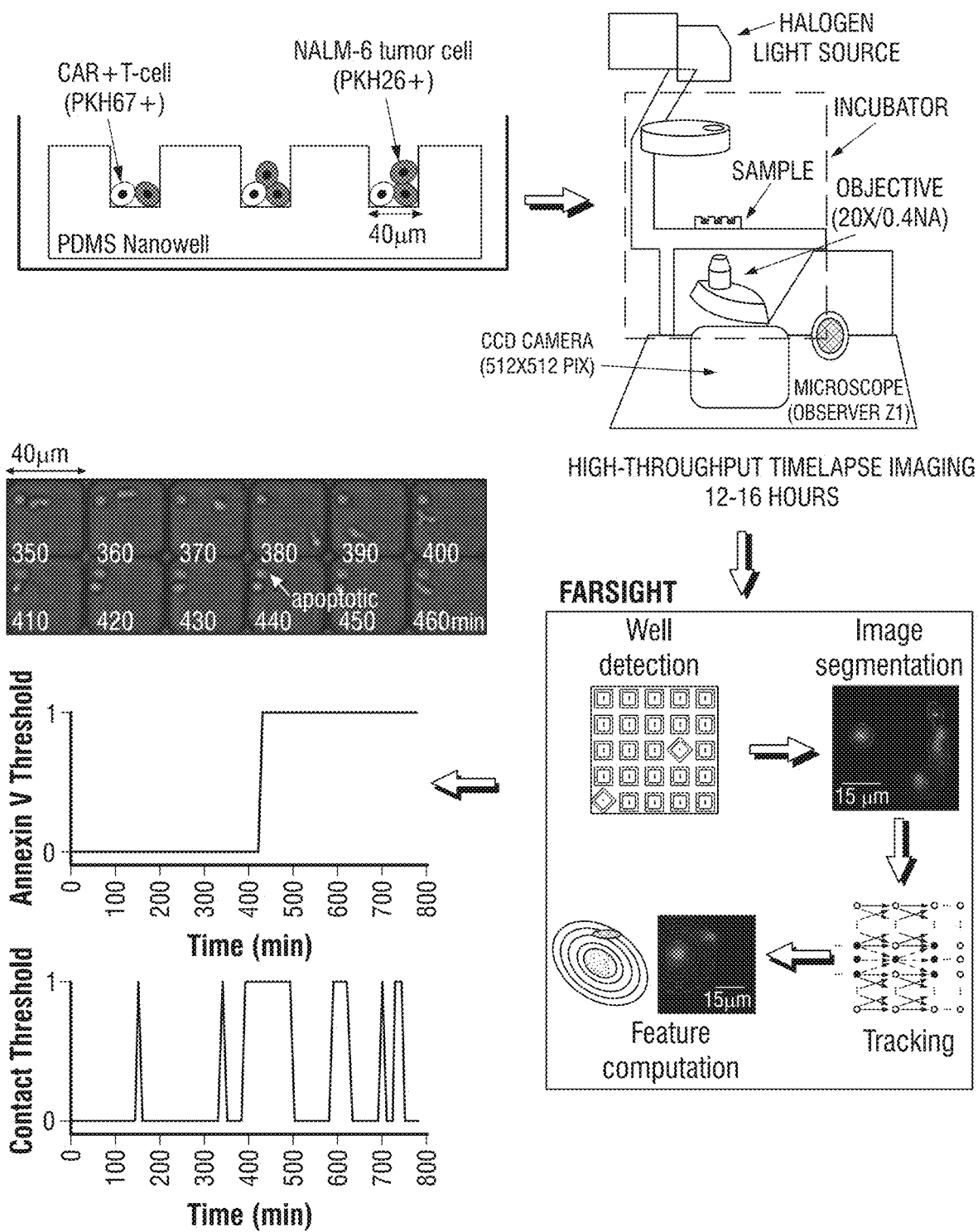
FIG. 33 shows a scheme of a TIMING assay. PDMS nanowell arrays (64 pL each nanowell) were fabricated to bond a 60 mm petridish. Labeled effectors and targets were loaded onto the nanowell array and the entire chip was immersed in cell-culture media containing fluorescent Annexin V. At least 6,000 nanowells are imaged every 7-10 minutes on the microscope for a total of 12-16 hours. Subsequently, an integrated pipeline within FARSIGHT is implemented to automatically enable well detection, image preprocessing and cell segmentation, tracking and feature computation. The images are fragmented such that each nanowell represents a single time series file. When analyzing time series data, only nanowells that yielded the exact same number of effectors and targets in >95% of time points were carried forward for analysis. Finally, the data is presented as time-series plots for each well along with the associated cell feature graphs.
Figure 34A:
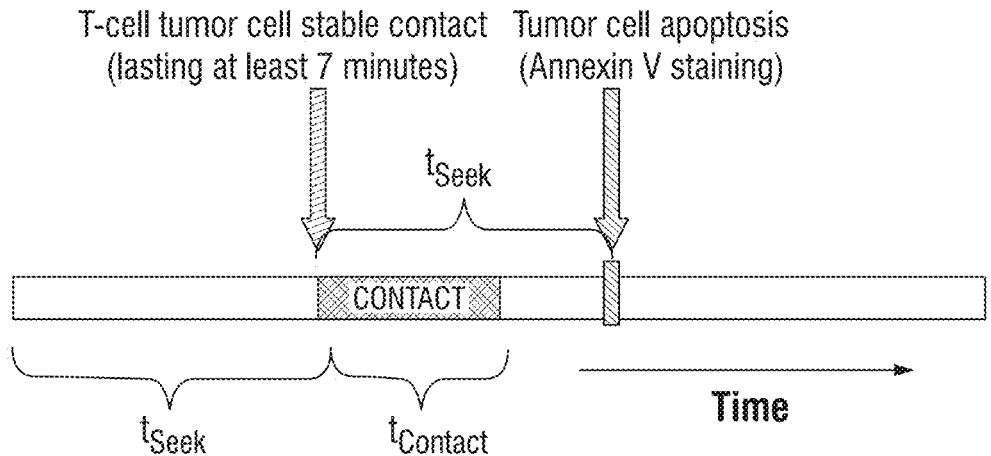
FIGS. 34A-34F show that CAR8 cells can be classified into different subgroups based on their the motility and conjugation periods with NALM-6 tumor cell (E:T 1:1). Schematic depicting the effector parameters used to describe their interaction with single NALM-6 tumor cells are shown.
Figure 34B:
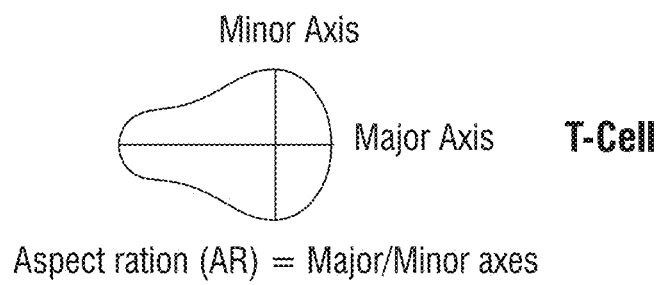
Figure 34C:
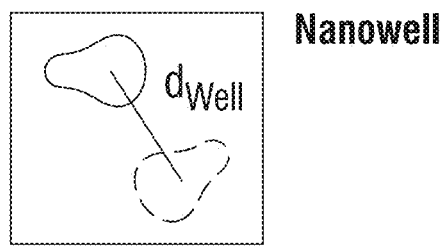

In order to gain an improved mechanistic understanding on the interaction between individual CAR$^+$ T cells and NALM-6 tumor cells, Applicants implemented the TIMING assay illustrated in FIG. 33. Six parameters describing T-cell intrinsic behavior motility ($d_{Well}$) 1 and aspect ratio of polarization (AR), conjugation (contact lasting>7 minutes, $t_{Seek}$ and $t_{Contact}$), and death ($t_{Death}$ and $t_{AICD}$) were computed to define each interacting pair of effector and tumor cells (FIGS. 34A-34C). At an E:T of 1:1, 77% ($N_{total}$=268) of single CD8$^+$CAR$^+$ T cells (CAR8 cells) that made at least one conjugate were able to kill the engaged leukemia cell. In order to identify subgroups of T cells that exhibited different behavioral interactions with the tumor cells leading to subsequent killing, the time series data for each of three features, total duration of conjugation, $d_{well}$ and AR, underwent hierarchical clustering (FIG. 35).

Figure 34D:
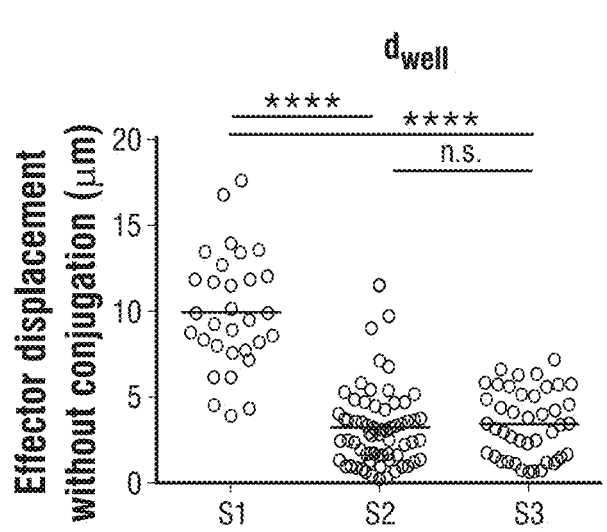
Figure 34E:
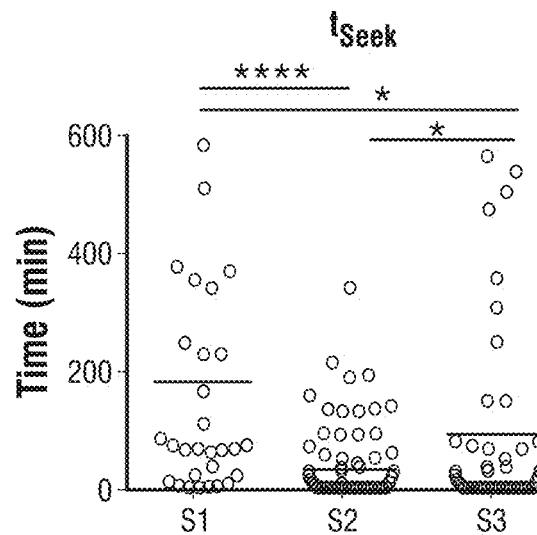
Figure 34F:
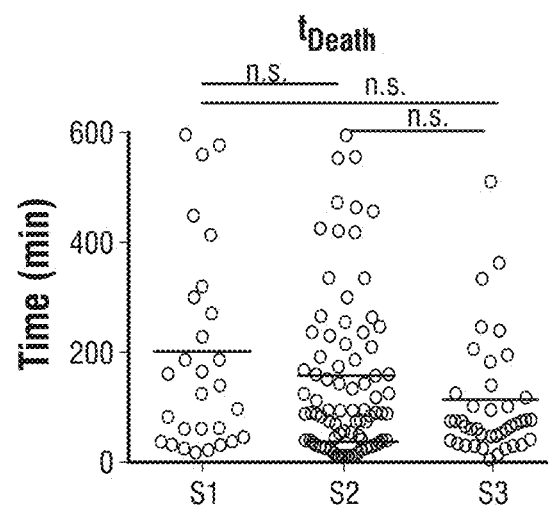

Three T-cell subgroups were described that collectively accounted for 70% of the single-killer CAR8 cells: S1 (14% [7-20%], range), low conjugation and high motility; S2 (49% [32-66%]), high conjugation and low motility; and S3 (21% [19-22%]), low conjugation and low motility (FIG. 35). The high-motility subgroup, S1, comprised predominantly of elongated T cells that had an initial "lag-phase" ($t_{Seek}$ 184±38 minutes, Mean±SEM), but formed stable conjugates ($t_{Contact}$ 98±13 minutes) prior to target apoptosis ($t_{Death}$ 204±35 minutes) (FIGS. 34D-34F). Predominantly, these T cells exhibited a decrease in motility and increased circularization during tumor-cell conjugation, detached after tumor-cell death, resumed normal migratory function and had only a low frequency of effector cells undergoing AICD (data now shown).

The representative cell in the dominant subgroup, S2, established conjugation quickly ($t_{Seek}$ 36±6 minutes), and displayed sustained conjugation ($t_{Contact}$ 145±16 minutes) prior to killing ($t_{Death}$ 158±18 minutes) (FIGS. 34E-34F). The majority of these T cells did not detach or resume migratory function after tumor-cell lysis, retained a predominantly circular morphology, and continued to remain conjugated for more than 10 hours, even subsequent to the death of the conjugated tumor-cell. Moreover, 88% of S2 effector cells underwent apoptosis within the first ten hours of observation (data not shown). Finally, T cells in the S3 subgroup were rapid killers ($t_{Contact}$ 84±8 minutes and $t_{Death}$ 118±20 minutes) that arrested after conjugation but failed to resume migration after tumor-cell detachment/killing (FIGS. 34E-34F). Although these S3 effectors detached from tumor-cells after delivering the lethal hit, 53% then underwent apoptosis (data not shown).

Taken together these results demonstrate that at an E:T ratio of 1:1, the dominant subgroup of cells, S2, identified by their lack of motility and early conjugation to tumor cell, underwent AICD. On the contrary, highly motile CAR8 cells, S1, detached efficiently and resumed exploration of the local microenvironment, indicating that the motility of CAR8 cells might help identify efficient killers with decreased propensity for AICD. The observation that the majority of the CAR8 cells (S2 subgroup) maintained extended contact even after the death of the tumor cell is consistent with investigations on HIV-specific CTLs.

Figure 36B:
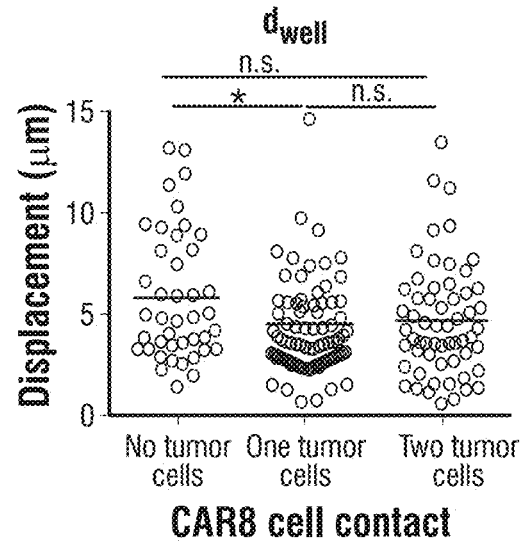

Example 3.12. CAR8 Cell Motility at Increased Tumor-Cell Densities Facilitates Multiplexed Killing The efficacy of CAR$^+$ T cells to eliminate tumor burden in excess of the number of effectors infused is due to their ability to persist and participate in serial killing. To facilitate identification of multi-killers, Applicants next profiled the interactions in nanowells containing a single CAR8 cell and 2 to 5 NALM-6 tumor cells (E:T 1:2-5). The frequency of CAR8 cells that were able to simultaneously conjugate to two or more tumor cells increased from 25% to 49% as the number of targets within the nanowell increased, indicating that multiplexed killing might be important (FIG. 36A). The frequency of simultaneous tumor conjugates that result in tumor cell deaths (46% [43-50%]) was not very different from true serial killers that attach, kill, detach and attach to a different tumor cell (49% [44-53%]), suggesting that CAR8 cells are capable of eliciting either mode of killing, likely dependent on tumor cell density. Individual multi-killer CAR8 cells ($N_{total}$=70) demonstrated only a small decrease in motility when conjugated to one tumor cell but showed no significant change in motility upon conjugation to multiple tumor cells ($d_{Well}$ (unconjugated): 5.9±0.5 µm vs $d_{Well}$ (single target): 4.6±0.3 µm vs $d_{Well}$ (two targets): 4.7±0.3 µm) (FIG. 36B).

Figure 36C:
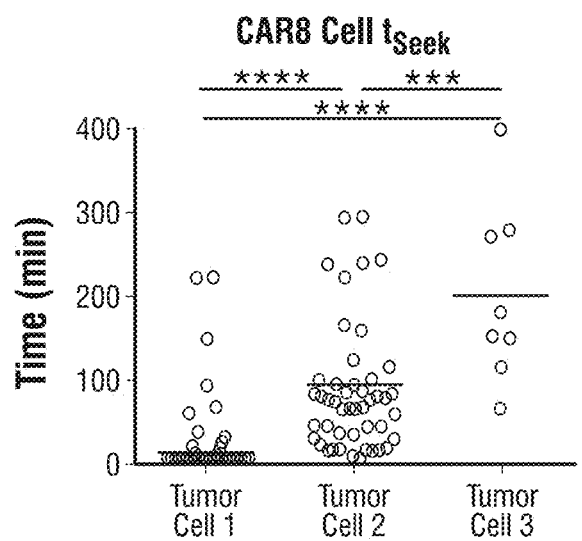
Figure 36D:
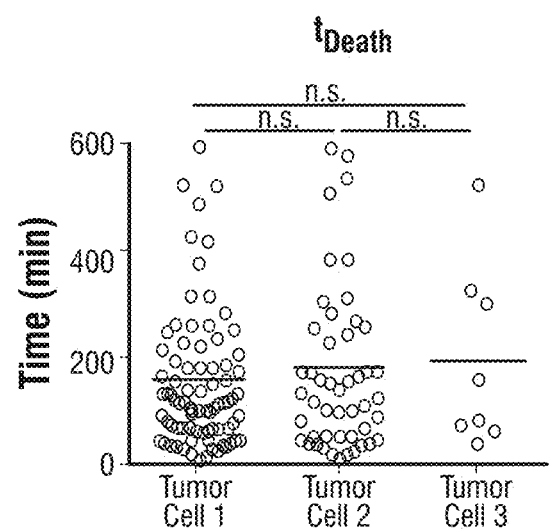

The only difference for multi-killers when contacting the different tumor cells was in their time to establish conjugates ($t_{Seek}$ Target$_1$: 18±4 minutes vs Target$_2$: 98±13 minutes, FIG. 36C). Both, duration of conjugation ($t_{Contact}$Target$_1$: 101±9 minutes vs Target$_2$: 113±15 minutes) and killing efficiency ($t_{Death}$Target$_1$: 156±17 minutes vs Target$_2$: 177±24 minutes) were no different (FIG. 36D).

In addition to contact duration, the number of CAR8 cell tumor cell conjugations that lead to killing during encounter with the first tumor cells (61% both donors) was also not significantly different from the number of conjugations that resulted in target cell killing during encounter with the second tumor cell (74% [70-79%]). These TIMING data suggest that the efficiency to kill a second tumor cell is largely unaffected by the hit on a first target (p-value>0.99). Furthermore, in comparison to single killer CAR8 cells, multi-killer CAR8 cells displayed greater motility when conjugated to the tumor cell despite the increased crowding because of higher tumor cell density.

Example 3.13. Motility can Identify a Subgroup of CAR4 Cells with Enhanced Cytotoxic Efficiency Next, the interaction of individual CAR4 cells from two donor-derived populations (FIG. 37A), with NALM-6 tumor cells were profiled using TIMING. At an E:T ratio of 1:1, 55% ($N_{total}$=549) of single CAR4 cells that conjugated to a NALM-6 cell subsequently killed the tumor cell. As with the CAR8 cells, the interaction behavior of CAR4 cells with the NALM-6 cells could be classified into three subgroups, S1-S3 (FIG. 38). CAR4 cells in the enhanced motility subgroup, S1 (11% both donors), displayed significantly faster kinetics of tumor cell death ($t_{Death}$ 157±17 minutes) compared to the dominant S2 (34% [31-36%]) subgroup ($t_{Death}$ 18±23 minutes, FIGS. 16A-16B). This increased kinetic efficiency was consistent with the decreased conjugation time required by the S1 subgroup of cells ($t_{Contact}$ 122±11 minutes) in comparison to the S2 subgroup ($t_{Contact}$ 300±21 minutes) (data not shown). These results suggest that similar to CAR8 cells, the motility of the CAR4 cells may help identify the most efficient killers.

Example 3.14. Both Single-Killer and Multi-Killer CAR4 Cells Required Longer Conjugation and Demonstrated Delayed Kinetics of Killing in Comparison to CAR8 Cells At the E:T ratio of 1:1, comparisons of the killing efficiency of CAR4 cells ($t_{Death}$ 284±11 minutes) and CAR8 cells (163±12 minutes) demonstrated that individual CAR4 cells on average required two extra hours to induce tumor cell death (FIG. 37E). Consistent with the observation that the S2 subgroup is the dominant population of CAR+ T cells, CAR4 cells in the S2 subgroup ($t_{Death}$ 318±23 minutes) demonstrated delayed kinetics of killing in comparison to CAR8 cells within the S2 subgroup ($t_{Death}$ 158±18 minutes) (data not shown). As mentioned herein, since the motility of CAR4 cells could be used to identify the most efficient killers (FIG. 37C), comparisons of the kinetic efficiency of CAR4 cells in the S1 subgroup ($t_{Death}$ 157±17 minutes) with CAR8 cells in the S1 subgroup ($t_{Death}$ 204±34 minutes) demonstrated no significant differences. This further supports the notion that motility might be a useful parameter in identifying efficient cytolytic CAR+ T cells.

Comparisons of the single-cell behavioral interactions of multi-killer CAR4 cells ($N_{total}$=78) with the CAR8 cells demonstrated that most features were conserved across cells of both phenotypes. First, the unconjugated motility of CAR4 cells ($d_{well}$ 6.9±0.5 µm) was no different than CAR8 cells ($d_{well}$ 5.9±0.5 µm, FIG. 39A). Second, like CAR8 cells, CAR4 cells demonstrated a matched decrease in motility (FIG. 39A) and increased circularization when conjugated to one or more tumor cells. Third, the preferred contact mode of the multi-killer CAR4 cells was also simultaneous conjugations to multiple tumor cells (data not shown). Fourth, simultaneous conjugates that result in killing accounted for 61% [60-63%] of multi killing events, indicating that this is an important mode of killing intrinsic to T cells and not just CD8+ T cells. Fifth, comparisons of $t_{Death}$ for the different tumor cells killed by individual multi-killer CAR4 cells demonstrated no differences (FIG. 39B). Lastly, the number of CAR4 cell tumor cell conjugations that lead to killing during the first tumor cell encounter (60% [58-61%]) is not significantly different from the number of contacts that leads to killing when encountering the second tumor cell (60% [57-63%]), suggesting that the killing efficiency is unchanged.

Consistent with the observations at an E:T of 1:1, multi-killer CAR4 cells required extended conjugation ($t_{Contact}$ 214±18 minutes) and demonstrated slower kinetics prior to killing the first tumor cell ($t_{Death}$ 310±23 minutes) in comparison to CAR8 cells (FIG. 39B). In aggregate, these results demonstrate that the major difference in CAR4 cells and CAR8 cells participating in either single killing or multi-killing is the kinetics of tumor cell death.

Example 3.15. Intracellular GzB Content can Explain Differences in Killing Efficiency To test the hypothesis that the varying efficiencies both between cells of the same population and in comparing CAR4 cells with CAR8 cells might be due to differences in expression of cytotoxic enzymes, Applicants employed intracellular staining at the single-cell level using flow cytometry to identify the expression GzB within these cells. To establish baseline controls, the intracellular GzB content of $CD3^+CD4^+$ cells (2.36±0.01) and $CD3^+CD8^+$ cells (3.89±0.04) in PBMC of two separate donors was determined (FIG. 39C). Consistent with our previous reports, both CAR4 cells (38.6±0.2) and CAR8 cells (267±2) showed significantly increased expression of GzB, in comparison to the controls (FIG. 39C). In agreement with the killing efficiency data (FIG. 39B), CAR4 cells expressed lower amounts of GzB in comparison to CAR8 cells, suggesting that the origin of the differing kinetic efficiencies of these cells might be the differences in GzB content (FIG. 39C).

In order to quantify the contribution GzB secretion to tumor cell killing at the single cell level, the ability of CAR4 cells to kill tumor cells in the presence of the calcium chelator EGTA was studied using flow cytometry. EGTA blocks cytotoxic granule exocytosis, and hence should eliminate GzB mediated killing. Not surprisingly, CAR4 cells co-cultured with tumor cells in the presence of 5 mM EGTA, demonstrated a substantial reduction in tumor cell killing across three different cell lines, Daudi-β2m, NALM-6 and $CD19^+EL4$ (FIGS. 39D-1 and 39D-2). The most striking reduction was seen with Daubi-β2m tumor cells, wherein CAR4 cell mediated killing was completely abolished (FIGS. 39D-1 and 39D-2).

Example 3.16. CAR+ T-Cell Fate is Dependent on Tumor-Cell Density

AICD is a mechanism by which T cells undergo programmed apoptosis in response to functional activation. The frequency and kinetics of individual cytolytic CAR+ T cells to undergo AICD was monitored under the two conditions: at high and low tumor densities. CAR8 cells inducing apoptosis of single targets demonstrated significantly faster kinetics of AICD ($t_{AICD}$ 221±14 minutes) in comparison to the multi-killer CAR8 cells from the same donors ($t_{AICD}$ 371±29 minutes, FIG. 40A). This trend of faster AICD kinetics at lower tumor cell density was also observed with CAR4 cells, although with delayed kinetics (FIG. 40A). Direct comparisons of the cells of different phenotypes at the same tumor cell density indicated that single-killer CAR8 cells underwent faster AICD ($t_{AICD}$, 221±14 minutes) in comparison to CAR4 cells ($t_{AICD}$ 328±19 minutes) (FIG. 40A). Consistent with the expectation that multi-killers efficiently resist AICD, these T cells from three of four donors displayed low frequencies of cells undergoing AICD (13-25%, FIG. 40B). However, multi-killer T cells from the last donor displayed AICD at elevated frequencies (58%)

underscoring that the efficiency of multi-killers to execute multiple tumor cells must be evaluated in the context of their ability to resist AICD (FIG. 40B).

Applicants confirmed that the effector apoptosis that was observed required functional antigenic stimulation by co-incubating CAR8 cells with CD19⁻EL4 cells within nanowell grids and imaged them using TIMING. The frequency of apoptotic effectors under these conditions was only 4% and this also confirmed that phototoxicity was negligible under the current imaging conditions.

Significantly, across all four donors, the frequencies of cytolytic CAR$^+$ T cells undergoing AICD was higher at an E:T of 1:1 in comparison to the multi-killer CAR$^+$ T cells, and this effect was more exaggerated with CAR8 cells (FIG. 40B). These data may help account for the decrease in number and even disappearance of infused CAR$^+$ T cells when the CD19$^+$ tumor mass is reduced.

Example 3.17. Summary

In this Example, Applicants implemented a high-throughput single-cell assay (TIMING) to dynamically profile the functionality of CAR$^+$ T cells. Applicants' analyses at the single-cell level demonstrate that much like CAR8 cells, CAR4 cells can directly engage in tumor cell killing, albeit with altered kinetics. Applicants further demonstrate that CAR4 cells can participate in multi-killing via simultaneous conjugation to multiple tumor cells.

At low tumor cell densities (E:T 1:1), the majority of the single killer CAR8 cells were significantly faster in killing tumor cells in comparison to individual CAR4 cells (FIG. 37E). By contrast, both single killer CAR8 and CAR4 cells within the S1 subgroup, characterized by their high basal motility, displayed no significant differences in the kinetics of tumor cell killing. Furthermore, in contrast to the rest of the population, effector apoptosis was infrequent amongst CAR8 and CAR4 cells in the 51 subgroup. Collectively, these data suggested that the high basal motility of CAR$^+$ T cells (CAR4 or CAR8) might help identify efficient killers with decreased propensity for AICD.

When interacting with increased numbers of tumor cells (E:T ratios of 1:2 to 1:5), both individual CAR4 and CAR8 cells efficiently conjugated to multiple tumor cells, facilitating multiplexed killing. Comparisons amongst the different tumor cells killed by these individual multi-killer CAR4/CAR8 cells demonstrated that they displayed an essentially unchanged efficiency ($t_{Contact}$) of killing of not only the first and second target killed, but also in comparison to (single-killer) CAR$^+$ T cells that were incubated with only one tumor cell (data not shown). In comparing CAR4 cells with CAR8 cells however, consistent with the observations at an E:T ratio of 1:1, CAR4 cells were significantly slower in tumor cell killing. Intracellular staining at the single-cell level indicated that the molecular origin of the differences in kinetic efficiency of the CAR4 and CAR8 cells could be attributed to their GzB content and this was further confirmed by blocking granule exocytosis using EGTA (FIGS. 39A-39D-2).

For both CAR4 and CAR8 cells, single killer effectors underwent apoptosis at higher frequencies and with faster kinetics in comparison to multi-killer CAR$^+$ T cells (FIGS. 29A-29E and 37A-37E). These data indicate that activation for lysis through multiple targets as opposed to prolonged conjugation with a single target reduces the propensity for effector apoptosis. Although the mechanistic basis for the responsiveness of these T cells to antigen/target density is not known, it is conceivable that the continuous propagation of these cells on irradiated aAPC at defined ratios, allows for balanced activation while minimizing AICD. Collectively, these data could provide mechanistic insights into observations that infused CAR$^+$ T cells swell in number in response to addressing large numbers of CD19$^+$ tumor cells, but then decline in number as the tumor bioburden is lowered due to the multi-killing by effector T cells.

In aggregate, comparisons of the CAR4 cells and CAR8 cells demonstrate that while CAR4 cells can participate in killing and multi-killing, they do so at slower rates, likely due to the lower GzB content. This decreased kinetic efficiency however is likely a minor disadvantage and is counter balanced by their decreased propensity of these cells to undergo AICD in the absence of help from other cells, as profiled in Applicants' nanowell system. Although Applicants have focused on the heterogeneity amongst CAR$^+$ T cells in this Example, the results presented here are also likely influenced by the underlying heterogeneity in tumor cells. While the expression of CD19 is uniform on the cells used as targets in Applicants' assays, it is feasible that there could be subpopulations of tumor cells that are resistant to CAR$^+$ T-cell mediated killing.

Example 4. Single-Cell Metrics of the Efficacy of CAR+ T Cells

CD19-specific CAR$^+$ T cells for the treatment of B-cell malignancies include a heterogeneous population. Among the most well described functional attributes of T-cell anti-tumor efficacy are cytotoxicity (against tumor cells) and ability to persist. Direct measurement of these T cell functions at the single-cell level requires the simultaneous monitoring of multiple parameters, including cell-cell interactions, cell migration, gene expression, their ability to kill target cells and the survival of the effector cells.

In this Example, Applicants demonstrate that single-cell methodologies can be used to characterize CAR$^+$ T cell potency a priori in vitro. In a comparison of two different CAR constructs, Applicants showed that in vitro potency defined as cytotoxicity against tumor cells was consistent with in vivo efficacy to control tumor cell progression. Further, the approach allowed Applicants to identify efficient killer CAR$^+$ T cells as expressing higher levels of granzyme B, (GZMB), CD137 (41BB) and TIM3 (HAVCR2).

As illustrated in FIG. 41, a TIMING assay followed by single cell gene expression profiling was utilized. As shown in FIG. 42, comparison of CAR constructs in vitro demonstrated optimal motility of T cells expressing CD8 hinge over IgG4 hinge. As shown in FIG. 43, CD8 hinge CAR$^+$ T cells kill tumor cells faster and in higher numbers.

Single CAR$^+$ T cells were retrieved after a 4 hour TIMING assay and assayed by multiplexed RT-qPCR. The gene expression profile of cytotoxic CAR$^+$ T cells reveals higher expression levels of CD137, TIM3 and GZMB transcripts. Volcano plot of genes transcripts (cytotoxic vs non cytotoxic) are shown in FIG. 44. A Venn diagram of differentially expressed genes for 3 donors is shown in FIG. 45.

FIG. 46 shows that CD137 is expressed at higher levels in activated CAR$^+$ T cells and in degranulating CAR$^+$ Tcells. FIG. 47 shows that CD137 stimulation decreases exhaustion markers while TIM3 targeting induces CTLA4. FIG. 48 shows that targeting CD137 and TIM3 increases cytotoxicity of CAR$^+$ T cells. FIG. 49 shows that targeting CD137 and TIM3 increases CAR$^+$ T cells kinetics of killing and serial killing.

In sum, this Example demonstrates that TIMING provides dynamic monitoring of individual T cells in vitro and allows for simultaneous measurement of cytotoxicity, cytokine secretion and gene expression at single cell resolution. Moreover, in vitro observations of the motility and functionality of individual CAR$^+$ T cells can predict efficacy in vivo.

Applicants also demonstrate in this Example that CD137 is dynamically induced on cytotoxic CAR$^+$ T cells. Moreover, subsequent targeting improves cytotoxicity of CAR$^+$ T cells while decreasing exhaustion. TIM3 transcripts are enriched in cytotoxic cells and targeting at the protein level boosts cytotoxicity of CAR$^+$ Tcells.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of evaluating or monitoring an effectiveness of an immunotherapy for cancer, wherein the method comprises:
receiving at least a first and a second single-cell measurement on at least one cell;
wherein each of the first and second single-cell measurement occurs at a single-cell level of the at least one cell, and wherein at least one of the first and second single-cell measurement is based on Time-lapse Imaging Microscopy In Nanowells Grids (TIMING), wherein TIMING comprises temporal imaging of at least three distinct timepoints of the at least one cell while the at least one cell is spatially confined to a well;
determining a value of responder/non-responder status of the tumor cell based at least in part on the first and second single-cell measurements at a single-cell level, wherein the value is indicative of a degree of responsiveness of the tumor cell to the immunotherapy with the at least one cell, thereby evaluating the effectiveness;
determining at least one treatment recommendation based at least in part on the value of responder/non-responder status, wherein the at least one treatment recommendation comprises an indication to administer or not administer the immunotherapy with the at least one cell based on the value; and
instructing the at least one treatment recommendation.

2. The method as recited in claim 1, wherein at least one of the first and second single-cell measurement comprises a level of expression of CD2 in the at least one cell at a single-cell level, wherein the level of expression of CD2 at the single-cell level is measured in at least one of:
a CD4+ T-cell population,
a CD8+ T cell population,
an NK cell population,
an apheresis sample, or
a manufactured CAR-expressing cell product sample.

3. The method as recited in claim 1, wherein at least one of the first and second single-cell measurement comprises measuring a level of expression of CD58 in the tumor cell at a single-cell level via an immunohistochemistry of a biopsy sample including the tumor cell.

4. The method as recited in claim 1, wherein at least one of the first and second single-cell measurement comprises measuring a level of motility of the at least one cell at a single-cell level in at least one of:
a CD4+ T-cell population,
a CD8+ T cell population,
an NK cell population,
an apheresis sample, or
a manufactured CAR-expressing cell product sample.

5. The method as recited in claim 1, wherein at least one of the first and second single-cell measurement comprises measuring a contact time that measures a time for the at least one cell to contact a tumor cell at a single-cell level, wherein the contact time is based on at least one microscopy image at the single-cell level.

6. The method as recited in claim 1, wherein at least one of the first and second single-cell measurement comprises measuring a contact time duration that measures a duration of contact of the at least one cell with the tumor cell at a single-cell level, wherein the contact time duration is based on at least one microscopy image at the single-cell level.

7. The method as recited in claim 1, wherein at least one of the first and second single-cell measurement comprises measuring a kill efficiency that measures an ability of the at least one cell to kill the tumor cell and at least one additional tumor cell at a single-cell level, wherein the kill efficiency at the single-cell level is based at least in part on a number of the at least one additional tumor cell of one or more matched tumor cells or tumor cell lines, or both, killed by the at least one cell, wherein the kill efficiency is measured for at least one of:
a CD4+ T-cell population,
a CD8+ T cell population, or
an NK cell population.

8. The method as recited in claim 1, wherein at least one of the first and second single-cell measurement comprises measuring a secretion amount that measures an amount of cytokines secreted by the at least one cell during a predetermined period of time at a single-cell level, wherein the cytokines comprise interferon gamma (IFN-γ) at the single-cell level.

9. The method as recited in claim 1, wherein at least one of the first and second single-cell measurement comprises measuring a survivability rate that measures a likelihood of the at least one cell to survive contact with one or more other cells at a single-cell level, wherein the measuring comprises measuring the survivability rate based on at least one microscopy image at the single-cell level.

10. The method as recited in claim 1, further comprising:
determining, by at least one processor, a statistical aggregation of the at least first and second single-cell measurements at the single-cell level; and
determining, by the at least one processor, the value based at least in part on a probability value for the statistical aggregation.

11. The method as recited in claim 1, wherein the TIMING data is analyzed in a method comprising: (i) auto-localizing a well containing the at least one cell by the use of image analysis algorithms to obtain an image of the well, and (ii) performing confinement-constrained cell segmentation and confinement-constrained cell tracking on the at least one cell.

12. A method for treating a subject having a cancer, comprising:
administering to the subject a therapeutically effective dose of an cell therapy upon the subject being identified as being responsive to a therapy comprising an immune-cell population, wherein said identifying comprises:

receiving at least a first and a second single-cell measurement on at least one cell, wherein each of the first and second single-cell measurement occurs at a single-cell level of the at least one cell, and wherein at least one of the first and second single-cell measurement is based on Timelapse Imaging Microscopy In Nanowells Grids (TIMING), wherein TIMING comprises temporal imaging of at least three distinct timepoints of the at least one cell while the at least one cell is spatially confined to a well;

determining a value of responder/non-responder status of the tumor cell based at least in part on the first and second single-cell measurements at a single-cell level; and wherein the value is indicative of a degree of responsiveness of the tumor cell to the immunotherapy with the at least one cell, thereby evaluating the subject.

13. The method of claim 1,
wherein the first single-cell measurement comprises at least one of:
- a level of expression of CD2 in the at least one cell at a single-cell level,
- a level of expression of CD58 in the at least one cell at a single-cell level,
- a level of expression of CD62L in the at least one cell at a single-cell level,
- a level of expression of CD45RA in the at least one cell at a single-cell level,
- a level of expression of CD28 in the at least one cell at a single-cell level,
- a level of expression of TIM3 in the at least one cell at a single-cell level,
- a level of expression of LAG3 in the at least one cell at a single-cell level,
- a level of expression of CTLA4 in the at least one cell at a single-cell level, wherein the second single-cell measurement comprises at least one of:
- a level of motility of the at least one cell based on a presence or absence of the tumor cell at a single-cell level,
- a contact time that measures a time for the at least one cell to contact the tumor cell at a single-cell level,
- a contact time duration that measures a duration of contact of the at least one cell with the tumor cell at a single-cell level,
- a kill efficiency that measures an ability of the at least one cell to kill the tumor cell and at least one additional tumor cell at a single-cell level,
- a secretion amount that measures an amount of cytokines secreted by the at least one cell during a predetermined period of time at a single-cell level, or
- a survivability rate that measures a likelihood of the at least one cell to survive contact with one or more other cells at a single-cell level.

14. The method of claim 1, wherein the first and second single-cell measurements occur at a single-cell level of the same cell.

15. The method of claim 1, wherein the first and second single-cell measurements occur at a single-cell level of two different cells.

16. The method of claim 15, wherein the first cell is an immune cell, and wherein the second cell is a tumor cell.

17. The method of claim 16,
wherein the first single-cell measurement comprises a level of expression of CD2 in the immune cell at a single-cell level, and
wherein the second single-cell measurement comprises a level of expression of CD58 in the tumor cell at a single-cell level.

* * * * *